US007847058B2

(12) United States Patent
Bock et al.

(10) Patent No.: US 7,847,058 B2
(45) Date of Patent: Dec. 7, 2010

(54) METHOD OF MODULATING CELL SURVIVAL, DIFFERENTIATION AND/OR SYNAPTIC PLASTICITY

(76) Inventors: Elisabeth Bock, Tonysvej 20, Charlottenlund (DK) DK-2920; Vladimir Berezin, Norrebrogade 223, 1.th., Copenhagen N (DK) DK-2200; Vladyslav Soroka, Olivenlunden 43, Hoge Taastrup (DK) DK-2630; Christina Kasper, Norredamsvej 93, Fredensborg (DK) DK-3480; Jette Sandholm Jensen Kastrup, Tokkekobvej, Allerod (DK) DK-3450

( * ) Notice: Subject to any disclaimer, the term of this patent is extended or adjusted under 35 U.S.C. 154(b) by 776 days.

(21) Appl. No.: 10/574,084

(22) PCT Filed: Sep. 29, 2004

(86) PCT No.: PCT/DK2004/000659

§ 371 (c)(1),
(2), (4) Date: May 15, 2007

(87) PCT Pub. No.: WO2005/030804

PCT Pub. Date: Apr. 7, 2005

(65) Prior Publication Data

US 2008/0249004 A1    Oct. 9, 2008

(30) Foreign Application Priority Data

Sep. 30, 2003    (DK) .............................. 2003 01418

(51) Int. Cl.
*A61K 38/00* (2006.01)
*C07K 4/00* (2006.01)
(52) U.S. Cl. .................................................. 530/300
(58) Field of Classification Search .................. None
See application file for complete search history.

(56) References Cited

U.S. PATENT DOCUMENTS

| 5,010,175 | A | 4/1991 | Rutter et al. |
|---|---|---|---|
| 5,223,409 | A | 6/1993 | Ladner et al. |
| 5,840,689 | A | 11/1998 | Daniloff |
| 6,723,344 | B2 | 4/2004 | Sakiyama-Elbert et al. |
| 2002/0104122 | A1 | 8/2002 | Kakitani et al. |
| 2005/0153888 | A1 | 7/2005 | Ronn et al. |
| 2008/0249004 | A1 | 10/2008 | Bocj et al. |
| 2009/0074774 | A1 | 3/2009 | Bock et al. |
| 2009/0074779 | A1 | 3/2009 | Bock et al. |
| 2009/0092617 | A1 | 4/2009 | Bock et al. |
| 2009/0105149 | A1 | 4/2009 | Albrechtsen et al. |
| 2009/0202554 | A1 | 8/2009 | Bock et al. |
| 2009/0221506 | A1 | 9/2009 | Bock et al. |
| 2009/0305951 | A1 | 12/2009 | Kiselyov et al. |

FOREIGN PATENT DOCUMENTS

| WO | WO99/54470 | 10/1999 |
|---|---|---|
| WO | WO 00/18801 | 4/2000 |
| WO | WO 01/07466 | * 2/2001 |

OTHER PUBLICATIONS

NCBI Accession polypeptide and identified as P13596—submitted Jan. 1, 1990.*
Small et al. (J. Cell Biol. 105:2335-2345 (1987).*
Atkins, A.R., Osborne, M.J., Lashuel, H.A., Edelman, G.M., Wright, P.E., Cunningham, B.A., and Dyson, H.J. (1999). "Association between the first two immunoglobulin-like domains of the neural cell adhesion molecule N-CAM". FEBS Lett. 451, 162-168.
Atkins, A.R, Chung, J., Deechongkit, S., Little, E.B., Edelman, G.M., Wright, P.E., Cunningham, B.A., and Dyson, H.J. (2001). "Solution structure of the third immunoglobulin domain of the neural cell adhesion molecule N-CAM: can solution studies define the mechanism of homophilic binding"? J. Mol. Biol. 311, 161-172.
Becker, J.W., Erickson, H.P., Hoffman, S., Cunningham, B.A., and Edelman, G.M. (1989). "Topology of cell adhesion molecules". Proc. Natl. Acad. Sci. USA 86, 1088-1092.
Berezin, V., Bock, E., and Poulsen, F.M. (2000)."The neural cell adhesion molecule". Curr. Opin. Drug Discovery Dev. 3, 605-609.
Bork, P., Downing, A.K., Kieffer, B., and Campbell, I.D. (1996). "Structure and distribution of modules in extracellular proteins". Q. Rev. Biophys. 29, 119-167.
Brieher, W.M., Yap, A.S., and Gumbiner, B.M. (1996). Lateral dimerization is required for the homophilic binding activity of C-cadherin. J Cell Biol. 135, 487-496.
Brünger, A.T., Adams, P.A., Clore, G.M., DeLano, W.L., Gros, P., Grosse-Kunstleve, R.W., Jiang, J-S., Kuszewski, J., Nilges, M., Pannu, N.S., Read, R.J., Rice, L.M., Simonson, T., and Warren, G.L. (1998). "Crystallography & NMR system: A new software suite for macromolecular structure determination". Acta Cryst. D54, 905-921.
Casasnovas, J.M., Stehle, T., Liu, J.H., Wang, J.H., and Springer, T.A. (1998)."A dimeric crystal structure for the N-terminal two domains of intercellular adhesion molecule-1". Proc. Natl. Acad. Sci. USA. 95, 4134-4139.
Chothia, C., and Jones, E.Y. (1997). "The molecular structure of cell adhesion molecules". Annu. Rev. Biochem. 66, 823-862.
Cole, G.J., and Akeson, R. (1989). "Identification of a heparin binding domain of the neural cell adhesion molecule N-CAM using synthetic peptides". Neuron 2, 1157-1165.
Collaborative Computational Project, No. 4. (1994). "The CCP4 Suite: Programs for Protein Crystallography". Acta Cryst. D50, 760-763.

(Continued)

*Primary Examiner*—Suzanne M. Noakes
(74) *Attorney, Agent, or Firm*—Iver P. Cooper

(57) ABSTRACT

The present invention relates to a method of modulating differentiation, adhesion and/or survival of the neural cell adhesion molecule (NCAM) presenting cells by providing compounds capable of modulating the interaction between the Ig1, Ig2 and/or Ig3 modules of NCAM. The invention provides candidate compounds capable of modulating the interaction between the Ig1, Ig2 and/or Ig3 modules of NCAM by using methods for screening and testing described in the application. The invention further relates to pharmaceutical compositions comprising compounds capable of modulating the interaction between the Ig1, Ig2 and/or Ig3 modules of NCAM and to use of the pharmaceutical compositions and compounds for the modulation of differentiation, adhesion and/or survival of NCAM presenting cells.

82 Claims, 63 Drawing Sheets

OTHER PUBLICATIONS

Covault, J., and Sanes, J.R. (1985)." Neural cell adhesion molecule (NCAM) accumulates in denervated and paralyzed skeletal muscles". Proc. Natl. Acad. Sci. USA 82, 4544-4548.

Conte, L.L., Chothia, C., and Janin, J. (1999). "The atomic structure of protein-protein recognition sites". J. Mol. Biol. 285, 2177-98.

Cremer, H., Lange, R., Christoph, A., Plomann, M., Vopper, G., Roes, J., Brown, R., Baldwin, S., Kraemer, P., Scheff, S., Barthels, D., Rajewsky, K., and Wille, W. (1994). "Inactivation of the N-CAM gene in mice results in size reduction of the olfactory bulb and deficits in spatial learning". Nature 367, 455-459.

Cunningham, B.A., Hemperly, J.J., Murray, B.A., Prediger, E.A., Brackenbury, R., and Edelman, G.M. (1987). "Neural cell adhesion molecule: Structure, immunoglobulin-like domains, cell surface modulation, and alternative RNA splicing". Science 236, 799-806.

Drejer J. and Schousboe A. (1989) "Selection of a pure cerebellar granule cell culture by kainate treatment". Neurochem Res. 14:751-4.

Edelman, G.M., and Crossin, K.L. (1991). "Cell adhesion molecules: implications for a molecular histology". Annu. Rev. Biochem. 60, 155-190.

Eksterowicz JE, Evensen E, Lemmen C, Brady GP, Lanctot JK, Bradley EK, Saiah E, Robinson LA, Grootenhuis PD, Blaney JM. ( 2002) "Coupling structure-based design with combinatorial chemistry: application of active site derived pharmacophores with informative library design". J Mol Graph Model. 20, 469-77.

Flocco, M.M., and Mowbray, S.L. (1994). "Planar stacking interactions of arginine and aromatic side-chains in proteins". J. Mol. Biol. 235, 709-717.

Freigang, J., Proba, K., Leder, L., Diederichs, K., Sonderegger, P., and Welte, W. (2000). "The crystal structure of the ligand binding module of axonin-1/TAG-1 suggests a zipper mechanism for neural cell adhesion". Cell 101, 425-433.

Gunning, P., Leavitt, J., Muscat, G., Ng, S.Y., and Kedes, L. (1987). "A human beta-actin expression vector system directs high-level accumulation of antisense transcripts". Proc. Natl. Acad. USA. 84, 4831-4835.

Hall, A.K., and Rutishauser, U. (1987). "Visualization of neural cell adhesion molecule by electron microscopy". J. Cell Biol. 104, 1579-1586.

Hunter, I., Sawa, H., Edlund, M., and Öbrink, B. (1996). "Evidence for regulated dimerization of cell-cell adhesion molecule (C-CAM) in epithelial cells". Biochem. J. 320, 847-853.

Janin, J. (1997). "Specific versus non-specific contacts in protein crystals". Nature Struct. Biol. 4, 973-974.

Jensen, P.H., Soroka, V., Thomsen, N.K., Ralets, I., Berezin, V., Bock, E., and Poulsen, F.M. (1999). "Structure and interactions of NCAM modules 1 and 2—basic elements in neural cell adhesion". Nature Struct. Biol. 6, 486-493.

Jones, T.A., Zou, J.Y., Cowan, S.W., and Kjeldgaard, M. (1991). "Improved methods for building protein models in electron density maps and the location of errors in these models". Acta Crystallogr. A47, 110-119.

Jones, E.Y., Davis, S.J., Williams, A.F., Harlos, K., and Stuart, D.I. (1992). "Crystal structure at 2.8 A resolution of a soluble form of the cell adhesion molecule CD2". Nature 360, 232-239.

Jones, S., and Thornton, J.M. (1996). "Principles of protein-protein interactions". Proc. Natl. Acad. Sci. USA 93, 13-20.

Jørgensen, O.S., and Bock, E. (1974). "Brain-specific synaptosomal membrane proteins demonstrated by crossed immunoelectrophoresis". J. Neurochem. 23, 879-880.

Kallapur, S.G., and Akeson, R.A. (1992). "The neural cell adhesion molecule (NCAM) heparin binding domain binds to cell surface heparan sulfate proteoglycans". J. Neurosci. Res. 33, 538-548.

Kasper, C., Stahlhut, M., Berezin, V., Maar, T.E., Edvardsen, K., Kiselyov, V.V., Soroka, V., and Bock, E. (1996)."Functional characterization of NCAM fibronectin type III domains: demonstration of modulatory effects of the proline-rich sequence encoded by alternatively spliced exons a and AAG". J. Neurosci. Res. 46, 173-186.

Kasper, C., Rasmussen, H., Kastrup, J.S., Ikemizu, S., Jones, E.Y., Berezin, V., Bock, E., and Larsen, I.K. (2000). "Structural basis of cell-cell adhesion by NCAM". Nature Struct. Biol. 7, 389-393.

Kiselyov, V.V., Berezin, V., Maar, T., Soroka, V., Edvardsen, K., Schousboe, A., and Bock, E. (1997). "The first Immunoglobulin-like NCAM domain is involved in both double reciprocal interaction with the second Immunoglobulin-like NCAM domain and in heparin binding". J.Biol.Chem. 272, 10125-10134.

Kleywegt, G.J., and Jones, T.A. (1996). "Phi/psi-chology: Ramachandran revisited". Structure 4, 1395-1400.

Kolkova, K., Novitskaya, V., Pedersen, N., Berezin, V., and Bock, E. (2000). "Neural cell adhesion molecule-stimulated neurite outgrowth depends on activation of protein kinase C and the Ras-mitogen-activated protein kinase pathway". J. Neurosci. 20, 2238-2246.

Kostrewa, D., Brockhaus, M., D'Arcy, A., Dale, G.E., Nelboeck, P., Schmid, G., Mueller, F., Bazzoni, G., Dejana, E., Bartfai, T., Winkler, F.K., and Hennig, M. (2001). "X-ray structure of junctional adhesion molecule: structural basis for homophilic adhesion via a novel dimerization motif". EMBO J. 20, 4391-4398.

Kraulis, P.J. (1991). "MOLSCRIPT: a program to produce both detailed and schematic plots of protein structures". J. Appl. Cryst. 24, 946-950.

Kristiansen, L.V., Marques, F.A., Soroka, V., Rønn, L.C., Kiselyov, V., Pedersen, N., Berezin, V., and Bock E. (1999). "Homophilic NCAM interactions interfere with L1 stimulated neurite outgrowth". FEBS Lett. 464, 30-34.

Leahy, D.J., Aukhil, I., and Erickson, H.P. (1996)."2.0 A crystal structure of a four-domain segment of human fibronectin encompassing the RGD loop and synergy region". Cell 84, 155-164.

Laskowski, R.A., MacArthur, M.W., Moss, D.S., and Thornton, J.M. (1993). "PROCHECK: a program to check the stereochemical quality of protein structures". J. Appl. Cryst. 26, 283-291.

Merritt, E.A. and Bacon, D.J. (1997). "Raster3D Photorealistic Molecular Graphics". Methods Enzymol. 277, 505-524.

Milev, P., Friedlander, D.R., Sakurai, T., Karthikeyan, L., Flad, M., Margolis, R.K., Grummet, M., and Margolis, R.U. (1994). "Interactions of the chondroitin sulfate proteoglican phosphacan, the extracellular domain of a receptor-type protein tyrosine phosphatase, with neurons, glia, and neural cell adhesion molecules". J. Cell Biol. 127, 1703-1715.

Miyahara, M., Nakanishi, H., Takahashi, K., Satoh-Horikawa, K., Tachibana, K., and Takai, Y. (2000). "Interaction of nectin with afadin is necessary for its clustering at cell-cell contact sites but not for its cis dimerization or trans interactions". J. Biol. Chem. 275, 613-618.

Muller, D., Wang, C., Skibo, G., Toni, N., Cremer, H., Calaora, V., Rougon, G., and Kiss, J.Z. (1996). "PSA-NCAM is required for activity-induced synaptic plasticity". Neuron 3, 413-422.

Navaza, J., and Saludjian, P. (1997). "AmoRe: An automated molecular replacement program package". Methods Enzymol. 276, 581-594.

Nybroe, O., Moran, N., and Bock, E. (1989). "Equilibrium binding analysis of neural cell adhesion molecule binding to heparin". J. Neurochem. 52, 1947-1949.

Otwinowski, Z., and Minor, W. (1997). "Processing of X-ray diffraction data collected in oscillation mode". Methods Enzymol. 276, 307-326.

Perrakis, A., Morris, R., and Lamzin, V.S. (1999). "Automated protein model building combined with iterative structure refinement". Nature Struct. Biol. 6, 458-463.

Probstmeier, R., Kuhn, K., and Schachner, M. (1989). "Binding properties of the neural cell adhesion molecule to different components of the extracellular matrix". J. Neurochem. 53, 1794-1801.

Ranheim, T.S., Edelman, G.M., and Cunningham, B.A. (1996). "Homophilic adhesion mediated by the neural cell adhesion molecule involves multiple immumoglobulin domains". Proc. Natl. Acad. Sci. USA. 93, 4071-4075.

Rao, Y., Wu, X-F., Gariepy J., Rutishauser, Urs., and Siu, C-H. (1992). "Identification of a peptide sequence involved in homophilic binding in the neural cell adhesion molecule NCAM". J. Cell Biol. 118, 937-949.

Rao, Y., Zhao, X., and Siu, C.H. (1994). "Mechanisms of homophilic binding mediated by the neural cell adhesion molecule NCAM. Evidence for isologous interaction". J. Biol. Chem. 269, 27540-275448.

Rønn, L.C., Ralets, I., Hartz, B.P., Bech, M., Berezin, A., Berezin, V., Moller, A., and Bock, E. (2000). "A simple procedure for quantification of neurite outgrowth based on stereological principles". J. Neurosci. Meth. 100, 25-32.

Sandig, M., Rao, Y., and Siu, C-H. (1994). "The homophilic binding site of the neural cell adhesion molecule NCAM is directly involved in promoting neurite outgrowth from cultured neural retinal cells". J. Biol. Chem. 269, 14841-14848.

Shapiro, L., Fannon, A.M., Kwong, Pd., Thompson, A., Lehmann, M.S., Grubel, G., Legrand, J-F., Als-Nielsen, J., Colman, D.R., and Hendrickson, W.A. (1995). Structural basis of cell-cell adhesion by cadherins. Nature 374, 327-337.

Soroka, V., Kiryushko, D., Novitskaya, V., Rønn, L.C., Poulsen, F.M., Holm, A., Bock, E., and Berezin, V. (2002). Induction of neuronal differentiation by a peptide corresponding to the homophilic binding site of the second Ig module of NCAM. J. Biol. Chem. 227, 24676-24683.

Su, X-D., Gastinel, L.N., Vaughn, D.E., Faye, I., Poon, P. and Bjorkman P.J. (1998). "Crystal structure of hemolin: A horseshoe shape with implications for homophilic adhesion". Science 281, 991-995.

Tomasiewicz, H., Ono, K., Yee, D., Thompson, C., Goridis, C., Rutishauser, U., and Magnuson, T. (1993). "Genetic deletion of a neural cell adhesion molecule variant (NCAM-180) produces defects in the central nervous system". Neuron 11, 1163-1174.

Thomsen, N.K., Soroka, V., Jensen, P.H., Berezin, V., Bock, E., and Poulsen, F.M. (1996). "The three-dimensional structure of the first domain of neural cell adhesion molecule". Nature Struct. Biol. 3, 581-585.

Wu, Y.Y., and Bradshaw, R.A. (1995). "PC12-E2 cells: a stable variant with altered responses to growth factor stimulation". J. Cell. Physiol. 164, 522-532.

Wu, H., Kwong, P.D., and Hendrickson, W.A. (1997). "Dimeric association and segmental variability in the structure of human CD4". Nature 387, 527-530.

Kasper, C., et al. "Extracellular modules of the cell adhesion molecules NCAM and L1", Database HTTP://WWW 'Online! 2002, XP002315066, retrieved from HTTP://WWW-HASYLAB.DESY.DE/SCIENCE/ANNUAL_REPORTS/2002_REPORT/PART2/CONTRIB/72/7824.

Huang, Z., et al. "Immunoglobulin Superfamily Proteins: Structure, Mechanisms, and Drug Discovery", Biopoly, vol. 43, pp. 367-382, 1997.

Rønn, L.C.B., et al. "Identification of a neuritogenic ligand of the neural cell adhesion molecule using a combinatorial library of synthetic peptides" Nature Biotechnology, vol. 17, Oct. 1999, 1000-1005.

Soroka, V., et al. "Structure and Interactions of NCAM Ig1-2-3 suggest a Novel Zipper Mechanism for Homophilic Adhesion" Structure, vol. 10, 1291-1301, Oct. 2003.

Takeda, et al. "E-Cadherin functions as a cis-dimer at the cell-cell adhesive interface in vivo"; Nature Structural Biology; vol. 6, No. 4, Apr. 1999.

U.S. Appl. No. 12/664,085, filed Dec. 11, 2009, Berezin et al.

U.S. Appl. No. 12/745,129, filed May 27, 2010, Berezin et al.

Andersen, et al., "Deciphering the Antibodyome—Peptide Arrays for Serum Antibody Biomarker Diagnostics", Current Proteomics, vol. 6, pp. 1-12, 2009.

Devlin, et al., "Random Peptide Libraries: A Source of Specific Protein Binding Molecules", Science, vol. 249, pp. 404-406, Jul. 27, 1990.

Fodor, et al., "Light-Directed, Spatially Addresable Parallel Chemical Synthesis", Science, vol. 251, pp. 767-773, Feb. 15, 1991.

Fret, et al., "Different Extracellular Domains of the Neural Cell Adhesion Molecule (N-CAM) Are Involved in Different Functions", The Journal of Cell Biology, vol. 118, No. 1, pp. 177-194, Jul. 1992.

Geysen, et al., "Use of peptide synthesis to probe viral antigens for epitopes to a resolution of a single amino acid", Proc. Natl. Acad. Sci. USA, vol. 81, pp. 3998-4002, Jul. 1984.

Geysen, et al., "Chemistry of Antibody Binding to a Protein", Science, vol. 235, pp. 1184-1190, Mar. 6, 1987.

Geysen, et al., "Strategies for epitope analysis using peptide synthesis", Journal of Immunological Methods, vol. 102, pp. 259-274, 1987.

Houghten, et al., "Generation and use of synthetic peptide combinatorial libraries for basic research and drug discovery", Nature, vol. 354, pp. 84-86, Nov. 7, 1991.

Kiselyov, et al., "Structure of the Second Fibronectin Type III Module of NCAM Identification of a Neuritogenic Site", European Journal of Neuroscience, vol. 12, suppl. 11, p. 274, 2000.

Kolkova, et al., "Neural Cell Adhesion Molecule-Stimulated Neurite Outgrowth Depends on Activation of Protein Kinase C and the Ras-Mitogen-Activated Protein Kinase Pathway", The Journal of Neuroscience, vol. 20(6), pp. 2238-2246, Mar. 15, 2000.

Lam, et al., "A new type of synthetic peptide library for identifying ligand-binding activity", Nature, vol. 354, pp. 82-84, Nov. 7, 1991.

Panicker, et al. "Recent Advances in Peptide-Based Microarray Technologies", Combinatorial Chemistry & High Throughput Screening, vol. 7, pp. 547-556, 2004.

Pavia, Michael, "The Chemical Generation of Molecular Diversity", http://www.netsci.org/Science/Combichem/feature01.html, pp. 1-11, May 14, 2010.

Pellois, et al., "Individually addressable parallel peptide synthesis on microchips", Nature Biotechnology, vol. 20, pp. 922-926, Sep. 2002.

Scott, et al., "Searching for Peptide Ligands with an Epitope Library", Science, vol. 249, pp. 386-390, Jul. 27, 1990.

Skladchikova, et al., "Extracellular Adenosine Triphosphate Affects Neural Cell Adhesion Molecule (NCAM)-Mediated Cell Adhesion and Neurite Outgrowth", Journal of Neuroscience Research, vol. 57, pp. 207-218, 1999.

Small, et al. "Identification of a cDNA Clone That Contains the Complete Coding Sequence for a 140-kD Rat NCAM Polypeptide", The Journal of Cell Biology, vol. 105, pp. 2335-2345, Nov. 1987.

Soroka, et al., "Structure and Interactions of NCAM Ig1-2-3 Suggest a Novel Zipper Mechanism for Homophilic Adhesion", Structure, vol. 10, pp. 1291-1301, Oct. 2003.

Uttamchandani, et al., "Combinatorial Peptide Microarrays for the Rapid Determination of Kinase Specificity", Bioorganic & Medicinal Chemistry Letters, vol. 13, pp. 2997-3000, 2003.

Schlessinger, "Immunoglobulin like domain of mouse N-CAM", Deposit AAR72860; Mar. 25, 2003 (revised), Nov. 21, 1995 (first entry).

Springer, "ICAM-1 related amino acid sequence NCAM #2", Deposit ABP53771; Jan. 3, 2003 (first entry).

* cited by examiner

Figure 1

Table 1. Crystallographic data and refinement statistics

|  | Native data set |
|---|---|
| Wavelength (Å) | 1.0526 |
| Resolution range (Å)[1] | 50.0-2.0 (2.07-2.0) |
| No. of observed reflections | 164,206 |
| No. of unique reflections | 27,881 |
| No. of reflections in $R_{free}$ set | 828 |
| Completeness (%) | 99.2(99.4) |
| I/σ(I) | 19.6(1.4) |
| $(R_{merge})$ (%)[2] | 3.9(20.9) |
| $R_{cryst}/R_{free}$ (%)[3] | 21.8/23.8 |
| No. of refined non-hydrogen atoms[4] |  |
| protein | 2248 |
| water | 265 |
| Average B-factor (all atoms, Å$^2$) | 60 |
| Wilson B-factor (Å$^2$) | 45 |
| R.m.s. Δ bond lengths/angles[5] | 0.0081/1.7 |
| Residues in allowed regions (%)[6] | 97% |

[1] Values in parentheses are statistics for the highest resolution bin.

[2] $R_{merge}(I) = \sum_{hkl}|Ihkl - <Ihkl>|/\sum_{hkl}Ihkl$, where $Ihkl$ is the measured intensity of the reflections with indices $hkl$.

[3] $R = \sum_{hkl}||Fo|-|Fc||/\sum|Fo|$, where $|Fo|$ and $|Fc|$ are the observed and calculated structure factor amplitudes for reflection hkl, applied to the work ($R_{cryst}$=97%) and test ($R_{free}$=3%) sets, respectively.

[4] Residues -2, 239 and 240 were not located. Residues originating from the cloning site were given negative integers.

[5] Root mean squared deviations (rms Δ) in bond length and angles from ideal values.

[6] The Ramachandran plot was calculated according to Kleywegt and Jones, (1996).

Figure 2 (Table 2 (page 1))

```
HEADER      CELL ADHESION                                    1QZ1
TITLE       CRYSTAL STRUCTURE OF THE IG 1-2-3 FRAGMENT OF NCAM
COMPND      MOL_ID: 1;
COMPND     2 MOLECULE: NEURAL CELL ADHESION MOLECULE 1, 140 KDA ISOFORM;
COMPND     3 CHAIN: A;
COMPND     4 FRAGMENT: IG MODULES 1-2-3;
COMPND     5 SYNONYM: N-CAM 140, NCAM-140;
COMPND     6 ENGINEERED: YES
SOURCE      MOL_ID: 1;
SOURCE     2 ORGANISM_SCIENTIFIC: RATTUS NORVEGICUS;
SOURCE     3 ORGANISM_COMMON: RAT;
SOURCE     4 GENE: NCAM1;
SOURCE     5 EXPRESSION_SYSTEM: PICHIA PASTORIS;
SOURCE     6 EXPRESSION_SYSTEM_COMMON: FUNGUS;
SOURCE     7 EXPRESSION_SYSTEM_STRAIN: GS-115;
SOURCE     8 EXPRESSION_SYSTEM_VECTOR_TYPE: PLASMID;
SOURCE     9 EXPRESSION_SYSTEM_PLASMID: PHIL-S1
KEYWDS      IG MODULES, CELL ADHESION, NCAM
EXPDTA      X-RAY DIFFRACTION
AUTHOR      V.SOROKA, K.KOLKOVA, J.S.KASTRUP, K.DIEDERICHS, J.BREED,
AUTHOR     2 V.V.KISELYOV, F.M.POULSEN, I.LARSEN, W.WELTE, V.BEREZIN,
AUTHOR     3 E.BOCK, C.KASPER
JRNL            AUTH   V.SOROKA, K.KOLKOVA, J.S.KASTRUP, K.DIEDERICHS,
JRNL            AUTH 2 J.BREED, V.V. KISELYOV, F.M.POULSEN, I.LARSEN,
JRNL            AUTH 3 W.WELTE, V.BEREZIN, E.BOCK, C.KASPER
JRNL            TITL   STRUCTURE AND INTERACTIONS OF NCAM IG1-2-3 SUGGEST
JRNL            TITL 2 A NOVEL ZIPPER MECHANISM FOR HOMOPHILIC ADHESION
JRNL            REF    TO BE PUBLISHED
JRNL            REFN
REMARK     1
REMARK     1 REFERENCE 1
REMARK     1  AUTH    C.KASPER,H.RASMUSSEN,J.S.KASTRUP,S.IKEMIZU,
REMARK     1  AUTH 2  E.Y.JONES,V.BEREZIN,E.BOCK,I.K.LARSEN
REMARK     1  TITL    STRUCTURAL BASIS OF CELL-CELL ADHESION BY NCAM
REMARK     1  REF     NAT.STRUCT.BIOL.                 V.   7  389 2000
REMARK     1  REFN    ASTM NSBIEW  US ISSN 1072-8368
REMARK     1 REFERENCE 2
REMARK     1  AUTH    C.KASPER,H.RASMUSSEN,V.BEREZIN,E.BOCK,I.K.LARSEN
REMARK     1  TITL    EXPRESSION, CRYSTALLIZATION AND PRELIMINARY X-RAY
REMARK     1  TITL 2  ANALYSIS OF THE TWO AMINO-TERMINAL IG DOMAINS OF
REMARK     1  TITL 3  THE NEURAL CELL ADHESION MOLECULE (NCAM)
REMARK     1  REF     ACTA CRYSTALLOGR.,SECT.D         V.  55 1598 1999
REMARK     1  REFN    ASTM ABCRE6  DK ISSN 0907-4449
REMARK     2
REMARK     2 RESOLUTION. 2.00 ANGSTROMS.
REMARK     3
REMARK     3 REFINEMENT.
REMARK     3   PROGRAM     : CNS 1.0
REMARK     3   AUTHORS     : BRUNGER,ADAMS,CLORE,DELANO,GROS,GROSSE-
REMARK     3               : KUNSTLEVE,JIANG,KUSZEWSKI,NILGES, PANNU,
REMARK     3               : READ,RICE,SIMONSON,WARREN
REMARK     3
REMARK     3   REFINEMENT TARGET : ENGH & HUBER
REMARK     3
REMARK     3   DATA USED IN REFINEMENT.
REMARK     3    RESOLUTION RANGE HIGH (ANGSTROMS) : 2.00
REMARK     3    RESOLUTION RANGE LOW  (ANGSTROMS) : 48.64
```

Figure 2 (Table 2 (page 2))

```
REMARK   3    DATA CUTOFF              (SIGMA(F)) : 0.000
REMARK   3    DATA CUTOFF HIGH         (ABS(F))   : NULL
REMARK   3    DATA CUTOFF LOW          (ABS(F))   : NULL
REMARK   3    COMPLETENESS (WORKING+TEST)   (%)   : 99.2
REMARK   3    NUMBER OF REFLECTIONS               : 28289
REMARK   3
REMARK   3   FIT TO DATA USED IN REFINEMENT.
REMARK   3    CROSS-VALIDATION METHOD            : THROUGHOUT
REMARK   3    FREE R VALUE TEST SET SELECTION    : RANDOM
REMARK   3    R VALUE            (WORKING SET)   : 0.218
REMARK   3    FREE R VALUE                       : 0.238
REMARK   3    FREE R VALUE TEST SET SIZE   (%)   : NULL
REMARK   3    FREE R VALUE TEST SET COUNT        : 828
REMARK   3    ESTIMATED ERROR OF FREE R VALUE    : NULL
REMARK   3
REMARK   3   FIT IN THE HIGHEST RESOLUTION BIN.
REMARK   3    TOTAL NUMBER OF BINS USED           : NULL
REMARK   3    BIN RESOLUTION RANGE HIGH     (A)   : 2.00
REMARK   3    BIN RESOLUTION RANGE LOW      (A)   : 2.13
REMARK   3    BIN COMPLETENESS (WORKING+TEST) (%) : 99.00
REMARK   3    REFLECTIONS IN BIN    (WORKING SET) : NULL
REMARK   3    BIN R VALUE           (WORKING SET) : 0.3730
REMARK   3    BIN FREE R VALUE                    : 0.4390
REMARK   3    BIN FREE R VALUE TEST SET SIZE  (%) : NULL
REMARK   3    BIN FREE R VALUE TEST SET COUNT     : 148
REMARK   3    ESTIMATED ERROR OF BIN FREE R VALUE : 0.036
REMARK   3
REMARK   3   NUMBER OF NON-HYDROGEN ATOMS USED IN REFINEMENT.
REMARK   3    PROTEIN ATOMS            : 2247
REMARK   3    NUCLEIC ACID ATOMS       : 0
REMARK   3    HETEROGEN ATOMS          : 0
REMARK   3    SOLVENT ATOMS            : 265
REMARK   3
REMARK   3   B VALUES.
REMARK   3    FROM WILSON PLOT           (A**2) : 42.00
REMARK   3    MEAN B VALUE      (OVERALL, A**2) : 60.60
REMARK   3    OVERALL ANISOTROPIC B VALUE.
REMARK   3     B11 (A**2) : 7.90000
REMARK   3     B22 (A**2) : -15.20000
REMARK   3     B33 (A**2) : 7.30000
REMARK   3     B12 (A**2) : 0.00000
REMARK   3     B13 (A**2) : 0.00000
REMARK   3     B23 (A**2) : 0.00000
REMARK   3
REMARK   3   ESTIMATED COORDINATE ERROR.
REMARK   3    ESD FROM LUZZATI PLOT        (A) : 0.30
REMARK   3    ESD FROM SIGMAA              (A) : 0.36
REMARK   3    LOW RESOLUTION CUTOFF        (A) : 5.00
REMARK   3
REMARK   3   CROSS-VALIDATED ESTIMATED COORDINATE ERROR.
REMARK   3    ESD FROM C-V LUZZATI PLOT    (A) : 0.35
REMARK   3    ESD FROM C-V SIGMAA          (A) : 0.42
REMARK   3
REMARK   3   RMS DEVIATIONS FROM IDEAL VALUES.
REMARK   3    BOND LENGTHS                 (A) : 0.008
REMARK   3    BOND ANGLES            (DEGREES) : 1.70
REMARK   3    DIHEDRAL ANGLES        (DEGREES) : 27.50
```

Figure 2 (Table 2 (page 3))

```
REMARK   3    IMPROPER ANGLES            (DEGREES) : 0.95
REMARK   3
REMARK   3   ISOTROPIC THERMAL MODEL : ANISOTROPIC
REMARK   3
REMARK   3   ISOTROPIC THERMAL FACTOR RESTRAINTS.    RMS     SIGMA
REMARK   3    MAIN-CHAIN BOND              (A**2) : NULL  ; NULL
REMARK   3    MAIN-CHAIN ANGLE             (A**2) : NULL  ; NULL
REMARK   3    SIDE-CHAIN BOND              (A**2) : NULL  ; NULL
REMARK   3    SIDE-CHAIN ANGLE             (A**2) : NULL  ; NULL
REMARK   3
REMARK   3   BULK SOLVENT MODELING.
REMARK   3    METHOD USED : NULL
REMARK   3    KSOL        : NULL
REMARK   3    BSOL        : NULL
REMARK   3
REMARK   3   NCS MODEL : NULL
REMARK   3
REMARK   3   NCS RESTRAINTS.                         RMS    SIGMA/WEIGHT
REMARK   3    GROUP  1  POSITIONAL            (A) : NULL  ; NULL
REMARK   3    GROUP  1  B-FACTOR           (A**2) : NULL  ; NULL
REMARK   3
REMARK   3   PARAMETER FILE  1  : NULL
REMARK   3   TOPOLOGY FILE   1  : NULL
REMARK   3
REMARK   3   OTHER REFINEMENT REMARKS: RESIDUES 241-242 WERE NOT LOCATED IN
REMARK   3   THE ELECTRON DENSITY MAP
REMARK   4
REMARK   4 1QZ1 COMPLIES WITH FORMAT V. 2.3, 09-JULY-1998
REMARK 100
REMARK 100 THIS ENTRY HAS BEEN PROCESSED BY RCSB ON 17-SEP-2003.
REMARK 100 THE RCSB ID CODE IS RCSB020242.
REMARK 200
REMARK 200 EXPERIMENTAL DETAILS
REMARK 200   EXPERIMENT TYPE                : X-RAY DIFFRACTION
REMARK 200   DATE OF DATA COLLECTION        : 06-NOV-2000; 04-DEC-2000
REMARK 200   TEMPERATURE       (KELVIN) : 100.0
REMARK 200   PH                             : 5.20
REMARK 200   NUMBER OF CRYSTALS USED        : 1
REMARK 200
REMARK 200   SYNCHROTRON            (Y/N) : Y; N
REMARK 200   RADIATION SOURCE             : MAX II ; ROTATING ANODE
REMARK 200   BEAMLINE                     : I711
REMARK 200   X-RAY GENERATOR MODEL        : NULL; HOME SOURCE
REMARK 200   MONOCHROMATIC OR LAUE  (M/L) : M
REMARK 200   WAVELENGTH OR RANGE      (A) : 1.0526; 1.54
REMARK 200   MONOCHROMATOR                : NULL
REMARK 200   OPTICS                       : NULL
REMARK 200
REMARK 200   DETECTOR TYPE                : IMAGE PLATE; IMAGE PLATE
REMARK 200   DETECTOR MANUFACTURER        : MARRESEARCH; MARRESEARCH
REMARK 200   INTENSITY-INTEGRATION SOFTWARE : DENZO
REMARK 200   DATA SCALING SOFTWARE        : SCALEPACK
REMARK 200
REMARK 200   NUMBER OF UNIQUE REFLECTIONS : 27881
REMARK 200   RESOLUTION RANGE HIGH    (A) : 2.000
REMARK 200   RESOLUTION RANGE LOW     (A) : 50.000
REMARK 200   REJECTION CRITERIA  (SIGMA(I)) : 0.000
```

Figure 2 (Table 2 (page 4))

```
REMARK 200
REMARK 200 OVERALL.
REMARK 200   COMPLETENESS FOR RANGE    (%) :  99.2
REMARK 200   DATA REDUNDANCY               :  5.900
REMARK 200   R MERGE                   (I) :  0.03900
REMARK 200   R SYM                     (I) :  0.03900
REMARK 200   <I/SIGMA(I)> FOR THE DATA SET :  19.6000
REMARK 200
REMARK 200 IN THE HIGHEST RESOLUTION SHELL.
REMARK 200   HIGHEST RESOLUTION SHELL, RANGE HIGH (A) :  2.00
REMARK 200   HIGHEST RESOLUTION SHELL, RANGE LOW  (A) :  2.07
REMARK 200   COMPLETENESS FOR SHELL    (%) :  99.4
REMARK 200   DATA REDUNDANCY IN SHELL      :  3.80
REMARK 200   R MERGE FOR SHELL         (I) :  0.20900
REMARK 200   R SYM FOR SHELL           (I) :  0.20900
REMARK 200   <I/SIGMA(I)> FOR SHELL        :  1.400
REMARK 200
REMARK 200 DIFFRACTION PROTOCOL: SINGLE WAVELENGTH
REMARK 200 METHOD USED TO DETERMINE THE STRUCTURE: MOLECULAR REPLACEMENT
REMARK 200 SOFTWARE USED: AMORE
REMARK 200 STARTING MODEL: PDB ENTRY 1EPF
REMARK 200
REMARK 200 REMARK: NULL
REMARK 280
REMARK 280 CRYSTAL
REMARK 280 SOLVENT CONTENT, VS    (%): NULL
REMARK 280 MATTHEWS COEFFICIENT, VM (ANGSTROMS**3/DA): NULL
REMARK 280
REMARK 280 CRYSTALLIZATION CONDITIONS: 14-17% PEG 4000, 450 MM LI SULFATE,
REMARK 280  100 MM NA ACETATE, PH 5.2, VAPOR DIFFUSION, HANGING DROP,
REMARK 280  TEMPERATURE 293K
REMARK 290
REMARK 290 CRYSTALLOGRAPHIC SYMMETRY
REMARK 290 SYMMETRY OPERATORS FOR SPACE GROUP: I 21 21 21
REMARK 290
REMARK 290      SYMOP    SYMMETRY
REMARK 290     NNNMMM    OPERATOR
REMARK 290       1555    X,Y,Z
REMARK 290       2555    1/2-X,-Y,1/2+Z
REMARK 290       3555    -X,1/2+Y,1/2-Z
REMARK 290       4555    1/2+X,1/2-Y,-Z
REMARK 290       5555    1/2+X,1/2+Y,1/2+Z
REMARK 290       6555    -X,1/2-Y,Z
REMARK 290       7555    1/2-X,Y,-Z
REMARK 290       8555    X,-Y,1/2-Z
REMARK 290
REMARK 290     WHERE NNN -> OPERATOR NUMBER
REMARK 290           MMM -> TRANSLATION VECTOR
REMARK 290
REMARK 290 CRYSTALLOGRAPHIC SYMMETRY TRANSFORMATIONS
REMARK 290 THE FOLLOWING TRANSFORMATIONS OPERATE ON THE ATOM/HETATM
REMARK 290 RECORDS IN THIS ENTRY TO PRODUCE CRYSTALLOGRAPHICALLY
REMARK 290 RELATED MOLECULES.
REMARK 290     SMTRY1   1  1.000000  0.000000  0.000000        0.00000
REMARK 290     SMTRY2   1  0.000000  1.000000  0.000000        0.00000
REMARK 290     SMTRY3   1  0.000000  0.000000  1.000000        0.00000
REMARK 290     SMTRY1   2 -1.000000  0.000000  0.000000       25.72000
```

Figure 2 (Table 2 (page 5))

```
REMARK 290   SMTRY2   2   0.000000  -1.000000   0.000000        0.00000
REMARK 290   SMTRY3   2   0.000000   0.000000   1.000000       74.65000
REMARK 290   SMTRY1   3  -1.000000   0.000000   0.000000        0.00000
REMARK 290   SMTRY2   3   0.000000   1.000000   0.000000       53.88000
REMARK 290   SMTRY3   3   0.000000   0.000000  -1.000000       74.65000
REMARK 290   SMTRY1   4   1.000000   0.000000   0.000000       25.72000
REMARK 290   SMTRY2   4   0.000000  -1.000000   0.000000       53.88000
REMARK 290   SMTRY3   4   0.000000   0.000000  -1.000000        0.00000
REMARK 290   SMTRY1   5   1.000000   0.000000   0.000000       25.72000
REMARK 290   SMTRY2   5   0.000000   1.000000   0.000000       53.88000
REMARK 290   SMTRY3   5   0.000000   0.000000   1.000000       74.65000
REMARK 290   SMTRY1   6  -1.000000   0.000000   0.000000        0.00000
REMARK 290   SMTRY2   6   0.000000  -1.000000   0.000000       53.88000
REMARK 290   SMTRY3   6   0.000000   0.000000   1.000000        0.00000
REMARK 290   SMTRY1   7  -1.000000   0.000000   0.000000       25.72000
REMARK 290   SMTRY2   7   0.000000   1.000000   0.000000        0.00000
REMARK 290   SMTRY3   7   0.000000   0.000000  -1.000000        0.00000
REMARK 290   SMTRY1   8   1.000000   0.000000   0.000000        0.00000
REMARK 290   SMTRY2   8   0.000000  -1.000000   0.000000        0.00000
REMARK 290   SMTRY3   8   0.000000   0.000000  -1.000000       74.65000
REMARK 290
REMARK 290 REMARK: NULL
REMARK 300
REMARK 300 BIOMOLECULE: 1
REMARK 300 THIS ENTRY CONTAINS THE CRYSTALLOGRAPHIC ASYMMETRIC UNIT
REMARK 300 WHICH CONSISTS OF 1 CHAIN(S). SEE REMARK 350 FOR
REMARK 300 INFORMATION ON GENERATING THE BIOLOGICAL MOLECULE(S).
REMARK 350
REMARK 350 GENERATING THE BIOMOLECULE
REMARK 350 COORDINATES FOR A COMPLETE MULTIMER REPRESENTING THE KNOWN
REMARK 350 BIOLOGICALLY SIGNIFICANT OLIGOMERIZATION STATE OF THE
REMARK 350 MOLECULE CAN BE GENERATED BY APPLYING BIOMT TRANSFORMATIONS
REMARK 350 GIVEN BELOW.  BOTH NON-CRYSTALLOGRAPHIC AND
REMARK 350 CRYSTALLOGRAPHIC OPERATIONS ARE GIVEN.
REMARK 350
REMARK 350 BIOMOLECULE: 1
REMARK 350 APPLY THE FOLLOWING TO CHAINS: A
REMARK 350    BIOMT1   1   1.000000   0.000000   0.000000        0.00000
REMARK 350    BIOMT2   1   0.000000   1.000000   0.000000        0.00000
REMARK 350    BIOMT3   1   0.000000   0.000000   1.000000        0.00000
REMARK 465
REMARK 465 MISSING RESIDUES
REMARK 465 THE FOLLOWING RESIDUES WERE NOT LOCATED IN THE
REMARK 465 EXPERIMENT. (M=MODEL NUMBER; RES=RESIDUE NAME; C=CHAIN
REMARK 465 IDENTIFIER; SSSEQ=SEQUENCE NUMBER; I=INSERTION CODE.)
REMARK 465
REMARK 465   M RES C SSSEQI
REMARK 465     ARG A    -2
REMARK 465     GLU A   239
REMARK 465     GLU A   240
REMARK 500
REMARK 500 GEOMETRY AND STEREOCHEMISTRY
REMARK 500 SUBTOPIC: COVALENT BOND ANGLES
REMARK 500
REMARK 500 THE STEREOCHEMICAL PARAMETERS OF THE FOLLOWING RESIDUES
REMARK 500 HAVE VALUES WHICH DEVIATE FROM EXPECTED VALUES BY MORE
REMARK 500 THAN 6*RMSD (M=MODEL NUMBER; RES=RESIDUE NAME; C=CHAIN
```

Figure 2 (Table 2(page 6))

```
REMARK 500 IDENTIFIER; SSEQ=SEQUENCE NUMBER; I=INSERTION CODE).
REMARK 500
REMARK 500 STANDARD TABLE:
REMARK 500 FORMAT: (10X,I3,1X,A3,1X,A1,I4,A1,3(1X,A4,2X),12X,F5.1)
REMARK 500
REMARK 500 EXPECTED VALUES: ENGH AND HUBER, 1991
REMARK 500
REMARK 500  M RES CSSEQI ATM1     ATM2     ATM3
REMARK 500    LEU A   1   N   -  CA   -  C     ANGL. DEV. =  11.0 DEGREES
REMARK 500    ASP A  27   N   -  CA   -  C     ANGL. DEV. =  11.4 DEGREES
REMARK 500    ALA A  28   N   -  CA   -  C     ANGL. DEV. = -17.5 DEGREES
REMARK 500    LYS A  29   N   -  CA   -  C     ANGL. DEV. =  12.7 DEGREES
REMARK 500    ASP A  56   N   -  CA   -  C     ANGL. DEV. = -11.4 DEGREES
REMARK 500    ALA A  89   N   -  CA   -  C     ANGL. DEV. = -10.5 DEGREES
REMARK 500    GLN A 108   N   -  CA   -  C     ANGL. DEV. = -10.5 DEGREES
REMARK 500    THR A 129   N   -  CA   -  C     ANGL. DEV. = -11.4 DEGREES
REMARK 500    ASP A 138   N   -  CA   -  C     ANGL. DEV. = -11.4 DEGREES
REMARK 500    ASP A 144   N   -  CA   -  C     ANGL. DEV. = -20.1 DEGREES
REMARK 500    THR A 194   N   -  CA   -  C     ANGL. DEV. = -11.0 DEGREES
REMARK 500    ARG A 257   N   -  CA   -  C     ANGL. DEV. =  17.3 DEGREES
REMARK 525
REMARK 525 SOLVENT
REMARK 525 THE FOLLOWING SOLVENT MOLECULES LIE FARTHER THAN EXPECTED
REMARK 525 FROM THE PROTEIN OR NUCLEIC ACID MOLECULE AND MAY BE
REMARK 525 ASSOCIATED WITH A SYMMETRY RELATED MOLECULE (M=MODEL
REMARK 525 NUMBER; RES=RESIDUE NAME; C=CHAIN IDENTIFIER; SSEQ=SEQUENCE
REMARK 525 NUMBER; I=INSERTION CODE):
REMARK 525
REMARK 525  M RES CSSEQI
REMARK 525     HOH    64         DISTANCE =  5.56 ANGSTROMS
REMARK 525     HOH    66         DISTANCE =  7.20 ANGSTROMS
REMARK 525     HOH    75         DISTANCE = 10.03 ANGSTROMS
REMARK 900
REMARK 900 RELATED ENTRIES
REMARK 900 RELATED ID: 2NCM   RELATED DB: PDB
REMARK 900 NMR STRUCTURE OF THE FIRST IMMUNOGLOBULIN DOMAIN OF THE
REMARK 900 NEURAL CELL ADHESION MOLECULE (NCAM)
REMARK 900 RELATED ID: 3NCM   RELATED DB: PDB
REMARK 900 NMR STRUCTURE OF THE SECOND IMMUNOGLOBULIN DOMAIN OF THE
REMARK 900 NEURAL CELL ADHESION MOLECULE (NCAM)
REMARK 900 RELATED ID: 1EPF   RELATED DB: PDB
REMARK 900 CRYSTAL STRUCTURE OF THE TWO N-TERMINAL IMMUNOGLOBULIN
REMARK 900 DOMAINS OF THE NEURAL CELL ADHESION MOLECULE (NCAM)
REMARK 999
REMARK 999 SEQUENCE
REMARK 999 RESIDUES -2, 239 AND 240 WERE NOT VISIBLE IN
REMARK 999 THE ELECTRON DENSITY.
DBREF  1QZ1 A    1   289  SWS    P13596   NCA1_RAT        20    308
SEQADV 1QZ1 ARG A   -2  SWS    P13596                  CLONING ARTIFACT
SEQADV 1QZ1 VAL A   -1  SWS    P13596                  CLONING ARTIFACT
SEQRES   1  A  291   ARG VAL LEU GLN VAL ASP ILE VAL PRO SER GLN GLY GLU
SEQRES   2  A  291   ILE SER VAL GLY GLU SER LYS PHE PHE LEU CYS GLN VAL
SEQRES   3  A  291   ALA GLY ASP ALA LYS ASP LYS ASP ILE SER TRP PHE SER
SEQRES   4  A  291   PRO ASN GLY GLU LYS LEU SER PRO ASN GLN GLN ARG ILE
SEQRES   5  A  291   SER VAL VAL TRP ASN ASP ASP SER SER THR LEU THR
SEQRES   6  A  291   ILE TYR ASN ALA ASN ILE ASP ASP ALA GLY ILE TYR LYS
SEQRES   7  A  291   CYS VAL VAL THR ALA GLU ASP GLY THR GLN SER GLU ALA
```

Figure 2 (Table 2 (page 7))

```
SEQRES   8 A  291  THR VAL ASN VAL LYS ILE PHE GLN LYS LEU MET PHE LYS
SEQRES   9 A  291  ASN ALA PRO THR PRO GLN GLU PHE LYS GLU GLY GLU ASP
SEQRES  10 A  291  ALA VAL ILE VAL CYS ASP VAL VAL SER SER LEU PRO PRO
SEQRES  11 A  291  THR ILE ILE TRP LYS HIS LYS GLY ARG ASP VAL ILE LEU
SEQRES  12 A  291  LYS LYS ASP VAL ARG PHE ILE VAL LEU SER ASN ASN TYR
SEQRES  13 A  291  LEU GLN ILE ARG GLY ILE LYS LYS THR ASP GLU GLY THR
SEQRES  14 A  291  TYR ARG CYS GLU GLY ARG ILE LEU ALA ARG GLY GLU ILE
SEQRES  15 A  291  ASN PHE LYS ASP ILE GLN VAL ILE VAL ASN VAL PRO PRO
SEQRES  16 A  291  THR VAL GLN ALA ARG GLN SER ILE VAL ASN ALA THR ALA
SEQRES  17 A  291  ASN LEU GLY GLN SER VAL THR LEU VAL CYS ASP ALA ASP
SEQRES  18 A  291  GLY PHE PRO GLU PRO THR MET SER TRP THR LYS ASP GLY
SEQRES  19 A  291  GLU PRO ILE GLU ASN GLU GLU GLU ASP ASP GLU LYS HIS
SEQRES  20 A  291  ILE PHE SER ASP ASP SER SER GLU LEU THR ILE ARG ASN
SEQRES  21 A  291  VAL ASP LYS ASN ASP GLU ALA GLU TYR VAL CYS ILE ALA
SEQRES  22 A  291  GLU ASN LYS ALA GLY GLU GLN ASP ALA SER ILE HIS LEU
SEQRES  23 A  291  LYS VAL PHE ALA LYS
FORMUL   2  HOH    *265(H2 O1)
HELIX    1   1 ASN A   68  ALA A   72  5                                   5
HELIX    2   2 LYS A  161  GLU A  165  5                                   5
HELIX    3   3 ASP A  260  GLU A  264  5                                   5
SHEET    1   A 4 VAL A    3  VAL A    6  0
SHEET    2   A 4 LYS A   18  VAL A   24 -1  O  GLN A   23   N  ASP A    4
SHEET    3   A 4 SER A   59  ILE A   64 -1  O  ILE A   64   N  LYS A   18
SHEET    4   A 4 ILE A   50  ASP A   56 -1  N  VAL A   53   O  THR A   61
SHEET    1   B 4 GLY A   10  SER A   13  0
SHEET    2   B 4 GLN A   86  PHE A   96  1  O  LYS A   94   N  GLY A    0
SHEET    3   B 4 GLY A   73  THR A   80 -1  N  VAL A   79   O  SER A   87
SHEET    4   B 4 ASP A   32  PHE A   36 -1  N  SER A   34   O  VAL A   78
SHEET    1   C 2 MET A  100  ASN A  103  0
SHEET    2   C 2 ASP A  121  VAL A  123 -1  O  ASP A  121   N  ASN A  103
SHEET    1   D 4 GLN A  108  LYS A  111  0
SHEET    2   D 4 GLU A  179  ALA A  197  1  O  ASN A  190   N  PHE A  110
SHEET    3   D 4 GLY A  166  ILE A  174 -1  N  GLY A  166   O  VAL A  187
SHEET    4   D 4 THR A  129  HIS A  134 -1  N  LYS A  133   O  ARG A  169
SHEET    1   E 5 GLN A  108  LYS A  111  0
SHEET    2   E 5 GLU A  179  ALA A  197  1  O  ASN A  190   N  PHE A  110
SHEET    3   E 5 VAL A  212  PHE A  221 -1  O  ASP A  217   N  GLN A  196
SHEET    4   E 5 GLU A  253  ILE A  256 -1  O  LEU A  254   N  LEU A  214
SHEET    5   E 5 HIS A  245  PHE A  247 -1  N  ILE A  246   O  THR A  255
SHEET    1   F 3 ALA A  116  ILE A  118  0
SHEET    2   F 3 LEU A  155  ILE A  157 -1  O  ILE A  157   N  ALA A  116
SHEET    3   F 3 PHE A  147  VAL A  149 -1  N  ILE A  148   O  GLN A  156
SHEET    1   G 5 ILE A  201  THR A  205  0
SHEET    2   G 5 GLY A  276  PHE A  287  1  O  PHE A  287   N  ALA A  204
SHEET    3   G 5 ALA A  265  ASN A  273 -1  N  TYR A  267   O  ILE A  282
SHEET    4   G 5 THR A  225  LYS A  230 -1  N  SER A  227   O  ILE A  270
SHEET    5   G 5 GLU A  233  PRO A  234 -1  O  GLU A  233   N  LYS A  230
SSBOND   1 CYS A   22    CYS A   77
SSBOND   2 CYS A  120    CYS A  170
SSBOND   3 CYS A  216    CYS A  269
CISPEP   1 VAL A    6    PRO A    7      0        -0.41
CISPEP   2 THR A  106    PRO A  107      0        -0.64
CISPEP   3 PHE A  221    PRO A  222      0        -0.72
CRYST1   51.440  107.760  149.300  90.00  90.00  90.00 I 21 21 21    8
ORIGX1     1.000000  0.000000  0.000000        0.00000
ORIGX2     0.000000  1.000000  0.000000        0.00000
ORIGX3     0.000000  0.000000  1.000000        0.00000
```

Figure 2 (Table 2 (page 8))

| | | | | | | | | | |
|---|---|---|---|---|---|---|---|---|---|
| SCALE1 | | | 0.019440 | 0.000000 | 0.000000 | | 0.00000 | | |
| SCALE2 | | | 0.000000 | 0.009280 | 0.000000 | | 0.00000 | | |
| SCALE3 | | | 0.000000 | 0.000000 | 0.006698 | | 0.00000 | | |
| ATOM | 1 | N | VAL | A | -1 | 21.197 | 71.826 | -24.060 | 1.00 110.27 N |
| ATOM | 2 | CA | VAL | A | -1 | 21.299 | 70.596 | -24.891 | 1.00 112.18 C |
| ATOM | 3 | C | VAL | A | -1 | 20.583 | 69.411 | -24.264 | 1.00 111.88 C |
| ATOM | 4 | O | VAL | A | -1 | 19.491 | 69.531 | -23.699 | 1.00 113.09 O |
| ATOM | 5 | CB | VAL | A | -1 | 22.778 | 70.161 | -25.114 | 1.00 111.00 C |
| ATOM | 6 | CG1 | VAL | A | -1 | 23.591 | 71.324 | -25.633 | 1.00 109.72 C |
| ATOM | 7 | CG2 | VAL | A | -1 | 23.374 | 69.625 | -23.817 | 1.00 106.12 C |
| ATOM | 8 | N | LEU | A | 1 | 21.255 | 68.270 | -24.364 | 1.00 107.51 N |
| ATOM | 9 | CA | LEU | A | 1 | 20.778 | 66.981 | -23.905 | 1.00 100.28 C |
| ATOM | 10 | C | LEU | A | 1 | 20.360 | 66.739 | -22.465 | 1.00 94.24 C |
| ATOM | 11 | O | LEU | A | 1 | 20.985 | 67.227 | -21.518 | 1.00 93.77 O |
| ATOM | 12 | CB | LEU | A | 1 | 21.808 | 65.936 | -24.296 | 1.00 100.43 C |
| ATOM | 13 | CG | LEU | A | 1 | 21.297 | 64.909 | -25.303 | 1.00 103.11 C |
| ATOM | 14 | CD1 | LEU | A | 1 | 20.253 | 65.528 | -26.233 | 1.00 106.65 C |
| ATOM | 15 | CD2 | LEU | A | 1 | 22.475 | 64.366 | -26.088 | 1.00 101.88 C |
| ATOM | 16 | N | GLN | A | 2 | 19.299 | 65.946 | -22.328 | 1.00 87.47 N |
| ATOM | 17 | CA | GLN | A | 2 | 18.771 | 65.575 | -21.028 | 1.00 86.76 C |
| ATOM | 18 | C | GLN | A | 2 | 18.937 | 64.075 | -20.822 | 1.00 80.18 C |
| ATOM | 19 | O | GLN | A | 2 | 18.520 | 63.264 | -21.656 | 1.00 82.58 O |
| ATOM | 20 | CB | GLN | A | 2 | 17.292 | 65.950 | -20.902 | 1.00 89.86 C |
| ATOM | 21 | CG | GLN | A | 2 | 16.819 | 65.996 | -19.458 | 1.00 102.22 C |
| ATOM | 22 | CD | GLN | A | 2 | 17.932 | 66.444 | -18.500 | 1.00 109.49 C |
| ATOM | 23 | OE1 | GLN | A | 2 | 18.786 | 67.260 | -18.859 | 1.00 112.97 O |
| ATOM | 24 | NE2 | GLN | A | 2 | 17.917 | 65.917 | -17.275 | 1.00 110.51 N |
| ATOM | 25 | N | VAL | A | 3 | 19.572 | 63.716 | -19.714 | 1.00 68.44 N |
| ATOM | 26 | CA | VAL | A | 3 | 19.790 | 62.317 | -19.375 | 1.00 65.80 C |
| ATOM | 27 | C | VAL | A | 3 | 19.290 | 62.058 | -17.959 | 1.00 63.80 C |
| ATOM | 28 | O | VAL | A | 3 | 19.588 | 62.816 | -17.029 | 1.00 61.99 O |
| ATOM | 29 | CB | VAL | A | 3 | 21.291 | 61.919 | -19.495 | 1.00 70.09 C |
| ATOM | 30 | CG1 | VAL | A | 3 | 22.157 | 62.831 | -18.653 | 1.00 66.37 C |
| ATOM | 31 | CG2 | VAL | A | 3 | 21.477 | 60.475 | -19.072 | 1.00 53.43 C |
| ATOM | 32 | N | ASP | A | 4 | 18.511 | 60.992 | -17.807 | 1.00 59.47 N |
| ATOM | 33 | CA | ASP | A | 4 | 17.957 | 60.635 | -16.507 | 1.00 62.16 C |
| ATOM | 34 | C | ASP | A | 4 | 18.056 | 59.137 | -16.281 | 1.00 61.45 C |
| ATOM | 35 | O | ASP | A | 4 | 17.973 | 58.337 | -17.222 | 1.00 54.28 O |
| ATOM | 36 | CB | ASP | A | 4 | 16.490 | 61.064 | -16.410 | 1.00 57.25 C |
| ATOM | 37 | CG | ASP | A | 4 | 16.312 | 62.564 | -16.536 | 1.00 81.12 C |
| ATOM | 38 | OD1 | ASP | A | 4 | 16.784 | 63.302 | -15.644 | 1.00 87.44 O |
| ATOM | 39 | OD2 | ASP | A | 4 | 15.702 | 63.010 | -17.531 | 1.00 84.62 O |
| ATOM | 40 | N | ILE | A | 5 | 18.226 | 58.760 | -15.024 | 1.00 54.90 N |
| ATOM | 41 | CA | ILE | A | 5 | 18.324 | 57.360 | -14.692 | 1.00 47.24 C |
| ATOM | 42 | C | ILE | A | 5 | 17.134 | 56.965 | -13.832 | 1.00 49.02 C |
| ATOM | 43 | O | ILE | A | 5 | 16.846 | 57.619 | -12.826 | 1.00 47.37 O |
| ATOM | 44 | CB | ILE | A | 5 | 19.625 | 57.077 | -13.934 | 1.00 42.30 C |
| ATOM | 45 | CG1 | ILE | A | 5 | 20.823 | 57.333 | -14.849 | 1.00 48.79 C |
| ATOM | 46 | CG2 | ILE | A | 5 | 19.638 | 55.615 | -13.450 | 1.00 40.90 C |
| ATOM | 47 | CD1 | ILE | A | 5 | 22.158 | 57.356 | -14.118 | 1.00 47.66 C |
| ATOM | 48 | N | VAL | A | 6 | 16.445 | 55.900 | -14.233 | 1.00 48.39 N |
| ATOM | 49 | CA | VAL | A | 6 | 15.300 | 55.401 | -13.480 | 1.00 48.78 C |
| ATOM | 50 | C | VAL | A | 6 | 15.545 | 53.939 | -13.119 | 1.00 52.24 C |
| ATOM | 51 | O | VAL | A | 6 | 15.905 | 53.130 | -13.980 | 1.00 51.37 O |
| ATOM | 52 | CB | VAL | A | 6 | 14.008 | 55.484 | -14.299 | 1.00 55.65 C |
| ATOM | 53 | CG1 | VAL | A | 6 | 12.857 | 54.882 | -13.515 | 1.00 53.36 C |
| ATOM | 54 | CG2 | VAL | A | 6 | 13.712 | 56.928 | -14.637 | 1.00 64.21 C |

Figure 2 (Table 2 (page 9))

```
ATOM     55  N    PRO A   7      15.418  53.594 -11.830  1.00 44.55  N
ATOM     56  CA   PRO A   7      15.074  54.460 -10.692  1.00 44.98  C
ATOM     57  C    PRO A   7      16.225  55.428 -10.411  1.00 52.07  C
ATOM     58  O    PRO A   7      17.391  55.112 -10.662  1.00 47.92  O
ATOM     59  CB   PRO A   7      14.842  53.462  -9.556  1.00 50.48  C
ATOM     60  CG   PRO A   7      15.718  52.291  -9.944  1.00 45.69  C
ATOM     61  CD   PRO A   7      15.446  52.181 -11.420  1.00 40.86  C
ATOM     62  N    SER A   8      15.894  56.604  -9.893  1.00 46.31  N
ATOM     63  CA   SER A   8      16.889  57.635  -9.634  1.00 49.55  C
ATOM     64  C    SER A   8      17.921  57.250  -8.592  1.00 53.48  C
ATOM     65  O    SER A   8      18.995  57.857  -8.515  1.00 54.87  O
ATOM     66  CB   SER A   8      16.198  58.940  -9.236  1.00 55.09  C
ATOM     67  OG   SER A   8      15.363  58.753  -8.111  1.00 61.93  O
ATOM     68  N    GLN A   9      17.597  56.255  -7.776  1.00 46.60  N
ATOM     69  CA   GLN A   9      18.538  55.781  -6.771  1.00 47.40  C
ATOM     70  C    GLN A   9      18.204  54.335  -6.448  1.00 44.46  C
ATOM     71  O    GLN A   9      17.103  53.864  -6.739  1.00 52.34  O
ATOM     72  CB   GLN A   9      18.494  56.658  -5.515  1.00 58.55  C
ATOM     73  CG   GLN A   9      17.103  56.860  -4.900  1.00 65.92  C
ATOM     74  CD   GLN A   9      17.149  57.765  -3.665  1.00 81.94  C
ATOM     75  OE1  GLN A   9      17.878  57.484  -2.713  1.00 86.13  O
ATOM     76  NE2  GLN A   9      16.374  58.853  -3.678  1.00 82.96  N
ATOM     77  N    GLY A  10      19.157  53.606  -5.883  1.00 46.46  N
ATOM     78  CA   GLY A  10      18.868  52.215  -5.589  1.00 50.99  C
ATOM     79  C    GLY A  10      19.637  51.600  -4.442  1.00 48.97  C
ATOM     80  O    GLY A  10      20.719  52.048  -4.070  1.00 46.47  O
ATOM     81  N    GLU A  11      19.051  50.559  -3.871  1.00 54.04  N
ATOM     82  CA   GLU A  11      19.684  49.842  -2.778  1.00 54.83  C
ATOM     83  C    GLU A  11      19.560  48.362  -3.127  1.00 47.65  C
ATOM     84  O    GLU A  11      18.499  47.918  -3.557  1.00 47.49  O
ATOM     85  CB   GLU A  11      18.970  50.150  -1.456  1.00 49.30  C
ATOM     86  CG   GLU A  11      19.627  49.508  -0.255  1.00 67.71  C
ATOM     87  CD   GLU A  11      19.026  49.974   1.061  1.00 68.83  C
ATOM     88  OE1  GLU A  11      17.829  49.704   1.305  1.00 70.78  O
ATOM     89  OE2  GLU A  11      19.758  50.620   1.843  1.00 73.96  O
ATOM     90  N    ILE A  12      20.636  47.599  -2.965  1.00 44.79  N
ATOM     91  CA   ILE A  12      20.587  46.178  -3.302  1.00 43.25  C
ATOM     92  C    ILE A  12      21.164  45.332  -2.185  1.00 49.76  C
ATOM     93  O    ILE A  12      22.261  45.610  -1.692  1.00 45.49  O
ATOM     94  CB   ILE A  12      21.402  45.856  -4.562  1.00 46.25  C
ATOM     95  CG1  ILE A  12      21.182  46.938  -5.621  1.00 48.07  C
ATOM     96  CG2  ILE A  12      20.984  44.481  -5.114  1.00 40.48  C
ATOM     97  CD1  ILE A  12      22.125  46.814  -6.795  1.00 44.46  C
ATOM     98  N    SER A  13      20.421  44.296  -1.796  1.00 50.25  N
ATOM     99  CA   SER A  13      20.880  43.384  -0.755  1.00 49.85  C
ATOM    100  C    SER A  13      21.869  42.416  -1.385  1.00 41.84  C
ATOM    101  O    SER A  13      21.690  41.973  -2.526  1.00 43.99  O
ATOM    102  CB   SER A  13      19.707  42.608  -0.156  1.00 48.85  C
ATOM    103  OG   SER A  13      20.157  41.794   0.916  1.00 55.47  O
ATOM    104  N    VAL A  14      22.926  42.114  -0.644  1.00 50.09  N
ATOM    105  CA   VAL A  14      23.955  41.214  -1.126  1.00 48.58  C
ATOM    106  C    VAL A  14      23.358  39.962  -1.742  1.00 53.11  C
ATOM    107  O    VAL A  14      22.481  39.320  -1.165  1.00 54.25  O
ATOM    108  CB   VAL A  14      24.924  40.814   0.004  1.00 51.58  C
ATOM    109  CG1  VAL A  14      25.880  39.739  -0.479  1.00 51.54  C
ATOM    110  CG2  VAL A  14      25.702  42.027   0.455  1.00 51.93  C
ATOM    111  N    GLY A  15      23.841  39.636  -2.935  1.00 45.67  N
```

Figure 2 (Table 2 (page 10))

| ATOM | 112 | CA  | GLY | A | 15 | 23.367 | 38.471 | -3.643  | 1.00 | 45.80  | C |
|------|-----|-----|-----|---|----|--------|--------|---------|------|--------|---|
| ATOM | 113 | C   | GLY | A | 15 | 22.174 | 38.738 | -4.546  | 1.00 | 49.51  | C |
| ATOM | 114 | O   | GLY | A | 15 | 21.845 | 37.910 | -5.395  | 1.00 | 44.42  | O |
| ATOM | 115 | N   | GLU | A | 16 | 21.516 | 39.885 | -4.390  | 1.00 | 48.69  | N |
| ATOM | 116 | CA  | GLU | A | 16 | 20.360 | 40.167 | -5.239  | 1.00 | 44.66  | C |
| ATOM | 117 | C   | GLU | A | 16 | 20.712 | 41.010 | -6.459  | 1.00 | 38.83  | C |
| ATOM | 118 | O   | GLU | A | 16 | 21.874 | 41.355 | -6.672  | 1.00 | 41.87  | O |
| ATOM | 119 | CB  | GLU | A | 16 | 19.239 | 40.800 | -4.403  | 1.00 | 44.40  | C |
| ATOM | 120 | CG  | GLU | A | 16 | 18.799 | 39.848 | -3.289  | 1.00 | 57.20  | C |
| ATOM | 121 | CD  | GLU | A | 16 | 17.666 | 40.373 | -2.428  | 1.00 | 67.70  | C |
| ATOM | 122 | OE1 | GLU | A | 16 | 17.111 | 41.448 | -2.739  | 1.00 | 72.10  | O |
| ATOM | 123 | OE2 | GLU | A | 16 | 17.328 | 39.695 | -1.433  | 1.00 | 77.10  | O |
| ATOM | 124 | N   | SER | A | 17 | 19.712 | 41.319 | -7.274  | 1.00 | 38.10  | N |
| ATOM | 125 | CA  | SER | A | 17 | 19.950 | 42.068 | -8.496  | 1.00 | 39.72  | C |
| ATOM | 126 | C   | SER | A | 17 | 19.039 | 43.283 | -8.655  | 1.00 | 43.71  | C |
| ATOM | 127 | O   | SER | A | 17 | 17.960 | 43.330 | -8.074  | 1.00 | 48.43  | O |
| ATOM | 128 | CB  | SER | A | 17 | 19.787 | 41.125 | -9.694  | 1.00 | 42.04  | C |
| ATOM | 129 | OG  | SER | A | 17 | 20.672 | 40.016 | -9.592  | 1.00 | 49.33  | O |
| ATOM | 130 | N   | LYS | A | 18 | 19.491 | 44.273 | -9.427  | 1.00 | 39.31  | N |
| ATOM | 131 | CA  | LYS | A | 18 | 18.725 | 45.495 | -9.689  | 1.00 | 40.44  | C |
| ATOM | 132 | C   | LYS | A | 18 | 19.194 | 46.068 | -11.004 | 1.00 | 36.17  | C |
| ATOM | 133 | O   | LYS | A | 18 | 20.310 | 45.799 | -11.447 | 1.00 | 41.18  | O |
| ATOM | 134 | CB  | LYS | A | 18 | 18.944 | 46.552 | -8.603  | 1.00 | 45.93  | C |
| ATOM | 135 | CG  | LYS | A | 18 | 17.902 | 46.558 | -7.506  | 1.00 | 63.96  | C |
| ATOM | 136 | CD  | LYS | A | 18 | 17.343 | 47.954 | -7.318  | 1.00 | 77.99  | C |
| ATOM | 137 | CE  | LYS | A | 18 | 16.408 | 48.029 | -6.120  | 1.00 | 91.67  | C |
| ATOM | 138 | NZ  | LYS | A | 18 | 15.285 | 47.049 | -6.198  | 1.00 | 104.95 | N |
| ATOM | 139 | N   | PHE | A | 19 | 18.355 | 46.866 | -11.632 | 1.00 | 39.73  | N |
| ATOM | 140 | CA  | PHE | A | 19 | 18.758 | 47.445 | -12.889 | 1.00 | 42.56  | C |
| ATOM | 141 | C   | PHE | A | 19 | 18.382 | 48.903 | -12.907 | 1.00 | 45.52  | C |
| ATOM | 142 | O   | PHE | A | 19 | 17.535 | 49.352 | -12.123 | 1.00 | 41.88  | O |
| ATOM | 143 | CB  | PHE | A | 19 | 18.131 | 46.681 | -14.058 | 1.00 | 37.12  | C |
| ATOM | 144 | CG  | PHE | A | 19 | 16.658 | 46.890 | -14.220 | 1.00 | 41.51  | C |
| ATOM | 145 | CD1 | PHE | A | 19 | 16.175 | 47.864 | -15.090 | 1.00 | 45.13  | C |
| ATOM | 146 | CD2 | PHE | A | 19 | 15.742 | 46.075 | -13.547 | 1.00 | 42.50  | C |
| ATOM | 147 | CE1 | PHE | A | 19 | 14.794 | 48.006 | -15.310 | 1.00 | 44.84  | C |
| ATOM | 148 | CE2 | PHE | A | 19 | 14.377 | 46.212 | -13.759 | 1.00 | 43.30  | C |
| ATOM | 149 | CZ  | PHE | A | 19 | 13.899 | 47.182 | -14.639 | 1.00 | 41.52  | C |
| ATOM | 150 | N   | PHE | A | 20 | 19.020 | 49.637 | -13.813 | 1.00 | 37.54  | N |
| ATOM | 151 | CA  | PHE | A | 20 | 18.816 | 51.062 | -13.938 | 1.00 | 38.86  | C |
| ATOM | 152 | C   | PHE | A | 20 | 18.816 | 51.437 | -15.408 | 1.00 | 46.44  | C |
| ATOM | 153 | O   | PHE | A | 20 | 19.702 | 51.035 | -16.165 | 1.00 | 47.88  | O |
| ATOM | 154 | CB  | PHE | A | 20 | 19.948 | 51.798 | -13.205 | 1.00 | 36.96  | C |
| ATOM | 155 | CG  | PHE | A | 20 | 20.112 | 51.368 | -11.784 | 1.00 | 46.76  | C |
| ATOM | 156 | CD1 | PHE | A | 20 | 20.904 | 50.267 | -11.460 | 1.00 | 48.63  | C |
| ATOM | 157 | CD2 | PHE | A | 20 | 19.427 | 52.027 | -10.765 | 1.00 | 42.55  | C |
| ATOM | 158 | CE1 | PHE | A | 20 | 21.008 | 49.826 | -10.138 | 1.00 | 46.86  | C |
| ATOM | 159 | CE2 | PHE | A | 20 | 19.525 | 51.591 | -9.436  | 1.00 | 40.53  | C |
| ATOM | 160 | CZ  | PHE | A | 20 | 20.317 | 50.489 | -9.126  | 1.00 | 44.32  | C |
| ATOM | 161 | N   | LEU | A | 21 | 17.816 | 52.209 | -15.806 | 1.00 | 46.01  | N |
| ATOM | 162 | CA  | LEU | A | 21 | 17.680 | 52.649 | -17.189 | 1.00 | 49.63  | C |
| ATOM | 163 | C   | LEU | A | 21 | 18.131 | 54.087 | -17.360 | 1.00 | 46.97  | C |
| ATOM | 164 | O   | LEU | A | 21 | 17.602 | 54.990 | -16.719 | 1.00 | 43.22  | O |
| ATOM | 165 | CB  | LEU | A | 21 | 16.218 | 52.530 | -17.641 | 1.00 | 54.55  | C |
| ATOM | 166 | CG  | LEU | A | 21 | 15.857 | 53.049 | -19.040 | 1.00 | 57.21  | C |
| ATOM | 167 | CD1 | LEU | A | 21 | 16.625 | 52.281 | -20.096 | 1.00 | 58.14  | C |
| ATOM | 168 | CD2 | LEU | A | 21 | 14.365 | 52.891 | -19.274 | 1.00 | 55.27  | C |

Figure 2 (Table 2 (page 11))

| ATOM | 169 | N   | CYS | A | 22 | 19.122 | 54.291 | -18.218 | 1.00 | 46.45  | N |
|------|-----|-----|-----|---|----|--------|--------|---------|------|--------|---|
| ATOM | 170 | CA  | CYS | A | 22 | 19.615 | 55.628 | -18.506 | 1.00 | 48.52  | C |
| ATOM | 171 | C   | CYS | A | 22 | 18.920 | 56.056 | -19.788 | 1.00 | 54.42  | C |
| ATOM | 172 | O   | CYS | A | 22 | 19.157 | 55.478 | -20.848 | 1.00 | 51.82  | O |
| ATOM | 173 | CB  | CYS | A | 22 | 21.115 | 55.601 | -18.730 | 1.00 | 49.72  | C |
| ATOM | 174 | SG  | CYS | A | 22 | 21.827 | 57.215 | -19.167 | 1.00 | 55.16  | S |
| ATOM | 175 | N   | GLN | A | 23 | 18.069 | 57.071 | -19.689 | 1.00 | 59.11  | N |
| ATOM | 176 | CA  | GLN | A | 23 | 17.312 | 57.546 | -20.837 | 1.00 | 66.68  | C |
| ATOM | 177 | C   | GLN | A | 23 | 17.718 | 58.941 | -21.314 | 1.00 | 63.21  | C |
| ATOM | 178 | O   | GLN | A | 23 | 17.951 | 59.839 | -20.509 | 1.00 | 57.50  | O |
| ATOM | 179 | CB  | GLN | A | 23 | 15.825 | 57.547 | -20.482 | 1.00 | 69.27  | C |
| ATOM | 180 | CG  | GLN | A | 23 | 14.900 | 57.940 | -21.618 | 1.00 | 83.38  | C |
| ATOM | 181 | CD  | GLN | A | 23 | 14.575 | 56.779 | -22.549 | 1.00 | 90.68  | C |
| ATOM | 182 | OE1 | GLN | A | 23 | 14.251 | 55.685 | -22.089 | 1.00 | 97.59  | O |
| ATOM | 183 | NE2 | GLN | A | 23 | 14.642 | 57.016 | -23.861 | 1.00 | 95.34  | N |
| ATOM | 184 | N   | VAL | A | 24 | 17.799 | 59.118 | -22.629 | 1.00 | 67.26  | N |
| ATOM | 185 | CA  | VAL | A | 24 | 18.145 | 60.415 | -23.197 | 1.00 | 74.82  | C |
| ATOM | 186 | C   | VAL | A | 24 | 16.857 | 61.028 | -23.739 | 1.00 | 75.90  | C |
| ATOM | 187 | O   | VAL | A | 24 | 16.039 | 60.338 | -24.356 | 1.00 | 76.41  | O |
| ATOM | 188 | CB  | VAL | A | 24 | 19.178 | 60.285 | -24.343 | 1.00 | 77.43  | C |
| ATOM | 189 | CG1 | VAL | A | 24 | 19.560 | 61.657 | -24.852 | 1.00 | 77.38  | C |
| ATOM | 190 | CG2 | VAL | A | 24 | 20.418 | 59.547 | -23.856 | 1.00 | 81.07  | C |
| ATOM | 191 | N   | ALA | A | 25 | 16.685 | 62.324 | -23.500 | 1.00 | 82.73  | N |
| ATOM | 192 | CA  | ALA | A | 25 | 15.490 | 63.053 | -23.933 | 1.00 | 92.22  | C |
| ATOM | 193 | C   | ALA | A | 25 | 15.455 | 63.428 | -25.424 | 1.00 | 99.21  | C |
| ATOM | 194 | O   | ALA | A | 25 | 16.491 | 63.734 | -26.019 | 1.00 | 99.63  | O |
| ATOM | 195 | CB  | ALA | A | 25 | 15.326 | 64.307 | -23.078 | 1.00 | 89.44  | C |
| ATOM | 196 | N   | GLY | A | 26 | 14.249 | 63.405 | -26.002 | 1.00 | 107.66 | N |
| ATOM | 197 | CA  | GLY | A | 26 | 14.040 | 63.735 | -27.410 | 1.00 | 117.13 | C |
| ATOM | 198 | C   | GLY | A | 26 | 14.697 | 62.739 | -28.348 | 1.00 | 123.74 | C |
| ATOM | 199 | O   | GLY | A | 26 | 14.060 | 62.088 | -29.188 | 1.00 | 126.85 | O |
| ATOM | 200 | N   | ASP | A | 27 | 16.010 | 62.671 | -28.187 | 1.00 | 127.93 | N |
| ATOM | 201 | CA  | ASP | A | 27 | 16.915 | 61.795 | -28.897 | 1.00 | 131.73 | C |
| ATOM | 202 | C   | ASP | A | 27 | 17.049 | 61.809 | -30.410 | 1.00 | 132.38 | C |
| ATOM | 203 | O   | ASP | A | 27 | 16.518 | 60.944 | -31.112 | 1.00 | 134.43 | O |
| ATOM | 204 | CB  | ASP | A | 27 | 16.721 | 60.353 | -28.433 | 1.00 | 133.67 | C |
| ATOM | 205 | CG  | ASP | A | 27 | 17.976 | 59.540 | -28.620 | 1.00 | 136.05 | C |
| ATOM | 206 | OD1 | ASP | A | 27 | 19.011 | 60.177 | -28.888 | 1.00 | 137.46 | O |
| ATOM | 207 | OD2 | ASP | A | 27 | 17.940 | 58.305 | -28.501 | 1.00 | 138.22 | O |
| ATOM | 208 | N   | ALA | A | 28 | 17.776 | 62.812 | -30.894 | 1.00 | 130.01 | N |
| ATOM | 209 | CA  | ALA | A | 28 | 18.098 | 62.888 | -32.301 | 1.00 | 127.19 | C |
| ATOM | 210 | C   | ALA | A | 28 | 19.203 | 61.826 | -32.208 | 1.00 | 125.97 | C |
| ATOM | 211 | O   | ALA | A | 28 | 19.562 | 61.453 | -31.091 | 1.00 | 125.76 | O |
| ATOM | 212 | CB  | ALA | A | 28 | 18.672 | 64.248 | -32.657 | 1.00 | 123.21 | C |
| ATOM | 213 | N   | LYS | A | 29 | 19.777 | 61.332 | -33.300 | 1.00 | 124.23 | N |
| ATOM | 214 | CA  | LYS | A | 29 | 20.754 | 60.267 | -33.095 | 1.00 | 120.04 | C |
| ATOM | 215 | C   | LYS | A | 29 | 22.237 | 60.419 | -33.356 | 1.00 | 114.93 | C |
| ATOM | 216 | O   | LYS | A | 29 | 22.773 | 61.503 | -33.593 | 1.00 | 109.02 | O |
| ATOM | 217 | CB  | LYS | A | 29 | 20.254 | 58.988 | -33.777 | 1.00 | 124.97 | C |
| ATOM | 218 | CG  | LYS | A | 29 | 19.095 | 58.340 | -33.030 | 1.00 | 125.66 | C |
| ATOM | 219 | CD  | LYS | A | 29 | 18.639 | 57.047 | -33.674 | 1.00 | 125.32 | C |
| ATOM | 220 | CE  | LYS | A | 29 | 17.462 | 56.460 | -32.915 | 1.00 | 120.15 | C |
| ATOM | 221 | NZ  | LYS | A | 29 | 16.388 | 57.477 | -32.740 | 1.00 | 120.03 | N |
| ATOM | 222 | N   | ASP | A | 30 | 22.875 | 59.260 | -33.286 | 1.00 | 110.94 | N |
| ATOM | 223 | CA  | ASP | A | 30 | 24.297 | 59.108 | -33.440 | 1.00 | 108.72 | C |
| ATOM | 224 | C   | ASP | A | 30 | 25.004 | 59.738 | -32.257 | 1.00 | 102.56 | C |
| ATOM | 225 | O   | ASP | A | 30 | 25.869 | 60.592 | -32.425 | 1.00 | 101.55 | O |

Figure 2 (Table 2 (page 12))

```
ATOM    226  CB  ASP A  30      24.800  59.729 -34.740  1.00114.65  C
ATOM    227  CG  ASP A  30      25.573  58.735 -35.584  1.00121.84  C
ATOM    228  OD1 ASP A  30      26.219  57.833 -35.001  1.00126.50  O
ATOM    229  OD2 ASP A  30      25.543  58.853 -36.824  1.00125.16  O
ATOM    230  N   LYS A  31      24.602  59.339 -31.055  1.00 90.62  N
ATOM    231  CA  LYS A  31      25.252  59.820 -29.845  1.00 86.82  C
ATOM    232  C   LYS A  31      25.645  58.547 -29.120  1.00 76.37  C
ATOM    233  O   LYS A  31      25.000  57.512 -29.280  1.00 76.59  O
ATOM    234  CB  LYS A  31      24.315  60.658 -28.965  1.00 87.55  C
ATOM    235  CG  LYS A  31      23.238  59.873 -28.261  1.00 90.62  C
ATOM    236  CD  LYS A  31      21.906  60.210 -28.856  1.00 90.82  C
ATOM    237  CE  LYS A  31      21.081  58.968 -28.999  1.00 94.15  C
ATOM    238  NZ  LYS A  31      20.424  58.901 -30.339  1.00 96.17  N
ATOM    239  N   ASP A  32      26.711  58.620 -28.341  1.00 66.33  N
ATOM    240  CA  ASP A  32      27.202  57.467 -27.607  1.00 64.69  C
ATOM    241  C   ASP A  32      26.732  57.503 -26.163  1.00 57.45  C
ATOM    242  O   ASP A  32      26.707  58.563 -25.532  1.00 61.27  O
ATOM    243  CB  ASP A  32      28.740  57.448 -27.669  1.00 59.49  C
ATOM    244  CG  ASP A  32      29.372  56.362 -26.791  1.00 67.93  C
ATOM    245  OD1 ASP A  32      29.627  56.626 -25.589  1.00 51.53  O
ATOM    246  OD2 ASP A  32      29.626  55.248 -27.308  1.00 61.79  O
ATOM    247  N   ILE A  33      26.336  56.342 -25.657  1.00 54.91  N
ATOM    248  CA  ILE A  33      25.911  56.210 -24.271  1.00 52.46  C
ATOM    249  C   ILE A  33      26.823  55.173 -23.640  1.00 53.58  C
ATOM    250  O   ILE A  33      26.875  54.022 -24.083  1.00 50.96  O
ATOM    251  CB  ILE A  33      24.470  55.712 -24.139  1.00 51.31  C
ATOM    252  CG1 ILE A  33      23.518  56.700 -24.800  1.00 52.96  C
ATOM    253  CG2 ILE A  33      24.116  55.563 -22.654  1.00 50.09  C
ATOM    254  CD1 ILE A  33      22.087  56.233 -24.828  1.00 54.31  C
ATOM    255  N   SER A  34      27.535  55.588 -22.603  1.00 43.80  N
ATOM    256  CA  SER A  34      28.463  54.716 -21.910  1.00 47.69  C
ATOM    257  C   SER A  34      28.262  54.831 -20.410  1.00 51.46  C
ATOM    258  O   SER A  34      27.899  55.892 -19.897  1.00 50.26  O
ATOM    259  CB  SER A  34      29.898  55.105 -22.255  1.00 44.86  C
ATOM    260  OG  SER A  34      30.197  54.768 -23.592  1.00 56.99  O
ATOM    261  N   TRP A  35      28.488  53.726 -19.714  1.00 47.72  N
ATOM    262  CA  TRP A  35      28.359  53.713 -18.270  1.00 42.75  C
ATOM    263  C   TRP A  35      29.741  53.598 -17.652  1.00 45.12  C
ATOM    264  O   TRP A  35      30.640  52.967 -18.223  1.00 44.07  O
ATOM    265  CB  TRP A  35      27.511  52.531 -17.800  1.00 39.02  C
ATOM    266  CG  TRP A  35      26.028  52.667 -18.015  1.00 43.96  C
ATOM    267  CD1 TRP A  35      25.323  52.308 -19.126  1.00 38.82  C
ATOM    268  CD2 TRP A  35      25.062  53.080 -17.041  1.00 36.18  C
ATOM    269  NE1 TRP A  35      23.974  52.454 -18.901  1.00 45.99  N
ATOM    270  CE2 TRP A  35      23.786  52.925 -17.632  1.00 47.03  C
ATOM    271  CE3 TRP A  35      25.150  53.556 -15.735  1.00 39.81  C
ATOM    272  CZ2 TRP A  35      22.605  53.232 -16.948  1.00 43.25  C
ATOM    273  CZ3 TRP A  35      23.962  53.865 -15.054  1.00 41.38  C
ATOM    274  CH2 TRP A  35      22.713  53.699 -15.668  1.00 42.80  C
ATOM    275  N   PHE A  36      29.907  54.225 -16.491  1.00 45.19  N
ATOM    276  CA  PHE A  36      31.160  54.178 -15.748  1.00 44.89  C
ATOM    277  C   PHE A  36      30.834  53.716 -14.345  1.00 44.82  C
ATOM    278  O   PHE A  36      29.858  54.166 -13.755  1.00 41.52  O
ATOM    279  CB  PHE A  36      31.819  55.556 -15.675  1.00 43.10  C
ATOM    280  CG  PHE A  36      32.286  56.062 -17.006  1.00 55.53  C
ATOM    281  CD1 PHE A  36      31.385  56.639 -17.893  1.00 51.14  C
ATOM    282  CD2 PHE A  36      33.610  55.883 -17.407  1.00 46.89  C
```

Figure 2 (Table 2 (page 13))

| ATOM | 283 | CE1 | PHE | A | 36 | 31.789 | 57.030 | -19.173 | 1.00 | 54.91 | C |
|---|---|---|---|---|---|---|---|---|---|---|---|
| ATOM | 284 | CE2 | PHE | A | 36 | 34.030 | 56.269 | -18.684 | 1.00 | 55.64 | C |
| ATOM | 285 | CZ | PHE | A | 36 | 33.110 | 56.846 | -19.573 | 1.00 | 50.29 | C |
| ATOM | 286 | N | SER | A | 37 | 31.641 | 52.795 | -13.832 | 1.00 | 42.90 | N |
| ATOM | 287 | CA | SER | A | 37 | 31.447 | 52.289 | -12.488 | 1.00 | 52.59 | C |
| ATOM | 288 | C | SER | A | 37 | 31.973 | 53.321 | -11.490 | 1.00 | 53.66 | C |
| ATOM | 289 | O | SER | A | 37 | 32.581 | 54.325 | -11.878 | 1.00 | 46.56 | O |
| ATOM | 290 | CB | SER | A | 37 | 32.176 | 50.950 | -12.322 | 1.00 | 56.49 | C |
| ATOM | 291 | OG | SER | A | 37 | 33.540 | 51.055 | -12.675 | 1.00 | 54.60 | O |
| ATOM | 292 | N | PRO | A | 38 | 31.729 | 53.096 | -10.192 | 1.00 | 55.82 | N |
| ATOM | 293 | CA | PRO | A | 38 | 32.169 | 54.004 | -9.124 | 1.00 | 58.18 | C |
| ATOM | 294 | C | PRO | A | 38 | 33.682 | 54.241 | -9.057 | 1.00 | 56.07 | C |
| ATOM | 295 | O | PRO | A | 38 | 34.135 | 55.248 | -8.519 | 1.00 | 57.12 | O |
| ATOM | 296 | CB | PRO | A | 38 | 31.619 | 53.338 | -7.864 | 1.00 | 55.81 | C |
| ATOM | 297 | CG | PRO | A | 38 | 30.327 | 52.731 | -8.377 | 1.00 | 51.53 | C |
| ATOM | 298 | CD | PRO | A | 38 | 30.764 | 52.107 | -9.677 | 1.00 | 50.32 | C |
| ATOM | 299 | N | ASN | A | 39 | 34.456 | 53.317 | -9.609 | 1.00 | 52.69 | N |
| ATOM | 300 | CA | ASN | A | 39 | 35.905 | 53.452 | -9.613 | 1.00 | 59.02 | C |
| ATOM | 301 | C | ASN | A | 39 | 36.396 | 54.175 | -10.881 | 1.00 | 61.73 | C |
| ATOM | 302 | O | ASN | A | 39 | 37.585 | 54.160 | -11.188 | 1.00 | 57.13 | O |
| ATOM | 303 | CB | ASN | A | 39 | 36.551 | 52.077 | -9.523 | 1.00 | 56.75 | C |
| ATOM | 304 | CG | ASN | A | 39 | 36.432 | 51.310 | -10.810 | 1.00 | 71.38 | C |
| ATOM | 305 | OD1 | ASN | A | 39 | 35.531 | 51.565 | -11.603 | 1.00 | 73.88 | O |
| ATOM | 306 | ND2 | ASN | A | 39 | 37.332 | 50.361 | -11.027 | 1.00 | 79.44 | N |
| ATOM | 307 | N | GLY | A | 40 | 35.471 | 54.777 | -11.626 | 1.00 | 54.18 | N |
| ATOM | 308 | CA | GLY | A | 40 | 35.839 | 55.523 | -12.825 | 1.00 | 58.26 | C |
| ATOM | 309 | C | GLY | A | 40 | 36.049 | 54.777 | -14.126 | 1.00 | 56.72 | C |
| ATOM | 310 | O | GLY | A | 40 | 36.311 | 55.385 | -15.161 | 1.00 | 59.14 | O |
| ATOM | 311 | N | GLU | A | 41 | 35.940 | 53.462 | -14.098 | 1.00 | 53.24 | N |
| ATOM | 312 | CA | GLU | A | 41 | 36.137 | 52.712 | -15.312 | 1.00 | 54.15 | C |
| ATOM | 313 | C | GLU | A | 41 | 34.887 | 52.572 | -16.152 | 1.00 | 52.64 | C |
| ATOM | 314 | O | GLU | A | 41 | 33.772 | 52.444 | -15.645 | 1.00 | 51.92 | O |
| ATOM | 315 | CB | GLU | A | 41 | 36.695 | 51.341 | -14.988 | 1.00 | 62.00 | C |
| ATOM | 316 | CG | GLU | A | 41 | 38.100 | 51.410 | -14.451 | 1.00 | 86.56 | C |
| ATOM | 317 | CD | GLU | A | 41 | 38.565 | 50.074 | -13.931 | 1.00 | 94.84 | C |
| ATOM | 318 | OE1 | GLU | A | 41 | 37.901 | 49.059 | -14.243 | 1.00 | 99.92 | O |
| ATOM | 319 | OE2 | GLU | A | 41 | 39.591 | 50.041 | -13.220 | 1.00 | 98.17 | O |
| ATOM | 320 | N | LYS | A | 42 | 35.104 | 52.625 | -17.457 | 1.00 | 48.52 | N |
| ATOM | 321 | CA | LYS | A | 42 | 34.050 | 52.475 | -18.430 | 1.00 | 45.24 | C |
| ATOM | 322 | C | LYS | A | 42 | 33.714 | 50.979 | -18.477 | 1.00 | 52.84 | C |
| ATOM | 323 | O | LYS | A | 42 | 34.607 | 50.126 | -18.534 | 1.00 | 47.42 | O |
| ATOM | 324 | CB | LYS | A | 42 | 34.536 | 52.971 | -19.796 | 1.00 | 46.19 | C |
| ATOM | 325 | CG | LYS | A | 42 | 33.502 | 52.863 | -20.930 | 1.00 | 58.73 | C |
| ATOM | 326 | CD | LYS | A | 42 | 34.006 | 53.553 | -22.205 | 1.00 | 60.30 | C |
| ATOM | 327 | CE | LYS | A | 42 | 33.004 | 53.446 | -23.353 | 1.00 | 69.24 | C |
| ATOM | 328 | NZ | LYS | A | 42 | 33.486 | 54.104 | -24.606 | 1.00 | 73.95 | N |
| ATOM | 329 | N | LEU | A | 43 | 32.425 | 50.659 | -18.441 | 1.00 | 42.58 | N |
| ATOM | 330 | CA | LEU | A | 43 | 31.986 | 49.270 | -18.453 | 1.00 | 44.33 | C |
| ATOM | 331 | C | LEU | A | 43 | 31.907 | 48.724 | -19.863 | 1.00 | 45.36 | C |
| ATOM | 332 | O | LEU | A | 43 | 31.315 | 49.351 | -20.734 | 1.00 | 49.42 | O |
| ATOM | 333 | CB | LEU | A | 43 | 30.613 | 49.177 | -17.778 | 1.00 | 37.59 | C |
| ATOM | 334 | CG | LEU | A | 43 | 30.672 | 49.579 | -16.302 | 1.00 | 45.02 | C |
| ATOM | 335 | CD1 | LEU | A | 43 | 29.276 | 49.708 | -15.713 | 1.00 | 48.59 | C |
| ATOM | 336 | CD2 | LEU | A | 43 | 31.489 | 48.538 | -15.550 | 1.00 | 45.09 | C |
| ATOM | 337 | N | SER | A | 44 | 32.507 | 47.566 | -20.100 | 0.50 | 34.43 | N |
| ATOM | 338 | CA | SER | A | 44 | 32.436 | 46.990 | -21.429 | 0.50 | 37.54 | C |
| ATOM | 339 | C | SER | A | 44 | 31.017 | 46.509 | -21.595 | 0.50 | 40.70 | C |

Figure 2 (Table 2 (page 14))

| | | | | | | | | | | |
|---|---|---|---|---|---|---|---|---|---|---|
| ATOM | 340 | O | SER | A | 44 | 30.404 | 45.984 | -20.672 | 0.50 31.07 | O |
| ATOM | 341 | CB | SER | A | 44 | 33.394 | 45.813 | -21.590 | 0.50 34.76 | C |
| ATOM | 342 | OG | SER | A | 44 | 34.730 | 46.238 | -21.418 | 0.50 37.63 | O |
| ATOM | 343 | N | PRO | A | 45 | 30.475 | 46.684 | -22.787 | 1.00 55.79 | N |
| ATOM | 344 | CA | PRO | A | 45 | 29.104 | 46.261 | -23.062 | 1.00 56.53 | C |
| ATOM | 345 | C | PRO | A | 45 | 28.910 | 44.761 | -23.041 | 1.00 53.37 | C |
| ATOM | 346 | O | PRO | A | 45 | 29.849 | 43.986 | -23.229 | 1.00 56.21 | O |
| ATOM | 347 | CB | PRO | A | 45 | 28.836 | 46.833 | -24.458 | 1.00 60.37 | C |
| ATOM | 348 | CG | PRO | A | 45 | 29.823 | 47.960 | -24.586 | 1.00 60.02 | C |
| ATOM | 349 | CD | PRO | A | 45 | 31.056 | 47.392 | -23.941 | 1.00 63.21 | C |
| ATOM | 350 | N | ASN | A | 46 | 27.667 | 44.370 | -22.800 | 1.00 57.48 | N |
| ATOM | 351 | CA | ASN | A | 46 | 27.279 | 42.973 | -22.812 | 1.00 57.72 | C |
| ATOM | 352 | C | ASN | A | 46 | 28.150 | 41.993 | -22.017 | 1.00 57.75 | C |
| ATOM | 353 | O | ASN | A | 46 | 28.534 | 40.950 | -22.541 | 1.00 60.65 | O |
| ATOM | 354 | CB | ASN | A | 46 | 27.179 | 42.508 | -24.272 | 1.00 67.80 | C |
| ATOM | 355 | CG | ASN | A | 46 | 26.285 | 43.417 | -25.119 | 1.00 71.96 | C |
| ATOM | 356 | OD1 | ASN | A | 46 | 25.090 | 43.557 | -24.850 | 1.00 81.33 | O |
| ATOM | 357 | ND2 | ASN | A | 46 | 26.862 | 44.033 | -26.146 | 1.00 70.84 | N |
| ATOM | 358 | N | GLN | A | 47 | 28.478 | 42.325 | -20.771 | 1.00 53.34 | N |
| ATOM | 359 | CA | GLN | A | 47 | 29.250 | 41.408 | -19.925 | 1.00 49.41 | C |
| ATOM | 360 | C | GLN | A | 47 | 28.202 | 40.672 | -19.091 | 1.00 50.32 | C |
| ATOM | 361 | O | GLN | A | 47 | 27.029 | 41.040 | -19.111 | 1.00 47.47 | O |
| ATOM | 362 | CB | GLN | A | 47 | 30.232 | 42.156 | -19.022 | 1.00 51.46 | C |
| ATOM | 363 | CG | GLN | A | 47 | 31.291 | 42.936 | -19.798 | 1.00 49.02 | C |
| ATOM | 364 | CD | GLN | A | 47 | 32.023 | 42.055 | -20.812 | 1.00 60.54 | C |
| ATOM | 365 | OE1 | GLN | A | 47 | 32.910 | 41.286 | -20.448 | 1.00 52.30 | O |
| ATOM | 366 | NE2 | GLN | A | 47 | 31.634 | 42.149 | -22.082 | 1.00 51.19 | N |
| ATOM | 367 | N | GLN | A | 48 | 28.630 | 39.669 | -18.336 | 1.00 52.29 | N |
| ATOM | 368 | CA | GLN | A | 48 | 27.728 | 38.807 | -17.566 | 1.00 56.49 | C |
| ATOM | 369 | C | GLN | A | 48 | 27.049 | 39.337 | -16.305 | 1.00 58.23 | C |
| ATOM | 370 | O | GLN | A | 48 | 25.818 | 39.453 | -16.238 | 1.00 50.89 | O |
| ATOM | 371 | CB | GLN | A | 48 | 28.486 | 37.524 | -17.199 | 1.00 69.79 | C |
| ATOM | 372 | CG | GLN | A | 48 | 27.606 | 36.324 | -16.903 | 1.00 85.42 | C |
| ATOM | 373 | CD | GLN | A | 48 | 27.071 | 35.675 | -18.172 | 1.00 96.52 | C |
| ATOM | 374 | OE1 | GLN | A | 48 | 27.848 | 35.302 | -19.052 | 1.00103.65 | O |
| ATOM | 375 | NE2 | GLN | A | 48 | 25.745 | 35.530 | -18.272 | 1.00 97.26 | N |
| ATOM | 376 | N | ARG | A | 49 | 27.866 | 39.613 | -15.297 | 1.00 46.27 | N |
| ATOM | 377 | CA | ARG | A | 49 | 27.376 | 40.069 | -14.009 | 1.00 49.02 | C |
| ATOM | 378 | C | ARG | A | 49 | 27.031 | 41.558 | -13.965 | 1.00 50.34 | C |
| ATOM | 379 | O | ARG | A | 49 | 25.951 | 41.929 | -13.518 | 1.00 44.46 | O |
| ATOM | 380 | CB | ARG | A | 49 | 28.404 | 39.724 | -12.937 | 1.00 43.05 | C |
| ATOM | 381 | CG | ARG | A | 49 | 27.841 | 39.691 | -11.541 | 1.00 50.00 | C |
| ATOM | 382 | CD | ARG | A | 49 | 28.920 | 39.301 | -10.560 | 1.00 46.14 | C |
| ATOM | 383 | NE | ARG | A | 49 | 29.847 | 40.402 | -10.332 | 1.00 50.29 | N |
| ATOM | 384 | CZ | ARG | A | 49 | 29.552 | 41.479 | -9.614 | 1.00 49.75 | C |
| ATOM | 385 | NH1 | ARG | A | 49 | 28.355 | 41.602 | -9.054 | 1.00 46.61 | N |
| ATOM | 386 | NH2 | ARG | A | 49 | 30.456 | 42.434 | -9.450 | 1.00 54.16 | N |
| ATOM | 387 | N | ILE | A | 50 | 27.950 | 42.413 | -14.404 | 1.00 45.13 | N |
| ATOM | 388 | CA | ILE | A | 50 | 27.693 | 43.846 | -14.431 | 1.00 47.45 | C |
| ATOM | 389 | C | ILE | A | 50 | 27.362 | 44.081 | -15.886 | 1.00 49.10 | C |
| ATOM | 390 | O | ILE | A | 50 | 28.236 | 44.288 | -16.718 | 1.00 46.05 | O |
| ATOM | 391 | CB | ILE | A | 50 | 28.927 | 44.633 | -13.989 | 1.00 46.67 | C |
| ATOM | 392 | CG1 | ILE | A | 50 | 29.309 | 44.197 | -12.569 | 1.00 49.39 | C |
| ATOM | 393 | CG2 | ILE | A | 50 | 28.645 | 46.122 | -14.047 | 1.00 45.96 | C |
| ATOM | 394 | CD1 | ILE | A | 50 | 28.175 | 44.305 | -11.547 | 1.00 38.44 | C |
| ATOM | 395 | N | SER | A | 51 | 26.069 | 44.019 | -16.172 | 1.00 45.97 | N |
| ATOM | 396 | CA | SER | A | 51 | 25.572 | 44.111 | -17.523 | 1.00 42.85 | C |

Figure 2 (Table 2 (page 15))

```
ATOM    397  C    SER A  51      25.123  45.464 -18.027  1.00 47.59  C
ATOM    398  O    SER A  51      24.300  46.145 -17.408  1.00 47.20  O
ATOM    399  CB   SER A  51      24.430  43.096 -17.676  1.00 42.67  C
ATOM    400  OG   SER A  51      23.643  43.375 -18.811  1.00 55.89  O
ATOM    401  N    VAL A  52      25.689  45.856 -19.159  1.00 45.49  N
ATOM    402  CA   VAL A  52      25.317  47.100 -19.802  1.00 46.68  C
ATOM    403  C    VAL A  52      24.768  46.706 -21.155  1.00 52.16  C
ATOM    404  O    VAL A  52      25.483  46.140 -21.991  1.00 52.43  O
ATOM    405  CB   VAL A  52      26.504  48.038 -20.028  1.00 51.87  C
ATOM    406  CG1  VAL A  52      26.064  49.202 -20.901  1.00 49.68  C
ATOM    407  CG2  VAL A  52      27.029  48.555 -18.694  1.00 46.22  C
ATOM    408  N    VAL A  53      23.491  46.999 -21.353  1.00 43.80  N
ATOM    409  CA   VAL A  53      22.813  46.679 -22.584  1.00 51.71  C
ATOM    410  C    VAL A  53      22.126  47.901 -23.192  1.00 60.49  C
ATOM    411  O    VAL A  53      21.288  48.550 -22.564  1.00 55.82  O
ATOM    412  CB   VAL A  53      21.770  45.573 -22.343  1.00 57.05  C
ATOM    413  CG1  VAL A  53      20.897  45.392 -23.569  1.00 61.58  C
ATOM    414  CG2  VAL A  53      22.478  44.269 -22.008  1.00 51.45  C
ATOM    415  N    TRP A  54      22.511  48.205 -24.422  1.00 65.48  N
ATOM    416  CA   TRP A  54      21.948  49.309 -25.178  1.00 74.11  C
ATOM    417  C    TRP A  54      20.581  48.813 -25.650  1.00 74.48  C
ATOM    418  O    TRP A  54      20.475  47.706 -26.167  1.00 72.95  O
ATOM    419  CB   TRP A  54      22.851  49.571 -26.365  1.00 82.17  C
ATOM    420  CG   TRP A  54      22.565  50.791 -27.135  1.00 99.79  C
ATOM    421  CD1  TRP A  54      22.877  52.073 -26.787  1.00102.50  C
ATOM    422  CD2  TRP A  54      22.021  50.849 -28.456  1.00107.53  C
ATOM    423  NE1  TRP A  54      22.573  52.929 -27.817  1.00109.34  N
ATOM    424  CE2  TRP A  54      22.045  52.205 -28.852  1.00111.35  C
ATOM    425  CE3  TRP A  54      21.515  49.889 -29.343  1.00108.73  C
ATOM    426  CZ2  TRP A  54      21.590  52.619 -30.108  1.00112.86  C
ATOM    427  CZ3  TRP A  54      21.061  50.305 -30.591  1.00109.55  C
ATOM    428  CH2  TRP A  54      21.100  51.662 -30.959  1.00110.38  C
ATOM    429  N    ASN A  55      19.537  49.612 -25.471  1.00 71.63  N
ATOM    430  CA   ASN A  55      18.205  49.185 -25.878  1.00 76.76  C
ATOM    431  C    ASN A  55      17.845  49.651 -27.281  1.00 81.91  C
ATOM    432  O    ASN A  55      17.573  48.846 -28.168  1.00 88.33  O
ATOM    433  CB   ASN A  55      17.197  49.689 -24.858  1.00 71.55  C
ATOM    434  CG   ASN A  55      17.474  49.141 -23.476  1.00 75.04  C
ATOM    435  OD1  ASN A  55      17.374  47.932 -23.246  1.00 72.25  O
ATOM    436  ND2  ASN A  55      17.841  50.021 -22.550  1.00 50.95  N
ATOM    437  N    ASP A  56      17.833  50.962 -27.455  1.00 88.42  N
ATOM    438  CA   ASP A  56      17.548  51.607 -28.722  1.00 96.25  C
ATOM    439  C    ASP A  56      18.566  52.727 -28.677  1.00101.81  C
ATOM    440  O    ASP A  56      19.369  52.797 -27.736  1.00102.77  O
ATOM    441  CB   ASP A  56      16.107  52.147 -28.744  1.00 95.48  C
ATOM    442  CG   ASP A  56      15.707  52.811 -27.433  1.00 93.76  C
ATOM    443  OD1  ASP A  56      16.451  53.704 -26.985  1.00 85.05  O
ATOM    444  OD2  ASP A  56      14.658  52.452 -26.849  1.00 93.98  O
ATOM    445  N    ASP A  57      18.599  53.607 -29.663  1.00102.50  N
ATOM    446  CA   ASP A  57      19.610  54.674 -29.562  1.00102.11  C
ATOM    447  C    ASP A  57      19.218  55.678 -28.491  1.00 97.41  C
ATOM    448  O    ASP A  57      19.933  56.652 -28.258  1.00 97.40  O
ATOM    449  CB   ASP A  57      19.781  55.395 -30.900  1.00112.19  C
ATOM    450  CG   ASP A  57      21.068  56.116 -30.995  1.00121.70  C
ATOM    451  OD1  ASP A  57      21.660  56.543 -29.959  1.00128.34  O
ATOM    452  OD2  ASP A  57      21.589  56.364 -32.125  1.00123.94  O
ATOM    453  N    ASP A  58      18.084  55.433 -27.843  1.00 90.49  N
```

Figure 2 (Table 2 (page 16))

```
ATOM    454  CA  ASP A  58      17.622  56.352 -26.826  1.00 87.06  C
ATOM    455  C   ASP A  58      18.071  55.997 -25.427  1.00 73.82  C
ATOM    456  O   ASP A  58      18.180  56.880 -24.577  1.00 62.84  O
ATOM    457  CB  ASP A  58      16.093  56.433 -26.809  1.00103.58  C
ATOM    458  CG  ASP A  58      15.487  56.564 -28.191  1.00113.84  C
ATOM    459  OD1 ASP A  58      15.498  57.677 -28.763  1.00117.69  O
ATOM    460  OD2 ASP A  58      14.997  55.534 -28.700  1.00121.72  O
ATOM    461  N   SER A  59      18.320  54.717 -25.174  1.00 64.75  N
ATOM    462  CA  SER A  59      18.681  54.313 -23.828  1.00 61.90  C
ATOM    463  C   SER A  59      19.628  53.131 -23.689  1.00 64.15  C
ATOM    464  O   SER A  59      19.869  52.359 -24.627  1.00 60.43  O
ATOM    465  CB  SER A  59      17.408  54.000 -23.052  1.00 55.02  C
ATOM    466  OG  SER A  59      16.760  52.881 -23.625  1.00 62.54  O
ATOM    467  N   SER A  60      20.145  53.005 -22.473  1.00 58.32  N
ATOM    468  CA  SER A  60      21.062  51.941 -22.111  1.00 53.12  C
ATOM    469  C   SER A  60      20.694  51.465 -20.708  1.00 51.38  C
ATOM    470  O   SER A  60      20.439  52.271 -19.815  1.00 50.11  O
ATOM    471  CB  SER A  60      22.502  52.451 -22.127  1.00 48.06  C
ATOM    472  OG  SER A  60      23.407  51.420 -21.751  1.00 54.93  O
ATOM    473  N   THR A  61      20.667  50.157 -20.509  1.00 41.41  N
ATOM    474  CA  THR A  61      20.308  49.618 -19.206  1.00 44.19  C
ATOM    475  C   THR A  61      21.489  48.979 -18.501  1.00 42.41  C
ATOM    476  O   THR A  61      22.227  48.188 -19.081  1.00 46.93  O
ATOM    477  CB  THR A  61      19.183  48.583 -19.353  1.00 47.49  C
ATOM    478  OG1 THR A  61      18.023  49.233 -19.880  1.00 56.06  O
ATOM    479  CG2 THR A  61      18.837  47.945 -18.004  1.00 45.18  C
ATOM    480  N   LEU A  62      21.674  49.359 -17.247  1.00 37.61  N
ATOM    481  CA  LEU A  62      22.731  48.797 -16.432  1.00 39.04  C
ATOM    482  C   LEU A  62      22.076  47.810 -15.475  1.00 38.19  C
ATOM    483  O   LEU A  62      21.171  48.185 -14.722  1.00 38.43  O
ATOM    484  CB  LEU A  62      23.431  49.896 -15.628  1.00 34.82  C
ATOM    485  CG  LEU A  62      24.273  49.373 -14.461  1.00 46.86  C
ATOM    486  CD1 LEU A  62      25.418  48.550 -14.996  1.00 41.11  C
ATOM    487  CD2 LEU A  62      24.797  50.517 -13.617  1.00 40.98  C
ATOM    488  N   THR A  63      22.488  46.548 -15.514  1.00 34.32  N
ATOM    489  CA  THR A  63      21.930  45.570 -14.583  1.00 42.11  C
ATOM    490  C   THR A  63      23.043  45.058 -13.694  1.00 38.02  C
ATOM    491  O   THR A  63      24.086  44.634 -14.181  1.00 39.91  O
ATOM    492  CB  THR A  63      21.312  44.333 -15.284  1.00 44.60  C
ATOM    493  OG1 THR A  63      20.291  44.746 -16.193  1.00 38.13  O
ATOM    494  CG2 THR A  63      20.709  43.388 -14.247  1.00 41.53  C
ATOM    495  N   ILE A  64      22.831  45.096 -12.390  1.00 32.30  N
ATOM    496  CA  ILE A  64      23.835  44.596 -11.464  1.00 40.27  C
ATOM    497  C   ILE A  64      23.288  43.299 -10.884  1.00 44.61  C
ATOM    498  O   ILE A  64      22.400  43.324 -10.032  1.00 43.38  O
ATOM    499  CB  ILE A  64      24.116  45.600 -10.319  1.00 43.07  C
ATOM    500  CG1 ILE A  64      24.757  46.868 -10.894  1.00 50.00  C
ATOM    501  CG2 ILE A  64      25.032  44.962  -9.265  1.00 36.35  C
ATOM    502  CD1 ILE A  64      25.080  47.930  -9.867  1.00 45.66  C
ATOM    503  N   TYR A  65      23.811  42.175 -11.373  1.00 41.50  N
ATOM    504  CA  TYR A  65      23.398  40.851 -10.917  1.00 41.75  C
ATOM    505  C   TYR A  65      24.239  40.399  -9.746  1.00 46.17  C
ATOM    506  O   TYR A  65      25.400  40.796  -9.628  1.00 46.44  O
ATOM    507  CB  TYR A  65      23.591  39.814 -12.023  1.00 39.24  C
ATOM    508  CG  TYR A  65      22.643  39.936 -13.177  1.00 46.02  C
ATOM    509  CD1 TYR A  65      23.074  40.408 -14.415  1.00 43.20  C
ATOM    510  CD2 TYR A  65      21.304  39.560 -13.035  1.00 40.19  C
```

Figure 2 (Table 2 (page 17))

```
ATOM    511  CE1 TYR A  65      22.198  40.503 -15.492  1.00 46.92  C
ATOM    512  CE2 TYR A  65      20.406  39.644 -14.117  1.00 42.02  C
ATOM    513  CZ  TYR A  65      20.868  40.117 -15.337  1.00 47.29  C
ATOM    514  OH  TYR A  65      20.008  40.185 -16.399  1.00 46.88  O
ATOM    515  N   ASN A  66      23.660  39.556  -8.897  1.00 43.81  N
ATOM    516  CA  ASN A  66      24.368  38.990  -7.756  1.00 48.17  C
ATOM    517  C   ASN A  66      25.277  40.002  -7.062  1.00 48.24  C
ATOM    518  O   ASN A  66      26.489  39.792  -6.955  1.00 48.04  O
ATOM    519  CB  ASN A  66      25.206  37.817  -8.241  1.00 44.79  C
ATOM    520  CG  ASN A  66      25.844  37.052  -7.100  1.00 58.80  C
ATOM    521  OD1 ASN A  66      26.868  36.393  -7.279  1.00 62.64  O
ATOM    522  ND2 ASN A  66      25.237  37.127  -5.919  1.00 60.17  N
ATOM    523  N   ALA A  67      24.684  41.080  -6.566  1.00 47.68  N
ATOM    524  CA  ALA A  67      25.448  42.151  -5.935  1.00 40.81  C
ATOM    525  C   ALA A  67      26.301  41.798  -4.739  1.00 49.08  C
ATOM    526  O   ALA A  67      25.937  40.963  -3.910  1.00 47.57  O
ATOM    527  CB  ALA A  67      24.523  43.290  -5.553  1.00 44.48  C
ATOM    528  N   ASN A  68      27.435  42.482  -4.649  1.00 50.95  N
ATOM    529  CA  ASN A  68      28.344  42.315  -3.529  1.00 54.43  C
ATOM    530  C   ASN A  68      28.763  43.719  -3.093  1.00 55.80  C
ATOM    531  O   ASN A  68      28.665  44.678  -3.872  1.00 45.45  O
ATOM    532  CB  ASN A  68      29.557  41.476  -3.922  1.00 51.73  C
ATOM    533  CG  ASN A  68      30.494  42.201  -4.854  1.00 61.49  C
ATOM    534  OD1 ASN A  68      30.920  43.322  -4.579  1.00 60.88  O
ATOM    535  ND2 ASN A  68      30.835  41.554  -5.963  1.00 52.62  N
ATOM    536  N   ILE A  69      29.235  43.835  -1.856  1.00 52.73  N
ATOM    537  CA  ILE A  69      29.630  45.118  -1.285  1.00 58.71  C
ATOM    538  C   ILE A  69      30.545  45.990  -2.137  1.00 51.79  C
ATOM    539  O   ILE A  69      30.483  47.208  -2.043  1.00 52.79  O
ATOM    540  CB  ILE A  69      30.299  44.937   0.095  1.00 60.50  C
ATOM    541  CG1 ILE A  69      31.681  44.301  -0.063  1.00 67.17  C
ATOM    542  CG2 ILE A  69      29.410  44.091   0.987  1.00 59.59  C
ATOM    543  CD1 ILE A  69      32.506  44.314   1.211  1.00 80.29  C
ATOM    544  N   ASP A  70      31.396  45.384  -2.956  1.00 46.36  N
ATOM    545  CA  ASP A  70      32.277  46.184  -3.781  1.00 50.45  C
ATOM    546  C   ASP A  70      31.587  46.792  -4.991  1.00 58.77  C
ATOM    547  O   ASP A  70      32.227  47.477  -5.784  1.00 53.61  O
ATOM    548  CB  ASP A  70      33.473  45.369  -4.241  1.00 50.41  C
ATOM    549  CG  ASP A  70      34.388  44.991  -3.088  1.00 69.82  C
ATOM    550  OD1 ASP A  70      34.622  45.851  -2.208  1.00 68.65  O
ATOM    551  OD2 ASP A  70      34.878  43.842  -3.064  1.00 67.67  O
ATOM    552  N   ASP A  71      30.290  46.540  -5.144  1.00 54.09  N
ATOM    553  CA  ASP A  71      29.554  47.102  -6.269  1.00 50.10  C
ATOM    554  C   ASP A  71      28.969  48.474  -5.898  1.00 52.41  C
ATOM    555  O   ASP A  71      28.508  49.224  -6.764  1.00 47.41  O
ATOM    556  CB  ASP A  71      28.406  46.166  -6.708  1.00 49.99  C
ATOM    557  CG  ASP A  71      28.892  44.834  -7.302  1.00 49.02  C
ATOM    558  OD1 ASP A  71      29.813  44.825  -8.146  1.00 46.46  O
ATOM    559  OD2 ASP A  71      28.324  43.784  -6.929  1.00 50.74  O
ATOM    560  N   ALA A  72      28.987  48.801  -4.610  1.00 42.72  N
ATOM    561  CA  ALA A  72      28.429  50.063  -4.133  1.00 45.31  C
ATOM    562  C   ALA A  72      29.129  51.291  -4.686  1.00 47.73  C
ATOM    563  O   ALA A  72      30.326  51.268  -4.977  1.00 47.41  O
ATOM    564  CB  ALA A  72      28.460  50.107  -2.604  1.00 47.05  C
ATOM    565  N   GLY A  73      28.378  52.374  -4.821  1.00 48.72  N
ATOM    566  CA  GLY A  73      28.976  53.593  -5.322  1.00 54.09  C
ATOM    567  C   GLY A  73      28.144  54.331  -6.341  1.00 51.98  C
```

Figure 2 (Table 2 (page 18))

| ATOM | 568 | O   | GLY | A | 73 | 27.018 | 53.939 | -6.653  | 1.00 | 49.57 | O |
|------|-----|-----|-----|---|----|--------|--------|---------|------|-------|---|
| ATOM | 569 | N   | ILE | A | 74 | 28.716 | 55.413 | -6.859  | 1.00 | 51.79 | N |
| ATOM | 570 | CA  | ILE | A | 74 | 28.052 | 56.242 | -7.850  | 1.00 | 48.58 | C |
| ATOM | 571 | C   | ILE | A | 74 | 28.428 | 55.760 | -9.237  | 1.00 | 47.75 | C |
| ATOM | 572 | O   | ILE | A | 74 | 29.603 | 55.780 | -9.620  | 1.00 | 46.87 | O |
| ATOM | 573 | CB  | ILE | A | 74 | 28.475 | 57.717 | -7.705  | 1.00 | 54.10 | C |
| ATOM | 574 | CG1 | ILE | A | 74 | 28.061 | 58.227 | -6.323  | 1.00 | 60.29 | C |
| ATOM | 575 | CG2 | ILE | A | 74 | 27.860 | 58.551 | -8.816  | 1.00 | 51.72 | C |
| ATOM | 576 | CD1 | ILE | A | 74 | 28.463 | 59.656 | -6.041  | 1.00 | 55.15 | C |
| ATOM | 577 | N   | TYR | A | 75 | 27.429 | 55.272 | -9.960  | 1.00 | 39.87 | N |
| ATOM | 578 | CA  | TYR | A | 75 | 27.637 | 54.826 | -11.330 | 1.00 | 48.23 | C |
| ATOM | 579 | C   | TYR | A | 75 | 27.168 | 56.010 | -12.126 | 1.00 | 48.15 | C |
| ATOM | 580 | O   | TYR | A | 75 | 26.293 | 56.764 | -11.682 | 1.00 | 46.43 | O |
| ATOM | 581 | CB  | TYR | A | 75 | 26.745 | 53.629 | -11.707 | 1.00 | 44.56 | C |
| ATOM | 582 | CG  | TYR | A | 75 | 27.137 | 52.331 | -11.050 | 1.00 | 47.56 | C |
| ATOM | 583 | CD1 | TYR | A | 75 | 26.925 | 52.133 | -9.682  | 1.00 | 39.03 | C |
| ATOM | 584 | CD2 | TYR | A | 75 | 27.789 | 51.326 | -11.773 | 1.00 | 43.44 | C |
| ATOM | 585 | CE1 | TYR | A | 75 | 27.356 | 50.967 | -9.045  | 1.00 | 39.99 | C |
| ATOM | 586 | CE2 | TYR | A | 75 | 28.230 | 50.162 | -11.146 | 1.00 | 32.79 | C |
| ATOM | 587 | CZ  | TYR | A | 75 | 28.010 | 49.990 | -9.778  | 1.00 | 35.84 | C |
| ATOM | 588 | OH  | TYR | A | 75 | 28.463 | 48.851 | -9.153  | 1.00 | 43.95 | O |
| ATOM | 589 | N   | LYS | A | 76 | 27.739 | 56.201 | -13.299 | 1.00 | 48.85 | N |
| ATOM | 590 | CA  | LYS | A | 76 | 27.270 | 57.305 | -14.090 | 1.00 | 48.84 | C |
| ATOM | 591 | C   | LYS | A | 76 | 27.178 | 56.938 | -15.532 | 1.00 | 44.98 | C |
| ATOM | 592 | O   | LYS | A | 76 | 27.912 | 56.092 | -16.052 | 1.00 | 47.18 | O |
| ATOM | 593 | CB  | LYS | A | 76 | 28.115 | 58.551 | -13.857 | 1.00 | 56.56 | C |
| ATOM | 594 | CG  | LYS | A | 76 | 29.442 | 58.619 | -14.520 | 1.00 | 59.09 | C |
| ATOM | 595 | CD  | LYS | A | 76 | 30.046 | 59.941 | -14.072 | 1.00 | 66.83 | C |
| ATOM | 596 | CE  | LYS | A | 76 | 31.142 | 60.452 | -14.968 | 1.00 | 71.43 | C |
| ATOM | 597 | NZ  | LYS | A | 76 | 31.553 | 61.794 | -14.449 | 1.00 | 73.15 | N |
| ATOM | 598 | N   | CYS | A | 77 | 26.194 | 57.553 | -16.153 | 1.00 | 45.89 | N |
| ATOM | 599 | CA  | CYS | A | 77 | 25.888 | 57.319 | -17.532 | 1.00 | 44.65 | C |
| ATOM | 600 | C   | CYS | A | 77 | 26.233 | 58.600 | -18.270 | 1.00 | 47.89 | C |
| ATOM | 601 | O   | CYS | A | 77 | 25.718 | 59.666 | -17.945 | 1.00 | 52.98 | O |
| ATOM | 602 | CB  | CYS | A | 77 | 24.401 | 57.004 | -17.652 | 1.00 | 42.61 | C |
| ATOM | 603 | SG  | CYS | A | 77 | 23.808 | 56.802 | -19.350 | 1.00 | 61.23 | S |
| ATOM | 604 | N   | VAL | A | 78 | 27.122 | 58.494 | -19.249 | 1.00 | 50.12 | N |
| ATOM | 605 | CA  | VAL | A | 78 | 27.547 | 59.658 | -20.019 | 1.00 | 46.50 | C |
| ATOM | 606 | C   | VAL | A | 78 | 27.082 | 59.581 | -21.471 | 1.00 | 43.99 | C |
| ATOM | 607 | O   | VAL | A | 78 | 27.222 | 58.552 | -22.131 | 1.00 | 48.45 | O |
| ATOM | 608 | CB  | VAL | A | 78 | 29.084 | 59.795 | -19.993 | 1.00 | 46.58 | C |
| ATOM | 609 | CG1 | VAL | A | 78 | 29.517 | 61.010 | -20.820 | 1.00 | 51.99 | C |
| ATOM | 610 | CG2 | VAL | A | 78 | 29.566 | 59.942 | -18.547 | 1.00 | 41.06 | C |
| ATOM | 611 | N   | VAL | A | 79 | 26.521 | 60.672 | -21.965 | 1.00 | 48.68 | N |
| ATOM | 612 | CA  | VAL | A | 79 | 26.047 | 60.720 | -23.343 | 1.00 | 57.39 | C |
| ATOM | 613 | C   | VAL | A | 79 | 26.945 | 61.666 | -24.119 | 1.00 | 54.87 | C |
| ATOM | 614 | O   | VAL | A | 79 | 27.194 | 62.792 | -23.691 | 1.00 | 52.91 | O |
| ATOM | 615 | CB  | VAL | A | 79 | 24.598 | 61.227 | -23.417 | 1.00 | 60.20 | C |
| ATOM | 616 | CG1 | VAL | A | 79 | 24.085 | 61.155 | -24.848 | 1.00 | 54.06 | C |
| ATOM | 617 | CG2 | VAL | A | 79 | 23.730 | 60.395 | -22.487 | 1.00 | 56.02 | C |
| ATOM | 618 | N   | THR | A | 80 | 27.452 | 61.191 | -25.247 | 1.00 | 48.32 | N |
| ATOM | 619 | CA  | THR | A | 80 | 28.313 | 62.011 | -26.066 | 1.00 | 52.81 | C |
| ATOM | 620 | C   | THR | A | 80 | 27.706 | 62.226 | -27.450 | 1.00 | 54.17 | C |
| ATOM | 621 | O   | THR | A | 80 | 27.501 | 61.266 | -28.187 | 1.00 | 49.22 | O |
| ATOM | 622 | CB  | THR | A | 80 | 29.691 | 61.371 | -26.241 | 1.00 | 54.94 | C |
| ATOM | 623 | OG1 | THR | A | 80 | 30.268 | 61.104 | -24.954 | 1.00 | 54.31 | O |
| ATOM | 624 | CG2 | THR | A | 80 | 30.601 | 62.318 | -27.012 | 1.00 | 41.33 | C |

Figure 2 (Table 2 (page 19))

| | | | | | | | | | |
|---|---|---|---|---|---|---|---|---|---|
| ATOM | 625 | N   | ALA | A | 81 | 27.430 | 63.487 | -27.787 | 1.00 56.76 N |
| ATOM | 626 | CA  | ALA | A | 81 | 26.859 | 63.866 | -29.088 | 1.00 58.85 C |
| ATOM | 627 | C   | ALA | A | 81 | 27.942 | 63.828 | -30.165 | 1.00 58.97 C |
| ATOM | 628 | O   | ALA | A | 81 | 29.131 | 63.922 | -29.847 | 1.00 53.72 O |
| ATOM | 629 | CB  | ALA | A | 81 | 26.263 | 65.265 | -29.005 | 1.00 60.88 C |
| ATOM | 630 | N   | GLU | A | 82 | 27.528 | 63.712 | -31.429 | 1.00 67.86 N |
| ATOM | 631 | CA  | GLU | A | 82 | 28.462 | 63.639 | -32.555 | 1.00 73.18 C |
| ATOM | 632 | C   | GLU | A | 82 | 29.599 | 64.664 | -32.507 | 1.00 68.06 C |
| ATOM | 633 | O   | GLU | A | 82 | 30.700 | 64.398 | -32.993 | 1.00 65.36 O |
| ATOM | 634 | CB  | GLU | A | 82 | 27.707 | 63.768 | -33.887 | 1.00 74.95 C |
| ATOM | 635 | CG  | GLU | A | 82 | 28.027 | 62.638 | -34.868 | 1.00 98.35 C |
| ATOM | 636 | CD  | GLU | A | 82 | 27.295 | 62.768 | -36.194 | 1.00111.66 C |
| ATOM | 637 | OE1 | GLU | A | 82 | 26.071 | 63.034 | -36.178 | 1.00118.11 O |
| ATOM | 638 | OE2 | GLU | A | 82 | 27.942 | 62.594 | -37.253 | 1.00117.01 O |
| ATOM | 639 | N   | ASP | A | 83 | 29.340 | 65.821 | -31.907 | 1.00 62.35 N |
| ATOM | 640 | CA  | ASP | A | 83 | 30.340 | 66.877 | -31.812 | 1.00 67.89 C |
| ATOM | 641 | C   | ASP | A | 83 | 31.171 | 66.830 | -30.533 | 1.00 71.00 C |
| ATOM | 642 | O   | ASP | A | 83 | 31.929 | 67.759 | -30.246 | 1.00 73.73 O |
| ATOM | 643 | CB  | ASP | A | 83 | 29.653 | 68.230 | -31.924 | 1.00 74.31 C |
| ATOM | 644 | CG  | ASP | A | 83 | 28.664 | 68.461 | -30.815 | 1.00 82.18 C |
| ATOM | 645 | OD1 | ASP | A | 83 | 27.939 | 67.508 | -30.462 | 1.00 93.75 O |
| ATOM | 646 | OD2 | ASP | A | 83 | 28.606 | 69.593 | -30.301 | 1.00 87.77 O |
| ATOM | 647 | N   | GLY | A | 84 | 31.017 | 65.760 | -29.759 | 1.00 69.26 N |
| ATOM | 648 | CA  | GLY | A | 84 | 31.790 | 65.617 | -28.533 | 1.00 61.95 C |
| ATOM | 649 | C   | GLY | A | 84 | 31.242 | 66.254 | -27.266 | 1.00 62.86 C |
| ATOM | 650 | O   | GLY | A | 84 | 31.851 | 66.139 | -26.197 | 1.00 65.82 O |
| ATOM | 651 | N   | THR | A | 85 | 30.106 | 66.936 | -27.361 | 1.00 55.77 N |
| ATOM | 652 | CA  | THR | A | 85 | 29.535 | 67.559 | -26.176 | 1.00 63.65 C |
| ATOM | 653 | C   | THR | A | 85 | 28.929 | 66.445 | -25.320 | 1.00 61.95 C |
| ATOM | 654 | O   | THR | A | 85 | 28.291 | 65.528 | -25.839 | 1.00 56.86 O |
| ATOM | 655 | CB  | THR | A | 85 | 28.471 | 68.614 | -26.555 | 1.00 61.72 C |
| ATOM | 656 | OG1 | THR | A | 85 | 27.458 | 68.019 | -27.373 | 1.00 73.83 O |
| ATOM | 657 | CG2 | THR | A | 85 | 29.125 | 69.749 | -27.325 | 1.00 69.89 C |
| ATOM | 658 | N   | GLN | A | 86 | 29.130 | 66.520 | -24.011 | 1.00 58.16 N |
| ATOM | 659 | CA  | GLN | A | 86 | 28.628 | 65.464 | -23.141 | 1.00 63.76 C |
| ATOM | 660 | C   | GLN | A | 86 | 27.696 | 65.900 | -22.030 | 1.00 62.47 C |
| ATOM | 661 | O   | GLN | A | 86 | 27.803 | 67.011 | -21.505 | 1.00 64.92 O |
| ATOM | 662 | CB  | GLN | A | 86 | 29.793 | 64.715 | -22.498 | 1.00 56.96 C |
| ATOM | 663 | CG  | GLN | A | 86 | 30.860 | 64.242 | -23.460 | 1.00 50.20 C |
| ATOM | 664 | CD  | GLN | A | 86 | 31.964 | 63.519 | -22.724 | 1.00 54.10 C |
| ATOM | 665 | OE1 | GLN | A | 86 | 32.390 | 63.965 | -21.663 | 1.00 54.08 O |
| ATOM | 666 | NE2 | GLN | A | 86 | 32.436 | 62.401 | -23.276 | 1.00 56.27 N |
| ATOM | 667 | N   | SER | A | 87 | 26.800 | 64.986 | -21.667 | 1.00 63.47 N |
| ATOM | 668 | CA  | SER | A | 87 | 25.836 | 65.182 | -20.588 | 1.00 68.11 C |
| ATOM | 669 | C   | SER | A | 87 | 25.889 | 63.906 | -19.749 | 1.00 65.62 C |
| ATOM | 670 | O   | SER | A | 87 | 26.194 | 62.829 | -20.270 | 1.00 69.37 O |
| ATOM | 671 | CB  | SER | A | 87 | 24.420 | 65.362 | -21.150 | 1.00 75.52 C |
| ATOM | 672 | OG  | SER | A | 87 | 24.344 | 66.449 | -22.057 | 1.00 88.36 O |
| ATOM | 673 | N   | GLU | A | 88 | 25.592 | 64.009 | -18.460 | 1.00 63.19 N |
| ATOM | 674 | CA  | GLU | A | 88 | 25.623 | 62.827 | -17.607 | 1.00 53.44 C |
| ATOM | 675 | C   | GLU | A | 88 | 24.532 | 62.803 | -16.556 | 1.00 59.13 C |
| ATOM | 676 | O   | GLU | A | 88 | 23.942 | 63.824 | -16.209 | 1.00 58.88 O |
| ATOM | 677 | CB  | GLU | A | 88 | 26.976 | 62.711 | -16.904 | 1.00 60.59 C |
| ATOM | 678 | CG  | GLU | A | 88 | 27.272 | 63.816 | -15.898 | 1.00 67.25 C |
| ATOM | 679 | CD  | GLU | A | 88 | 28.656 | 63.687 | -15.277 | 1.00 78.40 C |
| ATOM | 680 | OE1 | GLU | A | 88 | 29.631 | 63.494 | -16.035 | 1.00 79.36 O |
| ATOM | 681 | OE2 | GLU | A | 88 | 28.773 | 63.782 | -14.033 | 1.00 81.96 O |

Figure 2 (Table 2 (page 20))

```
ATOM    682  N    ALA A  89      24.254  61.602 -16.079  1.00 54.88   N
ATOM    683  CA   ALA A  89      23.283  61.384 -15.027  1.00 45.50   C
ATOM    684  C    ALA A  89      24.036  60.407 -14.149  1.00 52.74   C
ATOM    685  O    ALA A  89      24.777  59.552 -14.659  1.00 48.26   O
ATOM    686  CB   ALA A  89      22.022  60.736 -15.567  1.00 53.66   C
ATOM    687  N    THR A  90      23.887  60.549 -12.839  1.00 46.21   N
ATOM    688  CA   THR A  90      24.558  59.647 -11.932  1.00 49.08   C
ATOM    689  C    THR A  90      23.515  58.993 -11.051  1.00 49.13   C
ATOM    690  O    THR A  90      22.402  59.516 -10.861  1.00 49.24   O
ATOM    691  CB   THR A  90      25.587  60.376 -11.052  1.00 48.30   C
ATOM    692  OG1  THR A  90      24.932  61.366 -10.256  1.00 53.97   O
ATOM    693  CG2  THR A  90      26.640  61.041 -11.915  1.00 52.65   C
ATOM    694  N    VAL A  91      23.871  57.823 -10.539  1.00 45.14   N
ATOM    695  CA   VAL A  91      22.966  57.102  -9.667  1.00 48.65   C
ATOM    696  C    VAL A  91      23.736  56.474  -8.527  1.00 45.53   C
ATOM    697  O    VAL A  91      24.708  55.754  -8.740  1.00 47.93   O
ATOM    698  CB   VAL A  91      22.164  56.035 -10.433  1.00 50.62   C
ATOM    699  CG1  VAL A  91      23.113  55.013 -11.094  1.00 48.35   C
ATOM    700  CG2  VAL A  91      21.177  55.349  -9.474  1.00 54.01   C
ATOM    701  N    ASN A  92      23.304  56.773  -7.306  1.00 49.96   N
ATOM    702  CA   ASN A  92      23.964  56.255  -6.116  1.00 50.90   C
ATOM    703  C    ASN A  92      23.399  54.887  -5.780  1.00 45.05   C
ATOM    704  O    ASN A  92      22.220  54.742  -5.466  1.00 48.81   O
ATOM    705  CB   ASN A  92      23.757  57.200  -4.932  1.00 47.93   C
ATOM    706  CG   ASN A  92      24.569  56.786  -3.724  1.00 54.25   C
ATOM    707  OD1  ASN A  92      24.115  56.897  -2.584  1.00 56.44   O
ATOM    708  ND2  ASN A  92      25.784  56.304  -3.969  1.00 54.09   N
ATOM    709  N    VAL A  93      24.256  53.881  -5.851  1.00 46.44   N
ATOM    710  CA   VAL A  93      23.831  52.527  -5.574  1.00 47.68   C
ATOM    711  C    VAL A  93      24.387  52.085  -4.232  1.00 46.87   C
ATOM    712  O    VAL A  93      25.602  52.009  -4.053  1.00 45.39   O
ATOM    713  CB   VAL A  93      24.310  51.548  -6.679  1.00 44.88   C
ATOM    714  CG1  VAL A  93      23.834  50.143  -6.365  1.00 50.34   C
ATOM    715  CG2  VAL A  93      23.769  51.981  -8.042  1.00 51.13   C
ATOM    716  N    LYS A  94      23.490  51.807  -3.290  1.00 52.11   N
ATOM    717  CA   LYS A  94      23.902  51.347  -1.961  1.00 59.43   C
ATOM    718  C    LYS A  94      23.774  49.832  -1.886  1.00 55.63   C
ATOM    719  O    LYS A  94      22.871  49.241  -2.471  1.00 43.24   O
ATOM    720  CB   LYS A  94      23.033  51.960  -0.855  1.00 55.35   C
ATOM    721  CG   LYS A  94      23.173  53.464  -0.668  1.00 65.17   C
ATOM    722  CD   LYS A  94      22.156  53.977   0.356  1.00 67.48   C
ATOM    723  CE   LYS A  94      22.081  55.492   0.362  1.00 74.84   C
ATOM    724  NZ   LYS A  94      21.040  55.986   1.310  1.00 78.54   N
ATOM    725  N    ILE A  95      24.699  49.202  -1.181  1.00 56.66   N
ATOM    726  CA   ILE A  95      24.658  47.762  -1.004  1.00 56.71   C
ATOM    727  C    ILE A  95      24.467  47.546   0.495  1.00 59.65   C
ATOM    728  O    ILE A  95      25.004  48.298   1.305  1.00 53.96   O
ATOM    729  CB   ILE A  95      25.981  47.086  -1.451  1.00 50.11   C
ATOM    730  CG1  ILE A  95      26.247  47.361  -2.935  1.00 58.21   C
ATOM    731  CG2  ILE A  95      25.905  45.584  -1.206  1.00 55.81   C
ATOM    732  CD1  ILE A  95      25.141  46.878  -3.869  1.00 46.59   C
ATOM    733  N    PHE A  96      23.670  46.553   0.863  1.00 56.77   N
ATOM    734  CA   PHE A  96      23.464  46.249   2.269  1.00 56.57   C
ATOM    735  C    PHE A  96      23.070  44.791   2.380  1.00 52.33   C
ATOM    736  O    PHE A  96      22.921  44.087   1.375  1.00 55.58   O
ATOM    737  CB   PHE A  96      22.389  47.146   2.893  1.00 51.68   C
```

Figure 2 (Table 2 (page 21))

| | | | | | | | | | |
|---|---|---|---|---|---|---|---|---|---|
| ATOM | 738 | CG  | PHE | A | 96  | 20.984 | 46.731 | 2.570  | 1.00 55.80 C |
| ATOM | 739 | CD1 | PHE | A | 96  | 20.078 | 46.441 | 3.589  | 1.00 56.18 C |
| ATOM | 740 | CD2 | PHE | A | 96  | 20.565 | 46.630 | 1.249  | 1.00 53.68 C |
| ATOM | 741 | CE1 | PHE | A | 96  | 18.770 | 46.055 | 3.287  | 1.00 61.36 C |
| ATOM | 742 | CE2 | PHE | A | 96  | 19.268 | 46.249 | 0.932  | 1.00 54.41 C |
| ATOM | 743 | CZ  | PHE | A | 96  | 18.362 | 45.959 | 1.951  | 1.00 51.56 C |
| ATOM | 744 | N   | GLN | A | 97  | 22.929 | 44.323 | 3.607  | 1.00 44.80 N |
| ATOM | 745 | CA  | GLN | A | 97  | 22.565 | 42.945 | 3.819  | 1.00 41.35 C |
| ATOM | 746 | C   | GLN | A | 97  | 21.257 | 42.956 | 4.559  | 1.00 43.49 C |
| ATOM | 747 | O   | GLN | A | 97  | 21.185 | 43.352 | 5.725  | 1.00 48.61 O |
| ATOM | 748 | CB  | GLN | A | 97  | 23.639 | 42.220 | 4.639  | 1.00 50.03 C |
| ATOM | 749 | CG  | GLN | A | 97  | 23.239 | 40.811 | 5.074  | 1.00 42.38 C |
| ATOM | 750 | CD  | GLN | A | 97  | 22.968 | 39.885 | 3.899  | 1.00 45.87 C |
| ATOM | 751 | OE1 | GLN | A | 97  | 23.879 | 39.539 | 3.148  | 1.00 50.97 O |
| ATOM | 752 | NE2 | GLN | A | 97  | 21.712 | 39.485 | 3.725  | 1.00 43.50 N |
| ATOM | 753 | N   | LYS | A | 98  | 20.208 | 42.557 | 3.861  | 1.00 43.56 N |
| ATOM | 754 | CA  | LYS | A | 98  | 18.914 | 42.503 | 4.493  | 1.00 50.07 C |
| ATOM | 755 | C   | LYS | A | 98  | 18.988 | 41.436 | 5.594  | 1.00 45.12 C |
| ATOM | 756 | O   | LYS | A | 98  | 19.772 | 40.483 | 5.518  | 1.00 44.19 O |
| ATOM | 757 | CB  | LYS | A | 98  | 17.835 | 42.141 | 3.467  | 1.00 42.89 C |
| ATOM | 758 | CG  | LYS | A | 98  | 17.806 | 40.689 | 3.029  | 1.00 54.06 C |
| ATOM | 759 | CD  | LYS | A | 98  | 16.620 | 40.432 | 2.091  | 1.00 70.03 C |
| ATOM | 760 | CE  | LYS | A | 98  | 16.542 | 38.972 | 1.674  | 1.00 74.47 C |
| ATOM | 761 | NZ  | LYS | A | 98  | 15.366 | 38.722 | 0.799  | 1.00 87.06 N |
| ATOM | 762 | N   | LEU | A | 99  | 18.187 | 41.633 | 6.625  | 1.00 42.33 N |
| ATOM | 763 | CA  | LEU | A | 99  | 18.112 | 40.718 | 7.743  | 1.00 48.11 C |
| ATOM | 764 | C   | LEU | A | 99  | 17.731 | 39.322 | 7.271  | 1.00 51.43 C |
| ATOM | 765 | O   | LEU | A | 99  | 16.622 | 39.119 | 6.784  | 1.00 54.69 O |
| ATOM | 766 | CB  | LEU | A | 99  | 17.058 | 41.223 | 8.727  | 1.00 40.97 C |
| ATOM | 767 | CG  | LEU | A | 99  | 16.874 | 40.365 | 9.974  | 1.00 51.52 C |
| ATOM | 768 | CD1 | LEU | A | 99  | 18.114 | 40.494 | 10.829 | 1.00 49.68 C |
| ATOM | 769 | CD2 | LEU | A | 99  | 15.663 | 40.822 | 10.765 | 1.00 51.15 C |
| ATOM | 770 | N   | MET | A | 100 | 18.643 | 38.358 | 7.388  | 1.00 48.12 N |
| ATOM | 771 | CA  | MET | A | 100 | 18.321 | 36.984 | 6.995  | 1.00 51.56 C |
| ATOM | 772 | C   | MET | A | 100 | 19.033 | 35.977 | 7.907  | 1.00 51.77 C |
| ATOM | 773 | O   | MET | A | 100 | 19.991 | 36.322 | 8.621  | 1.00 39.76 O |
| ATOM | 774 | CB  | MET | A | 100 | 18.650 | 36.727 | 5.512  | 1.00 61.21 C |
| ATOM | 775 | CG  | MET | A | 100 | 20.116 | 36.564 | 5.166  | 1.00 69.49 C |
| ATOM | 776 | SD  | MET | A | 100 | 20.416 | 36.505 | 3.372  | 1.00 84.60 S |
| ATOM | 777 | CE  | MET | A | 100 | 19.818 | 34.884 | 2.949  | 1.00 92.44 C |
| ATOM | 778 | N   | PHE | A | 101 | 18.531 | 34.745 | 7.908  | 1.00 45.49 N |
| ATOM | 779 | CA  | PHE | A | 101 | 19.085 | 33.684 | 8.732  | 1.00 50.26 C |
| ATOM | 780 | C   | PHE | A | 101 | 20.138 | 32.893 | 7.995  | 1.00 43.40 C |
| ATOM | 781 | O   | PHE | A | 101 | 19.907 | 32.400 | 6.902  | 1.00 61.65 O |
| ATOM | 782 | CB  | PHE | A | 101 | 17.969 | 32.769 | 9.210  | 1.00 46.80 C |
| ATOM | 783 | CG  | PHE | A | 101 | 17.019 | 33.450 | 10.137 | 1.00 46.54 C |
| ATOM | 784 | CD1 | PHE | A | 101 | 15.900 | 34.112 | 9.652  | 1.00 52.32 C |
| ATOM | 785 | CD2 | PHE | A | 101 | 17.274 | 33.488 | 11.499 | 1.00 44.46 C |
| ATOM | 786 | CE1 | PHE | A | 101 | 15.054 | 34.822 | 10.516 | 1.00 43.20 C |
| ATOM | 787 | CE2 | PHE | A | 101 | 16.441 | 34.192 | 12.366 | 1.00 48.20 C |
| ATOM | 788 | CZ  | PHE | A | 101 | 15.322 | 34.858 | 11.869 | 1.00 48.40 C |
| ATOM | 789 | N   | LYS | A | 102 | 21.302 | 32.771 | 8.611  | 1.00 51.46 N |
| ATOM | 790 | CA  | LYS | A | 102 | 22.420 | 32.066 | 8.009  | 1.00 48.23 C |
| ATOM | 791 | C   | LYS | A | 102 | 22.516 | 30.619 | 8.468  | 1.00 54.86 C |
| ATOM | 792 | O   | LYS | A | 102 | 22.768 | 29.712 | 7.668  | 1.00 62.07 O |
| ATOM | 793 | CB  | LYS | A | 102 | 23.714 | 32.799 | 8.340  | 1.00 57.97 C |

Figure 2 (Table 2 (page 22))

| | | | | | | | | | | |
|---|---|---|---|---|---|---|---|---|---|---|
| ATOM | 794 | CG | LYS | A | 102 | 24.954 | 32.199 | 7.720 | 1.00 71.82 | C |
| ATOM | 795 | CD | LYS | A | 102 | 26.170 | 33.021 | 8.108 | 1.00 82.19 | C |
| ATOM | 796 | CE | LYS | A | 102 | 27.335 | 32.773 | 7.169 | 1.00 88.42 | C |
| ATOM | 797 | NZ | LYS | A | 102 | 28.516 | 33.602 | 7.540 | 1.00 98.10 | N |
| ATOM | 798 | N | ASN | A | 103 | 22.328 | 30.409 | 9.763 | 1.00 47.83 | N |
| ATOM | 799 | CA | ASN | A | 103 | 22.379 | 29.081 | 10.339 | 1.00 43.78 | C |
| ATOM | 800 | C | ASN | A | 103 | 21.419 | 29.084 | 11.525 | 1.00 45.04 | C |
| ATOM | 801 | O | ASN | A | 103 | 21.661 | 29.751 | 12.534 | 1.00 40.24 | O |
| ATOM | 802 | CB | ASN | A | 103 | 23.802 | 28.764 | 10.800 | 1.00 45.29 | C |
| ATOM | 803 | CG | ASN | A | 103 | 23.886 | 27.468 | 11.565 | 1.00 46.73 | C |
| ATOM | 804 | OD1 | ASN | A | 103 | 23.582 | 26.402 | 11.037 | 1.00 54.61 | O |
| ATOM | 805 | ND2 | ASN | A | 103 | 24.308 | 27.552 | 12.822 | 1.00 50.10 | N |
| ATOM | 806 | N | ALA | A | 104 | 20.312 | 28.369 | 11.379 | 1.00 40.89 | N |
| ATOM | 807 | CA | ALA | A | 104 | 19.304 | 28.264 | 12.422 | 1.00 48.41 | C |
| ATOM | 808 | C | ALA | A | 104 | 18.651 | 26.906 | 12.200 | 1.00 52.07 | C |
| ATOM | 809 | O | ALA | A | 104 | 17.490 | 26.811 | 11.829 | 1.00 51.94 | O |
| ATOM | 810 | CB | ALA | A | 104 | 18.280 | 29.359 | 12.241 | 1.00 53.18 | C |
| ATOM | 811 | N | PRO | A | 105 | 19.386 | 25.834 | 12.461 | 1.00 47.52 | N |
| ATOM | 812 | CA | PRO | A | 105 | 18.873 | 24.481 | 12.265 | 1.00 45.57 | C |
| ATOM | 813 | C | PRO | A | 105 | 17.700 | 24.096 | 13.112 | 1.00 47.49 | C |
| ATOM | 814 | O | PRO | A | 105 | 17.508 | 24.606 | 14.223 | 1.00 41.72 | O |
| ATOM | 815 | CB | PRO | A | 105 | 20.087 | 23.588 | 12.501 | 1.00 49.47 | C |
| ATOM | 816 | CG | PRO | A | 105 | 21.055 | 24.460 | 13.270 | 1.00 52.18 | C |
| ATOM | 817 | CD | PRO | A | 105 | 20.631 | 25.867 | 13.230 | 1.00 52.90 | C |
| ATOM | 818 | N | THR | A | 106 | 16.864 | 23.260 | 12.515 | 1.00 48.69 | N |
| ATOM | 819 | CA | THR | A | 106 | 15.717 | 22.758 | 13.215 | 1.00 52.32 | C |
| ATOM | 820 | C | THR | A | 106 | 15.529 | 21.322 | 12.759 | 1.00 58.90 | C |
| ATOM | 821 | O | THR | A | 106 | 15.672 | 20.999 | 11.581 | 1.00 55.09 | O |
| ATOM | 822 | CB | THR | A | 106 | 14.447 | 23.612 | 12.955 | 1.00 53.67 | C |
| ATOM | 823 | OG1 | THR | A | 106 | 13.355 | 23.053 | 13.698 | 1.00 54.59 | O |
| ATOM | 824 | CG2 | THR | A | 106 | 14.097 | 23.641 | 11.468 | 1.00 58.16 | C |
| ATOM | 825 | N | PRO | A | 107 | 15.275 | 20.424 | 13.714 | 1.00 52.16 | N |
| ATOM | 826 | CA | PRO | A | 107 | 15.184 | 20.737 | 15.138 | 1.00 43.22 | C |
| ATOM | 827 | C | PRO | A | 107 | 16.585 | 20.810 | 15.732 | 1.00 47.05 | C |
| ATOM | 828 | O | PRO | A | 107 | 17.578 | 20.532 | 15.064 | 1.00 45.59 | O |
| ATOM | 829 | CB | PRO | A | 107 | 14.426 | 19.539 | 15.688 | 1.00 49.39 | C |
| ATOM | 830 | CG | PRO | A | 107 | 15.052 | 18.411 | 14.902 | 1.00 55.45 | C |
| ATOM | 831 | CD | PRO | A | 107 | 15.065 | 18.986 | 13.480 | 1.00 55.64 | C |
| ATOM | 832 | N | GLN | A | 108 | 16.650 | 21.202 | 16.994 | 1.00 40.58 | N |
| ATOM | 833 | CA | GLN | A | 108 | 17.901 | 21.229 | 17.709 | 1.00 46.97 | C |
| ATOM | 834 | C | GLN | A | 108 | 17.566 | 20.339 | 18.896 | 1.00 44.47 | C |
| ATOM | 835 | O | GLN | A | 108 | 16.492 | 20.467 | 19.489 | 1.00 36.69 | O |
| ATOM | 836 | CB | GLN | A | 108 | 18.271 | 22.657 | 18.084 | 1.00 40.68 | C |
| ATOM | 837 | CG | GLN | A | 108 | 18.770 | 23.436 | 16.846 | 1.00 37.05 | C |
| ATOM | 838 | CD | GLN | A | 108 | 19.203 | 24.847 | 17.171 | 1.00 40.43 | C |
| ATOM | 839 | OE1 | GLN | A | 108 | 19.879 | 25.073 | 18.172 | 1.00 36.29 | O |
| ATOM | 840 | NE2 | GLN | A | 108 | 18.828 | 25.805 | 16.332 | 1.00 37.82 | N |
| ATOM | 841 | N | GLU | A | 109 | 18.469 | 19.413 | 19.203 | 1.00 38.32 | N |
| ATOM | 842 | CA | GLU | A | 109 | 18.261 | 18.425 | 20.257 | 1.00 39.59 | C |
| ATOM | 843 | C | GLU | A | 109 | 19.216 | 18.551 | 21.424 | 1.00 44.20 | C |
| ATOM | 844 | O | GLU | A | 109 | 20.380 | 18.922 | 21.254 | 1.00 41.88 | O |
| ATOM | 845 | CB | GLU | A | 109 | 18.364 | 17.033 | 19.637 | 1.00 39.87 | C |
| ATOM | 846 | CG | GLU | A | 109 | 17.437 | 16.885 | 18.448 | 1.00 45.54 | C |
| ATOM | 847 | CD | GLU | A | 109 | 17.358 | 15.478 | 17.912 | 1.00 49.95 | C |
| ATOM | 848 | OE1 | GLU | A | 109 | 17.335 | 14.518 | 18.713 | 1.00 54.48 | O |
| ATOM | 849 | OE2 | GLU | A | 109 | 17.295 | 15.330 | 16.678 | 1.00 54.37 | O |

Figure 2 (Table 2 (page 23))

```
ATOM    850  N    PHE A 110      18.713  18.223  22.609  1.00 36.31           N
ATOM    851  CA   PHE A 110      19.491  18.314  23.825  1.00 37.31           C
ATOM    852  C    PHE A 110      19.154  17.167  24.748  1.00 44.15           C
ATOM    853  O    PHE A 110      18.071  16.596  24.694  1.00 42.74           O
ATOM    854  CB   PHE A 110      19.202  19.643  24.531  1.00 29.73           C
ATOM    855  CG   PHE A 110      19.299  20.831  23.612  1.00 36.45           C
ATOM    856  CD1  PHE A 110      18.189  21.286  22.922  1.00 37.59           C
ATOM    857  CD2  PHE A 110      20.522  21.445  23.387  1.00 35.71           C
ATOM    858  CE1  PHE A 110      18.301  22.337  22.006  1.00 49.86           C
ATOM    859  CE2  PHE A 110      20.649  22.489  22.476  1.00 43.61           C
ATOM    860  CZ   PHE A 110      19.533  22.939  21.785  1.00 39.36           C
ATOM    861  N    LYS A 111      20.108  16.819  25.592  1.00 38.44           N
ATOM    862  CA   LYS A 111      19.909  15.745  26.533  1.00 39.53           C
ATOM    863  C    LYS A 111      19.327  16.395  27.769  1.00 33.66           C
ATOM    864  O    LYS A 111      19.832  17.419  28.238  1.00 37.40           O
ATOM    865  CB   LYS A 111      21.254  15.075  26.845  1.00 35.52           C
ATOM    866  CG   LYS A 111      21.185  13.974  27.890  1.00 45.41           C
ATOM    867  CD   LYS A 111      22.548  13.272  28.006  1.00 51.44           C
ATOM    868  CE   LYS A 111      22.515  12.114  29.000  1.00 58.54           C
ATOM    869  NZ   LYS A 111      23.657  11.172  28.765  1.00 62.26           N
ATOM    870  N    GLU A 112      18.255  15.810  28.287  1.00 39.60           N
ATOM    871  CA   GLU A 112      17.614  16.339  29.478  1.00 42.51           C
ATOM    872  C    GLU A 112      18.627  16.706  30.569  1.00 37.78           C
ATOM    873  O    GLU A 112      19.554  15.950  30.846  1.00 41.69           O
ATOM    874  CB   GLU A 112      16.621  15.312  30.034  1.00 42.05           C
ATOM    875  CG   GLU A 112      15.743  15.888  31.120  1.00 48.02           C
ATOM    876  CD   GLU A 112      14.735  14.886  31.675  1.00 67.88           C
ATOM    877  OE1  GLU A 112      13.582  15.304  31.937  1.00 64.90           O
ATOM    878  OE2  GLU A 112      15.093  13.700  31.865  1.00 70.27           O
ATOM    879  N    GLY A 113      18.448  17.875  31.175  1.00 41.71           N
ATOM    880  CA   GLY A 113      19.350  18.298  32.228  1.00 43.96           C
ATOM    881  C    GLY A 113      20.555  19.128  31.824  1.00 46.88           C
ATOM    882  O    GLY A 113      21.087  19.877  32.652  1.00 44.90           O
ATOM    883  N    GLU A 114      21.017  19.021  30.584  1.00 41.27           N
ATOM    884  CA   GLU A 114      22.181  19.830  30.227  1.00 49.33           C
ATOM    885  C    GLU A 114      21.739  21.260  29.927  1.00 46.85           C
ATOM    886  O    GLU A 114      20.539  21.551  29.864  1.00 45.47           O
ATOM    887  CB   GLU A 114      22.957  19.199  29.052  1.00 46.70           C
ATOM    888  CG   GLU A 114      22.319  19.293  27.682  1.00 49.46           C
ATOM    889  CD   GLU A 114      23.076  18.490  26.613  1.00 56.05           C
ATOM    890  OE1  GLU A 114      24.174  17.946  26.894  1.00 59.22           O
ATOM    891  OE2  GLU A 114      22.565  18.407  25.482  1.00 51.60           O
ATOM    892  N    ASP A 115      22.689  22.181  29.822  1.00 42.06           N
ATOM    893  CA   ASP A 115      22.323  23.554  29.512  1.00 46.33           C
ATOM    894  C    ASP A 115      22.184  23.568  28.018  1.00 46.24           C
ATOM    895  O    ASP A 115      23.107  23.195  27.299  1.00 51.16           O
ATOM    896  CB   ASP A 115      23.394  24.525  29.976  1.00 52.16           C
ATOM    897  CG   ASP A 115      23.530  24.535  31.475  1.00 58.98           C
ATOM    898  OD1  ASP A 115      22.515  24.291  32.169  1.00 56.34           O
ATOM    899  OD2  ASP A 115      24.647  24.785  31.959  1.00 74.61           O
ATOM    900  N    ALA A 116      21.009  23.943  27.536  1.00 40.21           N
ATOM    901  CA   ALA A 116      20.812  23.937  26.105  1.00 41.98           C
ATOM    902  C    ALA A 116      21.024  25.315  25.524  1.00 39.57           C
ATOM    903  O    ALA A 116      20.591  26.311  26.093  1.00 41.84           O
ATOM    904  CB   ALA A 116      19.406  23.428  25.761  1.00 37.59           C
ATOM    905  N    VAL A 117      21.711  25.374  24.396  1.00 35.34           N
```

Figure 2 (Table 2 (page 24))

```
ATOM    906  CA   VAL A 117      21.907  26.651  23.736  1.00 34.85  C
ATOM    907  C    VAL A 117      21.305  26.459  22.356  1.00 34.14  C
ATOM    908  O    VAL A 117      21.751  25.608  21.603  1.00 35.50  O
ATOM    909  CB   VAL A 117      23.391  26.997  23.612  1.00 40.36  C
ATOM    910  CG1  VAL A 117      23.573  28.240  22.764  1.00 35.45  C
ATOM    911  CG2  VAL A 117      23.957  27.265  24.994  1.00 46.40  C
ATOM    912  N    ILE A 118      20.276  27.244  22.046  1.00 35.04  N
ATOM    913  CA   ILE A 118      19.593  27.169  20.757  1.00 34.21  C
ATOM    914  C    ILE A 118      20.257  28.172  19.836  1.00 25.24  C
ATOM    915  O    ILE A 118      20.252  29.371  20.095  1.00 32.78  O
ATOM    916  CB   ILE A 118      18.106  27.535  20.901  1.00 34.79  C
ATOM    917  CG1  ILE A 118      17.471  26.651  21.978  1.00 43.37  C
ATOM    918  CG2  ILE A 118      17.384  27.289  19.578  1.00 35.72  C
ATOM    919  CD1  ILE A 118      16.071  27.043  22.340  1.00 58.55  C
ATOM    920  N    VAL A 119      20.829  27.649  18.771  1.00 31.01  N
ATOM    921  CA   VAL A 119      21.593  28.441  17.830  1.00 37.30  C
ATOM    922  C    VAL A 119      20.771  29.119  16.753  1.00 37.56  C
ATOM    923  O    VAL A 119      19.983  28.491  16.065  1.00 40.50  O
ATOM    924  CB   VAL A 119      22.670  27.549  17.175  1.00 35.82  C
ATOM    925  CG1  VAL A 119      23.467  28.340  16.136  1.00 34.06  C
ATOM    926  CG2  VAL A 119      23.582  27.004  18.258  1.00 34.59  C
ATOM    927  N    CYS A 120      20.980  30.414  16.620  1.00 36.81  N
ATOM    928  CA   CYS A 120      20.286  31.194  15.610  1.00 32.12  C
ATOM    929  C    CYS A 120      21.262  32.279  15.148  1.00 33.42  C
ATOM    930  O    CYS A 120      21.534  33.244  15.873  1.00 34.81  O
ATOM    931  CB   CYS A 120      19.027  31.819  16.211  1.00 41.13  C
ATOM    932  SG   CYS A 120      17.972  32.754  15.028  1.00 50.41  S
ATOM    933  N    ASP A 121      21.821  32.082  13.959  1.00 36.26  N
ATOM    934  CA   ASP A 121      22.778  33.020  13.370  1.00 38.88  C
ATOM    935  C    ASP A 121      22.109  33.906  12.333  1.00 36.35  C
ATOM    936  O    ASP A 121      21.607  33.429  11.326  1.00 41.43  O
ATOM    937  CB   ASP A 121      23.934  32.251  12.720  1.00 41.76  C
ATOM    938  CG   ASP A 121      24.766  31.509  13.744  1.00 40.59  C
ATOM    939  OD1  ASP A 121      25.129  32.153  14.749  1.00 47.54  O
ATOM    940  OD2  ASP A 121      25.047  30.306  13.560  1.00 45.40  O
ATOM    941  N    VAL A 122      22.099  35.202  12.584  1.00 41.75  N
ATOM    942  CA   VAL A 122      21.495  36.119  11.636  1.00 52.79  C
ATOM    943  C    VAL A 122      22.563  36.999  11.025  1.00 52.22  C
ATOM    944  O    VAL A 122      23.670  37.115  11.550  1.00 45.91  O
ATOM    945  CB   VAL A 122      20.458  37.052  12.302  1.00 53.37  C
ATOM    946  CG1  VAL A 122      19.391  36.242  12.998  1.00 50.48  C
ATOM    947  CG2  VAL A 122      21.153  37.986  13.275  1.00 58.84  C
ATOM    948  N    VAL A 123      22.215  37.609   9.901  1.00 47.92  N
ATOM    949  CA   VAL A 123      23.104  38.525   9.211  1.00 44.45  C
ATOM    950  C    VAL A 123      22.279  39.739   8.809  1.00 53.24  C
ATOM    951  O    VAL A 123      21.097  39.610   8.449  1.00 44.25  O
ATOM    952  CB   VAL A 123      23.713  37.910   7.941  1.00 53.12  C
ATOM    953  CG1  VAL A 123      24.633  36.758   8.307  1.00 58.99  C
ATOM    954  CG2  VAL A 123      22.610  37.442   7.012  1.00 54.51  C
ATOM    955  N    SER A 124      22.911  40.906   8.893  1.00 38.99  N
ATOM    956  CA   SER A 124      22.304  42.181   8.537  1.00 42.72  C
ATOM    957  C    SER A 124      23.383  43.252   8.618  1.00 46.36  C
ATOM    958  O    SER A 124      24.311  43.139   9.420  1.00 48.23  O
ATOM    959  CB   SER A 124      21.169  42.533   9.496  1.00 45.26  C
ATOM    960  OG   SER A 124      21.642  42.618  10.828  1.00 50.88  O
ATOM    961  N    SER A 125      23.257  44.283   7.787  1.00 48.24  N
```

Figure 2 (Table 2 (page 25))

| | | | | | | | | | | |
|---|---|---|---|---|---|---|---|---|---|---|
| ATOM | 962 | CA | SER | A | 125 | 24.221 | 45.387 | 7.755 | 1.00 | 54.08 C |
| ATOM | 963 | C | SER | A | 125 | 24.173 | 46.098 | 9.081 | 1.00 | 53.53 C |
| ATOM | 964 | O | SER | A | 125 | 25.201 | 46.357 | 9.694 | 1.00 | 54.81 O |
| ATOM | 965 | CB | SER | A | 125 | 23.874 | 46.373 | 6.641 | 1.00 | 45.61 C |
| ATOM | 966 | OG | SER | A | 125 | 23.901 | 45.724 | 5.391 | 1.00 | 46.33 O |
| ATOM | 967 | N | LEU | A | 126 | 22.961 | 46.408 | 9.519 | 1.00 | 51.93 N |
| ATOM | 968 | CA | LEU | A | 126 | 22.756 | 47.077 | 10.795 | 1.00 | 60.20 C |
| ATOM | 969 | C | LEU | A | 126 | 22.575 | 46.030 | 11.889 | 1.00 | 63.51 C |
| ATOM | 970 | O | LEU | A | 126 | 22.012 | 44.961 | 11.657 | 1.00 | 63.28 O |
| ATOM | 971 | CB | LEU | A | 126 | 21.521 | 47.987 | 10.726 | 1.00 | 67.31 C |
| ATOM | 972 | CG | LEU | A | 126 | 21.606 | 49.171 | 9.746 | 1.00 | 75.52 C |
| ATOM | 973 | CD1 | LEU | A | 126 | 20.323 | 49.998 | 9.750 | 1.00 | 66.85 C |
| ATOM | 974 | CD2 | LEU | A | 126 | 22.791 | 50.045 | 10.141 | 1.00 | 72.14 C |
| ATOM | 975 | N | PRO | A | 127 | 23.071 | 46.308 | 13.096 | 1.00 | 69.25 N |
| ATOM | 976 | CA | PRO | A | 127 | 22.925 | 45.331 | 14.185 | 1.00 | 64.19 C |
| ATOM | 977 | C | PRO | A | 127 | 21.463 | 45.007 | 14.524 | 1.00 | 57.99 C |
| ATOM | 978 | O | PRO | A | 127 | 20.655 | 45.913 | 14.728 | 1.00 | 62.20 O |
| ATOM | 979 | CB | PRO | A | 127 | 23.701 | 45.950 | 15.354 | 1.00 | 64.92 C |
| ATOM | 980 | CG | PRO | A | 127 | 23.957 | 47.367 | 14.952 | 1.00 | 66.17 C |
| ATOM | 981 | CD | PRO | A | 127 | 23.849 | 47.492 | 13.478 | 1.00 | 65.55 C |
| ATOM | 982 | N | PRO | A | 128 | 21.126 | 43.698 | 14.610 | 1.00 | 61.71 N |
| ATOM | 983 | CA | PRO | A | 128 | 19.782 | 43.195 | 14.906 | 1.00 | 61.85 C |
| ATOM | 984 | C | PRO | A | 128 | 19.470 | 43.143 | 16.362 | 1.00 | 62.11 C |
| ATOM | 985 | O | PRO | A | 128 | 20.351 | 42.980 | 17.192 | 1.00 | 64.26 O |
| ATOM | 986 | CB | PRO | A | 128 | 19.805 | 41.776 | 14.340 | 1.00 | 58.63 C |
| ATOM | 987 | CG | PRO | A | 128 | 21.070 | 41.714 | 13.493 | 1.00 | 66.61 C |
| ATOM | 988 | CD | PRO | A | 128 | 22.009 | 42.561 | 14.287 | 1.00 | 51.57 C |
| ATOM | 989 | N | THR | A | 129 | 18.196 | 43.270 | 16.669 | 1.00 | 56.05 N |
| ATOM | 990 | CA | THR | A | 129 | 17.759 | 43.128 | 18.039 | 1.00 | 50.88 C |
| ATOM | 991 | C | THR | A | 129 | 17.038 | 41.791 | 17.944 | 1.00 | 47.70 C |
| ATOM | 992 | O | THR | A | 129 | 16.192 | 41.597 | 17.072 | 1.00 | 52.86 O |
| ATOM | 993 | CB | THR | A | 129 | 16.801 | 44.243 | 18.457 | 1.00 | 59.29 C |
| ATOM | 994 | OG1 | THR | A | 129 | 17.564 | 45.360 | 18.933 | 1.00 | 64.98 O |
| ATOM | 995 | CG2 | THR | A | 129 | 15.885 | 43.769 | 19.562 | 1.00 | 68.98 C |
| ATOM | 996 | N | ILE | A | 130 | 17.377 | 40.868 | 18.827 | 1.00 | 47.42 N |
| ATOM | 997 | CA | ILE | A | 130 | 16.793 | 39.543 | 18.779 | 1.00 | 49.45 C |
| ATOM | 998 | C | ILE | A | 130 | 15.829 | 39.251 | 19.914 | 1.00 | 48.06 C |
| ATOM | 999 | O | ILE | A | 130 | 16.119 | 39.539 | 21.074 | 1.00 | 49.48 O |
| ATOM | 1000 | CB | ILE | A | 130 | 17.907 | 38.480 | 18.805 | 1.00 | 52.16 C |
| ATOM | 1001 | CG1 | ILE | A | 130 | 18.711 | 38.558 | 17.510 | 1.00 | 55.93 C |
| ATOM | 1002 | CG2 | ILE | A | 130 | 17.317 | 37.091 | 19.030 | 1.00 | 46.63 C |
| ATOM | 1003 | CD1 | ILE | A | 130 | 17.934 | 38.126 | 16.313 | 1.00 | 58.84 C |
| ATOM | 1004 | N | ILE | A | 131 | 14.681 | 38.675 | 19.568 | 1.00 | 45.61 N |
| ATOM | 1005 | CA | ILE | A | 131 | 13.707 | 38.318 | 20.588 | 1.00 | 50.29 C |
| ATOM | 1006 | C | ILE | A | 131 | 13.352 | 36.859 | 20.427 | 1.00 | 33.83 C |
| ATOM | 1007 | O | ILE | A | 131 | 12.993 | 36.426 | 19.330 | 1.00 | 50.28 O |
| ATOM | 1008 | CB | ILE | A | 131 | 12.374 | 39.104 | 20.474 | 1.00 | 55.23 C |
| ATOM | 1009 | CG1 | ILE | A | 131 | 12.620 | 40.610 | 20.479 | 1.00 | 61.34 C |
| ATOM | 1010 | CG2 | ILE | A | 131 | 11.470 | 38.737 | 21.647 | 1.00 | 58.84 C |
| ATOM | 1011 | CD1 | ILE | A | 131 | 12.630 | 41.236 | 19.085 | 1.00 | 60.34 C |
| ATOM | 1012 | N | TRP | A | 132 | 13.437 | 36.108 | 21.520 | 1.00 | 38.49 N |
| ATOM | 1013 | CA | TRP | A | 132 | 13.095 | 34.692 | 21.510 | 1.00 | 46.49 C |
| ATOM | 1014 | C | TRP | A | 132 | 11.668 | 34.498 | 22.042 | 1.00 | 48.20 C |
| ATOM | 1015 | O | TRP | A | 132 | 11.343 | 34.949 | 23.133 | 1.00 | 45.37 O |
| ATOM | 1016 | CB | TRP | A | 132 | 14.085 | 33.898 | 22.372 | 1.00 | 39.62 C |
| ATOM | 1017 | CG | TRP | A | 132 | 15.384 | 33.632 | 21.653 | 1.00 | 39.42 C |

Figure 2 (Table 2 (page 26))

| | | | | | | | | | | |
|---|---|---|---|---|---|---|---|---|---|---|
| ATOM | 1018 | CD1 | TRP | A | 132 | 16.536 | 34.369 | 21.728 | 1.00 36.55 | C |
| ATOM | 1019 | CD2 | TRP | A | 132 | 15.645 | 32.570 | 20.726 | 1.00 29.03 | C |
| ATOM | 1020 | NE1 | TRP | A | 132 | 17.502 | 33.826 | 20.901 | 1.00 34.64 | N |
| ATOM | 1021 | CE2 | TRP | A | 132 | 16.985 | 32.725 | 20.278 | 1.00 35.20 | C |
| ATOM | 1022 | CE3 | TRP | A | 132 | 14.883 | 31.502 | 20.229 | 1.00 33.72 | C |
| ATOM | 1023 | CZ2 | TRP | A | 132 | 17.572 | 31.848 | 19.364 | 1.00 32.11 | C |
| ATOM | 1024 | CZ3 | TRP | A | 132 | 15.470 | 30.632 | 19.318 | 1.00 35.81 | C |
| ATOM | 1025 | CH2 | TRP | A | 132 | 16.809 | 30.814 | 18.893 | 1.00 33.40 | C |
| ATOM | 1026 | N | LYS | A | 133 | 10.838 | 33.809 | 21.266 | 1.00 51.27 | N |
| ATOM | 1027 | CA | LYS | A | 133 | 9.451 | 33.579 | 21.645 | 1.00 57.47 | C |
| ATOM | 1028 | C | LYS | A | 133 | 9.043 | 32.124 | 21.741 | 1.00 59.45 | C |
| ATOM | 1029 | O | LYS | A | 133 | 9.408 | 31.298 | 20.903 | 1.00 53.79 | O |
| ATOM | 1030 | CB | LYS | A | 133 | 8.518 | 34.267 | 20.650 | 1.00 55.78 | C |
| ATOM | 1031 | CG | LYS | A | 133 | 8.672 | 35.771 | 20.593 | 1.00 66.61 | C |
| ATOM | 1032 | CD | LYS | A | 133 | 7.816 | 36.347 | 19.483 | 1.00 76.13 | C |
| ATOM | 1033 | CE | LYS | A | 133 | 7.989 | 37.857 | 19.385 | 1.00 82.76 | C |
| ATOM | 1034 | NZ | LYS | A | 133 | 7.076 | 38.469 | 18.372 | 1.00 81.20 | N |
| ATOM | 1035 | N | HIS | A | 134 | 8.274 | 31.824 | 22.781 | 1.00 63.05 | N |
| ATOM | 1036 | CA | HIS | A | 134 | 7.757 | 30.481 | 22.990 | 1.00 66.48 | C |
| ATOM | 1037 | C | HIS | A | 134 | 6.265 | 30.612 | 23.220 | 1.00 77.89 | C |
| ATOM | 1038 | O | HIS | A | 134 | 5.832 | 31.403 | 24.067 | 1.00 63.07 | O |
| ATOM | 1039 | CB | HIS | A | 134 | 8.370 | 29.816 | 24.221 | 1.00 70.22 | C |
| ATOM | 1040 | CG | HIS | A | 134 | 8.006 | 28.368 | 24.367 | 1.00 72.09 | C |
| ATOM | 1041 | ND1 | HIS | A | 134 | 8.057 | 27.704 | 25.574 | 1.00 72.16 | N |
| ATOM | 1042 | CD2 | HIS | A | 134 | 7.622 | 27.448 | 23.447 | 1.00 73.41 | C |
| ATOM | 1043 | CE1 | HIS | A | 134 | 7.723 | 26.440 | 25.392 | 1.00 77.82 | C |
| ATOM | 1044 | NE2 | HIS | A | 134 | 7.454 | 26.257 | 24.112 | 1.00 78.13 | N |
| ATOM | 1045 | N | LYS | A | 135 | 5.488 | 29.843 | 22.461 | 1.00 81.08 | N |
| ATOM | 1046 | CA | LYS | A | 135 | 4.034 | 29.850 | 22.574 | 1.00 91.79 | C |
| ATOM | 1047 | C | LYS | A | 135 | 3.435 | 31.264 | 22.532 | 1.00 92.61 | C |
| ATOM | 1048 | O | LYS | A | 135 | 2.397 | 31.511 | 23.139 | 1.00 95.56 | O |
| ATOM | 1049 | CB | LYS | A | 135 | 3.608 | 29.135 | 23.870 | 1.00 90.50 | C |
| ATOM | 1050 | CG | LYS | A | 135 | 3.832 | 29.955 | 25.143 | 1.00 96.62 | C |
| ATOM | 1051 | CD | LYS | A | 135 | 3.541 | 29.173 | 26.414 | 1.00 94.31 | C |
| ATOM | 1052 | CE | LYS | A | 135 | 3.714 | 30.058 | 27.643 | 1.00 94.84 | C |
| ATOM | 1053 | NZ | LYS | A | 135 | 3.553 | 29.294 | 28.915 | 1.00 95.67 | N |
| ATOM | 1054 | N | GLY | A | 136 | 4.082 | 32.194 | 21.828 | 1.00 91.50 | N |
| ATOM | 1055 | CA | GLY | A | 136 | 3.553 | 33.551 | 21.741 | 1.00 88.54 | C |
| ATOM | 1056 | C | GLY | A | 136 | 4.256 | 34.597 | 22.589 | 1.00 85.72 | C |
| ATOM | 1057 | O | GLY | A | 136 | 4.366 | 35.754 | 22.187 | 1.00 89.77 | O |
| ATOM | 1058 | N | ARG | A | 137 | 4.734 | 34.184 | 23.757 | 1.00 82.42 | N |
| ATOM | 1059 | CA | ARG | A | 137 | 5.426 | 35.064 | 24.698 | 1.00 83.81 | C |
| ATOM | 1060 | C | ARG | A | 137 | 6.867 | 35.398 | 24.329 | 1.00 80.74 | C |
| ATOM | 1061 | O | ARG | A | 137 | 7.372 | 35.029 | 23.272 | 1.00 83.63 | O |
| ATOM | 1062 | CB | ARG | A | 137 | 5.448 | 34.419 | 26.090 | 1.00 90.23 | C |
| ATOM | 1063 | CG | ARG | A | 137 | 4.111 | 34.360 | 26.790 | 1.00 99.62 | C |
| ATOM | 1064 | CD | ARG | A | 137 | 3.856 | 35.652 | 27.530 | 1.00105.25 | C |
| ATOM | 1065 | NE | ARG | A | 137 | 2.445 | 36.009 | 27.526 | 1.00113.79 | N |
| ATOM | 1066 | CZ | ARG | A | 137 | 1.973 | 37.181 | 27.937 | 1.00114.75 | C |
| ATOM | 1067 | NH1 | ARG | A | 137 | 2.805 | 38.109 | 28.390 | 1.00116.01 | N |
| ATOM | 1068 | NH2 | ARG | A | 137 | 0.672 | 37.432 | 27.883 | 1.00117.60 | N |
| ATOM | 1069 | N | ASP | A | 138 | 7.510 | 36.116 | 25.241 | 1.00 76.46 | N |
| ATOM | 1070 | CA | ASP | A | 138 | 8.907 | 36.497 | 25.132 | 1.00 75.03 | C |
| ATOM | 1071 | C | ASP | A | 138 | 9.464 | 35.773 | 26.328 | 1.00 76.03 | C |
| ATOM | 1072 | O | ASP | A | 138 | 9.139 | 36.102 | 27.476 | 1.00 73.85 | O |
| ATOM | 1073 | CB | ASP | A | 138 | 9.107 | 38.000 | 25.318 | 1.00 77.22 | C |

Figure 2 (Table 2 (page 27))

```
ATOM   1074  CG   ASP A 138      10.578  38.403  25.275  1.00 77.41 C
ATOM   1075  OD1  ASP A 138      11.410  37.736  25.931  1.00 76.27 O
ATOM   1076  OD2  ASP A 138      10.906  39.394  24.590  1.00 67.17 O
ATOM   1077  N    VAL A 139      10.292  34.776  26.069  1.00 63.30 N
ATOM   1078  CA   VAL A 139      10.838  33.992  27.152  1.00 58.22 C
ATOM   1079  C    VAL A 139      11.541  34.814  28.224  1.00 60.55 C
ATOM   1080  O    VAL A 139      11.799  34.320  29.321  1.00 71.06 O
ATOM   1081  CB   VAL A 139      11.785  32.935  26.595  1.00 62.13 C
ATOM   1082  CG1  VAL A 139      11.091  32.195  25.469  1.00 55.43 C
ATOM   1083  CG2  VAL A 139      13.068  33.588  26.091  1.00 47.09 C
ATOM   1084  N    ILE A 140      11.841  36.070  27.918  1.00 66.18 N
ATOM   1085  CA   ILE A 140      12.519  36.924  28.878  1.00 73.19 C
ATOM   1086  C    ILE A 140      11.594  37.514  29.925  1.00 77.32 C
ATOM   1087  O    ILE A 140      11.822  37.370  31.123  1.00 79.51 O
ATOM   1088  CB   ILE A 140      13.229  38.098  28.183  1.00 75.30 C
ATOM   1089  CG1  ILE A 140      14.357  37.569  27.300  1.00 79.57 C
ATOM   1090  CG2  ILE A 140      13.789  39.062  29.227  1.00 84.41 C
ATOM   1091  CD1  ILE A 140      15.381  36.752  28.065  1.00 75.80 C
ATOM   1092  N    LEU A 141      10.553  38.194  29.468  1.00 85.78 N
ATOM   1093  CA   LEU A 141       9.632  38.838  30.384  1.00 97.07 C
ATOM   1094  C    LEU A 141       8.966  37.937  31.409  1.00101.56 C
ATOM   1095  O    LEU A 141       8.177  38.408  32.225  1.00107.39 O
ATOM   1096  CB   LEU A 141       8.571  39.615  29.608  1.00101.80 C
ATOM   1097  CG   LEU A 141       9.106  40.905  28.991  1.00106.45 C
ATOM   1098  CD1  LEU A 141       7.949  41.736  28.461  1.00108.62 C
ATOM   1099  CD2  LEU A 141       9.882  41.699  30.046  1.00104.45 C
ATOM   1100  N    LYS A 142       9.276  36.650  31.384  1.00101.47 N
ATOM   1101  CA   LYS A 142       8.689  35.751  32.362  1.00101.64 C
ATOM   1102  C    LYS A 142       9.660  35.560  33.527  1.00101.85 C
ATOM   1103  O    LYS A 142       9.262  35.339  34.675  1.00105.32 O
ATOM   1104  CB   LYS A 142       8.346  34.404  31.702  1.00100.75 C
ATOM   1105  CG   LYS A 142       9.525  33.643  31.098  1.00 98.61 C
ATOM   1106  CD   LYS A 142       8.997  32.520  30.208  1.00 93.54 C
ATOM   1107  CE   LYS A 142      10.082  31.550  29.747  1.00 96.37 C
ATOM   1108  NZ   LYS A 142       9.503  30.522  28.822  1.00 91.06 N
ATOM   1109  N    LYS A 143      10.940  35.703  33.223  1.00102.59 N
ATOM   1110  CA   LYS A 143      11.992  35.519  34.206  1.00104.90 C
ATOM   1111  C    LYS A 143      11.852  34.206  34.942  1.00100.79 C
ATOM   1112  O    LYS A 143      11.372  34.122  36.080  1.00100.29 O
ATOM   1113  CB   LYS A 143      12.059  36.672  35.207  1.00107.17 C
ATOM   1114  CG   LYS A 143      13.224  36.510  36.183  1.00113.10 C
ATOM   1115  CD   LYS A 143      14.559  36.248  35.522  1.00116.78 C
ATOM   1116  CE   LYS A 143      15.786  36.228  36.466  1.00123.03 C
ATOM   1117  NZ   LYS A 143      17.123  36.187  35.780  1.00119.60 N
ATOM   1118  N    ASP A 144      12.237  33.182  34.199  1.00 94.81 N
ATOM   1119  CA   ASP A 144      12.319  31.828  34.669  1.00 85.45 C
ATOM   1120  C    ASP A 144      13.827  31.840  34.531  1.00 79.96 C
ATOM   1121  O    ASP A 144      14.365  31.687  33.436  1.00 88.63 O
ATOM   1122  CB   ASP A 144      11.718  30.833  33.677  1.00 85.69 C
ATOM   1123  CG   ASP A 144      11.884  29.398  34.137  1.00 89.87 C
ATOM   1124  OD1  ASP A 144      12.989  29.060  34.609  1.00 90.66 O
ATOM   1125  OD2  ASP A 144      10.913  28.608  34.041  1.00101.36 O
ATOM   1126  N    VAL A 145      14.490  32.118  35.642  1.00 68.69 N
ATOM   1127  CA   VAL A 145      15.946  32.226  35.721  1.00 67.87 C
ATOM   1128  C    VAL A 145      16.758  31.316  34.795  1.00 55.99 C
ATOM   1129  O    VAL A 145      17.915  31.598  34.490  1.00 61.04 O
```

Figure 2 (Table 2 (page 28))

```
ATOM   1130  CB   VAL A 145      16.415  31.974  37.167  1.00  76.83  C
ATOM   1131  CG1  VAL A 145      15.901  33.082  38.076  1.00  76.29  C
ATOM   1132  CG2  VAL A 145      15.902  30.617  37.655  1.00  77.74  C
ATOM   1133  N    ARG A 146      16.148  30.227  34.349  1.00  52.68  N
ATOM   1134  CA   ARG A 146      16.839  29.283  33.493  1.00  56.85  C
ATOM   1135  C    ARG A 146      16.984  29.771  32.055  1.00  48.40  C
ATOM   1136  O    ARG A 146      17.808  29.258  31.311  1.00  46.31  O
ATOM   1137  CB   ARG A 146      16.121  27.925  33.538  1.00  44.42  C
ATOM   1138  CG   ARG A 146      16.235  27.242  34.901  1.00  53.27  C
ATOM   1139  CD   ARG A 146      15.613  25.846  34.911  1.00  47.00  C
ATOM   1140  NE   ARG A 146      14.253  25.864  34.388  1.00  43.57  N
ATOM   1141  CZ   ARG A 146      13.898  25.279  33.253  1.00  53.19  C
ATOM   1142  NH1  ARG A 146      14.810  24.627  32.533  1.00  46.06  N
ATOM   1143  NH2  ARG A 146      12.646  25.359  32.825  1.00  49.59  N
ATOM   1144  N    PHE A 147      16.190  30.766  31.680  1.00  49.96  N
ATOM   1145  CA   PHE A 147      16.233  31.297  30.330  1.00  55.08  C
ATOM   1146  C    PHE A 147      17.068  32.568  30.213  1.00  55.40  C
ATOM   1147  O    PHE A 147      16.837  33.551  30.916  1.00  58.84  O
ATOM   1148  CB   PHE A 147      14.815  31.536  29.828  1.00  47.49  C
ATOM   1149  CG   PHE A 147      14.003  30.271  29.679  1.00  55.00  C
ATOM   1150  CD1  PHE A 147      13.520  29.598  30.796  1.00  50.35  C
ATOM   1151  CD2  PHE A 147      13.730  29.747  28.416  1.00  49.95  C
ATOM   1152  CE1  PHE A 147      12.773  28.416  30.654  1.00  61.13  C
ATOM   1153  CE2  PHE A 147      12.986  28.571  28.265  1.00  53.83  C
ATOM   1154  CZ   PHE A 147      12.508  27.905  29.386  1.00  56.75  C
ATOM   1155  N    ILE A 148      18.038  32.536  29.307  1.00  50.18  N
ATOM   1156  CA   ILE A 148      18.940  33.661  29.097  1.00  53.42  C
ATOM   1157  C    ILE A 148      19.348  33.856  27.636  1.00  45.25  C
ATOM   1158  O    ILE A 148      19.659  32.899  26.944  1.00  44.46  O
ATOM   1159  CB   ILE A 148      20.233  33.463  29.908  1.00  55.88  C
ATOM   1160  CG1  ILE A 148      19.907  33.427  31.399  1.00  65.94  C
ATOM   1161  CG2  ILE A 148      21.231  34.573  29.597  1.00  61.53  C
ATOM   1162  CD1  ILE A 148      21.093  33.081  32.279  1.00  69.07  C
ATOM   1163  N    VAL A 149      19.337  35.099  27.172  1.00  37.73  N
ATOM   1164  CA   VAL A 149      19.764  35.381  25.817  1.00  42.64  C
ATOM   1165  C    VAL A 149      21.236  35.794  25.962  1.00  46.84  C
ATOM   1166  O    VAL A 149      21.552  36.756  26.655  1.00  47.29  O
ATOM   1167  CB   VAL A 149      18.929  36.512  25.185  1.00  42.61  C
ATOM   1168  CG1  VAL A 149      19.472  36.844  23.791  1.00  44.21  C
ATOM   1169  CG2  VAL A 149      17.444  36.067  25.064  1.00  43.57  C
ATOM   1170  N    LEU A 150      22.127  35.036  25.328  1.00  40.34  N
ATOM   1171  CA   LEU A 150      23.568  35.289  25.400  1.00  42.16  C
ATOM   1172  C    LEU A 150      24.030  36.450  24.524  1.00  47.24  C
ATOM   1173  O    LEU A 150      23.262  36.965  23.723  1.00  39.70  O
ATOM   1174  CB   LEU A 150      24.305  34.019  25.001  1.00  36.82  C
ATOM   1175  CG   LEU A 150      23.885  32.825  25.860  1.00  50.79  C
ATOM   1176  CD1  LEU A 150      24.330  31.505  25.225  1.00  45.07  C
ATOM   1177  CD2  LEU A 150      24.473  32.999  27.252  1.00  55.15  C
ATOM   1178  N    SER A 151      25.295  36.849  24.666  1.00  50.63  N
ATOM   1179  CA   SER A 151      25.849  37.953  23.880  1.00  44.74  C
ATOM   1180  C    SER A 151      25.770  37.710  22.365  1.00  37.06  C
ATOM   1181  O    SER A 151      25.651  38.663  21.587  1.00  49.84  O
ATOM   1182  CB   SER A 151      27.320  38.200  24.273  1.00  45.09  C
ATOM   1183  OG   SER A 151      28.150  37.144  23.792  1.00  45.86  O
ATOM   1184  N    ASN A 152      25.866  36.455  21.937  1.00  38.65  N
ATOM   1185  CA   ASN A 152      25.784  36.140  20.506  1.00  40.49  C
```

Figure 2 (Table 2 (page 29))

```
ATOM   1186  C   ASN A 152      24.321  35.998  20.073  1.00 40.22  C
ATOM   1187  O   ASN A 152      24.036  35.583  18.936  1.00 34.75  O
ATOM   1188  CB  ASN A 152      26.476  34.821  20.207  1.00 39.82  C
ATOM   1189  CG  ASN A 152      26.097  33.752  21.199  1.00 54.90  C
ATOM   1190  OD1 ASN A 152      24.972  33.739  21.694  1.00 45.34  O
ATOM   1191  ND2 ASN A 152      27.029  32.850  21.504  1.00 46.13  N
ATOM   1192  N   ASN A 153      23.410  36.309  20.990  1.00 38.94  N
ATOM   1193  CA  ASN A 153      21.969  36.213  20.740  1.00 45.44  C
ATOM   1194  C   ASN A 153      21.352  34.827  20.723  1.00 42.99  C
ATOM   1195  O   ASN A 153      20.171  34.674  20.414  1.00 38.19  O
ATOM   1196  CB  ASN A 153      21.589  36.964  19.469  1.00 42.88  C
ATOM   1197  CG  ASN A 153      21.665  38.468  19.660  1.00 49.74  C
ATOM   1198  OD1 ASN A 153      21.300  38.990  20.720  1.00 57.35  O
ATOM   1199  ND2 ASN A 153      22.130  39.171  18.645  1.00 53.13  N
ATOM   1200  N   TYR A 154      22.121  33.810  21.080  1.00 31.78  N
ATOM   1201  CA  TYR A 154      21.563  32.463  21.151  1.00 37.05  C
ATOM   1202  C   TYR A 154      20.707  32.352  22.418  1.00 36.11  C
ATOM   1203  O   TYR A 154      20.918  33.107  23.357  1.00 35.56  O
ATOM   1204  CB  TYR A 154      22.675  31.425  21.247  1.00 35.50  C
ATOM   1205  CG  TYR A 154      23.535  31.329  20.021  1.00 40.10  C
ATOM   1206  CD1 TYR A 154      24.703  30.565  20.037  1.00 33.69  C
ATOM   1207  CD2 TYR A 154      23.179  31.990  18.837  1.00 35.06  C
ATOM   1208  CE1 TYR A 154      25.505  30.457  18.899  1.00 38.35  C
ATOM   1209  CE2 TYR A 154      23.979  31.892  17.676  1.00 34.58  C
ATOM   1210  CZ  TYR A 154      25.143  31.119  17.726  1.00 46.30  C
ATOM   1211  OH  TYR A 154      25.954  31.005  16.618  1.00 43.90  O
ATOM   1212  N   LEU A 155      19.757  31.415  22.450  1.00 37.10  N
ATOM   1213  CA  LEU A 155      18.936  31.237  23.650  1.00 33.06  C
ATOM   1214  C   LEU A 155      19.514  30.121  24.496  1.00 25.37  C
ATOM   1215  O   LEU A 155      19.688  28.989  24.037  1.00 33.57  O
ATOM   1216  CB  LEU A 155      17.482  30.866  23.303  1.00 33.13  C
ATOM   1217  CG  LEU A 155      16.635  30.561  24.545  1.00 39.86  C
ATOM   1218  CD1 LEU A 155      16.673  31.752  25.480  1.00 39.38  C
ATOM   1219  CD2 LEU A 155      15.185  30.269  24.142  1.00 35.14  C
ATOM   1220  N   GLN A 156      19.802  30.437  25.746  1.00 34.79  N
ATOM   1221  CA  GLN A 156      20.327  29.432  26.638  1.00 30.99  C
ATOM   1222  C   GLN A 156      19.212  28.964  27.568  1.00 33.82  C
ATOM   1223  O   GLN A 156      18.545  29.792  28.205  1.00 38.51  O
ATOM   1224  CB  GLN A 156      21.454  30.010  27.507  1.00 36.98  C
ATOM   1225  CG  GLN A 156      22.028  28.974  28.478  1.00 52.10  C
ATOM   1226  CD  GLN A 156      23.034  29.556  29.461  1.00 59.17  C
ATOM   1227  OE1 GLN A 156      22.750  30.542  30.134  1.00 58.98  O
ATOM   1228  NE2 GLN A 156      24.207  28.934  29.558  1.00 56.95  N
ATOM   1229  N   ILE A 157      19.012  27.651  27.655  1.00 35.15  N
ATOM   1230  CA  ILE A 157      18.001  27.104  28.570  1.00 39.14  C
ATOM   1231  C   ILE A 157      18.737  26.177  29.530  1.00 40.54  C
ATOM   1232  O   ILE A 157      19.028  25.030  29.189  1.00 41.38  O
ATOM   1233  CB  ILE A 157      16.928  26.304  27.832  1.00 36.32  C
ATOM   1234  CG1 ILE A 157      16.195  27.208  26.843  1.00 32.60  C
ATOM   1235  CG2 ILE A 157      15.943  25.728  28.842  1.00 42.84  C
ATOM   1236  CD1 ILE A 157      15.181  26.458  25.983  1.00 40.70  C
ATOM   1237  N   ARG A 158      19.068  26.674  30.718  1.00 38.99  N
ATOM   1238  CA  ARG A 158      19.804  25.857  31.673  1.00 45.51  C
ATOM   1239  C   ARG A 158      18.982  24.711  32.273  1.00 43.75  C
ATOM   1240  O   ARG A 158      17.781  24.851  32.484  1.00 47.32  O
ATOM   1241  CB  ARG A 158      20.381  26.749  32.778  1.00 53.96  C
```

Figure 2 (Table 2 (page 30))

```
ATOM   1242  CG   ARG A 158      21.475  27.697  32.272  1.00  70.32  C
ATOM   1243  CD   ARG A 158      22.155  28.453  33.405  1.00  65.23  C
ATOM   1244  NE   ARG A 158      21.287  29.449  34.012  1.00  68.48  N
ATOM   1245  CZ   ARG A 158      21.572  30.079  35.147  1.00  75.70  C
ATOM   1246  NH1  ARG A 158      22.704  29.808  35.792  1.00  65.00  N
ATOM   1247  NH2  ARG A 158      20.724  30.973  35.641  1.00  71.67  N
ATOM   1248  N    GLY A 159      19.653  23.589  32.544  1.00  47.20  N
ATOM   1249  CA   GLY A 159      18.998  22.415  33.096  1.00  48.68  C
ATOM   1250  C    GLY A 159      17.731  22.133  32.317  1.00  50.27  C
ATOM   1251  O    GLY A 159      16.658  21.983  32.897  1.00  44.17  O
ATOM   1252  N    ILE A 160      17.847  22.050  30.997  1.00  46.11  N
ATOM   1253  CA   ILE A 160      16.664  21.831  30.189  1.00  39.12  C
ATOM   1254  C    ILE A 160      15.872  20.590  30.606  1.00  46.02  C
ATOM   1255  O    ILE A 160      16.434  19.514  30.840  1.00  35.03  O
ATOM   1256  CB   ILE A 160      17.013  21.755  28.702  1.00  34.52  C
ATOM   1257  CG1  ILE A 160      15.727  21.917  27.874  1.00  37.12  C
ATOM   1258  CG2  ILE A 160      17.679  20.446  28.376  1.00  34.14  C
ATOM   1259  CD1  ILE A 160      15.993  22.199  26.392  1.00  28.22  C
ATOM   1260  N    LYS A 161      14.557  20.767  30.692  1.00  42.18  N
ATOM   1261  CA   LYS A 161      13.631  19.710  31.089  1.00  47.02  C
ATOM   1262  C    LYS A 161      12.855  19.202  29.899  1.00  43.66  C
ATOM   1263  O    LYS A 161      12.686  19.908  28.899  1.00  41.53  O
ATOM   1264  CB   LYS A 161      12.599  20.236  32.095  1.00  49.68  C
ATOM   1265  CG   LYS A 161      13.156  20.896  33.337  1.00  55.48  C
ATOM   1266  CD   LYS A 161      12.002  21.450  34.178  1.00  65.12  C
ATOM   1267  CE   LYS A 161      12.488  22.175  35.421  1.00  70.60  C
ATOM   1268  NZ   LYS A 161      11.350  22.563  36.307  1.00  76.58  N
ATOM   1269  N    LYS A 162      12.353  17.982  30.020  1.00  44.57  N
ATOM   1270  CA   LYS A 162      11.560  17.383  28.956  1.00  47.82  C
ATOM   1271  C    LYS A 162      10.372  18.311  28.670  1.00  43.43  C
ATOM   1272  O    LYS A 162       9.914  18.427  27.535  1.00  44.67  O
ATOM   1273  CB   LYS A 162      11.084  15.987  29.391  1.00  50.56  C
ATOM   1274  CG   LYS A 162      10.298  15.208  28.339  1.00  50.30  C
ATOM   1275  CD   LYS A 162      11.109  14.958  27.085  1.00  52.43  C
ATOM   1276  CE   LYS A 162      10.279  14.227  26.051  1.00  60.58  C
ATOM   1277  NZ   LYS A 162      10.963  14.149  24.731  1.00  59.55  N
ATOM   1278  N    THR A 163       9.897  19.010  29.691  1.00  44.12  N
ATOM   1279  CA   THR A 163       8.764  19.904  29.487  1.00  53.06  C
ATOM   1280  C    THR A 163       9.140  21.234  28.833  1.00  55.60  C
ATOM   1281  O    THR A 163       8.294  22.107  28.676  1.00  50.18  O
ATOM   1282  CB   THR A 163       8.022  20.195  30.812  1.00  53.57  C
ATOM   1283  OG1  THR A 163       8.942  20.712  31.780  1.00  55.40  O
ATOM   1284  CG2  THR A 163       7.372  18.914  31.349  1.00  55.53  C
ATOM   1285  N    ASP A 164      10.407  21.397  28.465  1.00  48.62  N
ATOM   1286  CA   ASP A 164      10.826  22.628  27.810  1.00  42.03  C
ATOM   1287  C    ASP A 164      10.764  22.477  26.299  1.00  44.90  C
ATOM   1288  O    ASP A 164      10.821  23.470  25.573  1.00  48.57  O
ATOM   1289  CB   ASP A 164      12.260  23.017  28.209  1.00  38.06  C
ATOM   1290  CG   ASP A 164      12.358  23.525  29.631  1.00  36.69  C
ATOM   1291  OD1  ASP A 164      11.469  24.295  30.052  1.00  49.63  O
ATOM   1292  OD2  ASP A 164      13.337  23.168  30.327  1.00  44.71  O
ATOM   1293  N    GLU A 165      10.639  21.251  25.798  1.00  44.64  N
ATOM   1294  CA   GLU A 165      10.602  21.116  24.353  1.00  53.09  C
ATOM   1295  C    GLU A 165       9.396  21.821  23.739  1.00  49.63  C
ATOM   1296  O    GLU A 165       8.465  22.215  24.440  1.00  52.65  O
ATOM   1297  CB   GLU A 165      10.681  19.650  23.909  1.00  50.75  C
```

Figure 2 (Table 2 (page 31))

| | | | | | | | | | | |
|---|---|---|---|---|---|---|---|---|---|---|
| ATOM | 1298 | CG | GLU | A | 165 | 9.828 | 18.702 | 24.683 | 1.00 | 65.76 C |
| ATOM | 1299 | CD | GLU | A | 165 | 9.940 | 17.283 | 24.155 | 1.00 | 72.74 C |
| ATOM | 1300 | OE1 | GLU | A | 165 | 11.040 | 16.884 | 23.691 | 1.00 | 69.18 O |
| ATOM | 1301 | OE2 | GLU | A | 165 | 8.922 | 16.565 | 24.220 | 1.00 | 65.52 O |
| ATOM | 1302 | N | GLY | A | 166 | 9.451 | 22.002 | 22.424 | 1.00 | 48.94 N |
| ATOM | 1303 | CA | GLY | A | 166 | 8.405 | 22.700 | 21.701 | 1.00 | 55.73 C |
| ATOM | 1304 | C | GLY | A | 166 | 9.067 | 23.579 | 20.655 | 1.00 | 47.37 C |
| ATOM | 1305 | O | GLY | A | 166 | 10.256 | 23.419 | 20.340 | 1.00 | 47.39 O |
| ATOM | 1306 | N | THR | A | 167 | 8.317 | 24.517 | 20.112 | 0.50 | 34.99 N |
| ATOM | 1307 | CA | THR | A | 167 | 8.865 | 25.386 | 19.099 | 0.50 | 35.61 C |
| ATOM | 1308 | C | THR | A | 167 | 9.253 | 26.706 | 19.720 | 0.50 | 31.90 C |
| ATOM | 1309 | O | THR | A | 167 | 8.524 | 27.264 | 20.526 | 0.50 | 30.91 O |
| ATOM | 1310 | CB | THR | A | 167 | 7.849 | 25.623 | 18.006 | 0.50 | 40.53 C |
| ATOM | 1311 | OG1 | THR | A | 167 | 6.633 | 26.081 | 18.602 | 0.50 | 51.84 O |
| ATOM | 1312 | CG2 | THR | A | 167 | 7.574 | 24.332 | 17.258 | 0.50 | 26.00 C |
| ATOM | 1313 | N | TYR | A | 168 | 10.434 | 27.191 | 19.360 | 1.00 | 43.71 N |
| ATOM | 1314 | CA | TYR | A | 168 | 10.922 | 28.467 | 19.871 | 1.00 | 42.97 C |
| ATOM | 1315 | C | TYR | A | 168 | 11.183 | 29.372 | 18.689 | 1.00 | 38.98 C |
| ATOM | 1316 | O | TYR | A | 168 | 11.801 | 28.965 | 17.705 | 1.00 | 43.48 O |
| ATOM | 1317 | CB | TYR | A | 168 | 12.205 | 28.283 | 20.682 | 1.00 | 44.02 C |
| ATOM | 1318 | CG | TYR | A | 168 | 11.968 | 27.702 | 22.047 | 1.00 | 36.86 C |
| ATOM | 1319 | CD1 | TYR | A | 168 | 11.676 | 26.353 | 22.206 | 1.00 | 38.88 C |
| ATOM | 1320 | CD2 | TYR | A | 168 | 12.000 | 28.512 | 23.179 | 1.00 | 36.72 C |
| ATOM | 1321 | CE1 | TYR | A | 168 | 11.419 | 25.821 | 23.466 | 1.00 | 41.93 C |
| ATOM | 1322 | CE2 | TYR | A | 168 | 11.739 | 27.997 | 24.440 | 1.00 | 42.88 C |
| ATOM | 1323 | CZ | TYR | A | 168 | 11.451 | 26.652 | 24.576 | 1.00 | 43.41 C |
| ATOM | 1324 | OH | TYR | A | 168 | 11.193 | 26.139 | 25.824 | 1.00 | 40.88 O |
| ATOM | 1325 | N | ARG | A | 169 | 10.715 | 30.610 | 18.787 | 1.00 | 44.05 N |
| ATOM | 1326 | CA | ARG | A | 169 | 10.871 | 31.533 | 17.681 | 1.00 | 41.18 C |
| ATOM | 1327 | C | ARG | A | 169 | 12.013 | 32.526 | 17.868 | 1.00 | 36.73 C |
| ATOM | 1328 | O | ARG | A | 169 | 12.102 | 33.216 | 18.877 | 1.00 | 40.52 O |
| ATOM | 1329 | CB | ARG | A | 169 | 9.552 | 32.289 | 17.444 | 1.00 | 50.40 C |
| ATOM | 1330 | CG | ARG | A | 169 | 9.655 | 33.416 | 16.430 | 1.00 | 60.69 C |
| ATOM | 1331 | CD | ARG | A | 169 | 8.284 | 33.861 | 15.925 | 1.00 | 46.23 C |
| ATOM | 1332 | NE | ARG | A | 169 | 7.716 | 32.865 | 15.022 | 1.00 | 56.58 N |
| ATOM | 1333 | CZ | ARG | A | 169 | 6.535 | 32.984 | 14.420 | 1.00 | 71.77 C |
| ATOM | 1334 | NH1 | ARG | A | 169 | 5.785 | 34.064 | 14.621 | 1.00 | 58.65 N |
| ATOM | 1335 | NH2 | ARG | A | 169 | 6.101 | 32.015 | 13.618 | 1.00 | 59.89 N |
| ATOM | 1336 | N | CYS | A | 170 | 12.888 | 32.576 | 16.875 | 1.00 | 42.37 N |
| ATOM | 1337 | CA | CYS | A | 170 | 13.998 | 33.506 | 16.919 | 1.00 | 45.65 C |
| ATOM | 1338 | C | CYS | A | 170 | 13.546 | 34.667 | 16.025 | 1.00 | 31.99 C |
| ATOM | 1339 | O | CYS | A | 170 | 13.423 | 34.505 | 14.810 | 1.00 | 41.21 O |
| ATOM | 1340 | CB | CYS | A | 170 | 15.253 | 32.840 | 16.357 | 1.00 | 42.01 C |
| ATOM | 1341 | SG | CYS | A | 170 | 16.748 | 33.898 | 16.241 | 1.00 | 52.42 S |
| ATOM | 1342 | N | GLU | A | 171 | 13.289 | 35.820 | 16.635 | 1.00 | 44.29 N |
| ATOM | 1343 | CA | GLU | A | 171 | 12.830 | 36.978 | 15.879 | 1.00 | 49.65 C |
| ATOM | 1344 | C | GLU | A | 171 | 13.814 | 38.129 | 15.844 | 1.00 | 40.68 C |
| ATOM | 1345 | O | GLU | A | 171 | 14.218 | 38.663 | 16.885 | 1.00 | 45.31 O |
| ATOM | 1346 | CB | GLU | A | 171 | 11.503 | 37.502 | 16.426 | 1.00 | 47.28 C |
| ATOM | 1347 | CG | GLU | A | 171 | 10.905 | 38.616 | 15.560 | 1.00 | 57.47 C |
| ATOM | 1348 | CD | GLU | A | 171 | 9.580 | 39.147 | 16.096 | 1.00 | 65.00 C |
| ATOM | 1349 | OE1 | GLU | A | 171 | 9.593 | 39.989 | 17.028 | 1.00 | 62.15 O |
| ATOM | 1350 | OE2 | GLU | A | 171 | 8.531 | 38.707 | 15.584 | 1.00 | 54.66 O |
| ATOM | 1351 | N | GLY | A | 172 | 14.163 | 38.525 | 14.625 | 1.00 | 46.09 N |
| ATOM | 1352 | CA | GLY | A | 172 | 15.086 | 39.624 | 14.436 | 1.00 | 49.63 C |
| ATOM | 1353 | C | GLY | A | 172 | 14.388 | 40.872 | 13.930 | 1.00 | 46.92 C |

Figure 2 (Table 2 (page 32))

```
ATOM   1354  O    GLY A 172      13.557  40.812  13.014  1.00 50.71      O
ATOM   1355  N    ARG A 173      14.753  41.998  14.535  1.00 40.06      N
ATOM   1356  CA   ARG A 173      14.222  43.309  14.215  1.00 44.00      C
ATOM   1357  C    ARG A 173      15.335  44.350  14.038  1.00 56.42      C
ATOM   1358  O    ARG A 173      16.328  44.354  14.768  1.00 47.64      O
ATOM   1359  CB   ARG A 173      13.310  43.800  15.345  1.00 42.90      C
ATOM   1360  CG   ARG A 173      12.048  42.970  15.527  1.00 41.21      C
ATOM   1361  CD   ARG A 173      11.096  43.649  16.488  1.00 49.33      C
ATOM   1362  NE   ARG A 173       9.880  42.862  16.656  1.00 55.21      N
ATOM   1363  CZ   ARG A 173       8.669  43.387  16.790  1.00 54.70      C
ATOM   1364  NH1  ARG A 173       8.518  44.704  16.773  1.00 54.11      N
ATOM   1365  NH2  ARG A 173       7.610  42.596  16.935  1.00 54.36      N
ATOM   1366  N    ILE A 174      15.135  45.245  13.080  1.00 51.94      N
ATOM   1367  CA   ILE A 174      16.068  46.331  12.821  1.00 48.52      C
ATOM   1368  C    ILE A 174      15.228  47.591  12.902  1.00 42.65      C
ATOM   1369  O    ILE A 174      14.485  47.901  11.973  1.00 40.81      O
ATOM   1370  CB   ILE A 174      16.687  46.193  11.436  1.00 51.33      C
ATOM   1371  CG1  ILE A 174      17.536  44.921  11.395  1.00 62.03      C
ATOM   1372  CG2  ILE A 174      17.536  47.417  11.128  1.00 57.79      C
ATOM   1373  CD1  ILE A 174      18.075  44.586  10.042  1.00 60.04      C
ATOM   1374  N    LEU A 175      15.348  48.327  14.004  1.00 43.83      N
ATOM   1375  CA   LEU A 175      14.514  49.513  14.203  1.00 50.67      C
ATOM   1376  C    LEU A 175      14.502  50.558  13.102  1.00 53.85      C
ATOM   1377  O    LEU A 175      13.435  51.017  12.694  1.00 54.58      O
ATOM   1378  CB   LEU A 175      14.853  50.223  15.520  1.00 52.93      C
ATOM   1379  CG   LEU A 175      14.067  51.544  15.693  1.00 69.90      C
ATOM   1380  CD1  LEU A 175      12.539  51.287  15.592  1.00 58.23      C
ATOM   1381  CD2  LEU A 175      14.423  52.195  17.026  1.00 61.03      C
ATOM   1382  N    ALA A 176      15.681  50.962  12.641  1.00 49.99      N
ATOM   1383  CA   ALA A 176      15.753  51.981  11.605  1.00 51.23      C
ATOM   1384  C    ALA A 176      14.902  51.629  10.385  1.00 45.44      C
ATOM   1385  O    ALA A 176      14.347  52.518   9.739  1.00 57.30      O
ATOM   1386  CB   ALA A 176      17.211  52.214  11.193  1.00 54.86      C
ATOM   1387  N    ARG A 177      14.776  50.341  10.074  1.00 50.42      N
ATOM   1388  CA   ARG A 177      13.987  49.924   8.917  1.00 45.08      C
ATOM   1389  C    ARG A 177      12.641  49.302   9.269  1.00 48.67      C
ATOM   1390  O    ARG A 177      11.862  48.974   8.377  1.00 45.39      O
ATOM   1391  CB   ARG A 177      14.778  48.918   8.081  1.00 57.24      C
ATOM   1392  CG   ARG A 177      16.084  49.467   7.544  1.00 64.35      C
ATOM   1393  CD   ARG A 177      16.813  48.460   6.666  1.00 64.31      C
ATOM   1394  NE   ARG A 177      17.880  49.138   5.939  1.00 77.29      N
ATOM   1395  CZ   ARG A 177      17.889  49.331   4.625  1.00 58.44      C
ATOM   1396  NH1  ARG A 177      16.892  48.883   3.873  1.00 54.23      N
ATOM   1397  NH2  ARG A 177      18.884  50.009   4.074  1.00 72.33      N
ATOM   1398  N    GLY A 178      12.373  49.130  10.562  1.00 44.96      N
ATOM   1399  CA   GLY A 178      11.122  48.508  10.972  1.00 44.41      C
ATOM   1400  C    GLY A 178      11.050  47.122  10.354  1.00 44.68      C
ATOM   1401  O    GLY A 178       9.976  46.574  10.092  1.00 40.98      O
ATOM   1402  N    GLU A 179      12.227  46.544  10.146  1.00 41.13      N
ATOM   1403  CA   GLU A 179      12.363  45.240   9.513  1.00 46.62      C
ATOM   1404  C    GLU A 179      12.204  44.076  10.496  1.00 46.51      C
ATOM   1405  O    GLU A 179      12.710  44.116  11.619  1.00 46.07      O
ATOM   1406  CB   GLU A 179      13.736  45.192   8.817  1.00 47.47      C
ATOM   1407  CG   GLU A 179      14.011  44.049   7.852  1.00 52.61      C
ATOM   1408  CD   GLU A 179      15.396  44.199   7.186  1.00 67.97      C
ATOM   1409  OE1  GLU A 179      16.232  44.974   7.709  1.00 52.50      O
```

Figure 2 (Table 2 (page 33))

```
ATOM   1410  OE2 GLU A 179      15.657  43.540   6.156  1.00 61.67 O
ATOM   1411  N   ILE A 180      11.504  43.037  10.044  1.00 46.98 N
ATOM   1412  CA  ILE A 180      11.260  41.843  10.844  1.00 44.57 C
ATOM   1413  C   ILE A 180      11.442  40.596  10.028  1.00 49.88 C
ATOM   1414  O   ILE A 180      11.018  40.531   8.878  1.00 50.41 O
ATOM   1415  CB  ILE A 180       9.820  41.784  11.371  1.00 60.91 C
ATOM   1416  CG1 ILE A 180       9.586  42.889  12.387  1.00 56.28 C
ATOM   1417  CG2 ILE A 180       9.544  40.416  11.996  1.00 58.36 C
ATOM   1418  CD1 ILE A 180       8.206  42.834  12.973  1.00 63.77 C
ATOM   1419  N   ASN A 181      12.088  39.607  10.632  1.00 49.49 N
ATOM   1420  CA  ASN A 181      12.269  38.308  10.010  1.00 44.31 C
ATOM   1421  C   ASN A 181      12.329  37.382  11.223  1.00 53.84 C
ATOM   1422  O   ASN A 181      12.789  37.776  12.297  1.00 49.42 O
ATOM   1423  CB  ASN A 181      13.555  38.240   9.189  1.00 50.86 C
ATOM   1424  CG  ASN A 181      13.527  37.117   8.165  1.00 58.63 C
ATOM   1425  OD1 ASN A 181      12.581  36.332   8.126  1.00 68.55 O
ATOM   1426  ND2 ASN A 181      14.567  37.031   7.331  1.00 62.99 N
ATOM   1427  N   PHE A 182      11.818  36.172  11.082  1.00 51.66 N
ATOM   1428  CA  PHE A 182      11.839  35.261  12.210  1.00 54.82 C
ATOM   1429  C   PHE A 182      12.052  33.843  11.711  1.00 62.75 C
ATOM   1430  O   PHE A 182      11.914  33.563  10.512  1.00 55.35 O
ATOM   1431  CB  PHE A 182      10.521  35.354  12.989  1.00 62.28 C
ATOM   1432  CG  PHE A 182       9.352  34.717  12.283  1.00 74.94 C
ATOM   1433  CD1 PHE A 182       9.292  33.333  12.120  1.00 82.11 C
ATOM   1434  CD2 PHE A 182       8.333  35.496  11.745  1.00 81.28 C
ATOM   1435  CE1 PHE A 182       8.244  32.733  11.429  1.00 84.02 C
ATOM   1436  CE2 PHE A 182       7.276  34.901  11.049  1.00 84.09 C
ATOM   1437  CZ  PHE A 182       7.236  33.516  10.892  1.00 83.03 C
ATOM   1438  N   LYS A 183      12.388  32.946  12.633  1.00 58.39 N
ATOM   1439  CA  LYS A 183      12.591  31.541  12.295  1.00 50.63 C
ATOM   1440  C   LYS A 183      12.106  30.678  13.459  1.00 53.23 C
ATOM   1441  O   LYS A 183      12.431  30.947  14.622  1.00 45.57 O
ATOM   1442  CB  LYS A 183      14.073  31.263  12.022  1.00 65.15 C
ATOM   1443  CG  LYS A 183      14.446  29.780  11.957  1.00 64.65 C
ATOM   1444  CD  LYS A 183      14.295  29.166  10.566  1.00 63.11 C
ATOM   1445  CE  LYS A 183      14.627  27.670  10.590  1.00 53.42 C
ATOM   1446  NZ  LYS A 183      15.665  27.264   9.599  1.00 53.61 N
ATOM   1447  N   ASP A 184      11.319  29.655  13.142  1.00 48.66 N
ATOM   1448  CA  ASP A 184      10.797  28.751  14.156  1.00 52.92 C
ATOM   1449  C   ASP A 184      11.722  27.567  14.333  1.00 45.71 C
ATOM   1450  O   ASP A 184      12.104  26.894  13.371  1.00 44.54 O
ATOM   1451  CB  ASP A 184       9.404  28.255  13.784  1.00 62.54 C
ATOM   1452  CG  ASP A 184       8.338  29.306  14.007  1.00 62.50 C
ATOM   1453  OD1 ASP A 184       8.407  30.010  15.038  1.00 56.56 O
ATOM   1454  OD2 ASP A 184       7.429  29.417  13.155  1.00 70.30 O
ATOM   1455  N   ILE A 185      12.085  27.313  15.576  1.00 40.93 N
ATOM   1456  CA  ILE A 185      12.993  26.219  15.849  1.00 39.71 C
ATOM   1457  C   ILE A 185      12.372  25.231  16.806  1.00 38.52 C
ATOM   1458  O   ILE A 185      11.958  25.590  17.909  1.00 38.65 O
ATOM   1459  CB  ILE A 185      14.326  26.752  16.417  1.00 41.45 C
ATOM   1460  CG1 ILE A 185      15.051  27.548  15.316  1.00 46.89 C
ATOM   1461  CG2 ILE A 185      15.199  25.580  16.922  1.00 37.86 C
ATOM   1462  CD1 ILE A 185      16.246  28.337  15.805  1.00 48.29 C
ATOM   1463  N   GLN A 186      12.291  23.984  16.355  1.00 42.25 N
ATOM   1464  CA  GLN A 186      11.744  22.916  17.181  1.00 41.47 C
ATOM   1465  C   GLN A 186      12.857  22.416  18.097  1.00 38.63 C
```

Figure 2 (Table 2 (page 34))

```
ATOM   1466  O    GLN A 186      13.916  21.991  17.630  1.00 42.48  O
ATOM   1467  CB   GLN A 186      11.247  21.755  16.307  1.00 52.01  C
ATOM   1468  CG   GLN A 186      10.732  20.542  17.100  1.00 64.38  C
ATOM   1469  CD   GLN A 186      10.353  19.348  16.204  1.00 79.51  C
ATOM   1470  OE1  GLN A 186      10.873  19.202  15.092  1.00 79.17  O
ATOM   1471  NE2  GLN A 186       9.465  18.481  16.701  1.00 80.31  N
ATOM   1472  N    VAL A 187      12.610  22.457  19.398  1.00 43.44  N
ATOM   1473  CA   VAL A 187      13.586  21.987  20.367  1.00 47.67  C
ATOM   1474  C    VAL A 187      13.146  20.607  20.866  1.00 49.13  C
ATOM   1475  O    VAL A 187      12.015  20.446  21.311  1.00 40.93  O
ATOM   1476  CB   VAL A 187      13.675  22.939  21.583  1.00 42.03  C
ATOM   1477  CG1  VAL A 187      14.563  22.315  22.652  1.00 41.16  C
ATOM   1478  CG2  VAL A 187      14.224  24.300  21.154  1.00 38.03  C
ATOM   1479  N    ILE A 188      14.035  19.621  20.785  1.00 41.32  N
ATOM   1480  CA   ILE A 188      13.733  18.273  21.255  1.00 42.62  C
ATOM   1481  C    ILE A 188      14.635  17.913  22.441  1.00 40.36  C
ATOM   1482  O    ILE A 188      15.835  18.224  22.442  1.00 42.29  O
ATOM   1483  CB   ILE A 188      13.945  17.213  20.142  1.00 45.03  C
ATOM   1484  CG1  ILE A 188      13.002  17.475  18.967  1.00 41.79  C
ATOM   1485  CG2  ILE A 188      13.687  15.806  20.702  1.00 46.59  C
ATOM   1486  CD1  ILE A 188      13.267  16.566  17.763  1.00 40.92  C
ATOM   1487  N    VAL A 189      14.050  17.285  23.455  1.00 36.36  N
ATOM   1488  CA   VAL A 189      14.808  16.867  24.627  1.00 42.50  C
ATOM   1489  C    VAL A 189      14.802  15.338  24.667  1.00 48.22  C
ATOM   1490  O    VAL A 189      13.748  14.705  24.672  1.00 41.17  O
ATOM   1491  CB   VAL A 189      14.206  17.455  25.921  1.00 44.30  C
ATOM   1492  CG1  VAL A 189      14.945  16.930  27.125  1.00 39.49  C
ATOM   1493  CG2  VAL A 189      14.304  18.966  25.894  1.00 40.56  C
ATOM   1494  N    ASN A 190      15.993  14.754  24.665  1.00 40.63  N
ATOM   1495  CA   ASN A 190      16.143  13.316  24.698  1.00 40.98  C
ATOM   1496  C    ASN A 190      16.395  12.885  26.148  1.00 45.73  C
ATOM   1497  O    ASN A 190      17.018  13.613  26.918  1.00 45.44  O
ATOM   1498  CB   ASN A 190      17.285  12.908  23.752  1.00 40.78  C
ATOM   1499  CG   ASN A 190      16.999  13.293  22.310  1.00 48.31  C
ATOM   1500  OD1  ASN A 190      15.917  13.005  21.782  1.00 44.75  O
ATOM   1501  ND2  ASN A 190      17.962  13.951  21.664  1.00 41.66  N
ATOM   1502  N    VAL A 191      15.877  11.710  26.509  1.00 42.84  N
ATOM   1503  CA   VAL A 191      15.982  11.151  27.863  1.00 39.39  C
ATOM   1504  C    VAL A 191      16.683   9.802  27.788  1.00 39.64  C
ATOM   1505  O    VAL A 191      16.261   8.910  27.043  1.00 47.40  O
ATOM   1506  CB   VAL A 191      14.574  10.954  28.470  1.00 44.63  C
ATOM   1507  CG1  VAL A 191      14.671  10.368  29.890  1.00 41.78  C
ATOM   1508  CG2  VAL A 191      13.848  12.310  28.499  1.00 41.72  C
ATOM   1509  N    PRO A 192      17.775   9.641  28.542  1.00 43.27  N
ATOM   1510  CA   PRO A 192      18.578   8.416  28.596  1.00 45.21  C
ATOM   1511  C    PRO A 192      17.722   7.224  28.990  1.00 42.00  C
ATOM   1512  O    PRO A 192      16.783   7.355  29.763  1.00 42.35  O
ATOM   1513  CB   PRO A 192      19.620   8.737  29.668  1.00 49.92  C
ATOM   1514  CG   PRO A 192      19.690  10.204  29.687  1.00 49.81  C
ATOM   1515  CD   PRO A 192      18.246  10.602  29.556  1.00 43.30  C
ATOM   1516  N    PRO A 193      18.075   6.034  28.515  1.00 40.57  N
ATOM   1517  CA   PRO A 193      17.301   4.848  28.838  1.00 39.79  C
ATOM   1518  C    PRO A 193      17.516   4.372  30.256  1.00 43.45  C
ATOM   1519  O    PRO A 193      18.552   4.666  30.864  1.00 44.20  O
ATOM   1520  CB   PRO A 193      17.842   3.809  27.853  1.00 41.07  C
ATOM   1521  CG   PRO A 193      18.661   4.630  26.843  1.00 46.01  C
```

Figure 2 (Table 2 (page 35))

```
ATOM   1522  CD   PRO A 193      19.250    5.657   27.729  1.00 47.13           C
ATOM   1523  N    THR A 194      16.516    3.665   30.779  1.00 45.04           N
ATOM   1524  CA   THR A 194      16.614    2.987   32.075  1.00 48.33           C
ATOM   1525  C    THR A 194      16.019    1.623   31.713  1.00 51.40           C
ATOM   1526  O    THR A 194      15.124    1.529   30.848  1.00 41.84           O
ATOM   1527  CB   THR A 194      15.792    3.630   33.225  1.00 48.61           C
ATOM   1528  OG1  THR A 194      14.414    3.724   32.862  1.00 54.30           O
ATOM   1529  CG2  THR A 194      16.338    4.992   33.574  1.00 57.24           C
ATOM   1530  N    VAL A 195      16.507    0.565   32.352  1.00 48.50           N
ATOM   1531  CA   VAL A 195      16.026   -0.760   32.017  1.00 45.60           C
ATOM   1532  C    VAL A 195      16.083   -1.715   33.200  1.00 42.61           C
ATOM   1533  O    VAL A 195      16.976   -1.644   34.021  1.00 46.25           O
ATOM   1534  CB   VAL A 195      16.853   -1.346   30.840  1.00 42.93           C
ATOM   1535  CG1  VAL A 195      18.314   -1.582   31.282  1.00 43.08           C
ATOM   1536  CG2  VAL A 195      16.218   -2.635   30.339  1.00 43.46           C
ATOM   1537  N    GLN A 196      15.104   -2.603   33.282  1.00 41.51           N
ATOM   1538  CA   GLN A 196      15.070   -3.577   34.355  1.00 48.63           C
ATOM   1539  C    GLN A 196      14.615   -4.928   33.817  1.00 46.66           C
ATOM   1540  O    GLN A 196      13.706   -5.009   32.992  1.00 45.71           O
ATOM   1541  CB   GLN A 196      14.119   -3.118   35.477  1.00 49.59           C
ATOM   1542  CG   GLN A 196      14.693   -2.064   36.393  1.00 55.69           C
ATOM   1543  CD   GLN A 196      13.790   -1.757   37.588  1.00 74.35           C
ATOM   1544  OE1  GLN A 196      14.268   -1.328   38.639  1.00 74.51           O
ATOM   1545  NE2  GLN A 196      12.482   -1.970   37.429  1.00 79.78           N
ATOM   1546  N    ALA A 197      15.257   -5.991   34.282  1.00 40.70           N
ATOM   1547  CA   ALA A 197      14.876   -7.329   33.873  1.00 39.75           C
ATOM   1548  C    ALA A 197      13.550   -7.650   34.550  1.00 42.61           C
ATOM   1549  O    ALA A 197      13.316   -7.246   35.687  1.00 48.54           O
ATOM   1550  CB   ALA A 197      15.940   -8.333   34.313  1.00 39.72           C
ATOM   1551  N    ARG A 198      12.671   -8.368   33.865  1.00 43.54           N
ATOM   1552  CA   ARG A 198      11.403   -8.720   34.485  1.00 44.25           C
ATOM   1553  C    ARG A 198      11.664   -9.866   35.479  1.00 53.02           C
ATOM   1554  O    ARG A 198      11.018   -9.960   36.528  1.00 45.60           O
ATOM   1555  CB   ARG A 198      10.392   -9.131   33.416  1.00 49.38           C
ATOM   1556  CG   ARG A 198       8.967   -8.992   33.873  1.00 56.08           C
ATOM   1557  CD   ARG A 198       7.991   -9.099   32.724  1.00 58.30           C
ATOM   1558  NE   ARG A 198       7.873   -7.869   31.947  1.00 47.20           N
ATOM   1559  CZ   ARG A 198       6.931   -7.675   31.030  1.00 54.23           C
ATOM   1560  NH1  ARG A 198       6.038   -8.633   30.793  1.00 47.47           N
ATOM   1561  NH2  ARG A 198       6.882   -6.541   30.339  1.00 50.85           N
ATOM   1562  N    GLN A 199      12.625  -10.722   35.133  1.00 51.86           N
ATOM   1563  CA   GLN A 199      13.047  -11.844   35.965  1.00 52.79           C
ATOM   1564  C    GLN A 199      14.564  -11.926   35.871  1.00 50.17           C
ATOM   1565  O    GLN A 199      15.107  -12.162   34.798  1.00 54.53           O
ATOM   1566  CB   GLN A 199      12.447  -13.159   35.472  1.00 58.34           C
ATOM   1567  CG   GLN A 199      10.941  -13.292   35.635  1.00 68.50           C
ATOM   1568  CD   GLN A 199      10.498  -13.315   37.100  1.00 83.24           C
ATOM   1569  OE1  GLN A 199      11.300  -13.596   37.996  1.00 85.74           O
ATOM   1570  NE2  GLN A 199       9.214  -13.035   37.347  1.00 71.40           N
ATOM   1571  N    SER A 200      15.247  -11.719   36.991  1.00 46.12           N
ATOM   1572  CA   SER A 200      16.715  -11.753   37.042  1.00 50.15           C
ATOM   1573  C    SER A 200      17.328  -13.157   37.004  1.00 47.60           C
ATOM   1574  O    SER A 200      18.458  -13.350   36.541  1.00 49.49           O
ATOM   1575  CB   SER A 200      17.194  -11.061   38.318  1.00 49.46           C
ATOM   1576  OG   SER A 200      16.702   -9.737   38.384  1.00 76.11           O
ATOM   1577  N    ILE A 201      16.576  -14.122   37.518  1.00 48.87           N
```

Figure 2 (Table 2 (page 36))

```
ATOM   1578  CA   ILE A 201      17.019 -15.504  37.591  1.00 50.62      C
ATOM   1579  C    ILE A 201      15.994 -16.400  36.925  1.00 47.35      C
ATOM   1580  O    ILE A 201      14.797 -16.328  37.216  1.00 51.41      O
ATOM   1581  CB   ILE A 201      17.181 -15.962  39.067  1.00 64.29      C
ATOM   1582  CG1  ILE A 201      18.080 -14.983  39.838  1.00 57.76      C
ATOM   1583  CG2  ILE A 201      17.768 -17.373  39.116  1.00 58.42      C
ATOM   1584  CD1  ILE A 201      19.476 -14.860  39.290  1.00 68.87      C
ATOM   1585  N    VAL A 202      16.469 -17.249  36.032  1.00 46.21      N
ATOM   1586  CA   VAL A 202      15.587 -18.157  35.339  1.00 49.25      C
ATOM   1587  C    VAL A 202      16.207 -19.540  35.336  1.00 47.17      C
ATOM   1588  O    VAL A 202      17.391 -19.687  35.045  1.00 43.79      O
ATOM   1589  CB   VAL A 202      15.371 -17.701  33.882  1.00 53.12      C
ATOM   1590  CG1  VAL A 202      14.436 -18.661  33.177  1.00 45.19      C
ATOM   1591  CG2  VAL A 202      14.820 -16.276  33.861  1.00 50.64      C
ATOM   1592  N    ASN A 203      15.393 -20.544  35.653  1.00 49.57      N
ATOM   1593  CA   ASN A 203      15.827 -21.937  35.680  1.00 51.28      C
ATOM   1594  C    ASN A 203      15.078 -22.676  34.575  1.00 55.81      C
ATOM   1595  O    ASN A 203      13.857 -22.541  34.440  1.00 50.57      O
ATOM   1596  CB   ASN A 203      15.473 -22.635  37.010  1.00 49.03      C
ATOM   1597  CG   ASN A 203      16.218 -22.067  38.217  1.00 47.83      C
ATOM   1598  OD1  ASN A 203      17.319 -21.530  38.105  1.00 47.54      O
ATOM   1599  ND2  ASN A 203      15.617 -22.217  39.390  1.00 44.22      N
ATOM   1600  N    ALA A 204      15.811 -23.487  33.825  1.00 53.79      N
ATOM   1601  CA   ALA A 204      15.249 -24.272  32.738  1.00 58.78      C
ATOM   1602  C    ALA A 204      15.827 -25.683  32.730  1.00 59.86      C
ATOM   1603  O    ALA A 204      16.909 -25.933  33.268  1.00 58.63      O
ATOM   1604  CB   ALA A 204      15.541 -23.592  31.408  1.00 54.08      C
ATOM   1605  N    THR A 205      15.088 -26.592  32.100  1.00 63.01      N
ATOM   1606  CA   THR A 205      15.483 -27.989  31.966  1.00 62.26      C
ATOM   1607  C    THR A 205      15.949 -28.248  30.546  1.00 59.60      C
ATOM   1608  O    THR A 205      15.282 -27.874  29.579  1.00 57.70      O
ATOM   1609  CB   THR A 205      14.323 -28.946  32.265  1.00 63.31      C
ATOM   1610  OG1  THR A 205      13.916 -28.799  33.634  1.00 64.86      O
ATOM   1611  CG2  THR A 205      14.760 -30.383  32.012  1.00 70.94      C
ATOM   1612  N    ALA A 206      17.089 -28.913  30.430  1.00 56.34      N
ATOM   1613  CA   ALA A 206      17.670 -29.203  29.134  1.00 60.33      C
ATOM   1614  C    ALA A 206      17.035 -30.352  28.375  1.00 64.54      C
ATOM   1615  O    ALA A 206      16.377 -31.228  28.940  1.00 68.98      O
ATOM   1616  CB   ALA A 206      19.156 -29.464  29.290  1.00 58.07      C
ATOM   1617  N    ASN A 207      17.246 -30.306  27.067  1.00 71.10      N
ATOM   1618  CA   ASN A 207      16.791 -31.322  26.140  1.00 71.82      C
ATOM   1619  C    ASN A 207      15.352 -31.788  26.216  1.00 70.92      C
ATOM   1620  O    ASN A 207      15.077 -32.971  26.023  1.00 73.91      O
ATOM   1621  CB   ASN A 207      17.724 -32.518  26.249  1.00 69.97      C
ATOM   1622  CG   ASN A 207      19.170 -32.119  26.105  1.00 75.29      C
ATOM   1623  OD1  ASN A 207      19.562 -31.531  25.097  1.00 81.94      O
ATOM   1624  ND2  ASN A 207      19.972 -32.421  27.115  1.00 80.72      N
ATOM   1625  N    LEU A 208      14.432 -30.877  26.496  1.00 67.07      N
ATOM   1626  CA   LEU A 208      13.026 -31.246  26.528  1.00 68.52      C
ATOM   1627  C    LEU A 208      12.347 -30.484  25.391  1.00 67.74      C
ATOM   1628  O    LEU A 208      11.122 -30.415  25.306  1.00 73.14      O
ATOM   1629  CB   LEU A 208      12.393 -30.904  27.877  1.00 68.09      C
ATOM   1630  CG   LEU A 208      12.930 -31.679  29.091  1.00 79.90      C
ATOM   1631  CD1  LEU A 208      12.105 -31.321  30.319  1.00 73.01      C
ATOM   1632  CD2  LEU A 208      12.854 -33.180  28.843  1.00 77.54      C
ATOM   1633  N    GLY A 209      13.175 -29.907  24.519  1.00 74.00      N
```

Figure 2 (Table 2 (page 37))

```
ATOM   1634  CA  GLY A 209      12.694 -29.159  23.364  1.00 81.72      C
ATOM   1635  C   GLY A 209      11.907 -27.893  23.667  1.00 87.49      C
ATOM   1636  O   GLY A 209      11.241 -27.341  22.788  1.00 95.12      O
ATOM   1637  N   GLN A 210      11.992 -27.420  24.905  1.00 84.00      N
ATOM   1638  CA  GLN A 210      11.254 -26.230  25.299  1.00 82.13      C
ATOM   1639  C   GLN A 210      12.033 -24.922  25.205  1.00 74.00      C
ATOM   1640  O   GLN A 210      13.265 -24.922  25.132  1.00 71.75      O
ATOM   1641  CB  GLN A 210      10.703 -26.400  26.711  1.00 86.64      C
ATOM   1642  CG  GLN A 210      11.770 -26.685  27.754  1.00 92.84      C
ATOM   1643  CD  GLN A 210      11.215 -27.469  28.932  1.00 98.28      C
ATOM   1644  OE1 GLN A 210      10.047 -27.856  28.930  1.00102.57      O
ATOM   1645  NE2 GLN A 210      12.049 -27.714  29.938  1.00100.49      N
ATOM   1646  N   SER A 211      11.295 -23.810  25.212  1.00 73.42      N
ATOM   1647  CA  SER A 211      11.873 -22.470  25.101  1.00 68.89      C
ATOM   1648  C   SER A 211      11.749 -21.688  26.394  1.00 59.63      C
ATOM   1649  O   SER A 211      10.995 -22.044  27.297  1.00 58.00      O
ATOM   1650  CB  SER A 211      11.181 -21.680  23.978  1.00 69.06      C
ATOM   1651  OG  SER A 211      11.312 -22.319  22.719  1.00 75.29      O
ATOM   1652  N   VAL A 212      12.515 -20.616  26.479  1.00 62.83      N
ATOM   1653  CA  VAL A 212      12.470 -19.749  27.638  1.00 57.69      C
ATOM   1654  C   VAL A 212      12.482 -18.343  27.056  1.00 51.71      C
ATOM   1655  O   VAL A 212      13.140 -18.086  26.044  1.00 48.36      O
ATOM   1656  CB  VAL A 212      13.697 -19.965  28.554  1.00 58.76      C
ATOM   1657  CG1 VAL A 212      14.970 -19.802  27.762  1.00 57.99      C
ATOM   1658  CG2 VAL A 212      13.665 -18.988  29.707  1.00 65.40      C
ATOM   1659  N   THR A 213      11.738 -17.438  27.672  1.00 48.53      N
ATOM   1660  CA  THR A 213      11.698 -16.079  27.171  1.00 50.94      C
ATOM   1661  C   THR A 213      12.279 -15.100  28.194  1.00 46.89      C
ATOM   1662  O   THR A 213      11.760 -14.969  29.301  1.00 48.85      O
ATOM   1663  CB  THR A 213      10.246 -15.669  26.820  1.00 50.59      C
ATOM   1664  OG1 THR A 213       9.720 -16.556  25.827  1.00 54.06      O
ATOM   1665  CG2 THR A 213      10.214 -14.255  26.276  1.00 56.06      C
ATOM   1666  N   LEU A 214      13.367 -14.430  27.823  1.00 50.67      N
ATOM   1667  CA  LEU A 214      14.015 -13.445  28.686  1.00 44.75      C
ATOM   1668  C   LEU A 214      13.444 -12.078  28.327  1.00 49.46      C
ATOM   1669  O   LEU A 214      13.339 -11.738  27.147  1.00 40.16      O
ATOM   1670  CB  LEU A 214      15.519 -13.469  28.464  1.00 40.05      C
ATOM   1671  CG  LEU A 214      16.140 -14.857  28.611  1.00 47.06      C
ATOM   1672  CD1 LEU A 214      17.647 -14.728  28.666  1.00 41.62      C
ATOM   1673  CD2 LEU A 214      15.623 -15.532  29.880  1.00 42.47      C
ATOM   1674  N   VAL A 215      13.089 -11.299  29.345  1.00 44.86      N
ATOM   1675  CA  VAL A 215      12.454 -10.004  29.143  1.00 46.92      C
ATOM   1676  C   VAL A 215      13.030  -8.850  29.928  1.00 48.90      C
ATOM   1677  O   VAL A 215      13.254  -8.937  31.135  1.00 50.91      O
ATOM   1678  CB  VAL A 215      10.969 -10.089  29.508  1.00 49.64      C
ATOM   1679  CG1 VAL A 215      10.265  -8.759  29.213  1.00 50.90      C
ATOM   1680  CG2 VAL A 215      10.332 -11.234  28.765  1.00 52.37      C
ATOM   1681  N   CYS A 216      13.254  -7.755  29.221  1.00 44.39      N
ATOM   1682  CA  CYS A 216      13.754  -6.542  29.826  1.00 45.29      C
ATOM   1683  C   CYS A 216      12.744  -5.449  29.501  1.00 52.26      C
ATOM   1684  O   CYS A 216      12.223  -5.399  28.393  1.00 47.28      O
ATOM   1685  CB  CYS A 216      15.122  -6.180  29.257  1.00 45.92      C
ATOM   1686  SG  CYS A 216      16.483  -7.140  29.998  1.00 51.48      S
ATOM   1687  N   ASP A 217      12.454  -4.598  30.478  1.00 44.49      N
ATOM   1688  CA  ASP A 217      11.523  -3.499  30.291  1.00 46.18      C
ATOM   1689  C   ASP A 217      12.330  -2.230  30.313  1.00 46.02      C
```

Figure 2 (Table 2 (page 38))

```
ATOM   1690  O    ASP A 217      12.974   -1.906   31.307  1.00 42.34  O
ATOM   1691  CB   ASP A 217      10.501   -3.453   31.419  1.00 43.07  C
ATOM   1692  CG   ASP A 217       9.576   -4.624   31.382  1.00 54.67  C
ATOM   1693  OD1  ASP A 217       8.860   -4.755   30.366  1.00 54.44  O
ATOM   1694  OD2  ASP A 217       9.573   -5.417   32.350  1.00 52.78  O
ATOM   1695  N    ALA A 218      12.279   -1.498   29.215  1.00 43.43  N
ATOM   1696  CA   ALA A 218      13.030   -0.269   29.129  1.00 51.56  C
ATOM   1697  C    ALA A 218      12.205    0.900   28.633  1.00 51.78  C
ATOM   1698  O    ALA A 218      11.150    0.731   28.031  1.00 48.04  O
ATOM   1699  CB   ALA A 218      14.221   -0.468   28.202  1.00 46.61  C
ATOM   1700  N    ASP A 219      12.704    2.096   28.901  1.00 47.98  N
ATOM   1701  CA   ASP A 219      12.076    3.287   28.377  1.00 53.40  C
ATOM   1702  C    ASP A 219      13.097    4.412   28.287  1.00 54.39  C
ATOM   1703  O    ASP A 219      14.214    4.308   28.791  1.00 53.10  O
ATOM   1704  CB   ASP A 219      10.876    3.693   29.214  1.00 67.27  C
ATOM   1705  CG   ASP A 219      11.226    3.878   30.644  1.00 73.00  C
ATOM   1706  OD1  ASP A 219      12.424    4.087   30.905  1.00 77.65  O
ATOM   1707  OD2  ASP A 219      10.315    3.824   31.502  1.00 83.21  O
ATOM   1708  N    GLY A 220      12.693    5.482   27.622  1.00 46.12  N
ATOM   1709  CA   GLY A 220      13.541    6.632   27.405  1.00 43.59  C
ATOM   1710  C    GLY A 220      13.035    7.286   26.135  1.00 46.49  C
ATOM   1711  O    GLY A 220      12.062    6.810   25.554  1.00 45.48  O
ATOM   1712  N    PHE A 221      13.700    8.341   25.678  1.00 43.50  N
ATOM   1713  CA   PHE A 221      13.283    9.017   24.465  1.00 42.29  C
ATOM   1714  C    PHE A 221      14.499    9.499   23.669  1.00 33.90  C
ATOM   1715  O    PHE A 221      15.313   10.265   24.178  1.00 43.58  O
ATOM   1716  CB   PHE A 221      12.391   10.215   24.797  1.00 41.04  C
ATOM   1717  CG   PHE A 221      11.792   10.861   23.572  1.00 44.52  C
ATOM   1718  CD1  PHE A 221      10.591   10.395   23.037  1.00 47.33  C
ATOM   1719  CD2  PHE A 221      12.482   11.863   22.891  1.00 44.34  C
ATOM   1720  CE1  PHE A 221      10.088   10.910   21.837  1.00 45.26  C
ATOM   1721  CE2  PHE A 221      11.989   12.380   21.693  1.00 48.97  C
ATOM   1722  CZ   PHE A 221      10.785   11.897   21.166  1.00 44.61  C
ATOM   1723  N    PRO A 222      14.645    9.050   22.400  1.00 40.11  N
ATOM   1724  CA   PRO A 222      13.780    8.122   21.655  1.00 40.06  C
ATOM   1725  C    PRO A 222      13.693    6.765   22.344  1.00 50.45  C
ATOM   1726  O    PRO A 222      14.546    6.419   23.172  1.00 43.37  O
ATOM   1727  CB   PRO A 222      14.480    8.000   20.307  1.00 44.90  C
ATOM   1728  CG   PRO A 222      15.163    9.311   20.158  1.00 43.89  C
ATOM   1729  CD   PRO A 222      15.733    9.547   21.536  1.00 38.16  C
ATOM   1730  N    GLU A 223      12.659    5.999   21.998  1.00 47.32  N
ATOM   1731  CA   GLU A 223      12.466    4.664   22.565  1.00 48.48  C
ATOM   1732  C    GLU A 223      13.778    3.917   22.403  1.00 44.89  C
ATOM   1733  O    GLU A 223      14.364    3.886   21.321  1.00 42.04  O
ATOM   1734  CB   GLU A 223      11.359    3.905   21.837  1.00 51.24  C
ATOM   1735  CG   GLU A 223       9.947    4.402   22.100  1.00 45.06  C
ATOM   1736  CD   GLU A 223       9.513    4.303   23.556  1.00 60.54  C
ATOM   1737  OE1  GLU A 223       9.950    3.368   24.263  1.00 71.83  O
ATOM   1738  OE2  GLU A 223       8.700    5.153   23.986  1.00 70.97  O
ATOM   1739  N    PRO A 224      14.249    3.296   23.483  1.00 46.34  N
ATOM   1740  CA   PRO A 224      15.507    2.559   23.453  1.00 48.92  C
ATOM   1741  C    PRO A 224      15.536    1.373   22.501  1.00 49.30  C
ATOM   1742  O    PRO A 224      14.535    0.692   22.311  1.00 47.42  O
ATOM   1743  CB   PRO A 224      15.678    2.113   24.911  1.00 47.68  C
ATOM   1744  CG   PRO A 224      14.893    3.128   25.698  1.00 57.81  C
ATOM   1745  CD   PRO A 224      13.673    3.314   24.843  1.00 47.48  C
```

Figure 2 (Table 2 (page 39))

| | | | | | | | | | | |
|---|---|---|---|---|---|---|---|---|---|---|
| ATOM | 1746 | N   | THR | A | 225 | 16.685 |   1.143 | 21.884 | 1.00 | 50.13 N |
| ATOM | 1747 | CA  | THR | A | 225 | 16.859 |  -0.016 | 21.021 | 1.00 | 60.61 C |
| ATOM | 1748 | C   | THR | A | 225 | 17.598 |  -1.033 | 21.907 | 1.00 | 59.15 C |
| ATOM | 1749 | O   | THR | A | 225 | 18.533 |  -0.663 | 22.631 | 1.00 | 47.10 O |
| ATOM | 1750 | CB  | THR | A | 225 | 17.723 |   0.319 | 19.810 | 1.00 | 58.08 C |
| ATOM | 1751 | OG1 | THR | A | 225 | 17.027 |   1.259 | 18.985 | 1.00 | 83.82 O |
| ATOM | 1752 | CG2 | THR | A | 225 | 18.009 |  -0.934 | 19.003 | 1.00 | 73.24 C |
| ATOM | 1753 | N   | MET | A | 226 | 17.189 |  -2.296 | 21.862 | 1.00 | 52.21 N |
| ATOM | 1754 | CA  | MET | A | 226 | 17.824 |  -3.310 | 22.692 | 1.00 | 53.46 C |
| ATOM | 1755 | C   | MET | A | 226 | 18.721 |  -4.265 | 21.927 | 1.00 | 56.38 C |
| ATOM | 1756 | O   | MET | A | 226 | 18.417 |  -4.657 | 20.802 | 1.00 | 51.69 O |
| ATOM | 1757 | CB  | MET | A | 226 | 16.766 |  -4.149 | 23.397 | 1.00 | 61.02 C |
| ATOM | 1758 | CG  | MET | A | 226 | 15.711 |  -3.339 | 24.112 | 1.00 | 73.13 C |
| ATOM | 1759 | SD  | MET | A | 226 | 16.515 |  -2.409 | 25.388 | 1.00 | 79.72 S |
| ATOM | 1760 | CE  | MET | A | 226 | 17.052 |  -3.791 | 26.474 | 1.00 | 72.80 C |
| ATOM | 1761 | N   | SER | A | 227 | 19.821 |  -4.649 | 22.564 | 1.00 | 51.74 N |
| ATOM | 1762 | CA  | SER | A | 227 | 20.755 |  -5.617 | 22.003 | 1.00 | 57.86 C |
| ATOM | 1763 | C   | SER | A | 227 | 21.169 |  -6.496 | 23.187 | 1.00 | 61.93 C |
| ATOM | 1764 | O   | SER | A | 227 | 21.204 |  -6.024 | 24.332 | 1.00 | 60.05 O |
| ATOM | 1765 | CB  | SER | A | 227 | 21.961 |  -4.912 | 21.403 | 1.00 | 41.57 C |
| ATOM | 1766 | OG  | SER | A | 227 | 22.546 |  -4.056 | 22.355 | 1.00 | 62.88 O |
| ATOM | 1767 | N   | TRP | A | 228 | 21.472 |  -7.765 | 22.924 | 1.00 | 57.15 N |
| ATOM | 1768 | CA  | TRP | A | 228 | 21.840 |  -8.689 | 23.998 | 1.00 | 55.47 C |
| ATOM | 1769 | C   | TRP | A | 228 | 23.243 |  -9.290 | 23.899 | 1.00 | 59.04 C |
| ATOM | 1770 | O   | TRP | A | 228 | 23.856 |  -9.273 | 22.829 | 1.00 | 49.40 O |
| ATOM | 1771 | CB  | TRP | A | 228 | 20.842 |  -9.840 | 24.050 | 1.00 | 49.35 C |
| ATOM | 1772 | CG  | TRP | A | 228 | 19.435 |  -9.439 | 24.308 | 1.00 | 47.96 C |
| ATOM | 1773 | CD1 | TRP | A | 228 | 18.630 |  -8.695 | 23.494 | 1.00 | 53.38 C |
| ATOM | 1774 | CD2 | TRP | A | 228 | 18.654 |  -9.760 | 25.462 | 1.00 | 47.76 C |
| ATOM | 1775 | NE1 | TRP | A | 228 | 17.394 |  -8.537 | 24.067 | 1.00 | 52.08 N |
| ATOM | 1776 | CE2 | TRP | A | 228 | 17.379 |  -9.177 | 25.279 | 1.00 | 45.77 C |
| ATOM | 1777 | CE3 | TRP | A | 228 | 18.906 | -10.482 | 26.637 | 1.00 | 42.71 C |
| ATOM | 1778 | CZ2 | TRP | A | 228 | 16.355 |  -9.291 | 26.227 | 1.00 | 37.55 C |
| ATOM | 1779 | CZ3 | TRP | A | 228 | 17.887 | -10.598 | 27.586 | 1.00 | 45.83 C |
| ATOM | 1780 | CH2 | TRP | A | 228 | 16.625 | -10.004 | 27.373 | 1.00 | 50.85 C |
| ATOM | 1781 | N   | THR | A | 229 | 23.749 |  -9.795 | 25.027 | 1.00 | 58.07 N |
| ATOM | 1782 | CA  | THR | A | 229 | 25.047 | -10.474 | 25.057 | 1.00 | 60.10 C |
| ATOM | 1783 | C   | THR | A | 229 | 24.918 | -11.741 | 25.902 | 1.00 | 61.83 C |
| ATOM | 1784 | O   | THR | A | 229 | 24.132 | -11.787 | 26.868 | 1.00 | 54.86 O |
| ATOM | 1785 | CB  | THR | A | 229 | 26.191 |  -9.610 | 25.652 | 1.00 | 53.98 C |
| ATOM | 1786 | OG1 | THR | A | 229 | 25.882 |  -9.252 | 26.999 | 1.00 | 57.01 O |
| ATOM | 1787 | CG2 | THR | A | 229 | 26.418 |  -8.373 | 24.816 | 1.00 | 57.89 C |
| ATOM | 1788 | N   | LYS | A | 230 | 25.677 | -12.765 | 25.515 | 1.00 | 58.82 N |
| ATOM | 1789 | CA  | LYS | A | 230 | 25.684 | -14.043 | 26.217 | 1.00 | 58.37 C |
| ATOM | 1790 | C   | LYS | A | 230 | 27.088 | -14.147 | 26.792 | 1.00 | 52.83 C |
| ATOM | 1791 | O   | LYS | A | 230 | 28.066 | -14.266 | 26.054 | 1.00 | 54.49 O |
| ATOM | 1792 | CB  | LYS | A | 230 | 25.396 | -15.173 | 25.227 | 1.00 | 55.01 C |
| ATOM | 1793 | CG  | LYS | A | 230 | 25.113 | -16.539 | 25.849 | 1.00 | 45.56 C |
| ATOM | 1794 | CD  | LYS | A | 230 | 24.973 | -17.615 | 24.757 | 1.00 | 59.41 C |
| ATOM | 1795 | CE  | LYS | A | 230 | 24.803 | -19.019 | 25.339 | 1.00 | 62.34 C |
| ATOM | 1796 | NZ  | LYS | A | 230 | 24.460 | -20.050 | 24.304 | 1.00 | 59.23 N |
| ATOM | 1797 | N   | ASP | A | 231 | 27.183 | -14.078 | 28.115 | 1.00 | 61.62 N |
| ATOM | 1798 | CA  | ASP | A | 231 | 28.479 | -14.105 | 28.781 | 1.00 | 69.33 C |
| ATOM | 1799 | C   | ASP | A | 231 | 29.439 | -13.118 | 28.113 | 1.00 | 69.66 C |
| ATOM | 1800 | O   | ASP | A | 231 | 30.612 | -13.429 | 27.916 | 1.00 | 73.37 O |
| ATOM | 1801 | CB  | ASP | A | 231 | 29.096 | -15.509 | 28.754 | 1.00 | 67.95 C |

Figure 2 (Table 2 (page 40))

```
ATOM   1802  CG   ASP A 231      28.359 -16.492  29.645  1.00 76.63  C
ATOM   1803  OD1  ASP A 231      27.830 -16.069  30.697  1.00 73.37  O
ATOM   1804  OD2  ASP A 231      28.327 -17.692  29.295  1.00 73.07  O
ATOM   1805  N    GLY A 232      28.939 -11.933  27.766  1.00 69.81  N
ATOM   1806  CA   GLY A 232      29.780 -10.925  27.147  1.00 62.92  C
ATOM   1807  C    GLY A 232      29.815 -10.953  25.633  1.00 57.21  C
ATOM   1808  O    GLY A 232      30.217  -9.985  24.999  1.00 64.11  O
ATOM   1809  N    GLU A 233      29.398 -12.058  25.039  1.00 60.24  N
ATOM   1810  CA   GLU A 233      29.407 -12.163  23.587  1.00 67.77  C
ATOM   1811  C    GLU A 233      28.086 -11.753  22.977  1.00 69.76  C
ATOM   1812  O    GLU A 233      27.019 -12.146  23.437  1.00 67.85  O
ATOM   1813  CB   GLU A 233      29.721 -13.589  23.156  1.00 73.47  C
ATOM   1814  CG   GLU A 233      31.174 -13.980  23.298  1.00 93.05  C
ATOM   1815  CD   GLU A 233      32.100 -13.154  22.416  1.00101.69  C
ATOM   1816  OE1  GLU A 233      31.753 -12.894  21.241  1.00104.10  O
ATOM   1817  OE2  GLU A 233      33.189 -12.771  22.898  1.00105.15  O
ATOM   1818  N    PRO A 234      28.146 -10.986  21.894  1.00 69.71  N
ATOM   1819  CA   PRO A 234      26.928 -10.527  21.227  1.00 69.07  C
ATOM   1820  C    PRO A 234      26.042 -11.660  20.747  1.00 63.95  C
ATOM   1821  O    PRO A 234      26.516 -12.774  20.513  1.00 68.33  O
ATOM   1822  CB   PRO A 234      27.463  -9.717  20.047  1.00 74.23  C
ATOM   1823  CG   PRO A 234      28.863  -9.346  20.458  1.00 78.24  C
ATOM   1824  CD   PRO A 234      29.349 -10.575  21.151  1.00 73.22  C
ATOM   1825  N    ILE A 235      24.756 -11.361  20.589  1.00 60.42  N
ATOM   1826  CA   ILE A 235      23.819 -12.347  20.075  1.00 59.30  C
ATOM   1827  C    ILE A 235      23.091 -11.707  18.887  1.00 73.94  C
ATOM   1828  O    ILE A 235      22.292 -10.780  19.062  1.00 69.18  O
ATOM   1829  CB   ILE A 235      22.785 -12.748  21.118  1.00 58.75  C
ATOM   1830  CG1  ILE A 235      23.480 -13.103  22.435  1.00 60.61  C
ATOM   1831  CG2  ILE A 235      21.986 -13.935  20.602  1.00 54.52  C
ATOM   1832  CD1  ILE A 235      22.535 -13.237  23.598  1.00 58.31  C
ATOM   1833  N    GLU A 236      23.341 -12.205  17.679  1.00 80.94  N
ATOM   1834  CA   GLU A 236      22.742 -11.605  16.488  1.00 90.13  C
ATOM   1835  C    GLU A 236      21.234 -11.755  16.308  1.00 93.13  C
ATOM   1836  O    GLU A 236      20.685 -12.857  16.339  1.00 89.58  O
ATOM   1837  CB   GLU A 236      23.493 -12.094  15.252  1.00 98.19  C
ATOM   1838  CG   GLU A 236      25.017 -12.039  15.429  1.00107.77  C
ATOM   1839  CD   GLU A 236      25.542 -10.662  15.844  1.00115.02  C
ATOM   1840  OE1  GLU A 236      24.988 -10.055  16.788  1.00121.81  O
ATOM   1841  OE2  GLU A 236      26.526 -10.191  15.233  1.00116.63  O
ATOM   1842  N    ASN A 237      20.585 -10.606  16.115  1.00 98.73  N
ATOM   1843  CA   ASN A 237      19.136 -10.494  15.944  1.00104.56  C
ATOM   1844  C    ASN A 237      18.609 -11.196  14.686  1.00110.81  C
ATOM   1845  O    ASN A 237      17.530 -11.792  14.705  1.00112.81  O
ATOM   1846  CB   ASN A 237      18.759  -9.004  15.930  1.00100.46  C
ATOM   1847  CG   ASN A 237      17.268  -8.761  16.142  1.00100.48  C
ATOM   1848  OD1  ASN A 237      16.868  -7.689  16.600  1.00 96.36  O
ATOM   1849  ND2  ASN A 237      16.443  -9.747  15.798  1.00 97.08  N
ATOM   1850  N    GLU A 238      19.382 -11.111  13.607  1.00114.86  N
ATOM   1851  CA   GLU A 238      19.072 -11.709  12.303  1.00120.04  C
ATOM   1852  C    GLU A 238      17.688 -12.328  12.095  1.00121.21  C
ATOM   1853  O    GLU A 238      16.975 -11.855  11.181  1.00121.72  O
ATOM   1854  CB   GLU A 238      20.152 -12.736  11.963  1.00121.17  C
ATOM   1855  CG   GLU A 238      21.557 -12.228  12.238  1.00126.14  C
ATOM   1856  CD   GLU A 238      21.808 -10.840  11.662  1.00130.48  C
ATOM   1857  OE1  GLU A 238      21.090  -9.885  12.034  1.00132.56  O
```

Figure 2 (Table 2 (page 41))

```
ATOM   1858  OE2 GLU A 238      22.731 -10.705  10.837  1.00134.55 O
ATOM   1859  N   ASP A 241      18.070 -14.713   9.305  1.00127.03 N
ATOM   1860  CA  ASP A 241      17.685 -16.080   9.767  1.00127.98 C
ATOM   1861  C   ASP A 241      17.960 -16.274  11.255  1.00129.18 C
ATOM   1862  O   ASP A 241      18.938 -15.754  11.803  1.00129.01 O
ATOM   1863  CB  ASP A 241      18.443 -17.152   8.972  1.00124.42 C
ATOM   1864  CG  ASP A 241      18.044 -18.574   9.365  1.00123.20 C
ATOM   1865  OD1 ASP A 241      18.114 -18.916  10.570  1.00119.17 O
ATOM   1866  OD2 ASP A 241      17.664 -19.356   8.464  1.00120.27 O
ATOM   1867  N   ASP A 242      17.080 -17.043  11.888  1.00129.87 N
ATOM   1868  CA  ASP A 242      17.157 -17.357  13.310  1.00128.52 C
ATOM   1869  C   ASP A 242      16.420 -18.676  13.544  1.00124.12 C
ATOM   1870  O   ASP A 242      15.291 -18.851  13.081  1.00127.28 O
ATOM   1871  CB  ASP A 242      16.509 -16.230  14.128  1.00134.37 C
ATOM   1872  CG  ASP A 242      15.076 -15.931  13.693  1.00137.89 C
ATOM   1873  OD1 ASP A 242      14.695 -16.306  12.560  1.00139.91 O
ATOM   1874  OD2 ASP A 242      14.335 -15.302  14.484  1.00138.48 O
ATOM   1875  N   GLU A 243      17.053 -19.614  14.237  1.00115.47 N
ATOM   1876  CA  GLU A 243      16.401 -20.892  14.492  1.00108.81 C
ATOM   1877  C   GLU A 243      16.219 -21.065  15.984  1.00101.77 C
ATOM   1878  O   GLU A 243      15.232 -21.637  16.453  1.00 97.50 O
ATOM   1879  CB  GLU A 243      17.243 -22.056  13.957  1.00113.03 C
ATOM   1880  CG  GLU A 243      18.587 -22.269  14.665  1.00119.77 C
ATOM   1881  CD  GLU A 243      19.736 -21.500  14.022  1.00123.96 C
ATOM   1882  OE1 GLU A 243      20.004 -21.723  12.821  1.00128.49 O
ATOM   1883  OE2 GLU A 243      20.380 -20.682  14.716  1.00125.21 O
ATOM   1884  N   LYS A 244      17.193 -20.552  16.719  1.00 90.55 N
ATOM   1885  CA  LYS A 244      17.196 -20.652  18.159  1.00 87.36 C
ATOM   1886  C   LYS A 244      16.847 -19.342  18.851  1.00 78.94 C
ATOM   1887  O   LYS A 244      15.944 -19.299  19.681  1.00 79.48 O
ATOM   1888  CB  LYS A 244      18.567 -21.157  18.623  1.00 85.94 C
ATOM   1889  CG  LYS A 244      18.973 -20.687  20.009  1.00 90.77 C
ATOM   1890  CD  LYS A 244      20.222 -21.392  20.527  1.00 85.35 C
ATOM   1891  CE  LYS A 244      19.960 -22.872  20.764  1.00 85.15 C
ATOM   1892  NZ  LYS A 244      18.698 -23.096  21.533  1.00 79.01 N
ATOM   1893  N   HIS A 245      17.566 -18.279  18.510  1.00 72.67 N
ATOM   1894  CA  HIS A 245      17.332 -16.978  19.121  1.00 73.65 C
ATOM   1895  C   HIS A 245      16.275 -16.150  18.398  1.00 71.43 C
ATOM   1896  O   HIS A 245      16.483 -15.726  17.264  1.00 73.85 O
ATOM   1897  CB  HIS A 245      18.636 -16.191  19.174  1.00 62.45 C
ATOM   1898  CG  HIS A 245      19.712 -16.860  19.968  1.00 73.56 C
ATOM   1899  ND1 HIS A 245      19.566 -17.183  21.301  1.00 75.57 N
ATOM   1900  CD2 HIS A 245      20.963 -17.251  19.624  1.00 74.25 C
ATOM   1901  CE1 HIS A 245      20.680 -17.740  21.742  1.00 69.91 C
ATOM   1902  NE2 HIS A 245      21.542 -17.792  20.747  1.00 78.21 N
ATOM   1903  N   ILE A 246      15.151 -15.907  19.066  1.00 71.28 N
ATOM   1904  CA  ILE A 246      14.061 -15.117  18.492  1.00 67.47 C
ATOM   1905  C   ILE A 246      13.820 -13.823  19.279  1.00 68.54 C
ATOM   1906  O   ILE A 246      13.465 -13.871  20.459  1.00 56.11 O
ATOM   1907  CB  ILE A 246      12.746 -15.912  18.494  1.00 71.39 C
ATOM   1908  CG1 ILE A 246      12.953 -17.270  17.829  1.00 73.66 C
ATOM   1909  CG2 ILE A 246      11.656 -15.114  17.803  1.00 69.42 C
ATOM   1910  CD1 ILE A 246      13.544 -17.182  16.451  1.00 82.71 C
ATOM   1911  N   PHE A 247      13.991 -12.675  18.625  1.00 57.64 N
ATOM   1912  CA  PHE A 247      13.783 -11.395  19.286  1.00 57.66 C
ATOM   1913  C   PHE A 247      12.444 -10.766  19.000  1.00 59.75 C
```

Figure 2 (Table 2 (page 42))

```
ATOM   1914  O    PHE A 247      11.842 -11.003  17.955  1.00 71.91  O
ATOM   1915  CB   PHE A 247      14.831 -10.386  18.866  1.00 58.61  C
ATOM   1916  CG   PHE A 247      16.205 -10.761  19.252  1.00 55.18  C
ATOM   1917  CD1  PHE A 247      16.931 -11.663  18.486  1.00 63.52  C
ATOM   1918  CD2  PHE A 247      16.791 -10.195  20.375  1.00 64.94  C
ATOM   1919  CE1  PHE A 247      18.233 -11.994  18.836  1.00 56.98  C
ATOM   1920  CE2  PHE A 247      18.084 -10.515  20.735  1.00 62.89  C
ATOM   1921  CZ   PHE A 247      18.813 -11.416  19.963  1.00 69.14  C
ATOM   1922  N    SER A 248      11.984  -9.948  19.939  1.00 60.62  N
ATOM   1923  CA   SER A 248      10.741  -9.211  19.761  1.00 59.42  C
ATOM   1924  C    SER A 248      11.135  -8.035  18.848  1.00 58.07  C
ATOM   1925  O    SER A 248      12.324  -7.793  18.605  1.00 50.63  O
ATOM   1926  CB   SER A 248      10.238  -8.684  21.107  1.00 51.67  C
ATOM   1927  OG   SER A 248      11.212  -7.849  21.713  1.00 56.47  O
ATOM   1928  N    ASP A 249      10.156  -7.286  18.364  1.00 62.87  N
ATOM   1929  CA   ASP A 249      10.433  -6.168  17.461  1.00 68.58  C
ATOM   1930  C    ASP A 249      11.414  -5.157  18.016  1.00 71.42  C
ATOM   1931  O    ASP A 249      12.289  -4.649  17.304  1.00 70.32  O
ATOM   1932  CB   ASP A 249       9.113  -5.519  17.102  1.00 78.97  C
ATOM   1933  CG   ASP A 249       8.122  -6.538  16.598  1.00 85.41  C
ATOM   1934  OD1  ASP A 249       8.266  -6.986  15.438  1.00 90.50  O
ATOM   1935  OD2  ASP A 249       7.218  -6.926  17.370  1.00 85.77  O
ATOM   1936  N    ASP A 250      11.274  -4.875  19.297  1.00 71.27  N
ATOM   1937  CA   ASP A 250      12.159  -3.942  19.964  1.00 74.17  C
ATOM   1938  C    ASP A 250      13.358  -4.713  20.521  1.00 70.10  C
ATOM   1939  O    ASP A 250      14.337  -4.113  20.971  1.00 70.84  O
ATOM   1940  CB   ASP A 250      11.390  -3.284  21.100  1.00 82.42  C
ATOM   1941  CG   ASP A 250      10.583  -4.296  21.895  1.00 86.25  C
ATOM   1942  OD1  ASP A 250      10.204  -5.350  21.328  1.00 87.71  O
ATOM   1943  OD2  ASP A 250      10.316  -4.044  23.082  1.00 99.42  O
ATOM   1944  N    SER A 251      13.266  -6.044  20.478  1.00 61.34  N
ATOM   1945  CA   SER A 251      14.301  -6.932  21.005  1.00 60.93  C
ATOM   1946  C    SER A 251      14.357  -6.787  22.529  1.00 55.43  C
ATOM   1947  O    SER A 251      15.398  -6.997  23.149  1.00 54.55  O
ATOM   1948  CB   SER A 251      15.667  -6.615  20.386  1.00 56.47  C
ATOM   1949  OG   SER A 251      15.608  -6.719  18.971  1.00 68.26  O
ATOM   1950  N    SER A 252      13.222  -6.419  23.120  1.00 44.12  N
ATOM   1951  CA   SER A 252      13.132  -6.262  24.565  1.00 54.67  C
ATOM   1952  C    SER A 252      12.961  -7.666  25.142  1.00 45.19  C
ATOM   1953  O    SER A 252      13.231  -7.900  26.321  1.00 45.23  O
ATOM   1954  CB   SER A 252      11.948  -5.359  24.957  1.00 50.26  C
ATOM   1955  OG   SER A 252      10.705  -6.019  24.785  1.00 68.26  O
ATOM   1956  N    GLU A 253      12.511  -8.586  24.288  1.00 39.14  N
ATOM   1957  CA   GLU A 253      12.351  -9.984  24.655  1.00 42.86  C
ATOM   1958  C    GLU A 253      13.245 -10.847  23.787  1.00 55.42  C
ATOM   1959  O    GLU A 253      13.322 -10.649  22.573  1.00 55.46  O
ATOM   1960  CB   GLU A 253      10.924 -10.475  24.459  1.00 46.35  C
ATOM   1961  CG   GLU A 253       9.898  -9.823  25.335  1.00 52.21  C
ATOM   1962  CD   GLU A 253       8.629 -10.640  25.406  1.00 55.68  C
ATOM   1963  OE1  GLU A 253       8.464 -11.550  24.569  1.00 60.84  O
ATOM   1964  OE2  GLU A 253       7.792 -10.370  26.296  1.00 63.61  O
ATOM   1965  N    LEU A 254      13.925 -11.798  24.423  1.00 49.11  N
ATOM   1966  CA   LEU A 254      14.793 -12.741  23.730  1.00 43.78  C
ATOM   1967  C    LEU A 254      14.260 -14.129  24.052  1.00 54.16  C
ATOM   1968  O    LEU A 254      14.179 -14.516  25.221  1.00 49.96  O
ATOM   1969  CB   LEU A 254      16.240 -12.617  24.212  1.00 48.13  C
```

Figure 2 (Table 2 (page 43))

```
ATOM   1970  CG   LEU A 254      17.132  -13.793   23.786  1.00  61.15  C
ATOM   1971  CD1  LEU A 254      17.129  -13.902   22.264  1.00  56.30  C
ATOM   1972  CD2  LEU A 254      18.561  -13.622   24.314  1.00  45.18  C
ATOM   1973  N    THR A 255      13.874  -14.873   23.024  1.00  52.09  N
ATOM   1974  CA   THR A 255      13.343  -16.214   23.233  1.00  55.30  C
ATOM   1975  C    THR A 255      14.371  -17.254   22.822  1.00  57.05  C
ATOM   1976  O    THR A 255      14.809  -17.279   21.677  1.00  56.25  O
ATOM   1977  CB   THR A 255      12.050  -16.444   22.419  1.00  62.05  C
ATOM   1978  OG1  THR A 255      10.999  -15.630   22.951  1.00  66.84  O
ATOM   1979  CG2  THR A 255      11.625  -17.908   22.491  1.00  69.28  C
ATOM   1980  N    ILE A 256      14.784  -18.085   23.774  1.00  57.59  N
ATOM   1981  CA   ILE A 256      15.740  -19.140   23.482  1.00  53.88  C
ATOM   1982  C    ILE A 256      14.863  -20.362   23.227  1.00  55.73  C
ATOM   1983  O    ILE A 256      14.031  -20.740   24.050  1.00  53.74  O
ATOM   1984  CB   ILE A 256      16.721  -19.325   24.635  1.00  60.39  C
ATOM   1985  CG1  ILE A 256      17.478  -18.003   24.865  1.00  49.75  C
ATOM   1986  CG2  ILE A 256      17.729  -20.408   24.263  1.00  67.76  C
ATOM   1987  CD1  ILE A 256      18.337  -17.959   26.113  1.00  52.15  C
ATOM   1988  N    ARG A 257      15.049  -20.980   22.070  1.00  60.13  N
ATOM   1989  CA   ARG A 257      14.153  -22.051   21.657  1.00  71.50  C
ATOM   1990  C    ARG A 257      14.176  -23.516   22.065  1.00  69.32  C
ATOM   1991  O    ARG A 257      13.160  -24.049   22.523  1.00  80.18  O
ATOM   1992  CB   ARG A 257      14.007  -21.955   20.148  1.00  74.93  C
ATOM   1993  CG   ARG A 257      13.281  -20.678   19.720  1.00  86.48  C
ATOM   1994  CD   ARG A 257      11.972  -21.046   19.067  1.00  94.98  C
ATOM   1995  NE   ARG A 257      12.243  -22.177   18.190  1.00 102.55  N
ATOM   1996  CZ   ARG A 257      11.403  -23.175   17.936  1.00 101.10  C
ATOM   1997  NH1  ARG A 257      10.194  -23.198   18.481  1.00  98.39  N
ATOM   1998  NH2  ARG A 257      11.805  -24.190   17.182  1.00  99.09  N
ATOM   1999  N    ASN A 258      15.287  -24.195   21.864  1.00  61.69  N
ATOM   2000  CA   ASN A 258      15.340  -25.602   22.253  1.00  64.49  C
ATOM   2001  C    ASN A 258      16.465  -25.618   23.247  1.00  62.07  C
ATOM   2002  O    ASN A 258      17.624  -25.892   22.925  1.00  55.85  O
ATOM   2003  CB   ASN A 258      15.636  -26.481   21.041  1.00  66.15  C
ATOM   2004  CG   ASN A 258      14.404  -26.716   20.191  1.00  68.75  C
ATOM   2005  OD1  ASN A 258      13.379  -27.234   20.673  1.00  64.25  O
ATOM   2006  ND2  ASN A 258      14.484  -26.329   18.926  1.00  70.00  N
ATOM   2007  N    VAL A 259      16.094  -25.272   24.468  1.00  62.90  N
ATOM   2008  CA   VAL A 259      17.049  -25.157   25.545  1.00  65.80  C
ATOM   2009  C    VAL A 259      17.876  -26.384   25.872  1.00  58.88  C
ATOM   2010  O    VAL A 259      17.365  -27.483   26.054  1.00  56.71  O
ATOM   2011  CB   VAL A 259      16.370  -24.703   26.858  1.00  64.49  C
ATOM   2012  CG1  VAL A 259      17.433  -24.328   27.883  1.00  63.04  C
ATOM   2013  CG2  VAL A 259      15.437  -23.546   26.599  1.00  62.50  C
ATOM   2014  N    ASP A 260      19.176  -26.159   25.951  1.00  60.37  N
ATOM   2015  CA   ASP A 260      20.110  -27.191   26.329  1.00  64.76  C
ATOM   2016  C    ASP A 260      21.141  -26.491   27.190  1.00  63.70  C
ATOM   2017  O    ASP A 260      21.185  -25.257   27.253  1.00  55.60  O
ATOM   2018  CB   ASP A 260      20.785  -27.829   25.120  1.00  61.25  C
ATOM   2019  CG   ASP A 260      21.602  -26.844   24.322  1.00  68.49  C
ATOM   2020  OD1  ASP A 260      22.091  -25.847   24.896  1.00  68.44  O
ATOM   2021  OD2  ASP A 260      21.775  -27.084   23.110  1.00  81.31  O
ATOM   2022  N    LYS A 261      21.986  -27.277   27.832  1.00  57.12  N
ATOM   2023  CA   LYS A 261      22.985  -26.711   28.711  1.00  51.64  C
ATOM   2024  C    LYS A 261      23.832  -25.591   28.141  1.00  46.97  C
ATOM   2025  O    LYS A 261      24.335  -24.757   28.895  1.00  48.66  O
```

Figure 2 (Table 2 (page 44))

```
ATOM   2026  CB  LYS A 261      23.874 -27.828  29.258  1.00 52.71  C
ATOM   2027  CG  LYS A 261      23.193 -28.612  30.358  1.00 61.87  C
ATOM   2028  CD  LYS A 261      24.105 -29.669  30.947  1.00 73.37  C
ATOM   2029  CE  LYS A 261      23.600 -30.117  32.308  1.00 76.85  C
ATOM   2030  NZ  LYS A 261      23.680 -29.007  33.304  1.00 77.99  N
ATOM   2031  N   ASN A 262      24.004 -25.534  26.827  1.00 51.62  N
ATOM   2032  CA  ASN A 262      24.834 -24.464  26.278  1.00 50.71  C
ATOM   2033  C   ASN A 262      24.189 -23.099  26.414  1.00 49.52  C
ATOM   2034  O   ASN A 262      24.835 -22.073  26.224  1.00 44.29  O
ATOM   2035  CB  ASN A 262      25.160 -24.707  24.815  1.00 63.69  C
ATOM   2036  CG  ASN A 262      26.545 -25.256  24.636  1.00 76.99  C
ATOM   2037  OD1 ASN A 262      27.466 -24.881  25.368  1.00 88.03  O
ATOM   2038  ND2 ASN A 262      26.713 -26.145  23.664  1.00 83.71  N
ATOM   2039  N   ASP A 263      22.911 -23.100  26.755  1.00 43.87  N
ATOM   2040  CA  ASP A 263      22.173 -21.864  26.915  1.00 49.29  C
ATOM   2041  C   ASP A 263      22.341 -21.257  28.307  1.00 56.55  C
ATOM   2042  O   ASP A 263      21.984 -20.103  28.532  1.00 45.77  O
ATOM   2043  CB  ASP A 263      20.705 -22.115  26.593  1.00 46.15  C
ATOM   2044  CG  ASP A 263      20.502 -22.558  25.148  1.00 47.16  C
ATOM   2045  OD1 ASP A 263      21.208 -22.006  24.272  1.00 50.06  O
ATOM   2046  OD2 ASP A 263      19.642 -23.440  24.894  1.00 53.96  O
ATOM   2047  N   GLU A 264      22.886 -22.033  29.241  1.00 52.20  N
ATOM   2048  CA  GLU A 264      23.126 -21.517  30.580  1.00 50.47  C
ATOM   2049  C   GLU A 264      24.217 -20.455  30.464  1.00 55.25  C
ATOM   2050  O   GLU A 264      25.286 -20.722  29.917  1.00 51.52  O
ATOM   2051  CB  GLU A 264      23.575 -22.644  31.526  1.00 49.18  C
ATOM   2052  CG  GLU A 264      23.865 -22.150  32.948  1.00 56.13  C
ATOM   2053  CD  GLU A 264      24.070 -23.270  33.968  1.00 59.96  C
ATOM   2054  OE1 GLU A 264      23.144 -24.088  34.166  1.00 52.27  O
ATOM   2055  OE2 GLU A 264      25.161 -23.319  34.575  1.00 63.96  O
ATOM   2056  N   ALA A 265      23.936 -19.254  30.971  1.00 50.58  N
ATOM   2057  CA  ALA A 265      24.882 -18.143  30.932  1.00 49.56  C
ATOM   2058  C   ALA A 265      24.285 -16.892  31.553  1.00 44.28  C
ATOM   2059  O   ALA A 265      23.138 -16.876  32.020  1.00 44.60  O
ATOM   2060  CB  ALA A 265      25.275 -17.839  29.485  1.00 55.17  C
ATOM   2061  N   GLU A 266      25.084 -15.837  31.565  1.00 46.95  N
ATOM   2062  CA  GLU A 266      24.597 -14.566  32.052  1.00 58.95  C
ATOM   2063  C   GLU A 266      24.233 -13.782  30.796  1.00 54.06  C
ATOM   2064  O   GLU A 266      25.077 -13.547  29.937  1.00 49.16  O
ATOM   2065  CB  GLU A 266      25.662 -13.784  32.824  1.00 49.59  C
ATOM   2066  CG  GLU A 266      25.188 -12.371  33.185  1.00 68.76  C
ATOM   2067  CD  GLU A 266      26.312 -11.461  33.655  1.00 79.04  C
ATOM   2068  OE1 GLU A 266      27.442 -11.585  33.135  1.00 92.30  O
ATOM   2069  OE2 GLU A 266      26.071 -10.604  34.534  1.00 84.00  O
ATOM   2070  N   TYR A 267      22.969 -13.405  30.682  1.00 56.50  N
ATOM   2071  CA  TYR A 267      22.539 -12.620  29.539  1.00 53.55  C
ATOM   2072  C   TYR A 267      22.379 -11.175  29.973  1.00 53.33  C
ATOM   2073  O   TYR A 267      21.857 -10.899  31.051  1.00 56.26  O
ATOM   2074  CB  TYR A 267      21.216 -13.131  29.000  1.00 41.05  C
ATOM   2075  CG  TYR A 267      21.302 -14.503  28.392  1.00 52.19  C
ATOM   2076  CD1 TYR A 267      21.310 -15.645  29.200  1.00 46.18  C
ATOM   2077  CD2 TYR A 267      21.374 -14.669  27.010  1.00 42.85  C
ATOM   2078  CE1 TYR A 267      21.385 -16.907  28.649  1.00 36.41  C
ATOM   2079  CE2 TYR A 267      21.447 -15.926  26.447  1.00 47.87  C
ATOM   2080  CZ  TYR A 267      21.454 -17.043  27.269  1.00 46.20  C
ATOM   2081  OH  TYR A 267      21.534 -18.289  26.709  1.00 46.42  O
```

Figure 2 (Table 2 (page 45))

```
ATOM   2082  N    VAL A 268      22.849  -10.259   29.134  1.00 54.55           N
ATOM   2083  CA   VAL A 268      22.744   -8.833   29.420  1.00 51.27           C
ATOM   2084  C    VAL A 268      21.939   -8.121   28.325  1.00 53.04           C
ATOM   2085  O    VAL A 268      22.238   -8.268   27.140  1.00 49.32           O
ATOM   2086  CB   VAL A 268      24.149   -8.164   29.507  1.00 51.72           C
ATOM   2087  CG1  VAL A 268      24.008   -6.653   29.697  1.00 53.25           C
ATOM   2088  CG2  VAL A 268      24.954   -8.757   30.667  1.00 53.72           C
ATOM   2089  N    CYS A 269      20.909   -7.372   28.708  1.00 47.02           N
ATOM   2090  CA   CYS A 269      20.130   -6.631   27.712  1.00 46.07           C
ATOM   2091  C    CYS A 269      20.572   -5.192   27.825  1.00 48.28           C
ATOM   2092  O    CYS A 269      20.513   -4.568   28.893  1.00 54.75           O
ATOM   2093  CB   CYS A 269      18.645   -6.725   27.972  1.00 47.89           C
ATOM   2094  SG   CYS A 269      18.154   -6.060   29.588  1.00 57.20           S
ATOM   2095  N    ILE A 270      21.040   -4.684   26.705  1.00 44.49           N
ATOM   2096  CA   ILE A 270      21.542   -3.334   26.618  1.00 54.21           C
ATOM   2097  C    ILE A 270      20.492   -2.429   25.984  1.00 51.98           C
ATOM   2098  O    ILE A 270      20.057   -2.665   24.858  1.00 52.39           O
ATOM   2099  CB   ILE A 270      22.804   -3.333   25.757  1.00 58.16           C
ATOM   2100  CG1  ILE A 270      23.777   -4.385   26.287  1.00 59.14           C
ATOM   2101  CG2  ILE A 270      23.451   -1.964   25.768  1.00 58.07           C
ATOM   2102  CD1  ILE A 270      24.907   -4.698   25.332  1.00 62.65           C
ATOM   2103  N    ALA A 271      20.068   -1.413   26.725  1.00 46.08           N
ATOM   2104  CA   ALA A 271      19.081   -0.463   26.220  1.00 43.82           C
ATOM   2105  C    ALA A 271      19.811    0.838   25.863  1.00 41.91           C
ATOM   2106  O    ALA A 271      20.461    1.454   26.713  1.00 41.51           O
ATOM   2107  CB   ALA A 271      18.010   -0.212   27.272  1.00 40.50           C
ATOM   2108  N    GLU A 272      19.709    1.242   24.601  1.00 43.98           N
ATOM   2109  CA   GLU A 272      20.375    2.453   24.128  1.00 50.40           C
ATOM   2110  C    GLU A 272      19.526    3.346   23.255  1.00 40.39           C
ATOM   2111  O    GLU A 272      18.635    2.880   22.548  1.00 43.66           O
ATOM   2112  CB   GLU A 272      21.589    2.115   23.251  1.00 46.89           C
ATOM   2113  CG   GLU A 272      22.738    1.366   23.863  1.00 76.32           C
ATOM   2114  CD   GLU A 272      23.835    1.101   22.832  1.00 88.35           C
ATOM   2115  OE1  GLU A 272      23.496    0.886   21.643  1.00 95.66           O
ATOM   2116  OE2  GLU A 272      25.031    1.096   23.206  1.00 91.47           O
ATOM   2117  N    ASN A 273      19.843    4.635   23.316  1.00 46.76           N
ATOM   2118  CA   ASN A 273      19.260    5.648   22.438  1.00 47.59           C
ATOM   2119  C    ASN A 273      20.335    6.718   22.340  1.00 52.11           C
ATOM   2120  O    ASN A 273      21.366    6.622   23.008  1.00 44.76           O
ATOM   2121  CB   ASN A 273      17.897    6.201   22.916  1.00 46.27           C
ATOM   2122  CG   ASN A 273      17.964    6.980   24.211  1.00 44.51           C
ATOM   2123  OD1  ASN A 273      19.012    7.471   24.611  1.00 44.37           O
ATOM   2124  ND2  ASN A 273      16.808    7.126   24.866  1.00 38.00           N
ATOM   2125  N    LYS A 274      20.128    7.723   21.504  1.00 56.80           N
ATOM   2126  CA   LYS A 274      21.154    8.740   21.317  1.00 51.83           C
ATOM   2127  C    LYS A 274      21.618    9.485   22.567  1.00 54.11           C
ATOM   2128  O    LYS A 274      22.667   10.123   22.545  1.00 58.51           O
ATOM   2129  CB   LYS A 274      20.718    9.742   20.238  1.00 55.02           C
ATOM   2130  CG   LYS A 274      19.590   10.658   20.644  1.00 47.96           C
ATOM   2131  CD   LYS A 274      18.892   11.218   19.403  1.00 52.54           C
ATOM   2132  CE   LYS A 274      19.784   12.175   18.622  1.00 65.50           C
ATOM   2133  NZ   LYS A 274      19.120   12.652   17.364  1.00 68.41           N
ATOM   2134  N    ALA A 275      20.869    9.403   23.659  1.00 47.65           N
ATOM   2135  CA   ALA A 275      21.275   10.100   24.868  1.00 48.41           C
ATOM   2136  C    ALA A 275      21.944    9.233   25.930  1.00 49.48           C
ATOM   2137  O    ALA A 275      22.294    9.735   26.988  1.00 50.34           O
```

Figure 2 (Table 2 (page 46))

```
ATOM   2138  CB   ALA A 275      20.084  10.814  25.487  1.00 44.55  C
ATOM   2139  N    GLY A 276      22.122   7.942  25.691  1.00 49.34  N
ATOM   2140  CA   GLY A 276      22.755   7.177  26.746  1.00 51.88  C
ATOM   2141  C    GLY A 276      22.482   5.694  26.738  1.00 50.21  C
ATOM   2142  O    GLY A 276      21.907   5.164  25.779  1.00 51.48  O
ATOM   2143  N    GLU A 277      22.868   5.026  27.824  1.00 50.99  N
ATOM   2144  CA   GLU A 277      22.696   3.586  27.906  1.00 53.05  C
ATOM   2145  C    GLU A 277      22.598   3.056  29.316  1.00 51.11  C
ATOM   2146  O    GLU A 277      23.116   3.655  30.249  1.00 52.32  O
ATOM   2147  CB   GLU A 277      23.873   2.915  27.194  1.00 58.98  C
ATOM   2148  CG   GLU A 277      23.900   1.389  27.218  1.00 74.31  C
ATOM   2149  CD   GLU A 277      24.570   0.797  28.462  1.00 89.46  C
ATOM   2150  OE1  GLU A 277      25.277   1.537  29.183  1.00 96.28  O
ATOM   2151  OE2  GLU A 277      24.398  -0.420  28.705  1.00 89.19  O
ATOM   2152  N    GLN A 278      21.907   1.927  29.453  1.00 49.66  N
ATOM   2153  CA   GLN A 278      21.783   1.228  30.724  1.00 45.13  C
ATOM   2154  C    GLN A 278      21.513  -0.239  30.415  1.00 50.42  C
ATOM   2155  O    GLN A 278      20.877  -0.568  29.417  1.00 46.75  O
ATOM   2156  CB   GLN A 278      20.662   1.789  31.607  1.00 48.09  C
ATOM   2157  CG   GLN A 278      20.812   1.327  33.064  1.00 46.69  C
ATOM   2158  CD   GLN A 278      19.700   1.822  33.976  1.00 57.97  C
ATOM   2159  OE1  GLN A 278      18.572   1.330  33.917  1.00 44.46  O
ATOM   2160  NE2  GLN A 278      20.012   2.800  34.826  1.00 53.33  N
ATOM   2161  N    ASP A 279      22.013  -1.132  31.257  1.00 45.92  N
ATOM   2162  CA   ASP A 279      21.795  -2.541  31.014  1.00 47.69  C
ATOM   2163  C    ASP A 279      21.345  -3.251  32.270  1.00 47.71  C
ATOM   2164  O    ASP A 279      21.357  -2.687  33.366  1.00 48.35  O
ATOM   2165  CB   ASP A 279      23.062  -3.186  30.451  1.00 60.02  C
ATOM   2166  CG   ASP A 279      24.316  -2.707  31.154  1.00 69.17  C
ATOM   2167  OD1  ASP A 279      24.456  -2.954  32.370  1.00 75.17  O
ATOM   2168  OD2  ASP A 279      25.157  -2.073  30.490  1.00 75.70  O
ATOM   2169  N    ALA A 280      20.892  -4.480  32.079  1.00 49.27  N
ATOM   2170  CA   ALA A 280      20.428  -5.314  33.172  1.00 57.28  C
ATOM   2171  C    ALA A 280      20.804  -6.748  32.833  1.00 54.10  C
ATOM   2172  O    ALA A 280      20.868  -7.126  31.659  1.00 47.63  O
ATOM   2173  CB   ALA A 280      18.909  -5.184  33.341  1.00 47.77  C
ATOM   2174  N    SER A 281      21.043  -7.560  33.854  1.00 53.68  N
ATOM   2175  CA   SER A 281      21.429  -8.931  33.599  1.00 48.69  C
ATOM   2176  C    SER A 281      20.402  -9.952  34.031  1.00 45.20  C
ATOM   2177  O    SER A 281      19.595  -9.718  34.934  1.00 45.89  O
ATOM   2178  CB   SER A 281      22.768  -9.219  34.279  1.00 61.38  C
ATOM   2179  OG   SER A 281      22.718  -8.863  35.646  1.00 57.59  O
ATOM   2180  N    ILE A 282      20.427 -11.086  33.349  1.00 43.38  N
ATOM   2181  CA   ILE A 282      19.524 -12.185  33.637  1.00 41.38  C
ATOM   2182  C    ILE A 282      20.392 -13.429  33.671  1.00 47.86  C
ATOM   2183  O    ILE A 282      21.235 -13.631  32.799  1.00 51.03  O
ATOM   2184  CB   ILE A 282      18.436 -12.316  32.548  1.00 40.14  C
ATOM   2185  CG1  ILE A 282      17.557 -11.056  32.557  1.00 46.94  C
ATOM   2186  CG2  ILE A 282      17.576 -13.549  32.807  1.00 42.53  C
ATOM   2187  CD1  ILE A 282      16.484 -10.998  31.476  1.00 45.40  C
ATOM   2188  N    HIS A 283      20.204 -14.248  34.695  1.00 45.39  N
ATOM   2189  CA   HIS A 283      20.998 -15.458  34.816  1.00 46.01  C
ATOM   2190  C    HIS A 283      20.145 -16.651  34.501  1.00 41.84  C
ATOM   2191  O    HIS A 283      19.164 -16.923  35.197  1.00 51.27  O
ATOM   2192  CB   HIS A 283      21.570 -15.575  36.230  1.00 53.96  C
ATOM   2193  CG   HIS A 283      22.617 -14.551  36.543  1.00 60.28  C
```

Figure 2 (Table 2 (page 47))

```
ATOM   2194  ND1 HIS A 283      23.908  -14.633  36.065  1.00 69.25 N
ATOM   2195  CD2 HIS A 283      22.554  -13.401  37.260  1.00 68.71 C
ATOM   2196  CE1 HIS A 283      24.593  -13.578  36.473  1.00 75.43 C
ATOM   2197  NE2 HIS A 283      23.796  -12.816  37.199  1.00 66.88 N
ATOM   2198  N   LEU A 284      20.499  -17.349  33.427  1.00 41.70 N
ATOM   2199  CA  LEU A 284      19.752  -18.534  33.050  1.00 45.86 C
ATOM   2200  C   LEU A 284      20.533  -19.778  33.469  1.00 49.53 C
ATOM   2201  O   LEU A 284      21.683  -19.963  33.058  1.00 45.44 O
ATOM   2202  CB  LEU A 284      19.515  -18.576  31.532  1.00 41.74 C
ATOM   2203  CG  LEU A 284      18.782  -19.827  31.028  1.00 47.91 C
ATOM   2204  CD1 LEU A 284      17.407  -19.888  31.680  1.00 45.59 C
ATOM   2205  CD2 LEU A 284      18.648  -19.810  29.500  1.00 48.70 C
ATOM   2206  N   LYS A 285      19.913  -20.625  34.285  1.00 48.59 N
ATOM   2207  CA  LYS A 285      20.557  -21.863  34.711  1.00 53.60 C
ATOM   2208  C   LYS A 285      19.797  -23.008  34.061  1.00 46.75 C
ATOM   2209  O   LYS A 285      18.570  -23.061  34.109  1.00 49.33 O
ATOM   2210  CB  LYS A 285      20.531  -21.991  36.239  1.00 56.58 C
ATOM   2211  CG  LYS A 285      21.302  -20.880  36.942  1.00 63.01 C
ATOM   2212  CD  LYS A 285      21.254  -21.021  38.459  1.00 71.05 C
ATOM   2213  CE  LYS A 285      21.853  -19.795  39.148  1.00 76.77 C
ATOM   2214  NZ  LYS A 285      20.993  -18.583  39.020  1.00 73.22 N
ATOM   2215  N   VAL A 286      20.525  -23.922  33.436  1.00 44.47 N
ATOM   2216  CA  VAL A 286      19.888  -25.047  32.759  1.00 53.73 C
ATOM   2217  C   VAL A 286      20.271  -26.367  33.410  1.00 58.55 C
ATOM   2218  O   VAL A 286      21.446  -26.709  33.489  1.00 58.02 O
ATOM   2219  CB  VAL A 286      20.283  -25.078  31.268  1.00 49.11 C
ATOM   2220  CG1 VAL A 286      19.618  -26.248  30.572  1.00 52.83 C
ATOM   2221  CG2 VAL A 286      19.872  -23.760  30.597  1.00 49.45 C
ATOM   2222  N   PHE A 287      19.267  -27.100  33.875  1.00 56.62 N
ATOM   2223  CA  PHE A 287      19.493  -28.379  34.528  1.00 60.81 C
ATOM   2224  C   PHE A 287      19.172  -29.540  33.607  1.00 64.78 C
ATOM   2225  O   PHE A 287      18.208  -29.487  32.846  1.00 64.16 O
ATOM   2226  CB  PHE A 287      18.645  -28.461  35.795  1.00 58.95 C
ATOM   2227  CG  PHE A 287      18.868  -27.314  36.724  1.00 61.24 C
ATOM   2228  CD1 PHE A 287      17.963  -26.259  36.783  1.00 56.19 C
ATOM   2229  CD2 PHE A 287      20.036  -27.237  37.477  1.00 62.69 C
ATOM   2230  CE1 PHE A 287      18.224  -25.139  37.575  1.00 53.03 C
ATOM   2231  CE2 PHE A 287      20.304  -26.124  38.266  1.00 58.31 C
ATOM   2232  CZ  PHE A 287      19.397  -25.073  38.314  1.00 59.07 C
ATOM   2233  N   ALA A 288      19.997  -30.583  33.666  1.00 66.33 N
ATOM   2234  CA  ALA A 288      19.795  -31.766  32.834  1.00 73.18 C
ATOM   2235  C   ALA A 288      18.428  -32.377  33.119  1.00 78.08 C
ATOM   2236  O   ALA A 288      17.960  -32.349  34.259  1.00 78.39 O
ATOM   2237  CB  ALA A 288      20.887  -32.785  33.106  1.00 69.96 C
ATOM   2238  N   LYS A 289      17.794  -32.931  32.087  1.00 80.55 N
ATOM   2239  CA  LYS A 289      16.476  -33.541  32.240  1.00 84.08 C
ATOM   2240  C   LYS A 289      16.535  -34.855  33.016  1.00 88.56 C
ATOM   2241  O   LYS A 289      15.585  -35.127  33.785  1.00 92.60 O
ATOM   2242  CB  LYS A 289      15.830  -33.779  30.872  1.00 82.11 C
ATOM   2243  CG  LYS A 289      16.538  -34.804  30.009  1.00 82.83 C
ATOM   2244  CD  LYS A 289      15.739  -35.066  28.748  1.00 81.13 C
ATOM   2245  CE  LYS A 289      16.362  -36.164  27.910  1.00 87.98 C
ATOM   2246  NZ  LYS A 289      15.562  -36.424  26.677  1.00 90.82 N
ATOM   2247  OXT LYS A 289      17.519  -35.608  32.835  1.00 94.14 O
TER    2248      LYS A 289
HETATM 2249  O   HOH     1      26.862   53.829  -2.499  1.00 53.80 O
```

Figure 2 (Table 2 (page 48))

```
HETATM 2250  O    HOH     2      31.435  56.206  -5.661  1.00 53.53    O
HETATM 2251  O    HOH     4      18.815  60.633 -12.908  1.00 43.98    O
HETATM 2252  O    HOH     5      16.291  34.157   5.585  1.00 64.41    O
HETATM 2253  O    HOH     6      24.283  23.825  11.233  1.00 59.48    O
HETATM 2254  O    HOH     7      21.204  19.365  17.749  1.00 60.83    O
HETATM 2255  O    HOH     8      15.430  12.803  19.226  1.00 45.67    O
HETATM 2256  O    HOH     9      22.245  15.815  31.410  1.00 50.19    O
HETATM 2257  O    HOH    10      25.429  21.325  30.709  1.00 49.37    O
HETATM 2258  O    HOH    11      23.048  36.010  15.248  1.00 51.13    O
HETATM 2259  O    HOH    12      29.692  33.165  19.866  1.00 37.03    O
HETATM 2260  O    HOH    13       9.169  23.139  31.247  1.00 61.40    O
HETATM 2261  O    HOH    14      17.022  56.166   8.038  1.00 75.27    O
HETATM 2262  O    HOH    15       8.769  40.002   7.174  1.00 48.91    O
HETATM 2263  O    HOH    16      10.231  43.238   7.473  1.00 47.42    O
HETATM 2264  O    HOH    17      15.641  26.081   5.720  1.00 78.13    O
HETATM 2265  O    HOH    18      20.551  14.627  22.658  1.00 46.05    O
HETATM 2266  O    HOH    19      11.221  -2.472  26.804  1.00 52.85    O
HETATM 2267  O    HOH    20      13.041  60.224  -4.320  1.00 64.49    O
HETATM 2268  O    HOH    21      14.835  48.897  -2.048  1.00 85.96    O
HETATM 2269  O    HOH    22      29.546  51.498 -21.147  1.00 47.61    O
HETATM 2270  O    HOH    23      24.511  42.141 -28.698  1.00 76.55    O
HETATM 2271  O    HOH    25      21.636  45.365 -18.499  1.00 37.40    O
HETATM 2272  O    HOH    26      15.790  47.805 -19.728  1.00 64.11    O
HETATM 2273  O    HOH    27      20.999  58.533  -6.980  1.00 47.49    O
HETATM 2274  O    HOH    28      14.534  40.436   5.659  1.00 59.32    O
HETATM 2275  O    HOH    29      18.746  16.322  14.473  1.00 79.28    O
HETATM 2276  O    HOH    30      25.965  40.212   9.533  1.00 52.16    O
HETATM 2277  O    HOH    31      16.482  55.396  13.144  1.00 59.76    O
HETATM 2278  O    HOH    32       9.922  15.732  20.883  1.00 48.37    O
HETATM 2279  O    HOH    33      11.915  -0.137  41.445  1.00 73.91    O
HETATM 2280  O    HOH    34      11.044   7.531  19.815  1.00 49.89    O
HETATM 2281  O    HOH    35       6.902   3.742  25.922  1.00 63.36    O
HETATM 2282  O    HOH    37      21.399  -1.338  20.994  1.00 76.17    O
HETATM 2283  O    HOH    38      18.329  53.773  -1.977  1.00 62.61    O
HETATM 2284  O    HOH    39      18.014  43.718  -2.937  1.00 49.73    O
HETATM 2285  O    HOH    40      32.281  40.568 -12.177  1.00 66.60    O
HETATM 2286  O    HOH    41      19.381  44.469 -19.805  1.00 64.16    O
HETATM 2287  O    HOH    42      25.046  41.566 -20.577  1.00 61.50    O
HETATM 2288  O    HOH    46       7.104   2.690  28.661  1.00 90.82    O
HETATM 2289  O    HOH    48      29.774 -14.171  32.170  1.00 72.60    O
HETATM 2290  O    HOH    49      36.677  48.530 -18.261  1.00 57.32    O
HETATM 2291  O    HOH    50      33.317  46.204 -17.946  1.00 47.09    O
HETATM 2292  O    HOH    52      22.357  37.802  16.682  1.00 62.95    O
HETATM 2293  O    HOH    54      11.598   9.583  18.307  1.00 51.71    O
HETATM 2294  O    HOH    55      22.448  12.959  33.086  1.00 71.24    O
HETATM 2295  O    HOH    56      12.323 -25.457  30.778  1.00 69.54    O
HETATM 2296  O    HOH    57      22.080  16.779  21.536  1.00 49.07    O
HETATM 2297  O    HOH    58      17.068   4.212  19.556  1.00 71.54    O
HETATM 2298  O    HOH    59      21.824  23.695  19.290  1.00 44.38    O
HETATM 2299  O    HOH    60      17.965   7.263  19.831  1.00 45.41    O
HETATM 2300  O    HOH    61      19.593  -1.710  35.113  1.00 49.69    O
HETATM 2301  O    HOH    62      18.642  -7.793  36.955  1.00 68.54    O
HETATM 2302  O    HOH    63      23.848  -0.227  33.498  1.00 54.90    O
HETATM 2303  O    HOH    64      31.052 -17.541  34.986  1.00 68.80    O
HETATM 2304  O    HOH    65       5.551  -4.238   9.968  1.00 64.86    O
HETATM 2305  O    HOH    66      10.472  -3.423   9.588  1.00 81.77    O
```

Figure 2 (Table 2 (page 49))

```
HETATM 2306  O  HOH   67    6.705   -3.198  12.269  1.00 59.36 O
HETATM 2307  O  HOH   68   18.934    8.523  16.255  1.00 70.67 O
HETATM 2308  O  HOH   69   26.373  -11.223  28.910  1.00 53.04 O
HETATM 2309  O  HOH   70   26.631    6.184  27.729  1.00 74.30 O
HETATM 2310  O  HOH   71   26.466  -20.918  34.876  1.00 70.68 O
HETATM 2311  O  HOH   72    8.293   12.647  18.395  1.00 56.61 O
HETATM 2312  O  HOH   74   17.106   -5.693  36.496  1.00 48.96 O
HETATM 2313  O  HOH   75    1.311   -8.583   8.383  1.00 70.05 O
HETATM 2314  O  HOH   76   26.233   40.015   4.081  1.00 64.69 O
HETATM 2315  O  HOH   77   21.018   39.423   0.780  1.00 63.73 O
HETATM 2316  O  HOH   78   30.385   47.077  -9.984  1.00 47.01 O
HETATM 2317  O  HOH   80   17.757   22.465   9.580  1.00 54.37 O
HETATM 2318  O  HOH   81   25.847   39.446  18.635  1.00 61.83 O
HETATM 2319  O  HOH   82   23.903  -18.248  35.163  1.00 66.46 O
HETATM 2320  O  HOH   83   17.550   29.059   7.625  1.00 69.50 O
HETATM 2321  O  HOH   84   22.192   30.581  38.779  1.00 45.18 O
HETATM 2322  O  HOH   85   19.724   26.758   8.865  1.00 62.11 O
HETATM 2323  O  HOH   87   29.601   58.691 -24.045  1.00 49.94 O
HETATM 2324  O  HOH   88   22.701   60.581  -7.832  1.00 65.08 O
HETATM 2325  O  HOH   89   21.940   62.739 -12.104  1.00 60.23 O
HETATM 2326  O  HOH   90   28.142   44.638 -19.542  1.00 52.86 O
HETATM 2327  O  HOH   91   19.926   59.567 -10.713  1.00 54.05 O
HETATM 2328  O  HOH   92   23.841   23.097  24.364  1.00 55.20 O
HETATM 2329  O  HOH   93   14.026   37.104  24.024  1.00 50.35 O
HETATM 2330  O  HOH   94   28.637   30.316  16.747  1.00 47.63 O
HETATM 2331  O  HOH   95   13.597  -12.079  32.292  1.00 47.38 O
HETATM 2332  O  HOH   96   20.525    6.030  31.726  1.00 59.12 O
HETATM 2333  O  HOH   97   12.219   25.294  38.142  1.00 74.46 O
HETATM 2334  O  HOH   98   17.582   46.166 -21.327  1.00 58.26 O
HETATM 2335  O  HOH   99   18.462    3.098  17.614  1.00 74.29 O
HETATM 2336  O  HOH  100    7.657   -6.217  21.068  1.00 54.31 O
HETATM 2337  O  HOH  101   31.973   58.468 -22.566  1.00 51.37 O
HETATM 2338  O  HOH  102   25.581   34.891  15.303  1.00 62.92 O
HETATM 2339  O  HOH  103    9.781    4.793  26.865  1.00 52.97 O
HETATM 2340  O  HOH  104   27.113   28.768  14.346  1.00 46.27 O
HETATM 2341  O  HOH  105   20.934   59.591  -4.081  1.00 63.10 O
HETATM 2342  O  HOH  106   29.101   39.039  -6.576  1.00 50.94 O
HETATM 2343  O  HOH  107   20.829   -6.266  36.888  1.00 67.77 O
HETATM 2344  O  HOH  108   14.801   -6.395  38.213  1.00 57.81 O
HETATM 2345  O  HOH  109   21.412  -19.178  24.173  1.00 57.65 O
HETATM 2346  O  HOH  110   29.742   32.206  15.564  1.00 51.50 O
HETATM 2347  O  HOH  111   27.197   38.482  -3.772  1.00 57.43 O
HETATM 2348  O  HOH  112   23.730   20.567  24.733  1.00 63.78 O
HETATM 2349  O  HOH  113   15.996   50.339  -4.519  1.00 68.59 O
HETATM 2350  O  HOH  114   10.665   -4.867  34.503  1.00 53.34 O
HETATM 2351  O  HOH  115    6.955   17.535  26.540  1.00 72.17 O
HETATM 2352  O  HOH  116   15.712  -29.078  24.014  1.00 65.77 O
HETATM 2353  O  HOH  118   32.255   44.366  -7.537  1.00 62.15 O
HETATM 2354  O  HOH  119   29.827   41.068  -0.664  1.00 57.67 O
HETATM 2355  O  HOH  122   14.630  -27.859  26.706  1.00 65.41 O
HETATM 2356  O  HOH  123    8.521  -18.764  25.803  1.00 74.48 O
HETATM 2357  O  HOH  125   15.199   60.049 -12.759  1.00 63.41 O
HETATM 2358  O  HOH  126   10.378   14.473  18.707  1.00 52.05 O
HETATM 2359  O  HOH  127   28.187  -10.553  30.862  1.00 65.81 O
HETATM 2360  O  HOH  128    7.837   37.705   8.662  1.00 62.54 O
HETATM 2361  O  HOH  130   23.744   37.155   1.565  1.00 65.13 O
```

Figure 2 (Table 2 (page 50))

| | | | | | | | | | |
|---|---|---|---|---|---|---|---|---|---|
| HETATM | 2362 | O | HOH | 131 | 13.354 | 57.052 | -9.380 | 1.00 | 64.16 O |
| HETATM | 2363 | O | HOH | 132 | 31.235 | 44.417 | -16.467 | 1.00 | 58.09 O |
| HETATM | 2364 | O | HOH | 134 | 18.966 | 44.757 | 7.268 | 1.00 | 51.54 O |
| HETATM | 2365 | O | HOH | 135 | 22.888 | 3.287 | 35.759 | 1.00 | 66.29 O |
| HETATM | 2366 | O | HOH | 136 | 10.345 | 29.244 | 10.371 | 1.00 | 53.80 O |
| HETATM | 2367 | O | HOH | 137 | 21.314 | -8.331 | 20.298 | 1.00 | 59.91 O |
| HETATM | 2368 | O | HOH | 138 | 38.747 | 55.169 | -17.210 | 1.00 | 61.68 O |
| HETATM | 2369 | O | HOH | 139 | 14.760 | 55.271 | 10.174 | 1.00 | 55.52 O |
| HETATM | 2370 | O | HOH | 140 | 23.711 | 55.591 | 3.512 | 1.00 | 78.73 O |
| HETATM | 2371 | O | HOH | 142 | 5.285 | 37.922 | 7.977 | 1.00 | 63.10 O |
| HETATM | 2372 | O | HOH | 143 | 24.355 | 15.578 | 30.186 | 1.00 | 68.63 O |
| HETATM | 2373 | O | HOH | 144 | 23.201 | 9.987 | 31.463 | 1.00 | 64.84 O |
| HETATM | 2374 | O | HOH | 145 | 15.111 | -8.434 | 40.304 | 1.00 | 70.85 O |
| HETATM | 2375 | O | HOH | 146 | 34.105 | 49.705 | -9.362 | 1.00 | 66.43 O |
| HETATM | 2376 | O | HOH | 147 | 22.545 | 50.730 | 2.853 | 1.00 | 70.28 O |
| HETATM | 2377 | O | HOH | 149 | 23.888 | 38.804 | -17.868 | 1.00 | 69.84 O |
| HETATM | 2378 | O | HOH | 150 | 26.301 | 66.907 | -32.270 | 1.00 | 69.82 O |
| HETATM | 2379 | O | HOH | 151 | 29.578 | 51.924 | -24.078 | 1.00 | 67.26 O |
| HETATM | 2380 | O | HOH | 152 | 31.935 | 49.759 | -6.982 | 1.00 | 72.11 O |
| HETATM | 2381 | O | HOH | 153 | 11.771 | 12.964 | 31.927 | 1.00 | 70.57 O |
| HETATM | 2382 | O | HOH | 154 | 14.696 | 6.619 | 31.148 | 1.00 | 64.86 O |
| HETATM | 2383 | O | HOH | 155 | 33.398 | 69.714 | -31.980 | 1.00 | 74.81 O |
| HETATM | 2384 | O | HOH | 156 | 26.480 | 50.982 | 0.230 | 1.00 | 59.10 O |
| HETATM | 2385 | O | HOH | 157 | 22.798 | 7.195 | 30.848 | 1.00 | 68.26 O |
| HETATM | 2386 | O | HOH | 158 | 19.477 | -6.906 | 18.703 | 1.00 | 72.82 O |
| HETATM | 2387 | O | HOH | 159 | 13.208 | 60.522 | -15.082 | 1.00 | 57.68 O |
| HETATM | 2388 | O | HOH | 160 | 34.799 | 47.949 | -14.048 | 1.00 | 71.55 O |
| HETATM | 2389 | O | HOH | 161 | 12.156 | -20.278 | 36.293 | 1.00 | 63.41 O |
| HETATM | 2390 | O | HOH | 162 | 12.064 | 0.618 | 21.733 | 1.00 | 59.67 O |
| HETATM | 2391 | O | HOH | 163 | 13.025 | 12.470 | 18.298 | 1.00 | 57.94 O |
| HETATM | 2392 | O | HOH | 164 | 11.241 | -6.036 | 37.279 | 1.00 | 66.37 O |
| HETATM | 2393 | O | HOH | 165 | 15.326 | 30.761 | 7.083 | 1.00 | 72.54 O |
| HETATM | 2394 | O | HOH | 166 | 24.166 | 26.288 | 8.146 | 1.00 | 80.46 O |
| HETATM | 2395 | O | HOH | 167 | 18.532 | 37.307 | 28.877 | 1.00 | 52.52 O |
| HETATM | 2396 | O | HOH | 169 | 19.929 | 10.591 | 15.027 | 1.00 | 79.89 O |
| HETATM | 2397 | O | HOH | 171 | 18.161 | 19.995 | 12.208 | 1.00 | 88.12 O |
| HETATM | 2398 | O | HOH | 172 | 25.181 | -23.987 | 37.247 | 1.00 | 83.59 O |
| HETATM | 2399 | O | HOH | 174 | 18.136 | -3.696 | 37.260 | 1.00 | 58.69 O |
| HETATM | 2400 | O | HOH | 175 | 9.790 | 35.898 | 8.924 | 1.00 | 68.04 O |
| HETATM | 2401 | O | HOH | 176 | 39.649 | 55.783 | -13.588 | 1.00 | 75.74 O |
| HETATM | 2402 | O | HOH | 177 | 11.431 | -13.326 | 32.112 | 1.00 | 68.92 O |
| HETATM | 2403 | O | HOH | 178 | 15.462 | 13.080 | 15.436 | 1.00 | 72.04 O |
| HETATM | 2404 | O | HOH | 179 | 10.845 | -23.387 | 30.834 | 1.00 | 75.68 O |
| HETATM | 2405 | O | HOH | 180 | 8.771 | -8.704 | 37.430 | 1.00 | 69.36 O |
| HETATM | 2406 | O | HOH | 181 | 21.236 | 41.306 | -18.704 | 1.00 | 71.93 O |
| HETATM | 2407 | O | HOH | 182 | 15.632 | 39.325 | 24.779 | 1.00 | 76.42 O |
| HETATM | 2408 | O | HOH | 184 | 9.633 | 7.268 | 24.170 | 1.00 | 59.85 O |
| HETATM | 2409 | O | HOH | 185 | 8.212 | -4.659 | 26.095 | 1.00 | 73.13 O |
| HETATM | 2410 | O | HOH | 187 | 22.544 | -23.667 | 22.886 | 1.00 | 67.43 O |
| HETATM | 2411 | O | HOH | 190 | 38.135 | 52.923 | -18.866 | 1.00 | 60.86 O |
| HETATM | 2412 | O | HOH | 192 | 13.987 | -13.566 | 39.379 | 1.00 | 64.17 O |
| HETATM | 2413 | O | HOH | 194 | 8.678 | 19.753 | 34.818 | 1.00 | 74.26 O |
| HETATM | 2414 | O | HOH | 195 | 16.248 | 11.313 | 17.210 | 1.00 | 71.99 O |
| HETATM | 2415 | O | HOH | 196 | 21.583 | 37.449 | -18.466 | 1.00 | 74.25 O |
| HETATM | 2416 | O | HOH | 197 | 18.608 | 13.183 | 13.886 | 1.00 | 69.55 O |
| HETATM | 2417 | O | HOH | 199 | 32.100 | 47.030 | -11.918 | 1.00 | 55.13 O |

Figure 2 (Table 2 (page 51))

```
HETATM 2418  O   HOH   200      8.309  -2.904  23.865  1.00 78.50  O
HETATM 2419  O   HOH   201     27.690  42.102   3.955  1.00 77.78  O
HETATM 2420  O   HOH   204     13.069  56.872  -6.846  1.00 79.77  O
HETATM 2421  O   HOH   205     13.299   3.871  18.787  1.00 66.67  O
HETATM 2422  O   HOH   206     29.245  60.023 -30.224  1.00 60.72  O
HETATM 2423  O   HOH   208     14.879  -4.423  17.190  1.00 90.36  O
HETATM 2424  O   HOH   209     10.483  17.298  32.627  1.00 73.09  O
HETATM 2425  O   HOH   210     11.855  61.308 -30.434  1.00 88.84  O
HETATM 2426  O   HOH   211     13.217  40.439  25.017  1.00 85.86  O
HETATM 2427  O   HOH   213      7.822 -16.528  22.942  1.00 78.51  O
HETATM 2428  O   HOH   214     23.675  20.955  33.560  1.00 73.68  O
HETATM 2429  O   HOH   215      8.958 -13.070  31.871  1.00 66.49  O
HETATM 2430  O   HOH   216     13.965   9.052  16.630  1.00 67.53  O
HETATM 2431  O   HOH   220      8.596  -0.069  28.112  1.00 61.80  O
HETATM 2432  O   HOH   221     31.299  38.557 -18.341  1.00 61.93  O
HETATM 2433  O   HOH   222     20.516  15.336  17.249  1.00 62.41  O
HETATM 2434  O   HOH   223     32.487  45.347 -13.991  1.00 67.08  O
HETATM 2435  O   HOH   224      9.634  26.343  28.605  1.00 80.33  O
HETATM 2436  O   HOH   225     26.881  41.843   6.770  1.00 66.49  O
HETATM 2437  O   HOH   226     21.933  62.656  -9.449  1.00 77.20  O
HETATM 2438  O   HOH   227     16.939  -0.959  38.266  1.00 47.64  O
HETATM 2439  O   HOH   228      1.517  27.871  29.550  1.00 69.94  O
HETATM 2440  O   HOH   229     25.455  67.088 -17.467  1.00 70.28  O
HETATM 2441  O   HOH   231     22.761  36.354 -14.024  1.00 67.12  O
HETATM 2442  O   HOH   233      9.742 -18.263  29.864  1.00 71.11  O
HETATM 2443  O   HOH   236      9.749  -1.644  39.210  1.00 68.73  O
HETATM 2444  O   HOH   238     18.795  37.370  -0.374  1.00 70.06  O
HETATM 2445  O   HOH   239     28.893 -23.822  27.314  1.00 63.21  O
HETATM 2446  O   HOH   240     20.653  54.689  -2.794  1.00 69.17  O
HETATM 2447  O   HOH   241     32.703  57.255  -7.932  1.00 73.68  O
HETATM 2448  O   HOH   242     26.839  45.754 -28.862  1.00 73.66  O
HETATM 2449  O   HOH   243     21.145  36.229  -1.718  1.00 67.47  O
HETATM 2450  O   HOH   244     24.749  63.978 -31.459  1.00 70.06  O
HETATM 2451  O   HOH   245     15.031  42.223  -0.424  1.00 65.72  O
HETATM 2452  O   HOH   246     13.421  46.493   5.518  1.00 68.84  O
HETATM 2453  O   HOH   247     31.086  37.829 -20.633  1.00 67.16  O
HETATM 2454  O   HOH   249     16.331  24.733   8.656  1.00 80.75  O
HETATM 2455  O   HOH   250     34.686  48.482 -11.577  1.00 67.41  O
HETATM 2456  O   HOH   252     26.863 -21.667  27.711  1.00 73.87  O
HETATM 2457  O   HOH   253     25.486  24.675   5.799  1.00 94.36  O
HETATM 2458  O   HOH   255     19.570 -18.069  15.539  1.00 68.87  O
HETATM 2459  O   HOH   256      7.507  24.181  27.128  1.00 75.95  O
HETATM 2460  O   HOH   257     18.214  50.275  13.595  1.00 77.43  O
HETATM 2461  O   HOH   258     24.259   5.598  21.754  1.00 80.04  O
HETATM 2462  O   HOH   259     23.644  -9.401  38.458  1.00 73.87  O
HETATM 2463  O   HOH   260     29.288  57.908 -36.191  1.00 83.70  O
HETATM 2464  O   HOH   261     14.644 -13.020  15.667  1.00 67.62  O
HETATM 2465  O   HOH   262     16.016  47.827  16.745  1.00 77.21  O
HETATM 2466  O   HOH   263     19.538 -33.347  29.648  1.00 64.40  O
HETATM 2467  O   HOH   265      2.949  33.426  13.572  1.00 75.54  O
HETATM 2468  O   HOH   266     25.030  51.698 -23.955  1.00 72.53  O
HETATM 2469  O   HOH   267     29.126  34.667  -5.967  1.00 87.07  O
HETATM 2470  O   HOH   268     21.351   0.866  18.679  1.00 81.24  O
HETATM 2471  O   HOH   270     11.563 -28.282  33.256  1.00 88.99  O
HETATM 2472  O   HOH   273     25.953  36.560 -14.131  1.00 68.45  O
HETATM 2473  O   HOH   275      3.498  32.668  11.344  1.00 60.17  O
```

Figure 2 (Table 2 (page 52))

```
HETATM 2474  O   HOH 277    24.261 -20.185  20.738 1.00 69.47 O
HETATM 2475  O   HOH 279    16.935  12.111  32.241 1.00 61.50 O
HETATM 2476  O   HOH 281     6.985  31.018  33.495 1.00 82.04 O
HETATM 2477  O   HOH 282    29.259  66.155 -18.386 1.00 76.82 O
HETATM 2478  O   HOH 283     7.960  15.959  16.209 1.00 82.31 O
HETATM 2479  O   HOH 284    10.497 -27.436  17.219 1.00 87.04 O
HETATM 2480  O   HOH 286    26.964  63.396 -39.492 1.00 92.90 O
HETATM 2481  O   HOH 288    24.134  68.136 -30.170 1.00 73.68 O
HETATM 2482  O   HOH 289    21.035  57.596  -2.427 1.00 63.71 O
HETATM 2483  O   HOH 290     5.098  -6.663   9.498 1.00 71.30 O
HETATM 2484  O   HOH 291    28.355  60.022 -32.628 1.00 84.14 O
HETATM 2485  O   HOH 292    27.829 -18.993  32.106 1.00 83.61 O
HETATM 2486  O   HOH 294    25.765  53.781 -27.581 1.00 80.50 O
HETATM 2487  O   HOH 295    24.969 -15.013  17.181 1.00 79.45 O
HETATM 2488  O   HOH 296    21.804 -31.840  29.638 1.00 63.37 O
HETATM 2489  O   HOH 297    24.675  41.475  22.470 1.00 76.81 O
HETATM 2490  O   HOH 298    21.097 -16.469  16.858 1.00 76.40 O
HETATM 2491  O   HOH 299    10.492   1.947  39.785 1.00 73.55 O
HETATM 2492  O   HOH 300    24.883  60.577  -6.394 1.00 83.17 O
HETATM 2493  O   HOH 301    12.022  63.003 -25.379 1.00 82.86 O
HETATM 2494  O   HOH 302    29.658  36.500 -13.658 1.00 76.81 O
HETATM 2495  O   HOH 303    28.183  35.860 -10.762 1.00 71.74 O
HETATM 2496  O   HOH 304    33.215  39.854  -9.262 1.00 79.17 O
HETATM 2497  O   HOH 305    22.138  35.777 -10.127 1.00 75.26 O
HETATM 2498  O   HOH 306    34.862  51.476  -6.285 1.00 73.10 O
HETATM 2499  O   HOH 307    40.147  51.580  -7.567 1.00 79.78 O
HETATM 2500  O   HOH 308    28.423  71.917 -29.800 1.00 75.06 O
HETATM 2501  O   HOH 309    31.298  68.573 -22.781 1.00 78.92 O
HETATM 2502  O   HOH 310    22.252  33.788   4.586 1.00 75.58 O
HETATM 2503  O   HOH 311    26.312  13.773  26.214 1.00 71.75 O
HETATM 2504  O   HOH 312    24.723  12.029  25.114 1.00 75.67 O
HETATM 2505  O   HOH 313    23.485  49.266   5.646 1.00 72.55 O
HETATM 2506  O   HOH 314    25.648  43.055  12.920 1.00 71.36 O
HETATM 2507  O   HOH 315     4.653  34.503  32.710 1.00 77.71 O
HETATM 2508  O   HOH 316     2.456  37.131  32.175 1.00 78.77 O
HETATM 2509  O   HOH 317     6.881  27.100  34.488 1.00 80.24 O
HETATM 2510  O   HOH 318    10.082  23.711  13.099 1.00 81.07 O
HETATM 2511  O   HOH 319    18.524 -28.499  21.428 1.00 79.53 O
HETATM 2512  O   HOH 321    26.684   3.017  30.716 1.00 82.34 O
HETATM 2513  O   HOH 322    27.178  -5.228  32.903 1.00 82.07 O
CONECT  174  603
CONECT  603  174
CONECT  932 1341
CONECT 1341  932
CONECT 1686 2094
CONECT 2094 1686
MASTER       303    0    0    3   27    0    0    6 2512    1    6   23
END
```

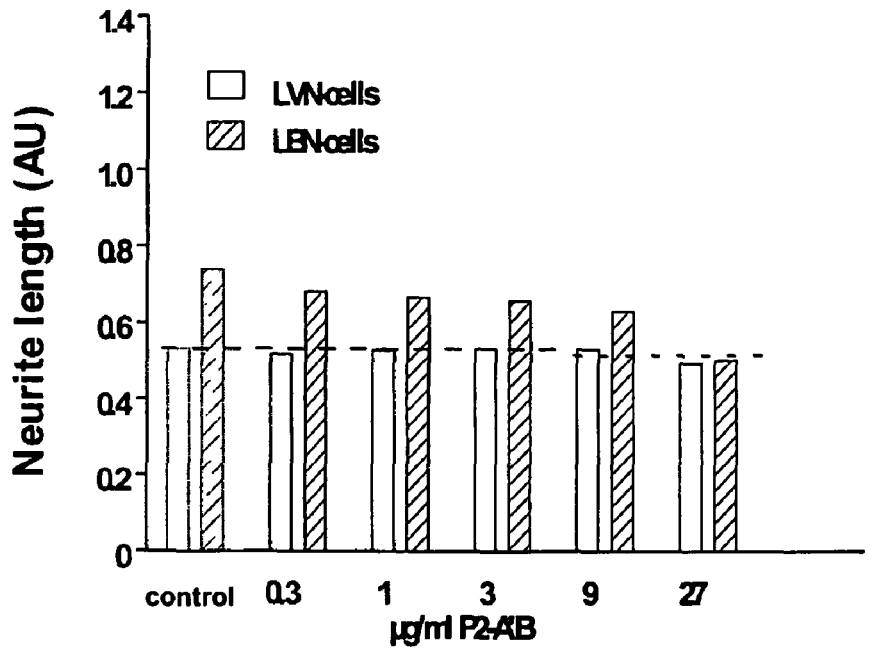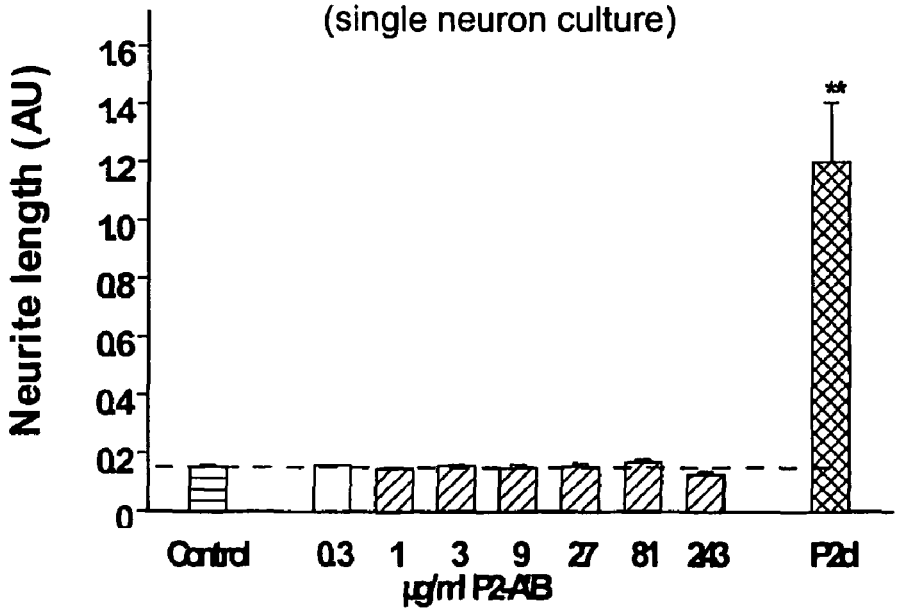
Figure 12

US 7,847,058 B2

METHOD OF MODULATING CELL SURVIVAL, DIFFERENTIATION AND/OR SYNAPTIC PLASTICITY

FIELD OF INVENTION

The present invention relates to a method of modulating cell differentiation and/or survival by providing compounds capable of modulating the interaction between two individual neural cell adhesion molecules (NCAM). The invention further relates to a method of screening for candidate compounds capable of modulating the interaction between the Ig1, Ig2 and/or Ig3 modules of two individual NCAM. The invention also concerns the use of the identified candidate compounds for the manufacture of a medicament.

BACKGROUND OF INVENTION

The neural cell adhesion molecule, NCAM, mediates cell-cell adhesion via homophilic (NCAM-NCAM) binding. NCAM plays a key role in neural development, neuronal differentiation and synaptic plasticity, including learning and memory consolidation.

Intercellular interactions play a crucial role in a wide range of biological processes, including cell migration, survival and differentiation. These phenomena depend upon protein recognition at the cell surface mediated by cell-cell adhesion molecules (CAMs).

The neural cell adhesion molecule, NCAM, originally described as a synaptic membrane protein (Jorgensen and Bock, 1974), and later shown to mediate cell-cell adhesion was the first mammalian cell adhesion molecule identified. NCAM belongs to the immunoglobulin (Ig) superfamily. Alternative splicing of mRNA and post-translational modifications generate a large number of NCAM isoforms. The three major NCAM isoforms have identical extracellular parts consisting of five Ig modules and two fibronectin type III modules.

NCAM is known to mediate $Ca^{2+}$-independent cell-cell and cell-substratum adhesion via homophilic (NCAM binding to NCAM) and heterophilic (NCAM binding to other molecules) interactions (Berezin et al., 2000). The different modules of NCAM have been shown to perform distinct functions. NCAM binds various extracellular matrix components such as heparin/heparan sulfate, chondroitin sulfate proteoglyeans, and different types of collagen. The heparin binding sequence is localized to the Ig2 module. NCAM also binds to the neural cell adhesion molecule L1. This interaction is believed to take place between the fourth Ig module of NCAM and an oligomannosidic moiety expressed on L1.

Despite extensive studies, the precise mechanism of the homophilic binding of NCAM remains unclear, and the published results are to some extent contradictory. NCAM homophilic binding was originally reported to depend on an antiparallel interaction between Ig3 modules from two opposing NCAM molecules. Cell aggregation experiments performed on mouse L-cells expressing chicken NCAM with deletions of different Ig modules indicated an involvement of the Ig3 module. Later, employing microspheres coated with individual recombinant Ig modules of chicken NCAM, binding was demonstrated between the Ig1 and Ig5 modules, and between the Ig2 and Ig4 modules, whereas microspheres coated with Ig3 exhibited strong self-aggregation (Ranheim et al., 1996). However, a study by Atkins et al. (2001) on the solution structure of the Ig3 module of chicken NCAM including ultracentrifugation experiments did not support the suggested dimerization of Ig3.

A binding between recombinant modules of rat Ig1 and Ig2 was demonstrated by means of surface plasmon resonance analysis (Kiselyov et al., 1997). The three-dimensional structures of individual modules of rat Ig1 and Ig2, and the chicken Ig1 module, have been determined by nuclear magnetic resonance (NMR) spectroscopy, resulting in the identification of amino acid residues involved in the homophilic binding between the Ig1 and Ig2 modules (Thomsen et al., 1996; Jensen et al., 1999; Atkins et al., 1999). The crystal structure of the Ig1-2 fragment of rat NCAM provided detailed information on the cross-like Ig1-2 dimer, and pointed out the key residues in this interaction, namely F19 and Y65 (Kasper et al., 2000). Recently, it was demonstrated that a point mutation of F19 (F19S) did not affect cell aggregation mediated by full length NCAM, even though it abolished dimerization of the Ig1-2-3 fragment, which otherwise takes place in solution (Atkins et al., 2001). These results therefore question the suggested Ig3-to-Ig3 (Rao et al., 1992; Ranheim et al., 1996) and Ig1-to-Ig2 (Kiselyov et al., 1997; Kasper et al., 2000) models of NCAM homophilic binding.

Thus, two non-overlapping homophylic binding sites of NCAM have been described in scientific literature: the Ig3-to-Ig3 and Ig1-to-Ig2 binding sites. The sequences derived from these two sites have been shown to be capable of stimulating neurite outgrowth and modulating adhesion of neural cells (WO03020749, Soroka et al, 2002; Rao et al., 1992; Ranheim et al., 1996). It has also been shown that peptide sequences, which are capable to bind to the Ig3-to-Ig3 binding site, do not interfere with the biological effects mediated by the Ig1-to-Ig2 binding site, and vice versa. The latter finding indicate that NCAM homophylic adhesion has a much more complex mechanism, then just the mechanism of mechanistic binding of two individual NCAM molecules though the multiple homophylic binding sites, and that the involvement of one or another homophylic binding site in a process mediated by NCAM may depend on a particular NCAM environment, such as for example the presence of a ligand of one or another binding site, or availability of one or another site for binding.

The present invention provides a method of modulating such processes by providing compounds capable of binding to NCAM modules Ig1, Ig2 and/or Ig3 through a novel homophylic binding site.

SUMMARY OF INVENTION

According to the present invention, providing the ligands directed to different homophylic binding sites of NCAM may allow a fine regulation of involvement of NCAM in molecular mechanisms underlying different processes related to placticity of neural cells and thereby modulation of these processes. Thus, the present invention concerns the compounds, which are capable of modulating adhesion, induce differentiation, and promote regeneration, neuronal plasticity and survival of cells expressing NCAM, and methods for screening and using such compounds.

In one aspect the present invention relates to a method of modulating cell differentiation and/or survival of the neural cell adhesion molecule (NCAM) presenting cells comprising
a) providing a candidate compound capable of
i) interacting with the Ig1 module of NCAM, and thereby mimicking and/or modulating the interaction between the Ig1 and Ig3 modules of NCAM, wherein said modules are from two individual NCAM molecules, and/or
ii) interacting with the Ig3 module of NCAM, and thereby mimicking and/or modulating the interaction between the Ig3 and Ig1 modules of NCAM, wherein said modules are from two individual NCAM molecules, and/or iii) interacting with the Ig2 module of NCAM, and thereby mimicking the interaction between Ig2 and Ig3 modules of NCAM, wherein said modules are from two individual NCAM molecules, and/or iv) interacting with the Ig3 module of NCAM, and thereby mimicking and/or modulating the interaction between the Ig3 and Ig2 modules of NCAM, wherein said modules are from two individual NCAM molecules, and/or v) interacting with the Ig2 module of NCAM, and thereby mimicking and/or modulating the interaction between the Ig2 and Ig2 modules of NCAM, wherein said modules are from two individual NCAM molecules, b) providing at least one NCAM presenting cell;

c) contacting the at least one NCAM presenting cell with said candidate compound, and thereby modulating cell differentiation and/or survival of the at least one NCAM presenting cell.

In another aspect the present invention is concerned with a method for testing a compound whether it is capable of modulating interaction between two individual NCAM molecules through a homophylic binding site composed of the Ig1, Ig2 and Ig3 modules of said NCAM molecules by modulating the interaction of i) the Ig1 module of one individual NCAM molecule with the Ig3 module of another individual NCAM molecule, and/or ii) the Ig2 module of one individual NCAM molecule with the Ig3 module of another individual NCAM molecule, and/or iii) the Ig2 module of one individual NCAM molecule with the Ig2 module of another individual NCAM molecule said method comprising a) providing a compound;

b) providing at least one individual fragment of an NCAM molecule, wherein said fragment comprising a sequence of consecutive amino acid residues corresponding to the sequence of the Ig1-2-3 module of NCAM comprising residues 1 to 289 of the sequence set forth in SEQ ID NO: 44, or a fragment of said individual fragment;

c) testing whether the compound is capable of i) interacting with the Ig1 module of NCAM, and thereby mimicking and/or modulating the interaction between the Ig1 and Ig3 modules of NCAM, wherein said modules are from the two individual fragments of (b) interacting to each other, and/or ii) interacting with the Ig3 module of NCAM, and thereby mimicking and/or modulating the interaction between the Ig3 and Ig1 modules of NCAM, wherein said modules are from the two individual fragments of (b) interacting to each other, and/or iii) interacting with the Ig2 module of NCAM, and thereby mimicking the interaction between Ig2 and Ig3 modules of NCAM, wherein said modules are from the two individual fragments of (b) interacting to each other, and/or iv) interacting with the Ig3 module of NCAM, and thereby mimicking and/or modulating the interaction between the Ig3 and Ig2 modules of NCAM, wherein said modules are from the two individual fragments of (b) interacting to each other, and/or v) interacting with the Ig2 module of NCAM, and thereby mimicking and/or modulating the interaction between the Ig2 and Ig2 modules of NCAM, wherein said modules are from the two individual fragments of (b) interacting to each other.

by contacting the compound with a fragment of (b);

d) selecting a compound capable of at least one interaction of (c) as a candidate compound capable of modulating differentiation, adhesion and/or survival of a cell presenting NCAM.

In still another aspect the present invention provide a method for selecting a candidate compound capable of modulating differentiation, adhesion and/or survival of NCAM presenting cells by modulating the interaction of i) the Ig1 module of one individual NCAM molecule with the Ig3 module of another individual NCAM molecule, and/or ii) the Ig2 module of one individual NCAM molecule with the Ig3 module of another individual NCAM molecule, and/or iii) the Ig2 module of one individual NCAM molecule with the Ig2 module of another individual NCAM molecule, said method comprising the steps of a) providing a soluble or a crystalline polypeptide comprising the Ig1-2-3 module of NCAM, b) generating a structural model of the Ig1-2-3 module of NCAM of (a) by using the computer modelling techniques;

c) in-silico evaluating compounds for the capability of i) interacting with the Ig1 module of NCAM, and thereby mimicking and/or modulating the interaction between the Ig1 and Ig3 modules of NCAM, wherein said modules are from two individual NCAM molecules, and/or ii) interacting with the Ig3 module of NCAM, and thereby mimicking and/or modulating the interaction between the Ig3 and Ig1 modules of NCAM, wherein said modules are from two individual NCAM molecules, and/or iii) interacting with the Ig2 module of NCAM, and thereby mimicking the interaction between Ig2 and Ig3 modules of NCAM, wherein said modules are from two individual NCAM molecules, and/or iv) interacting with the Ig3 module of NCAM, and thereby mimicking and/or modulating the interaction between the Ig3 and Ig2 modules of NCAM, wherein said modules are from two individual NCAM molecules, and/or v) interacting with the Ig2 module of NCAM, and thereby mimicking and/or modulating the interaction between the Ig2 and Ig2 modules of NCAM, wherein said modules are from two individual NCAM molecules, by using the structural model(s) of the Ig1-2-3 module of NCAM of (c);

d) selecting a candidate compound capable of at least one interaction of (b), and e) testing the candidate compound of (d) in an in vitro or in vivo assay for the capability of modulating differentiation, adhesion and/or survival of NCAM presenting cells, said assays comprising at least one NCAM presenting cell, and/or f) testing the candidate compound of (d) in an assay comprising evaluating the capability of the compound of at least one interaction of (b) by contacting the compound with at least one individual fragment of an NCAM molecule, said fragment comprising a sequence of consecutive amino acid residues corresponding to the sequence of the Ig1-2-3 module of NCAM comprising residues 1 to 289 of the sequence set forth in SEQ ID NO: 44.

Thus, it is an objective of the present invention to provide a crystalline protein comprising the Ig1-2-3 module of NCAM and a method of preparing said crystalline protein.

The invention further provides the compounds capable of i) interacting with the Ig1 module of NCAM, and thereby mimicking and/or modulating the interaction between the Ig1 and Ig3 modules of NCAM, wherein said modules are from two individual NCAM molecules, and/or ii) interacting with the Ig3 module of NCAM, and thereby mimicking and/or modulating the interaction between the Ig3 and Ig1 modules of NCAM, wherein said modules are from two individual NCAM molecules, and/or iii) interacting with the Ig2 module of NCAM, and thereby mimicking the interaction between Ig2 and Ig3 modules of NCAM, wherein said modules are from two individual NCAM molecules, and/or iv) interacting with the Ig3 module of NCAM, and thereby mimicking and/or modulating the interaction between the Ig3 and Ig2 modules of NCAM, wherein said modules are from two individual NCAM molecules, and/or v) interacting with the Ig2 module of NCAM, and thereby mimicking and/or modulating the interaction between the Ig2 and Ig2 modules of NCAM, wherein said modules are from two individual NCAM molecules.

The invention also concerns using the compounds selected by the above methods for the manufacture of a medicament and features pharmaceutical compositions comprising thereof.

DESCRIPTION OF DRAWINGS

FIG. 1 presents crystallographic data and refinement statistics.

FIG. 2 presents the atomic structure coordinates of the Ig1-2-3 module crystal (sequence is SEQ ID NO:46. This sequence is amino acids 20-308 of SEQ ID NO:44, preceded by Arg-Val).

(A) Cα backbone diagram in stereo with every $10^{th}$ residue labeled.

(B) Ribbon diagram with β-strands labeled according to Ig 1 set nomenclature.

Figure 4:
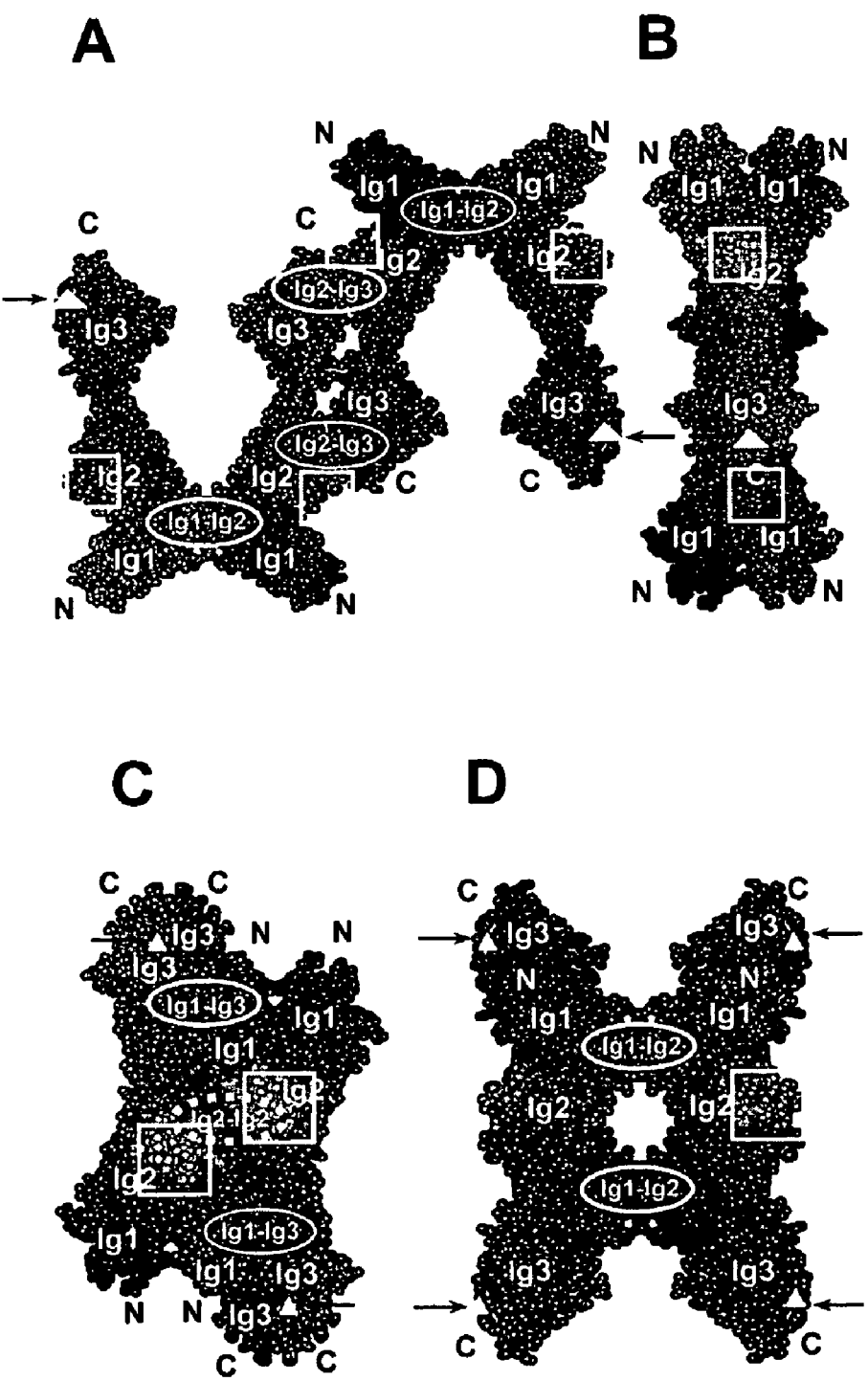

FIG. 4. Crystal structure of the Ig1-2-3 fragment of NCAM reveals four major module-module interactions and two kinds of Ig1-2-3 arrays. Space-filling models of interacting Ig1-2-3 cis dimers (mediated by Ig1-Ig2 binding) are shown. The Ig1-to-Ig2, Ig1-to-Ig3, Ig2-to-Ig2, and Ig2-to-Ig3 interaction sites are indicated by white ellipses. The heparin binding sites of the Ig2 modules (residues 133-148) are indicated by white squares. The arrows indicate the position of N-linked glycosylation at Asn203 (Asn203 is marked by white triangle). The termini are denoted by N and C.

(A,B) The Ig1-2 mediated cis dimers of the Ig1-2-3 fragment form a "flat" zipper via an Ig2-to-Ig3 mediated trans interaction, reflecting an interaction between NCAM molecules on opposing cells.

(C,D) The Ig1-2-3 fragment cis dimers also form a non-symmetrical "compact" zipper via Ig1-to-Ig3 and Ig2-to-Ig2 trans interactions. Two cis dimers are held together by two Ig1-to-Ig3 interactions (full ellipses) on one side and one Ig2-to-Ig2 interaction (stippled ellipse) on the opposite side of the zipper. The views in B and D are perpendicular to A and C, respectively.

Figure 5:
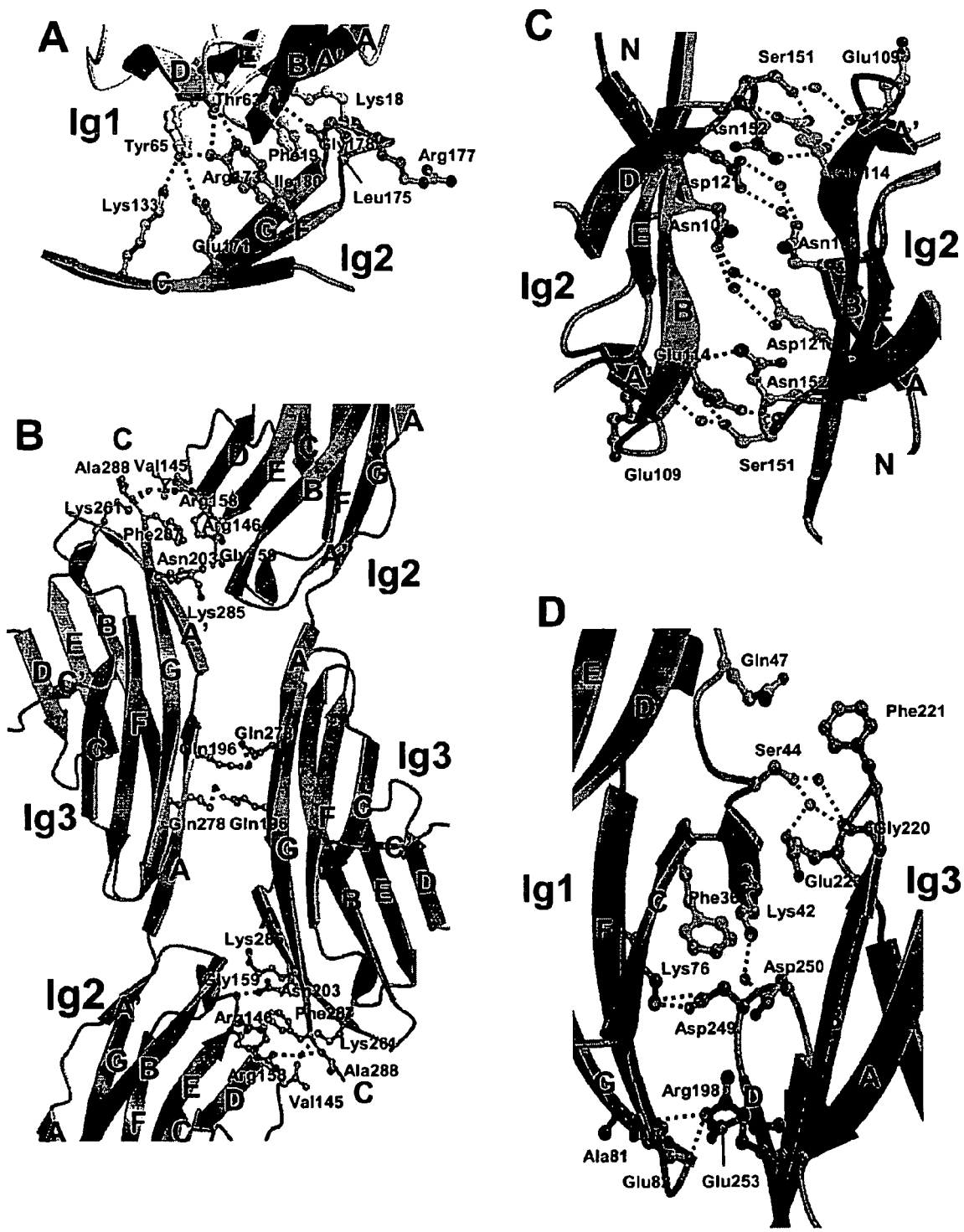

FIG. 5. Close-up view of the interaction interfaces in the NCAM Ig1-2-3 fragment.

(A) The Ig1-to-Ig2 interaction interface. The Ig1 and Ig2 modules are belong to two different individual Ig1-2-3 fragments that form one Ig1-2-3 cis dimer.

(B) The Ig2-to-Ig3 interaction interface.

(C) The Ig2-to-Ig2 interaction interface.

(D) The Ig1-to-Ig3 interaction interface. In B-D, the ribbon representations of modules from two interacting Ig1-2-3 fragments belonging to different individual Ig1-2-3 cis dimers. The hydrogen bonds are shown as dashed lines.

Figure 6:
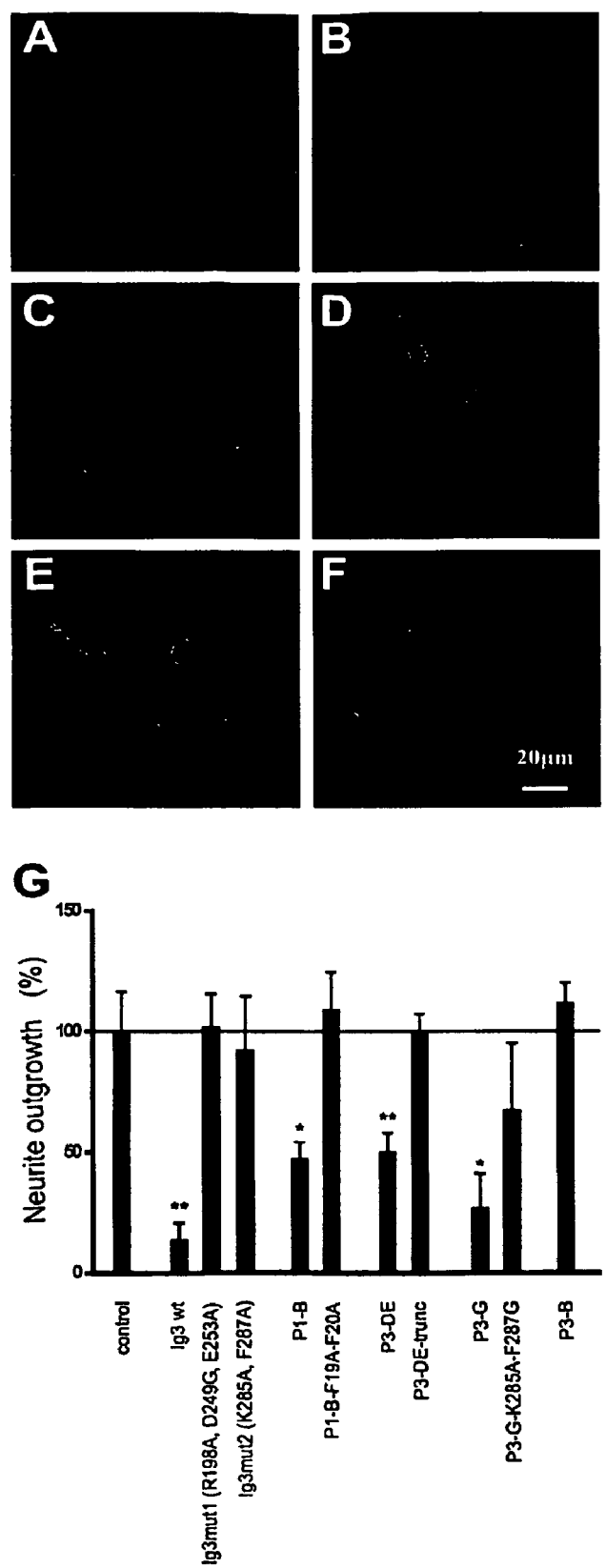

FIG. 6. The effect of the Ig3 module, the P1-B, P3-DE, P3-G, P3-B peptides, and their derivatives, on neurite outgrowth from the NCAM-expressing PC12-E2 cells grown on top of a confluent monolayer of NCAM-transfected fibroblasts.

(A-F) Confocal micrographs of NCAM-expressing pheochromocytoma PC12-E2 cells grown on top of a confluent monolayer of vector-transfected A,C,E or NCAM-140 transfected B,D,F L929 fibroblasts. NCAM-NCAM interaction stimulates neurite outgrowth in PC12-E2 cells grown on top of NCAM-expressing (LBN) B versus NCAM-negative (LVN) A fibroblasts. Introduction of the recombinant Ig3 module does not affect PC12-E2 cells grown on vector-transfected fibroblasts C but clearly inhibits neurite outgrowth in PC12-E2 cells grown on NCAM-transfected fibroblasts D as a result of disruption of NCAM-NCAM interactions. In contrast, Ig3mut2 neither affects PC12-E2 cells grown on vector-transfected fibroblasts E nor inhibits NCAM-induced neurite outgrowth F. Peptides P1-B, P3-DE, and P3-G have inhibitory effects comparable to the effect of Ig3 wt C,D, whereas effects of the Ig3mut1, P3-B peptide, and control peptides are similar to the effect of Ig3mut2 E,F. Scale bar, 20 µm.

(G) The effect of the Ig3 module, P1-B, P3-DE, P3-G, P3-B peptides, and their derivatives, is shown as percent of control, setting the difference between the average neurite length of PC12-E2 cells grown on NCAM-140-transfected and vector-transfected fibroblasts to 100%. Results are given as mean±SEM. *$P<0.05$, **$P<0.01$ (compared to the induction of neurite outgrowth from PC12-E2 cells grown on top of monolayer of NCAM-transfected fibroblasts).

Figure 7:
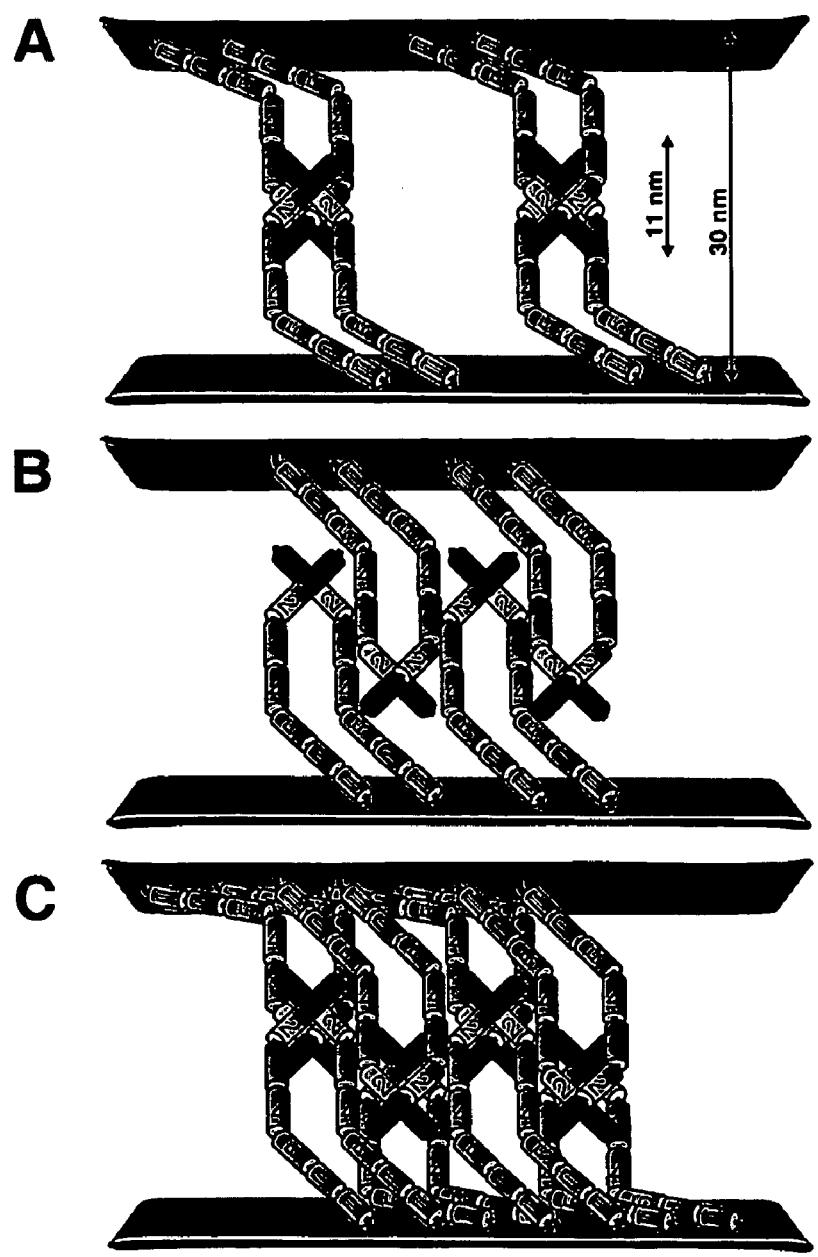

FIG. 7. Schematic representations of the "compact", "flat", and "double" zipper adhesion complexes formed by NCAM, as observed in the crystal structure of the NCAM Ig1-2-3 fragment. The individual NCAM modules are shown as cylinders. The Ig and FnIII modules are numbered by Arabic and Roman numerals, respectively. In order to accommodate all seven extracellular modules of NCAM a bend has been introduced after Ig4 according to electron microscopy studies (Hall and Rutishauser, 1987; Becker et al., 1989). The size of the Ig1-2-3 fragment and distance between opposing cell membranes are indicated.

(A) The "compact" zippers are stabilized by Ig1-to-Ig3 and Ig2-to-Ig2 interactions between Ig1-2-3 cis dimers originating from two opposing cell membranes.

(B) The "flat" zipper is stabilized by Ig2-to-Ig3 interactions between Ig1-2-3 cis dimers originating from two opposing cell membranes.

(C) The two types of zippers may co-exist as observed in the crystal and will result in formation of a double zipper-like adhesion complex.

Figure 8:
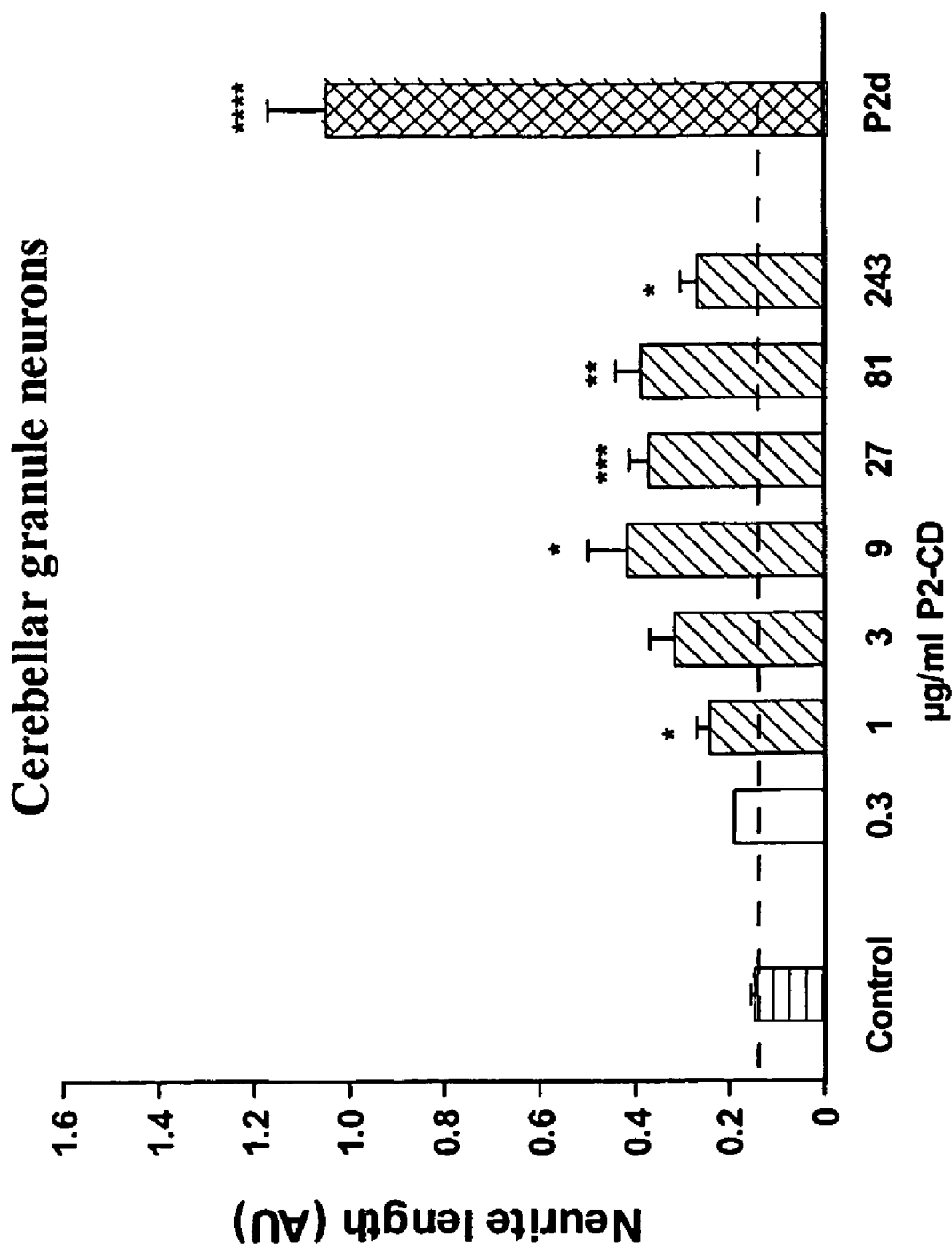

FIG. 8. demonstrates the effect of the P2-CD peptide on neurite outgrowth of CGN grown as single neurons in primary culture for 24 h in the presence of different concentrations of the peptide in growth media. The length of neurites is expressed in Arbitrary Units (AU). The length of neurites in treated cultures is compared to the length of neurite in cultures without treatment (control) (*$p<0.05$; $p<0.02$; *$p<0.001$ ****$p<0.0005$). P2d, which is a peptide fragment of NCAM Ig2 module (see Soroka et al., 2002), was used as a positive control to indicate responsiveness of the cells to the treatment.

Figure 9:
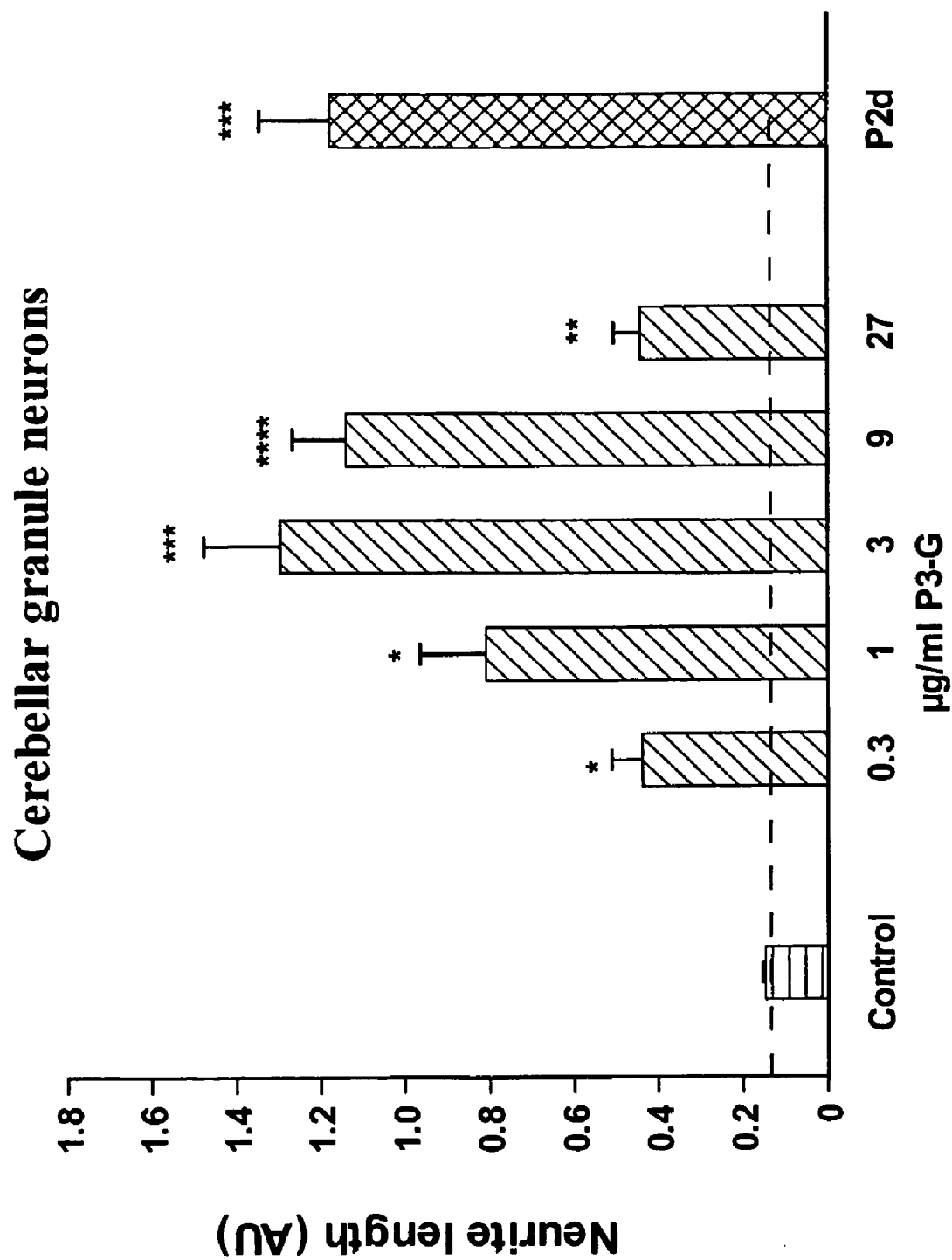

FIG. 9 demonstrates the effect of the P3-G peptide on neurite outgrowth of CGN grown as single neurons in primary culture for 24 h in the presence of different concentrations of the peptide in growth media. The length of neurites is expressed in Arbitrary Units (AU). The length of neurites in treated cultures is compared to the length of neurite in cultures without treatment (control). P2d was used as a positive control. *$p<0.05$; $p<0.02$; *$p<0.001$ ****$p<0.0005$ FIG. 10 demonstrates the effect of the P2-EF peptide on neurite outgrowth of CGN grown as single neurons in primary culture for 24 h in the presence of different concentrations of the peptide in growth media. The length of neurites is expressed in Arbitrary Units (AU). The length of neurites in treated cultures is compared to the length of neurite in cultures without treatment (control). P2d as used as a positive control. *$p<0.05$; $p<0.02$; *$p<0.001$ **$p<0.0005$ FIG. 11 demonstrates the effects of the P1-CD peptide on neurite outgrowth of CGN grown as single neurons in primary culture for 24 h in the presence of different concentrations of the peptide in growth media and in co-culture of CGN with genetically modified fibroblasts with (LBN) or without (LVN) NCAM expression. It can be seen that the peptide does not affect NCAM-independent neurite outgrowth of CGN in both cultures, but inhibits NCAM-dependent neurite outgrowth by interfering with NCAM homophylic adhesion in co-cultures of CGN and LBN-cells. The length of neurites is expressed in Arbitrary Units (AU). The length of neurites in treated cultures is compared to the length of neurite in cultures without treatment (control). P2d was used as a positive control. *$p<0.001$ FIG. 12 demonstrates the effect of the P2-A'B peptide on neurite outgrowth of CGN grown as single neurons in primary culture for 24 h in the presence of different concentrations of the peptide in growth media and in co-culture of CGN with genetically modified fibroblasts with (LBN) or without (LVN) NCAM expression. From the figure it can be seen that the peptide does not affect NCAM-independent neurite outgrowth of CGN in both cultures, and inhibits NCAM-dependent neurite outgrowth by interfering with NCAM homophylic adhesion in co-cultures of CGN and LBN-cells. The length of neurites is expressed in Arbitrary Units (AU). The length of neurites in treated cultures is compared to the length of neurite in cultures without treatment (control). P2d was used as a positive control. ***$p<0.001$

DETAILED DESCRIPTION OF THE INVENTION

Molecules with the potential to promote neurite outgrowth as well as stimulate survival, regeneration and modulate adhesion of neuronal cells, such as certain endogenous trophic factors and adhesion molecules, for example NCAM, are prime targets in the search for compounds that facilitate for example neuronal regeneration and other forms of neuronal plasticity. To evaluate the potential of compounds to interfere with cell adhesion, the ability to stimulate neurite outgrowth, regeneration and the survival of neuronal cells a capability of the compounds to interact with NCAM may be investigated. It is an object of the present invention to provide compounds capable of binding to one or more positions in the NCAM molecule. In particular, positions in the NCAM Ig1, Ig2 and/or Ig3 modules which constitute a homophylic binding site of NCAM described in the present application.

NCAM is a multifunctional adhesion molecule. It is involved as a key molecule in different processes associated with neural plasticity during embryonic development, in the adult brain and in association with disease. Involvement of NCAM in different processes underlying neural plasticity is provided by a capability of NCAM to cis- and trans-homophylic interactions and heterophylic interactions with a number of cellular receptors and other cellular and extracellular molecules. The NCAM molecule has multiple non-ovelapping and overlapping binding sites for the interaction with these molecules, which are located in different extracellular NCAM modules and in the intracellular domain of NCAM.

The present invention relates to a method of modulating the differentiation, adhesion and/or survival of NCAM presenting cells, said method comprising providing a compound capable of interacting with a novel NCAM homophylic binding site composed of amino acid residues of the Ig1, Ig2 and Ig3 modules of NCAM. Amino acid residues of the binding site are capable of the following interactions:

amino acid residues of the binding site located in the Ig1 module of one NCAM molecule of the interaction with the amino acid residues of the binding site located in the Ig3 module of another, the counter NCAM molecule, but not with the residues of the binding site located in Ig1 or Ig2 modules of this counter NCAM molecule, amino acid residues of the binding site located in the Ig2 module of one NCAM molecule of interaction with the amino acid residues of the binding site located in the Ig2 module of another, the counter NCAM molecule, but not with the residues of the binding site located in the Ig1 or Ig3 modules of this counter NCAM molecule, and amino acid residues of the binding site located in the Ig2 module of one NCAM molecule of the interaction with the amino acid residues of the binding site located in the Ig3 module of another, the counter NCAM molecule, but not with the residues of the binding site located in the Ig2 or Ig1 modules of this counter NCAM molecule, amino acid residues of the binding site located in the Ig3 module of one NCAM molecule of the interaction with the amino acid residues of the binding site located in the Ig2 module of another, the counter NCAM molecule, but not with the residues of the binding site located in the Ig3 or Ig1 modules of this counter NCAM molecule, amino acid residues of the binding site located in the Ig3 module of one NCAM molecule of the interaction with the amino acid residues of the binding site located on the Ig1 module of another, counter NCAM molecule, but not with the residues of the binding site located on the Ig3 or Ig2 modules of this counter NCAM molecule.

According to the invention, a compound, which is capable of i) interacting with the Ig1 module of NCAM, and thereby mimicking and/or modulating the interaction between the Ig1 and Ig3 modules of NCAM, wherein said modules are from two individual NCAM molecules, and/or ii) interacting with the Ig3 module of NCAM, and thereby mimicking and/or modulating the interaction between the Ig3 and Ig1 modules of NCAM, wherein said modules are from two individual NCAM molecules, and/or iii) interacting with the Ig2 module of NCAM, and thereby mimicking the interaction between Ig2 and Ig3 modules of NCAM, wherein said modules are from two individual NCAM molecules, and/or iv) interacting with the Ig3 module of NCAM, and thereby mimicking and/or modulating the interaction between the Ig3 and Ig2 modules of NCAM, wherein said modules are from two individual NCAM molecules, and/or v) interacting with the Ig2 module of NCAM, and thereby mimicking and/or modulating the interaction between the Ig2 and Ig2 modules of NCAM, wherein said modules are from two individual NCAM molecules, is a ligand of the above homophylic binding site and is capable of modulating a process assisted by NCAM homophylic binding through the above binding site by interacting with this binding site.

The term "individual" in relation to two or more molecules/modules/fragments is used to indicate that these two or more molecules/modules/fragments are present as separate, non-connected, substances.

The term "interacting" is used herein synonymously with the term "binding". The term "ligand" is defined as a compound, which binds to the binding site of above and mimics NCAM homophylic binding. The term "to mimic" is understood as a capability of the ligand to induce/stimulate or inhibit a biological process, which is mediated by NCAM through homophylic interaction through the above binding site. The ligand may also inhibit naturally occurring interactions, such as by binding to parts of NCAM which are not a part of the binding site, and wherein the interference is merely a steric interference.

The compounds capable of interaction/binding to the binding site of the invention are favourable for the promotion of neurite outgrowth. Compounds of the invention are therefore considered to be good promoters of regeneration of neuronal connections, and thereby of functional recovery after damages, as well as promoters of neuronal function in other conditions where such an effect is required.

In the present context "differentiation" is related to the processes of maturation of cells, such as for example extension of neurites from neurons which takes place after the last cell division of said neurons has ended. The compounds of the present invention may be capable of stopping cell division and initiate maturation and/or extension of neurites In the present invention a compound is considered promising when it is capable of stimulating neurite outgrowth, for example when it is capable of stimulating neurite outgrowth of cultured cells when compared to control cells, such as improving neurite outgrowth by 50% or more, such as 75%, for example 100% or more.

Further, in the present context the wording "stimulate/promoting survival" is used synonymously with the wording "preventing cell death" or "neuro-protection". By stimulating/promoting survival it is possible to prevent diseases or prevent further degeneration of the nervous system in individuals suffering from a neuro-degenerative disorder.

"Survival" refers to the process, wherein a cell has been traumatised and would under normal circumstances, with a high probability die, if not the compound of the invention was used to prevent said cell from degenerating, and thus promoting or stimulating survival of said traumatised cell.

By the term "modulation" is meant a change, such as either stimulation or inhibition. A compound of the invention is capable of modulation of the processes mediated by NCAM homophylic binding. Thus, the compound is capable of stimulation or inhibition of neural cell differentiation and/or survival. The latter processes may involve activating or inhibiting of NCAM signalling. Thus, the compound, which is capable of modulating the above NCAM dependent processes, is considered by the invention as a compound, which is capable of modulating NCAM signalling. Under the capability of a compound "to modulate the NCAM signalling" is understood a capability of a molecule to modulate the process of initiating of the production of second messenger molecules and/or activation or inhibition of an intracellular cascade reaction leading to a physiological response of the cell, such as for example an increase in neurite length in response to ligand binding to the homophylic binding site of the invention.

The invention also provides for a compound capable of "interfering with cell adhesion". This refers to the process wherein cells are attracted to one another and where the present compound is capable of either stimulating or inhibiting said attraction.

The compounds according to the invention also relates to the prevention of neuronal cell death. Peripheral nerve cells possess to a limited extent a potential to regenerate and re-establish functional connections with their targets after various injuries. However, functional recovery is rarely complete and peripheral nerve cell damage remains a considerable problem. In the central nervous system, the potential for regeneration is even more limited. Therefore, the identification of substances with the ability to prevent neuronal cell death in the peripheral and the central nervous system is significant and of great commercial value.

The compounds of the invention may be peptides, such as the peptide fragments/parts of the binding site, or peptides comprising the amino acid sequences of the binding site.

In a further embodiment of the invention the compounds may comprise other chemical entities, such as sugar, cholesterol, and fatty acid. Preferably, the chemical entity is bound to the N-terminal or C-terminal of the peptide of the compound.

It is an aspect of the present invention that the compounds are capable of binding to the NCAM Ig1 and/or Ig2 and/or Ig3 modules at the homophilic binding site of the invention, or at any other sites of the NCAM module consisting of the Ig1, Ig2 and Ig3 modules and mimicking the effect of the binding at said homophilic binding site, or modulating said effect.

Without being bound by theory, the present inventors believe that active ligands to the NCAM Ig1 and/or Ig2 and/or Ig3 modules are ligands which bind to the NCAM Ig1 and/or Ig2 and/or Ig3 modules and thus trigger a conformational change of the module resulting in a signalling cascade being initiated, wherein said signalling results in a physiological change in the cell, such as influencing survival of cells, cellular adhesion and/or neurite outgrowth. Thus, a compound according to the invention may be any compound described above which can trigger a conformational change of the NCAM Ig1 and/or the NCAM Ig2 and/or the NCAM Ig3 module resulting in a change in downstream signalling cascade.

Method of Modulating

Thus, it is an object of the present invention to provide a method of modulating adhesion, differentiation and/or survival of NCAM presenting cells by
a) providing a compound capable of interacting with an NCAM homophylic binding site composed of the amino acid residues of the Ig1, Ig2 and Ig3 modules of NCAM by
  i) interacting with the Ig1 module of NCAM, and thereby mimicking and/or modulating the interaction between the Ig1 and Ig3 modules of NCAM, wherein said modules are from two individual NCAM molecules, and/or
  ii) interacting with the Ig3 module of NCAM, and thereby mimicking and/or modulating the interaction between the Ig3 and Ig1 modules of NCAM, wherein said modules are from two individual NCAM molecules, and/or
  iii) interacting with the Ig2 module of NCAM, and thereby mimicking the interaction between Ig2 and Ig3 modules of NCAM, wherein said modules are from two individual NCAM molecules, and/or iv) interacting with the Ig3 module of NCAM, and thereby mimicking and/or modulating the interaction between the Ig3 and Ig2 modules of NCAM, wherein said modules are from two individual NCAM molecules, and/or
v) interacting with the Ig2 module of NCAM, and thereby mimicking and/or modulating the interaction between the Ig2 and Ig2 modules of NCAM, wherein said modules are from two individual NCAM molecules,
b) providing at least one NCAM presenting cell;
c) modulating cell differentiation and/or survival of the at least one NCAM presenting cell by contacting the at least one NCAM presenting cell with said compound, and thereby.

The invention concerns the NCAM presenting cell being
i) a cell, which naturally express an NCAM molecule on the cell surface, such as for example a neural cell, a muscle cell or a cell of any other tissue,
ii) a cancer cell, which express an NCAM molecule on the cell surface;
iii) a recombinant cell, which was genetically modified to express an NCAM molecule on the cell surface.

The NCAM presenting cell of above may be an in vivo cell, such as a cell of the body of an animal, or it may be a cell cultured in vitro. Accordingly, the above method may be used for modulating differentiation, survival and/or adhesion of NCAM presenting cells both in vivo and in vitro. In some embodiments the method is for the in vitro use, in other embodiments the method is for the in vivo use.

The method of above comprises providing a compound capable of interacting with the NCAM homophylic binding site composed by the amino acid residues of the Ig1, Ig2 and Ig3 modules of NCAM. In one embodiment it may be a compound capable of interacting with the residues of Ig1 module of NCAM, and thereby mimicking and/or modulating the interaction between the Ig1 and Ig3 modules of NCAM, wherein said modules are from two individual NCAM molecules.

In another embodiment this may be a compound capable of interacting with the residues of Ig3 module of NCAM, and thereby mimicking and/or modulating the interaction between the Ig3 and Ig1 modules of NCAM, wherein said modules are from two individual NCAM molecules.

In still another embodiment the compound is capable of interacting with the residues of the Ig2 module, and thereby mimicking the interaction between Ig2 and Ig3 modules of NCAM, wherein said modules are from two individual NCAM molecules.

In yet another embodiment the compound may be capable of interacting with the residues of the Ig3 module, and thereby mimicking and/or modulating the interaction between the Ig3 and Ig2 modules of NCAM, wherein said modules are from two individual NCAM molecules.

In yet still another embodiment the compound may be capable of interacting with the residues of the Ig2 module of NCAM, and thereby mimicking and/or modulating the interaction between the Ig2 and Ig2 modules of NCAM, wherein said modules are from two individual NCAM molecules.

The above compounds may be represented by a) the molecules, which are capable of all the above interactions (i) to (v), or some of the above interaction, such as for example the interaction of (i) and (ii), or (i) and (iii) or any other combinations of the interactions of (i) to (v), or b) the molecules, which are capable of only one interaction selected from any of the interactions (i) to (v).

Providing a compound capable of one or more of the above interactions may be done in one embodiment by using a method for selecting a candidate compound described in the present application. In another embodiment it may be dome by using a method for testing a compound described in the application below.

All the compounds of (a) and (b) are presumed to be capable of modulating the NCAM functions, if the executing of said functions by an NCAM molecule involves one or more interactions (i) to (v) of above.

Under the compound capable of "mimicking" the interaction means a compound acting as a ligand of the homophylic binding site of above capable of binding to the Ig1, Ig2 or Ig3 modules, and thereby replacing the binding to these modules of the Ig3, Ig2 or Ig1 modules of another, the counter, NCAM molecule, respectfully, as described above. The mimicking is results according to the invention in stimulating or inhibiting a biological process related to the latter binding.

The present inventors present herein a model for NCAM homophilic binding, wherein the Ig1 and Ig2 modules mediate dimerization of individual NCAM molecules situated on the same cell surface (cis interaction), and wherein the Ig3 module mediates interactions between individual NCAM molecules expressed on the surface of opposing cells (trans interaction) through simultaneous binding to the Ig1 and Ig2 modules. This arrangement results in the formation of a double zipper-like NCAM adhesion complex.

Sequences from NCAM

A compound of the invention may be a peptide fragment derived from the sequence of NCAM, or a variant of said peptide fragment. The peptide fragment may be a fragment of the NCAM sequence identified as SwissProt accession number NP_113709 (SEQ ID NO: 44) or SwissProt accession number P13591 (SEQ ID NO: 45).

A preferred peptide fragment may be selected from the amino acid sequences identified below:

| Sequence | |
|---|---|
| WFSPNGEKLSPNQ | (SEQ ID NO: 1) |
| YKCVVTAEDGTQSE | (SEQ ID NO: 2) |
| TLVADADGFPEP | (SEQ ID NO: 3) |
| QIRGIKKTD | (SEQ ID NO: 4) |
| DVR | (SEQ ID NO: 5) |
| RGIKKTD | (SEQ ID NO: 6) |
| DVRRGIKKTD | (SEQ ID NO: 7 |
| KEGED | (SEQ ID NO: 8) |
| IRGIKKTD | (SEQ ID NO: 9) |
| KEGEDGIRGIKKTD | (SEQ ID NO: 10) |
| DKNDE | (SEQ ID NO: 11) |
| TVQARNSIVNAT | (SEQ ID NO: 12) |
| SIHLKVFAK | (SEQ ID NO: 13) |
| LSNNYLQIR | (SEQ ID NO: 14) |
| RFIVLSNNYLQI | (SEQ ID NO: 15) |
| KKDVRFIVLSNNYLQI | (SEQ ID NO: 16) |
| QEFKEGEDAVIV | (SEQ ID NO: 17) |
| KEGEDAVIVCD | (SEQ ID NO: 18) |

```
                        -continued
GEISVGESKFFL                (SEQ ID NO: 19)

KHIFSDDSSELTIRNVDKNDE,      (SEQ ID NO: 20)

AFSPNGEKLSPNQ,              (SEQ ID NO: 40)

AKSVVTAEDGTQSE              (SEQ ID NO: 41)

DVRRGIKKTD                  (SEQ ID NO: 42)

QIRGIKKTD.                  (SEQ ID NO: 43)
```

The above amino acid sequences are derived from the sequence of rat NCAM having the SwissProt accession number NP_113709 (SEQ ID NO: 40).

Another preferred peptide fragment may be selected from fragments or variants of the above identified sequences.

The "variant" is to be understood as being any peptide sequence capable of interacting with the Ig1, Ig2 and/or Ig3 modules of NCAM, and via said interacting induce differentiation, modulate cellular adhesion, stimulate regeneration, neuronal plasticity and survival of cells. Thus, fragment or variant is a biologically active compound and may be defined as a compound i) comprising an amino acid sequence capable of being recognised by an antibody, which is also capable of recognising the predetermined NCAM amino acid sequence, and/or ii) comprising an amino acid sequence capable of binding to a receptor moiety, which is also capable of binding the predetermined NCAM amino acid sequence, and/or iii) having a substantially similar binding affinity to at least one of the Ig1, Ig2 or Ig3 modules as said predetermined NCAM amino acid sequence.

Thus, according to the invention, a variant as defined above is the functional equivalent of a preferred peptide fragment of above.

A variant of the full length NCAM protein, such as the NCAM of SEQ ID NO: 44 or 45, may be represented by a natural isoform of the protein, such as natural soluble molecules of NCAM, shorter or longer polypeptides of NCAM generated as a result of alternative splicing, or it may be a recombinant protein containing a fragment of NCAM comprising 30-100% of the residues the full length protein, or it may a natural protein, which has homology to NCAM. The homology between amino acid sequences may be calculated using well known algorithms such as BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, or BLOSUM 90. Homologues are to be considered as falling within the scope of the present invention when they are at least about 40 percent homologous with the NCAM of SEQ ID NO: 44 or 45, such as at least about 50 percent homologous, for example at least about 60 percent homologous, such as at least about 70 percent homologous, for example at least about 75 percent homologous, such as at least about 80 percent homologous, for example at least about 85 percent homologous, such as at least about 90 percent homologous, for example at least 92 percent homologous, such as at least 94 percent homologous, for example at least 95 percent homologous, such as at least 96 percent homologous, for example at least 97 percent homologous, such as at least 98 percent homologous, for example at least 99 percent homologous. According to one embodiment of the invention the homology percentages refer to identity percentages.

The NCAM variant is according to invention a functional variant, such as an variant that remains a capability of the full length protein to homophylic binding through the binding site of the invention and executing the functions assisted by this binding.

The binding affinity of the compound according to the invention preferably has a binding affinity (Kd value) to the NCAM modules in the range of $10^{-3}$ to $10^{-10}$ M, such as preferably in the range of $10^{-4}$ to $10^{-8}$ M. According to the present invention the binding affinity is determined by one of the following assays of surface plasmon resonance analysis or nuclear magnetic resonance spectroscopy.

In one embodiment variants may be understood as exhibiting amino acid sequences gradually differing from the preferred predetermined sequence, as the number and scope of insertions, deletions and substitutions including conservative substitutions increase. This difference is measured as a reduction in homology between the predetermined sequence and the variant.

"Variants of peptide sequences" means that the peptides may be modified, for example by substitution of one or more of the amino acid residues. Both L-amino acids and D-amino acids may be used. Other modification may comprise derivatives such as esters, sugars, etc. Examples are methyl and acetyl esters. Polymerisation such as repetitive sequences or attachment to various carriers are well-known in the art, e.g. lysine backbones, such as lysine dendrimers carrying 4 peptides, 8 peptides, 16 peptides, or 32 peptides. Other carriers may be protein moieties, such as bovine serum albumin (BSA), or lipophilic dendrimers, or micelle-like carriers formed by lipophilic derivatives, or starburst (star-like) carbon chain polymer conjugates, or ligand presenting assembly (LPA) based on derivatives of diethylaminomethane.

Variants of the peptide fragments according to the invention may comprise, within the same variant, or fragments thereof or among different variants, or fragments thereof, at least one substitution, such as a plurality of substitutions introduced independently of one another. Variants of the complex, or fragments thereof may thus comprise conservative substitutions independently of one another, wherein at least one glycine (Gly) of said variant, or fragments thereof is substituted with an amino acid selected from the group of amino acids consisting of Ala, Val, Leu, and Ile, and independently thereof, variants, or fragments thereof, wherein at least one alanine (Ala) of said variants, or fragments thereof is substituted with an amino acid selected from the group of amino acids consisting of Gly, Val, Leu, and Ile, and independently thereof, variants, or fragments thereof, wherein at least one valine (Val) of said variant, or fragments thereof is substituted with an amino acid selected from the group of amino acids consisting of Gly, Ala, Leu, and Ile, and independently thereof, variants, or fragments thereof, wherein at least one leucine (Leu) of said variant, or fragments thereof is substituted with an amino acid selected from the group of amino acids consisting of Gly, Ala, Val, and Ile, and independently thereof, variants, or fragments thereof, wherein at least one isoleucine (Ile) of said variants, or fragments thereof is substituted with an amino acid selected from the group of amino acids consisting of Gly, Ala, Val and Leu, and independently thereof, variants, or fragments thereof wherein at least one aspartic acids (Asp) of said variant, or fragments thereof is substituted with an amino acid selected from the group of amino acids consisting of Glu, Asn, and Gln, and independently thereof, variants, or fragments thereof, wherein at least one asparagine (Asn) of said variants, or fragments thereof is substituted with an amino acid selected from the group of amino acids consisting of Asp, Glu, and Gln, and independently thereof, variants, or fragments thereof, wherein at least one glutamine (Gln) of said variants, or fragments thereof is substituted with an amino acid selected from the group of amino acids consisting of Asp, Glu, and Asn, and wherein at least one phenylalanine (Phe) of said variants, or fragments thereof is substituted with an amino acid selected from the group of amino acids consisting of Tyr, Trp, His, Pro, and preferably selected from the group of amino acids consisting of Tyr and Trp, and independently thereof, variants, or fragments thereof, wherein at least one tyrosine (Tyr) of said variants, or fragments thereof is substituted with an amino acid selected from the group of amino acids consisting of Phe, Trp, His, Pro, preferably an amino acid selected from the group of amino acids consisting of Phe and Trp, and independently thereof, variants, or fragments thereof, wherein at least one arginine (Arg) of said fragment is substituted with an amino acid selected from the group of amino acids consisting of Lys and His, and independently thereof, variants, or fragments thereof, wherein at least one lysine (Lys) of said variants, or fragments thereof is substituted with an amino acid selected from the group of amino acids consisting of Arg and His, and independently thereof, variants, or fragments thereof, and independently thereof, variants, or fragments thereof, and wherein at least one proline (Pro) of said variants, or fragments thereof is substituted with an amino acid selected from the group of amino acids consisting of Phe, Tyr, Trp, and His, and independently thereof, variants, or fragments thereof, wherein at least one cysteine (Cys) of said variants, or fragments thereof is substituted with an amino acid selected from the group of amino acids consisting of Asp, Glu, Lys, Arg, His, Asn, Gln, Ser, Thr, and Tyr.

It thus follows from the above that the same functional equivalent of a peptide fragment, or fragment of said functional equivalent may comprise more than one conservative amino acid substitution from more than one group of conservative amino acids as defined herein above. The term "conservative amino acid substitution" is used synonymously herein with the term "homologous amino acid substitution".

The groups of conservative amino acids are as the following:

P, A, G, S, T (neutral, weakly hydrophobic)

Q, N, E, D, B, Z (hydrophilic, acid amine)

H, K, R (hydrophilic, basic)

F, Y, W (hydrophobic, aromatic)

L, I, V, M (hydrophobic)

C (cross-link forming)

Conservative substitutions may be introduced in any position of a preferred predetermined peptide of the invention or fragment thereof. It may however also be desirable to introduce non-conservative substitutions, particularly, but not limited to, a non-conservative substitution in any one or more positions.

A non-conservative substitution leading to the formation of a functionally equivalent fragment of the peptide of the invention would for example differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on peptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Substitution of amino acids may in one embodiment be made based upon their hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

The addition or deletion of an amino acid may be an addition or deletion of from 2 to preferably 10 amino acids, such as from 2 to 8 amino acids, for example from 2 to 6 amino acids, such as from 2 to 4 amino acids. However, additions of more than 10 amino acids, such as additions from 2 to 10 amino acids, are also comprised within the present invention. In the multimeric forms additions/deletions may be made individually in each monomer of the multimer.

The invention also concerns non-peptide variants of the compounds disclosed herein. In particular, such variants should be understood to be compounds which bind to or in other ways interact with the Ig1, Ig2 or the Ig3 modules of NCAM and thereby stimulate Ig1, Ig2 or Ig3 signalling and/or modulate proliferation and/or induce differentiation and/or stimulate regeneration, neuronal plasticity and/or survival of cells presenting an NCAM receptor.

Functional Equivalent

A functional equivalent may be obtained by substitution an amino acid in the sequence, which has a functional activity according to the invention. Functionally similar in the present content refers to dominant characteristics of the side chains such as hydrophobic, basic, neutral or acidic, or the presence or absence of steric bulk. Accordingly, in one embodiment of the invention, the degree of identity between i) a given functional equivalent capable of effect and ii) a preferred predetermined fragment, is not a principal measure of the fragment as a variant or functional equivalent of a preferred predetermined peptide fragment according to the present invention.

Fragments sharing at least some homology with a preferred predetermined fragment of at least 3 amino acids, more preferably at least 5 amino acids, are to be considered as falling within the scope of the present invention when they are at least about 25 percent homologous with the preferred predetermined NCAM peptide, or fragment thereof, such as at least about 30 percent homologous, for example at least about 40 percent homologous, such as at least about 50 percent homologous, for example at least about 55 percent homologous, such as at least about 60 percent homologous, for example at least about 65 percent homologous, such as at least about 70 percent homologous, such as at least about 75 percent homologous, for example at least about 80 percent homologous, such as at least about 85 percent homologous.

Sequence identity can be measured using sequence analysis software (for example, the Sequence Analysis Software Package of the Genetics Computer Group, University of Wisconsin Biotechnology Centre, 1710 University Avenue, Madison, Wis. 53705), with the default parameters as specified therein.

Where nothing is specified it is to be understood that the C-terminal amino acid of a polypeptide of the invention exists as the free carboxylic acid, this may also be specified as "—OH". However, the C-terminal amino acid of a compound of the invention may be the amidated derivative, which is indicated as "—NH$_2$". Where nothing else is stated the N-terminal amino acid of a polypeptide comprise a free amino-group, this may also be specified as "H—".

Where nothing else is specified amino acid can be selected from any amino acid, whether naturally occurring or not, such as alpha amino acids, beta amino acids, and/or gamma amino acids. Accordingly, the group comprises but are not limited to: Ala, Val, Leu, Ile, Pro, Phe, Trp, Met, Gly, Ser, Thr, Cys, Tyr, Asn, Gln, Asp, Glu, Lys, Arg, His Aib, Nal, Sar, Orn, Lysine analogues DAP and DAPA, 4Hyp Method for Testing According to the present invention, compounds capable of modulating the interaction between two individual NCAM molecules through the homophylic binding site composed by the Ig1, Ig2 and Ig3 modules of said NCAM molecules may be identified by testing their capability of
  i) interacting with the Ig1 module of NCAM, and thereby mimicking and/or modulating the interaction between the Ig1 and Ig3 modules of NCAM, wherein said modules are from the two individual fragments of (b) interacting to each other, and/or
  ii) interacting with the Ig3 module of NCAM, and thereby mimicking and/or modulating the interaction between the Ig3 and Ig1 modules of NCAM, wherein said modules are from the two individual fragments of (b) interacting to each other, and/or
  iii) interacting with the Ig2 module of NCAM, and thereby mimicking the interaction between Ig2 and Ig3 modules of NCAM, wherein said modules are from the two individual fragments of (b) interacting to each other, and/or
  iv) interacting with the Ig3 module of NCAM, and thereby mimicking and/or modulating the interaction between the Ig3 and Ig2 modules of NCAM, wherein said modules are from the two individual fragments of (b) interacting to each other, and/or
  v) interacting with the Ig2 module of NCAM, and thereby mimicking and/or modulating the interaction between the Ig2 and Ig2 modules of NCAM, wherein said modules are from the two individual fragments of (b) interacting to each other The method according to the invention comprises the steps of
a) providing a compound;
b) providing at least one individual fragment of an NCAM molecule, wherein said fragment comprises a sequence of consecutive amino acid residues corresponding to the sequence of the Ig1-2-3 module of NCAM comprising residues 1 to 289 of the sequence set forth in SEQ ID NO: 40 or fragments of said sequence;
c) contacting the compound of (a) with the individual NCAM fragment of (b), and
d) testing whether the compound is capable of
  interacting with the Ig1 module of NCAM, and thereby mimicking and/or modulating the interaction between the Ig1 and Ig3 modules of NCAM, wherein said modules are from the two individual fragments of (b) interacting to each other, and/or
  interacting with the Ig3 module of NCAM, and thereby mimicking and/or modulating the interaction between the Ig3 and Ig1 modules of NCAM, wherein said modules are from the two individual fragments of (b) interacting to each other, and/or
  interacting with the Ig2 module of NCAM, and thereby mimicking the interaction between Ig2 and Ig3 modules of NCAM, wherein said modules are from the two individual fragments of (b) interacting to each other, and/or
  interacting with the Ig3 module of NCAM, and thereby mimicking and/or modulating the interaction between the Ig3 and Ig2 modules of NCAM, wherein said modules are from the two individual fragments of (b) interacting to each other, and/or
  interacting with the Ig2 module of NCAM, and thereby mimicking and/or modulating the interaction between the Ig2 and Ig2 modules of NCAM, wherein said modules are from the two individual fragments of (b) interacting to each other.

d) providing a candidate compound capable of any of the above interaction(s).

In a preferred embodiment of the invention the individual fragment of NCAM is represented by the Ig1-2-3 module of NCAM comprising a consecutive sequence of at least 289 amino acids from the sequence of NCAM. In more preferred embodiment the sequence comprises aa 1 to 289 of NCAM, wherein NCAM is rat NCAM having the NCBI accession number NP_113709 identified as SEQ ID NO: 40 of the present application.

By the "Ig1-2-3 module of NCAM" in the present context is meant a contiguous amino acid sequence as described above consisting of the sequences of Ig1, Ig2, and Ig3, and linker sequences connecting said modules in the following order: N-terminus<Ig1-linker-Ig2-linker-Ig3>C-terminus. The Ig1-2-3 module may be a recombinant molecule consisting of the Ig1, Ig2 and Ig3 modules, or it may be a recombinant fusion protein containing the Ig1, Ig2 and Ig3 modules and a fusion partner, or it may be a fragment of a full-length NCAM molecule obtained by any known in the art method. According to the above invention the Ig1-2-3 module of the above method is in solution. In one embodiment the solution is an aquatic solution. In a preferred embodiment the solution is phosphate buffered saline (PBS) solution or a TRIS-HCl buffer, pH 7.4.

The contacting of a compound with the individual NCAM fragment of step (c) preferably occurs in solution of the Ig1-2-3 module.

Testing whether the compound is capable of the above interactions may be done by any available in the art method currently used for the detection of protein interactions. For example the NMR spectroscopy may be selected as an appropriate method, or it may be done by using the Plasmon Resonance Analysis. According to the invention the NMR evaluation is preferred.

A compound capable of the above interaction(s) is identified by the above method is designated according to the invention as a candidate compound. The candidate compound may further be tested for its capability of modulating the interaction between at least two individual modules of NCAM, such as
  i) the Ig1 module and the Ig3 module, and/or
  ii) the Ig2 module and the Ig3 module, and/or
  iii) the Ig2 module and the Ig2 module.

The latter testing may for example be done by using gel-filtration of the Ig1-2-3 module in solution in the presence of the selected candidate compound. Or it may be done by using gel-filtration of a mixture of the individual Ig1 and Ig3 modules, or a mixture of the individual Ig2 and Ig3 modules, or a mixture of two individual NCAM fragments, each of which is consisting of the contiguous sequence of the Ig1 and Ig3 modules, or the fragments consisting of Ig2 and Ig3 modules. Gel-filtration chromatography is one of the most commonly used laboratory techniques and a skilful artisan can easily perform such a testing.

According to the present invention, the candidate compound may be any molecule capable of modulating the interactions of the Ig1, Ig2 and Ig3 NCAM modules of above. Such a compound may, for example, be selected from the group comprising combinatorial libraries of peptides, lipids, carbohydrates or other organic molecules, or co-polymers of amino acids with other organic compounds. In a preferred embodiment, the candidate compound of the invention is a peptide.

The purpose of the above testing method is the identification and selection of interesting compounds (candidate compounds) capable of interacting with the Ig1-2-3 module of NCAM at the binding site of the invention and thereby modulating NCAM-dependent cell differentiation, adhesion and/or survival.

Crystal

According to the invention the identification of a candidate compound may comprise the use of a crystalline protein comprising either the individual Ig1, Ig2 and Ig3 modules or a combination of said modules.

A crystalline protein of the Ig1-2-3 module of NCAM consisting of the amino acid sequence corresponding to amino acid residues 1-289 of rat NCAM (SwissProt accession number NP_113709) (SEQ ID NO: 40) is made by the authors of the present invention to determine the structure of NCAM homophylic binding site and the computer generated 3D structure of the module is proposed herein for the in-silico screening compounds capable of binding to the identified homophylic binding site.

In a preferred embodiment the crystalline protein of the invention is a crystal of a polypeptide comprising the Ig1-2-3 module of NCAM comprising a homophilic binding site of NCAM. The crystal may comprise more than one polypeptide, for example two polypeptides. In a preferred embodiment the crystal comprises the Ig1, Ig2 and Ig3 modules of NCAM co-jointed in one fragment by interconnecting amino acid sequences, said one fragment termed herein "the Ig1-2-3 fragment".

Hence, it is preferred that the crystal diffracts X-rays for determination of atomic co-ordinates to a resolution of at least 4 Å, preferably at least 3 Å, more preferably at least 2.8 Å, even more preferably at least 2.5 Å, most preferably at least 2.0 Å.

In a very preferred embodiment of the invention the crystal comprises atoms arranged in a spatial relationship represented by the structure co-ordinates of table 2 shown on FIG. 2, or by co-ordinates having a root mean square deviation there from of not more than 2.5 Å, preferably not more than 2.25 Å, more preferably not more than 2.0 Å, even more preferably not more than 1.75 Å, yet more preferably not more than 1.5 Å, for example not more than 1.25 Å, such as not more than 1.0 Å. Preferably, the co-ordinates has a root mean square deviation there from, of not more than 2.5 Å, preferably not more than 2.25 Å, more preferably not more than 2.0 Å, even more preferably not more than 1.75 Å, yet more preferably not more than 1.5 Å, for example not more than 1.25 Å, such as not more than 1.0 Å.

Preferably, the crystal comprises or more preferably consists of the structure as deposited to the PDB with id 1QZ1.

The crystal may comprise more than one polypeptide of the Ig1-2-3 fragment NCAM per asymmetric unit, in a preferred embodiment of the invention the crystal comprises polypeptides of the one Ig1-2-3 module of NCAM per asymmetric unit.

It is preferred that the crystal has unit cell dimensions of in the range of a=50 to 52, preferably 50.5 to 51.0, more preferably around 51.5 b=107.5 to 109.5, preferably 108 to 109, more preferably around 108.5 c=146 to 151, preferably 148 to 150, more preferably around 149.0

α=85.5 to 95.5, preferably 88 to 92, more preferably around 90

β=85.5 to 95.5, preferably 88 to 92, more preferably around 90

γ=85.5 to 95.5, preferably 88 to 92, more preferably around 90.

Most preferably the crystal has the following characteristics:

Spacegroup: $I2_12_12_1$, with 1 molecule per asymmetric unit, unit cell dimensions of a=51.5 b=108.5 c=149.0 Å alpha=90° beta=90° gamma=90°.

Preparing Crystals

After several unsuccessful attempts, suitable conditions for preparing crystals of a polypeptide corresponding to the Ig 1-2-3 module of NCAM were identified.

It is therefore also an aspect of the present invention to provide a crystal comprising a polypeptide comprising at least 289 consecutive amino acid residues corresponding to amino acid residues 1-289 of rat NCAM (NCBI accession number NP_113709) (SEQ ID NO: 40), said consecutive amino acids correspond to the Ig1-2-3 fragment of rat NCAM using a method of preparing a crystal, wherein said method comprises the steps of i) providing said polypeptide;

ii) growing crystals under conditions wherein said polypeptide is incubated in a buffer comprising in the range of 14 to 17% polyethylene glycol 4000 (PEG4k), in the range of 0.150 M to 0.5 M Li sulfate salt wherein said buffer has a pH in the range of 4.8-5.8;

iii) thereby preparing said crystals

In one embodiment of the invention, co-crystals of said polypeptide and a compound capable of interacting with said polypeptide are prepared. Said compound may have been identified by any of the methods outlined herein below. Hence, the compound may in one aspect of the invention be a modulator, such as a modulator of NCAM-homophilic interaction mediated by the Ig 1-2-3 module of NCAM.

The co-crystals are useful for designing optimised compounds, with enhanced binding properties. In particular, the co-crystals may be useful for designing better inhibitors of homophilic interaction mediated by the Ig 1-2-3 module of NCAM, or stabilizers of said interaction.

The buffer preferably comprises in the range of 5 to 25% polyethylene glycol, more preferably in the range of 10 to 20%, even more preferably in the range of 12 to 18%, yet more preferably in the range of 14 to 16%, most preferably around 15% polyethylene glycol. Polyethylene glycol (PEG) may be any suitable PEG for example a PEG selected from the group consisting of PEG 4000, PEG 6000 and PEG 8000, preferably polyethylene glycol is PEG 4000.

The buffer preferably comprises in the range of 0.15 M to 0.5 M salt, more preferably in the range of 0.2 to 0.5 M, even more preferably in the range of 0.3 to 0.5 M, yet more preferably in the range of 0.4 to 0.5 M, most preferably around 0.45 M salt. The salt may be any useful salt, preferably the salt is Li sulfate ($Li_2SO_4$)

The buffer preferably has a pH in the range of 4.0 to 8.5, more preferably in the range of 4.5 to 7.5, even more preferably in the range of 5.0 to 6.5, yet more preferably in the range of 5.0 to 5.2. The buffer may be any useful buffer, preferably the Na-acetate buffer.

Incubation should be performed at a suitable temperature, preferably at a temperature in the range of 5 to 25° C., more preferably in the range of 10 to 25° C., even more preferably in the range of 15 to 25° C., even more preferably in the range of 17 to 21° C., yet more preferably around 18° C.

The crystals may be grown by any suitable method, for example by the hanging drop method.

Determination of Structure

The structure of crystals may be determined by any method known to the person skilled in the art, for example using X-ray diffraction. Once a structure has been identified, said structure may be refined using suitable software.

In one embodiment of the invention a molecular replacement technique may be used. Such techniques involves that the structure is determined by obtaining x-ray diffraction data for crystals of the polypeptide or complex for which one wishes to determine the three dimensional structure. Then, one determines the three-dimensional structure of that polypeptide or complex by analysing the x-ray diffraction data using molecular replacement techniques with reference to known structural co-ordinates of a structurally similar protein. In the case of polypeptide comprising the Ig1-2 modules of NCAM, structural co-ordinates of said modules may be used. As described in U.S. Pat. No. 5,353,236, for instance, molecular replacement uses a molecule having a known structure as a starting point to model the structure of an unknown crystalline sample. This technique is based on the principle that two molecules, which have similar structures, orientations and positions in the unit cell, diffract similarly. Molecular replacement involves positioning the known structure in the unit cell in the same location and orientation as the unknown structure. Once positioned, the atoms of the known structure in the unit cell are used to calculate the structure factors that would result from a hypothetical diffraction experiment. This involves rotating the known structure in the six dimensions (three angular and three spatial dimensions) until alignment of the known structure with the experimental data is achieved. This approximate structure can be fine-tuned to yield a more accurate and often higher resolution structure using various refinement techniques. For instance, the resultant model for the structure defined by the experimental data may be subjected to rigid body refinement in which the model is subjected to limited additional rotation in the six dimensions yielding positioning shifts of under about 5%. The refined model may then be further refined using other known refinement methods.

Another method for determining the three-dimensional structure of a polypeptide corresponding to the Ig 1-2-3 module of NCAM, or a complex of said polypeptide with an interacting compound, is homology modelling techniques. Homology modelling involves constructing a model of an unknown structure using structural co-ordinates of one or more related proteins, protein domains and/or subdomains. Homology modelling may be conducted by fitting common or homologous portions of the protein or peptide whose three dimensional structure is to be solved to the three dimensional structure of homologous structural elements. Homology modelling can include rebuilding part or all of a three dimensional structure with replacement of amino acids (or other components) by those of the related structure to be solved.

An example of structure determination is outlined in example 2.

Structural coordinates of a crystalline polypeptide of this invention may be stored in a machine-readable form on a machine-readable storage medium, e.g. a computer hard drive, diskette, DAT tape, CD-ROM etc., for display as a three-dimensional shape or for other uses involving computer-assisted manipulation of, or computation based on, the structural coordinates or the three-dimensional structures they define. For example, data defining the three dimensional structure of a polypeptide corresponding to the Ig 1-2-3 module of NCAM, may be stored in a machine-readable storage medium, and may be displayed as a graphical three-dimensional representation of the protein structure, typically using a computer capable of reading the data from said storage medium and programmed with instructions for creating the representation from such data. This invention thus encompasses a machine, such as a computer, having a memory that contains data representing the structural coordinates of a crystalline composition of this invention, e.g. the coordinates set forth in table 2 (FIG. 2), together with additional optional data and instructions for manipulating such data. Such data may be used for a variety of purposes, such as the elucidation of other related structures and drug discovery.

A first set of such machine readable data may be combined with a second set of machine-readable data using a machine programmed with instructions for using the first data set and the second data set to determine at least a portion of the coordinates corresponding to the second set of machine-readable data. For instance, the first set of data may comprise a Fourier transform of at least a portion of the coordinates for the complex set forth in table 2 (FIG. 2), while the second data set may comprise X-ray diffraction data of a molecule or molecular complex.

More specifically, one of the objects of this invention is to provide three-dimensional structural information of co-complexes comprising the homophilic binding site of the Ig 1-2-3 module of NCAM. To that end, we provide for the use of the structural co-ordinates of a crystalline composition of this invention, or portions thereof, to solve, e.g. by molecular replacement or by homology modelling techniques, the three dimensional structure of a crystalline form of another similar cell adhesion molecule (CAM), for example another CAM comprising the Ig modules capable of homophilic interaction or a polypeptide:interacting compound complex.

For example, one may use molecular replacement to exploit a set of coordinates such as set forth in table 2 (FIG. 2) to determine the structure of a crystalline co-complex of a polypeptide corresponding to the Ig 1-2-3 module of NCAM comprising a homophilic binding site and an interacting compound.

Uses of the Structures

A 3D representation of the polypeptides described in the present invention may be useful for several purposes, for example for determining the structure of similar proteins or polypeptides (see also herein above) or for designing compounds capable of interacting with said polypeptides.

For example, the three dimensional structure defined by the machine readable data for the polypeptide of the Ig1-2-3 module of NCAM may be computationally evaluated for its ability to associate with various chemical entities or test compounds. The term "chemical entity", as used herein, refers to chemical compounds, complexes of at least two chemical compounds, and fragments of such compounds or complexes.

For instance, a first set of machine-readable data defining the 3-D structure of polypeptide corresponding to the Ig1-2-3 module of NCAM or complex thereof, is combined with a second set of machine-readable data defining the structure of a chemical entity or test compound of interest using a machine programmed with instructions for evaluating the ability of the chemical entity or compound to associate with the Ig1-2-3 module of NCAM or complex thereof and/or the location and/or orientation of such association. Such methods provide insight into the location, orientation and energies of association of protein surfaces with such chemical entities.

The three dimensional structure defined by the data may be displayed in a graphical format permitting visual inspection of the structure, as well as visual inspection of the association of the polypeptide component(s) with an interacting compound. Alternatively, more quantitative or computational methods may be used. For example, one method of this invention for evaluating the ability of a chemical entity to associate with any of the molecules or molecular complexes set forth herein comprises the steps of: (a) employing computational means to perform a fitting operation between the chemical entity and a binding site or other surface feature of the molecule or molecular complex; and (b) analysing the results of said fitting operation to quantify the association between the chemical entity and the binding site.

This invention further provides for the use of the structural coordinates of a crystalline composition of this invention, or portions thereof, to identify reactive amino acids, such as cysteine residues, within the three-dimensional structure, preferably within or adjacent to a binding site; to generate and visualise a molecular surface, such as a water-accessible surface or a surface comprising the space-filling van der Waals surface of all atoms; to calculate and visualise the size and shape of surface features of the protein or complex, e.g., substrate binding sites; to locate potential H-bond donors and acceptors within the three-dimensional structure, preferably within or adjacent to a ligand binding site; to calculate regions of hydrophobicity and hydrophilicity within the three-dimensional structure, preferably within or adjacent to a ligand binding site; and to calculate and visualize regions on or adjacent to the protein surface of favourable interaction energies with respect to selected functional groups of interest (e.g. amino, hydroxyl, carboxyl, methylene, alkyl, alkenyl, aromatic carbon, aromatic rings, heteroaromatic rings, etc.). One may use the foregoing approaches for characterising the polypeptide corresponding to the Ig1-2-3 module of NCAM and its interactions with moieties of potential interacting compounds to design or select compounds capable of specific covalent attachment to reactive amino acids (e.g., cysteine) and to design or select compounds of complementary characteristics (e.g., size, shape, charge, hydrophobicity/hydrophilicity, ability to participate in hydrogen bonding, etc.) to surface features of the protein, a set of which may be preselected. Using the structural coordinates, one may also predict or calculate the orientation, binding constant or relative affinity of a given ligand to the protein in the complexed state, and use that information to design or select compounds of improved affinity.

In such cases, the structural coordinates of the polypeptide of the Ig1-2-3 module of NCAM, or portion or complex thereof, are entered in machine readable form into a machine programmed with instructions for carrying out the desired operation and containing any necessary additional data, e.g. data defining structural and/or functional characteristics of a potential interacting compound or moiety thereof, defining molecular characteristics of the various amino acids, etc.

One method of this invention provides for selecting from a database of chemical structures a compound capable of binding to the Ig1-2-3 module of NCAM. The method starts with structural co-ordinates of a crystalline composition of the invention, e.g., co-ordinates defining the three dimensional structure of the Ig 1-2-3 module of NCAM or a portion thereof or a complex thereof. Points associated with that three-dimensional structure are characterised with respect to the favourable ability of interactions with one or more functional groups. A database of chemical structures is then searched for candidate compounds containing one or more functional groups disposed for favourable interaction with the protein based on the prior characterisation. Compounds having structures which best fit the points of favourable interaction with the three dimensional structure are thus identified.

It is often preferred, although not required, that such searching be conducted with the aid of a computer. In that case a first set of machine-readable data defining the 3D structure of a polypeptide corresponding to the Ig1-2-3 module of NCAM, or a portion or polypeptide/interacting compound complex thereof, is combined with a second set of machine readable data defining one or more moieties or functional groups of interest, using a machine programmed with instructions for identifying preferred locations for favourable interaction between the functional group(s) and atoms of the polypeptide. A third set of data, i.e. data defining the location(s) of favourable interaction between polypeptide and functional group(s) is so generated. That third set of data is then combined with a fourth set of data defining the 3D structures of one or more chemical entities using a machine programmed with instructions for identifying chemical entities containing functional groups so disposed as to best fit the locations of their respective favourable interaction with the polypeptide.

Compounds having the structures selected or designed by any of the foregoing means may be tested for their ability to bind to the Ig 1-2-3 module of NCAM.

In one preferred embodiment of the invention, the compound is preferably a modulator of NCAM homophilic interaction mediated by the Ig 1-2-3 fragment. For example, a compound capable of interacting with the Ig1-2-3 homophilic binding site may be a good inhibitor of NCAM homophilic binding and NCAM function that requires this binding. Hence, compounds having the structures selected or designed by any of the foregoing means may be tested for their ability to modulate NCAM activity, such as mediation of cell differentiation and/or survival of NCAM presenting cells.

As practitioners in this art will appreciate, various computational analyses may be used to determine the degree of similarity between the three dimensional structure of a given polypeptide (or a portion or complex thereof) and a polypeptide corresponding to the Ig1-2-3 module of NCAM or complex thereof such as are described herein. Such analyses may be carried out with commercially available software applications, such as the Molecular Similarity application of QUANTA (Molecular Simulations Inc., Waltham, Mass.) version 3.3, and as described in the accompanying User's Guide, Volume 3 pgs. 134-135.

The Molecular Similarity application permits comparisons between different structures, different conformations of the same structure, and different parts of the same structure. The procedure used in Molecular Similarity to compare structures is divided into four steps: (1) load the structures to be compared; (2) define the atom equivalences in these structures; (3) perform a fitting operation; and (4) analyse the results.

Each structure is identified by a name. One structure is identified as the target (i.e., the fixed structure); all remaining structures are working structures (i.e., moving structures). Since atom equivalency within QUANTA is defined by user input, for the purpose of this invention we define equivalent atoms as protein backbone atoms (N, Cα, C and O) for all conserved residues between the two structures being compared and consider only rigid fitting operations.

When a rigid fitting method is used, the working structure is translated and rotated to obtain an optimum fit with the target structure. The fitting operation uses a least squares fitting algorithm that computes the optimum translation and rotation to be applied to the moving structure, such that the root mean square difference of the fit over the specified pairs of equivalent atom is an absolute minimum. This number, given in angstroms, is reported by QUANTA.

For the purpose of this invention, any set of structural co-ordinates of a polypeptide corresponding to Ig 1-2-3 module of NCAM or molecular complex thereof that has a root mean square deviation of conserved residue backbone atoms (N, Cα, C, O) of less than 1.5 Å when superimposed—using backbone atoms—on the relevant structural co-ordinates of a protein or complex of this invention, e.g. the co-ordinates listed in table 2 (FIG. 2), are considered identical. More preferably, the root mean square deviation is less than 1.0 Å. Most preferably, the root mean square deviation is less than 0.5 Å.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein from the backbone of a protein of this invention, such as a homophilic binding site of the Ig 1-2-3 module of NCAM as defined by the structural co-ordinates of table 2 (FIG. 2) and described herein.

The term "least squares" refers to a method based on the principle that the best estimate of a value is that in which the sum of the squares of the deviations of observed values is a minimum.

In order to use the structural co-ordinates generated for a crystalline substance of this invention, e.g. the structural co-ordinates set forth in table 2 (FIG. 2), it is often necessary or desirable to display them as, or convert them to, a three-dimensional shape, or to otherwise manipulate them. This is typically accomplished by the use of commercially available software such as a program, which is capable of generating three-dimensional graphical representations of molecules or portions thereof from a set of structural co-ordinates.

By way of illustration, a non-exclusive list of computer programs for viewing or otherwise manipulating protein structures include the following:

Midas (Univ. of California, San Francisco),

MidasPlus (Univ. of Cal., San Francisco)

MOIL (University of Illinois)

Yummie (Yale University)

Sybyl (Tripos, Inc.)

Insight/Discover (Biosym Technologies)

MacroModel (Columbia University)

Quanta (Molecular Simulations, Inc.)

Cerius (Molecular Simulations, Inc.)

Alchemy (Tripos, Inc.)

LabVision (Tripos, Inc.)

Rasmol (Glaxo Research and Development)

Ribbon (University of Alabama)

NAOMI (Oxford University)

Explorer Eyechem (Silicon Graphics, Inc.)

Univision (Cray Research)

Molscript (Uppsala University)

Chem-3D (Cambridge Scientific)

Chain (Baylor College of Medicine)

O (Uppsala University)

GRASP (Columbia University)

X-Plor (Molecular Simulations, Inc.; Yale Univ.)

Spartan (Wavefunction, Inc.)

Catalyst (Molecular Simulations, Inc.)

Molcadd (Tripos, Inc.)

VMD (Univ. of Illinois/Beckman Institute)

Sculpt (Interactive Simulations, Inc.)

Procheck (Brookhaven Nat'l Laboratory)

DGEOM (QCPE)

RE_VIEW (Brunel University)

Modeller (Birbeck Col., Univ. of London)

Xmol (Minnesota Supercomputing Center)

Protein Expert (Cambridge Scientific)

HyperChem (Hypercube)

MD Display (University of Washington)

PKB (Nat'l Center for Biotech. Info., NIH)

ChemX (Chemical Design, Ltd.)

Cameleon (Oxford Molecular, Inc.)

Iditis (Oxford Molecular, Inc.)

For storage, transfer and use with such programs of structural coordinates for a crystalline substance of this invention, a machine-readable storage medium is provided comprising a data storage material encoded with machine readable data which, when using a machine programmed with instructions for using said data, e.g. a computer loaded with one or more programs of the sort identified above, is capable of displaying a graphical three-dimensional representation of any of the molecules or molecular complexes described herein. Machine-readable storage media comprising a data storage material include conventional computer hard drives, floppy disks, DAT tape, CD-ROM, and other magnetic, magneto-optical, optical, floptical and other media which may be adapted for use with a computer.

Figure 3:
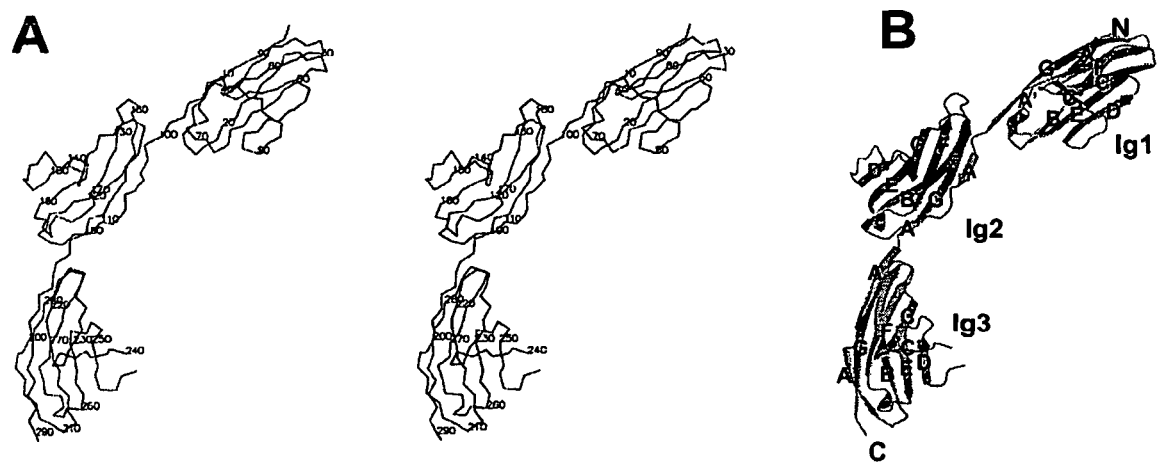
FIG. 3. Crystal structure of the rat NCAM Ig1-2-3 fragment at 2.0 Å resolution.

Even more preferred is a machine-readable data storage medium that is capable of displaying a graphical three-dimensional representation of a molecule or molecular complex that is defined by the structural co-ordinates of the Ig1-2-3 module of NCAM, such as the co-ordinates set forth in table 2 (FIG. 2) +/− a root mean square deviation from the conserved backbone atoms of the amino acids thereof of not more than 1.5 Å. An illustrative embodiment of this aspect of the invention is a conventional 3.5" diskette, DAT tape or hard drive encoded with a data set, preferably in PDB format, comprising the co-ordinates of table 2 (FIG. 2). FIG. 3 illustrates a print-out of a graphical three-dimensional representation of such a polypeptide.

In another embodiment, the machine-readable data storage medium comprises a data storage material encoded with a first set of machine readable data which comprises the Fourier transform of the structural co-ordinates set forth in table 2 (FIG. 2) (or again, a derivative thereof), and which, when using a machine programmed with instructions for using said data, can be combined with a second set of machine readable data comprising the X-ray diffraction pattern of a molecule or molecular complex to determine at least a portion of the structural co-ordinates corresponding to the second set of machine readable data.

Such a system may for example include a computer comprising a central processing unit ("CPU"), a working memory which may be, e.g., RAM (random-access memory) or "core" memory, mass storage memory (such as one or more disk drives or CD-ROM drives), one or more cathode-ray tube ("CRT") display terminals, one or more keyboards, one or more input lines (IP), and one or more output lines (OP), all of which are interconnected by a conventional bidirectional system bus.

Input hardware, coupled to the computer by input lines, may be implemented in a variety of ways. Machine-readable data of this invention may be inputted via the use of a modem or modems connected by a telephone line or dedicated data line. Alternatively or additionally, the input hardware may comprise CD-ROM drives or disk drives. In conjunction with the CRT display terminal, a keyboard may also be used as an input device.

Output hardware, coupled to the computer by output lines, may similarly be implemented by conventional devices. By way of example, output hardware may include a CRT display terminal for displaying a graphical representation of a protein of this invention (or portion thereof) using a program such as QUANTA as described herein. Output hardware might also include a printer, so that hard copy output may be produced, or a disk drive, to store system output for later use.

In operation, the CPU coordinates the use of the various input and output devices, co-ordinates data accesses from mass storage and accesses to and from working memory, and determines the sequence of data processing steps. A number of programs may be used to process the machine-readable data of this invention. Examples of such programs are discussed herein above. Algorithms suitable for this purpose are also implemented in programs such as Cast-3D (Chemical Abstracts Service), 3 DB Unity (Tripos, Inc.), Quest-3D (Cambridge Crystallographic Data Center), and MACCS/ISIS-3D (Molecular Design Limited). These geometric searches can be augmented by steric searching, in which the size and shape requirements of the binding site are used to weed out hits that have prohibitive dimensions. Programs that may be used to synchronize the geometric and steric requirements in a search applied to the FRB of FRAP include CAVEAT (P. Bartlett, University of California, Berkeley), HOOK (MSI), ALADDIN (Daylight Software) and DOCK (http://www.cmpharm.ucsf.edu/kuntz-/kuntz.html and references cited therein). All of these searching protocols may be used in conjunction with existing corporate databases, the Cambridge Structural Database, or available chemical databases from chemical suppliers.

In one embodiment of the invention the methods involve identifying a number of compounds potentially capable of interacting with the Ig 1-2-3 module of NCAM or a fragment thereof, for example the methods may involve identification of a sub-library of compounds potentially interacting with the Ig 1-2-3 module of NCAM or fragments thereof. This may be accomplished using any conventional method. For example, all the possible members of a combinatorial library may first be enumerated, according to the available reagents and the established synthetic chemistries. Individual members may then separately be docked into a binding site of a polypeptide of MASP-2. Finally, an optimal sub-library may be selected for synthesis, based on the ranking of their docking scores and/or diversity measures. Software for fast library enumeration has been developed, including for example CombiLibMaker in Sybyl, Analog Builder in Cerius2, and the QuaSAR-CombiGen module available in MOE (MOE Software, Chemical Computing Group, 1010 Sherbrooke Street W., Suite 910, Montreal, Canada H3A 2R7). Most of these programs can easily generate all of the 2D or 3D structures for a combinatorial library containing millions of compounds, using either fragment-based or reaction-based schemes. Other tools within these software packages are also available for decreasing the size of a virtual library prior to docking. For example, a library enumerated through CombiLibMaker can subsequently be analysed with diverse solutions (available in Sybyl) to provide a sub-library that adequately samples chemical space. QuaSAR-CombiDesign is another combinatorial library design tool available in MOE that provides a non-enumerative method for combinatorial library generation, and can, e.g. test against rule of five filters using statistical sampling techniques during library creation, creating smaller sub-libraries with user-defined property ranges. In principle, the docking step that follows library creation can be conducted using any of the available docking programs like DOCK or FlexX©, while the diversity selection for example may be performed using software available from Daylight, Tripos (diverse solutions), or BCI or by high throughput docking as for example described by Diller and Merz.

In another example a 'divide-and-conquer' approach may be used. With this strategy, all of the product structures in a combinatorial library are viewed as having variable substituents attached through one or multiple sites on a common template. The template is first docked into the binding site and only the top-scoring poses are saved for the further consideration. Individual substituents are then independently attached onto each pose of the template, to assess which substituents can fit well into the binding site. Only those combinations of top-scoring substituents are further considered and scored to identify the whole product structures that can dock really well into the binding site. This may be done with the aid of suitable software for example PRO SELECT, CombiBUILD, Combi-DOCK, DREAM++ and FlexX©.

In one embodiment the methods of invention comprise application of pharmacophores obtained using active site maps. Herein the term "active site" is meant to describe a site responsible of interaction with a compound and not a catalytically active site. The method may for example be a computational approach comprising the generation of multiple, promising, structurally diverse test-compounds. The search for multiple structural series may be accomplished by coupling protein structural information with combinatorial library design using any suitable method. For example the "design in receptor" method (Murrary et al., 1999) or the method outlined herein below may be used. Methods to account for multiple protein conformations for example as described by Mason et al., 2000 may also be used, including the creation of a dynamic pharmacophore model (as for example described by Carlson et al., 2000) from molecular dynamics simulations. Also experimental and computational needle screening approaches for mapping active sites with molecular fragments may be used for example as described in Boehm et al., 2000. Any suitable software tools for mapping site points (e.g. GRID and SITEPOINT) may be used with the invention. Also MCSS techniques for generating site maps may be used.

Suitable methods may for example comprise generation of active site maps from protein structures. Then all possible 2-, 3- and 4-point pharmacophores can be enumerated from the site map and encoded as a bit string (signature) these pharmacophores define a space to be probed by compounds that are selected using the informative library design tool. The metric used to evaluate the success of the approach is the number of active scaffolds selected in the library design, with the number of active compounds as a secondary measure. Any suitable algorithm for site map generation may be used, for example algorithms generating between 10 and 80 feature positions for each active site. An example of such a method is described for example by Eksterowicz et al J Mol Graph Model. 2002 June; 20(6):469-77.

Information of the various binding sites of the Ig1-2-3 module along with the crystal structure of the invention provide a tool for the examination of the biological significance of the observed Ig1-to-Ig2, Ig1-to-Ig3, and Ig2-to-Ig3 contacts, and for the screening for compounds capable of mimicking the binding of the Ig1-to-Ig2, Ig1-to-Ig3, Ig3-to-Ig1, Ig2-to-Ig3 and Ig2-to-Ig2 modules of NCAM.

The Structure of the Ig1-2-3 Module in Solution

Alternatively, the 3D structure of soluble Ig1-2-3 module may be determined and used for in-silico screening of the compounds for evaluation their potential to interact with the binding site comprised by the module. The NMR spectroscopy may ultimately be used for solving the structure of the proteins in solution.

Screening the Compounds

The identification of a new compound capable of modulating adhesion, differentiation and/or survival of NCAM presenting cells may in one aspect be performed by screening a computer model template, such as for example the three-dimensional structure of the Ig1-2-3 module of NCAM as crystalline or soluble protein. Accordingly, the invention also relates to providing a screening method for selecting a compound capable of modulating cell differentiation and/or survival of NCAM presenting cells, comprising the steps of i) providing a polypeptide comprising the Ig1-2-3 module of NCAM;

ii) preparing a crystalline protein comprising the polypeptide of (i);

iii) generating a structural model of the Ig1-2-3 module of NCAM as a crystalline protein of (ii);

iv) designing a compound into the structure of said generated model of step i);

v) selecting a compound capable of interacting with the homophylic binding site according to the structural model of (iii);

vi) testing the compound of step (vi) in an in vitro or in vivo assay whether the compound is capable of modulating neural cell differentiation, adhesion and/or survival.

The above screening method may in some embodiments comprise using a computer generated model of the Ig1-2-3 module of NCAM, or fragments of said module, such as Ig1, Ig2, Ig3, or Ig1-2, or Ig2-3 modules in a solution. Such a model may be generated on the basis of the data obtained, for example, from Nuclear Magnetic Resonance spectroscopy of samples of the above modules. However, preferably, a computer generated model is a structural model of a crystal of the above modules.

The invention provides a computer generated structural structure model of the Ig1-2-3 module for the screening a compound capable of modulating NCAM homophylic binding-dependent cell adhesion, survival and differentiation.

Designing Interacting Compounds

Designing Interacting Compounds

Generating a Site Map

Feature points complementary to the active site are computed using an internally developed software tool. For example, a hydrogen bond donor feature is mapped in the proximity of a hydrogen bond acceptor in the protein active site. The collection of 3D coordinates and labels (acceptors, donors, negatives, positives, hydrophobes and aromatics) is called a site map. Technically, the site map is the union of three separately computed maps, ESMap which contains the electrostatic feature points (P, N, and H) HBMap with hydrogen-bonding feature points (D and A) and AroMap containing aromatic feature points (Ar).

The electrostatic feature map, ESMap, is computed by first using the sphere placement algorithm employed in the program PASS (Brady et al., 2000). It generates an evenly-distributed set of points (ProbeMap) in regions of buried volume along the protein surface. A subset of points in the ProbeMap comprises the P, N, and H feature points depending upon the local electrostatic character of the protein. The CVFF molecular mechanics force field is used to compute the electrostatic potential, $\phi i$, at each point i of ProbeMap, along with the mean potential $\phi$ and mean magnitude $|\phi|$ averaged over all points in ProbeMap. The value of $\phi i$ determines whether or not point i is included as a P, N, or H feature point, according to the following definitions $i > \phi + 1.5*\sigma(\phi)$, $i = N$ feature point $i > \phi - 1.5*\sigma(\phi)$, $i = P$ feature point $|\phi| - 1.0*\sigma(|\phi|) < |\phi i| < (|\phi|) + 1.0*\sigma(|\phi|)$, $i = H$ feature point Here $\sigma(X)$ denotes the standard deviation about the mean of quantity X. This normalizes the point assignments relative to the overall electrostatic environment of the active site. This presents non charge-neutral protein structures (which may result from counter ions not being resolved or present in the crystal structures) from skewing feature point assignments unreasonably.

The hydrogen-bonding feature map, HBMap, is determined by projecting complementary points outward from known hydrogen-bonding atoms of the protein. The resulting superset of points is filtered on the basis of steric clash, insufficient burial and minimal proximity of alike feature points. Ideal hydrogen-bonding points are positioned on the basis of the mean angle and distance as observed in the PDB (see for example table 2 shown on FIG. 1). Points that clash with the protein are removed. However, for robustness, small positional perturbations are applied to retain potentially important hydrogen-bonding positions. Bifurcated hydrogen-bonding joints are computed heuristically by investigating full rings of points equally is bifurcated between protein atoms that are considered moderate or strong hydrogen bond participants.

Points on such rings are retained as bifurcated HB points if they do not violate steric clash, burial and mutual proximity conditions. To build the final HBMap, the surviving sets of ideal and bifurcated HB points are combined and subjected to filtration on the basis of mutual proximity.

The AroMap set of aromatic feature points is computed by repeatedly docking a benzene ring into the protein active site and retaining the centroids of the top-scoring configurations. The protein is represented using a polar-hydrogen CVFF force field. The docking is performed using internal code in local optimization mode. One hundred separate local docking trials with different starting positions are performed. Any of the docked configurations whose score lies within an energy window of 5 kcal/mol of the minimum-energy configuration is included in AroMap. Again points are subjected to filtration on the basis of burial and mutual proximity.

Converting Pharmacophores into a Signature

Pharmacophores are generated on the basis of feature points in the active site by exhaustive enumeration of all 2-, 3-, and 4-point subsets of the feature points. For all pairs of feature points their distance in 3D-space is precomputed. In order to arrive at a discrete representation of a pharmacophore, the distances are binned, applying a user-defined binning scheme. Chirality is denoted by encoding the handedness of 4-point pharmacophores. Each pharmacophore is mapped onto a unique address, such that any possible combination of up to four features and distances is represented. The address is taken for a binary representation of the pharmacophores, called a signature. The length of the signature is the highest possible address for an encoding of a 4-point pharmacophore. All bits in the signature are initially set to 0. In order to represent a pharmacophore the bit at the respective address in the signature is turned on (set to 1). For the representation of the active site all pharmacophores are exhaustively enumerated and the respective bits are turned on.

Union of Signatures for Multiple Structures

Multiple signatures may be combined. The binary union of multiple signatures yields a single bit string representing all pharmacophores present in any structure. Any consensus threshold c can be used to define the consensus representation of multiple active sites. That is, a pharmacophore is present in at least c of active site conformations. Note that this way of handling multiple active site snapshots is quite expedient.

Molecular Signatures

Test compounds are encoded as follows. First, conformers are generated for each compound using an internal tool that generates a fairly complete conformational model of the molecule. Features are assigned using a substructure-based set of rules. Pharmacophores are enumerated from these three-dimensional feature positions following the same protocol as for the active site, thus ensuring compatibility of the binary encodings. However, multiple conformers need to be represented simultaneously here. This is done by wrapping the exhaustive enumeration of pharmacophores for a single conformer into an extra loop over all the conformers of a compound. That is, any pharmacophore on any conformer of a compound is represented by turning the respective bit in the signature on.

Molecular Signature Masking

With the binary representation of the active site and the binary representation of the molecules being defined analogously, the meaning of a bit at a certain address is the same (the same pharmacophore, within the tolerances of the distance binning). Therefore, representing a design space amounts to masking all molecule signatures by the active site signature. Masking a signature means taking the logical and of the bits of the site signature and the molecule signature. For a given molecule, bits representing pharmacophores not present in the active site are turned off, whereas the bits of the pharmacophores in the active site can be either on or off, depending on their presence or absence in the molecules. This way only the pharmacophore space defined by the active site is taken into account.

Informative Library Design

Informative library design is a molecule selection strategy that optimises information return for a given virtual library. The goal is to detect a set of features (pharmacophores) that determine activity against a particular test compound. Informative design aims at selecting a set of compounds such that the resulting subset will interrogate the test compound in different, but overlapping ways. Molecules are selected for synthesis and screening such that each pharmacophore in the design space has a unique pattern of occurrence in the molecules of the set. This unique 'code' enables the identification and retention of the important pharmacophores when the set of compounds is assayed, regardless of the actual experimental outcome. This is in contrast to diversity methods that seek to produce a unique pattern of pharmacophore occurrences in each molecule.

Given a design space, the algorithm seeks to optimize decoding as many pharmacophores as possible, with the smoothest distribution across the size of pharmacophore classes. A pharmacophore class refers to the subset of pharmacophores that all have the same code or pattern. Note that the optimum solution is a set of compounds that enables decoding each individual pharmacophore. However, this may not be possible due either to the source pool, bit correlation or to limited size of selection. The cost function for an unconstrained optimisation in terms of molecule selection is the entropy of the class distribution. The entropy is given by $$H = -\sum_{i=1}^{C} \frac{|Ci|}{f} \ln \frac{|Ci|}{f}$$

where H is the entropy of the feature classes, C the number of distinct classes, f the number of features in the design space and |c| is the size of class i. During the course of the optimisation, molecules are selected, such as to maximize H.

Testing

A compound selected by in-silico screening of the above is to be further tested whether it has a capability to modulate cellular adhesion, differentiation and/or survival of cells presenting NCAM.

Biological assays for the testing a capability of compounds to modulate adhesion, differentiation and/or survival of NCAM presenting cells are well known in the art. In particular, the assays described in WO03020749, WO0247719, WO03016351 and in the present application may be used.

The testing of the identified compound of (vi) may in some embodiments be additionally or alternatively performed by using the testing method described above.

Compound

A compound of the present invention is preferably selected by any of the above screening methods. According to the invention a selected compound is the candidate compound.

By the term "candidate compound" is meant a compound capable of i) interacting with the Ig1 module of NCAM, and thereby mimicking and/or modulating the interaction between the Ig1 and Ig3 modules of NCAM, wherein said modules are from two individual NCAM molecules, and/or ii) interacting with the Ig3 module of NCAM, and thereby mimicking and/or modulating the interaction between the Ig3 and Ig1 modules of NCAM, wherein said modules are from two individual NCAM molecules, and/or iii) interacting with the Ig2 module of NCAM, and thereby mimicking the interaction between Ig2 and Ig3 modules of NCAM, wherein said modules are from two individual NCAM molecules, and/or iv) interacting with the Ig3 module of NCAM, and thereby mimicking and/or modulating the interaction between the Ig3 and Ig2 modules of NCAM, wherein said modules are from two individual NCAM molecules, and/or v) interacting with the Ig2 module of NCAM, and thereby mimicking and/or modulating the interaction between the Ig2 and Ig2 modules of NCAM, wherein said modules are from two individual NCAM molecules.

A candidate compound, which is capable of at least one of the above interactions, is according to the invention also capable of modulating cell differentiation, adhesion and survival mediated by NCAM homophylic binding though the homophylic binding site described herein.

On one preferred embodiment a candidate compound is capable of interacting with the Ig1 module of NCAM, and thereby mimicking and/or modulating the interaction between the Ig1 and Ig3 modules of NCAM, wherein said modules are from two individual NCAM molecules, and thereby modulating cell differentiation, adhesion and survival mediated by NCAM homophylic binding through the homophylic binding site of the invention.

In another preferred embodiment a candidate compound is capable of interacting with the Ig3 module of NCAM, and thereby mimicking and/or modulating the interaction between the Ig3 and Ig1 modules of NCAM, wherein said modules are from two individual NCAM molecules, and thereby modulating cell differentiation, adhesion and survival mediated by NCAM homophylic binding through the homophylic binding site of the invention.

A candidate compound, which is capable of interacting with the Ig2 module of NCAM, and thereby mimicking the interaction between Ig2 and Ig3 modules of NCAM, wherein said modules are from two individual NCAM molecules, and thereby modulating cell differentiation, adhesion and survival mediated by NCAM homophylic binding through the homophylic binding site of the invention is another preferred embodiment of the invention.

In still another preferred embodiment a candidate compound is capable of interacting with the Ig3 module of NCAM, and thereby mimicking and/or modulating the interaction between the Ig3 and Ig2 modules of NCAM, wherein said modules are from two individual NCAM molecules, and thereby modulating cell differentiation, adhesion and survival mediated by NCAM homophylic binding through the homophylic binding site of the invention.

In yet another preferred embodiment a candidate compound is capable of interacting with the Ig2 module of NCAM, and thereby mimicking and/or modulating the interaction between the Ig2 and Ig2 modules of NCAM, wherein said modules are from two individual NCAM molecules, and thereby modulating cell differentiation, adhesion and survival mediated by NCAM homophylic binding through the homophylic binding site of the invention.

Other preferred embodiments of the invention concern the i) candidate compounds, which are capable of simultaneous interaction with amino acid residues of the Ig1 and Ig3 modules of the same NCAM molecule and thereby mimicking and/or modulating the interaction between the Ig1-to-Ig3 and the Ig3-to-Ig1 modules of two individual NCAM molecules interacting through said modules, ii) candidate compounds, which are capable of simultaneous interaction with amino acid residues of the Ig1 and Ig2 modules of the same NCAM molecule and thereby mimicking and/or modulating the interaction the Ig1-to-Ig3 and the Ig2-to-Ig3 modules of two individual NCAM molecules interacting through said modules, iii) candidate compounds, which are capable of simultaneous interaction with amino acid residues of the Ig1 and Ig3 modules of the same NCAM molecule and thereby mimicking and/or modulating the interaction between the Ig1-to-Ig3 and the Ig3-to-Ig2 modules of two individual NCAM molecules interacting through said modules, iv) candidate compounds, which are capable of simultaneous interaction with amino acid residues of the Ig1 and Ig2 modules of the same NCAM molecule and thereby mimicking and/or modulating the interaction between the Ig1-to-Ig3 and the Ig2-to-Ig2 modules of two individual NCAM molecules interacting through said modules, v) candidate compounds, which are capable of simultaneous interaction with amino acid residues of the Ig2 and Ig3 modules of the same NCAM molecule and thereby mimicking and/or modulating the interaction between the Ig2-to-Ig3 and the Ig3-to-Ig1 modules of two individual NCAM molecules interacting through said modules, vi) candidate compounds, which are capable of simultaneous interaction with amino acid residues of the Ig2 and Ig3 modules of the same NCAM molecule and thereby mimicking and/or modulating the interaction between the Ig2-to-Ig2 and the Ig3-to-Ig1 modules of two individual NCAM molecules interacting through said modules, vii) candidate compounds, which are capable of simultaneous interaction with amino acid residues of the Ig2 and Ig3 modules of the same NCAM molecule and thereby mimicking and/or modulating the interaction between the Ig2-to-Ig3 and the Ig3-to-Ig1 modules of two individual NCAM molecules interacting through said modules, viii) candidate compounds, which are capable of simultaneous interaction with amino acid residues of the Ig2 and Ig3 modules of the same NCAM molecule and thereby mimicking and/or modulating the interaction between the Ig2-to-Ig3 and the Ig3-to-Ig2 modules of two individual NCAM molecules interacting through said modules.

The candidate compound may be any compound, which as capable of the above interactions. Such a compound may, for example, be selected from the group comprising combinatorial libraries of peptides, lipids, carbohydrates or other organic molecules, or co-polymers of amino acids with other organic compounds. In a preferred embodiment, the candidate compound of the invention is a peptide. Alternatively, the compound may an antibody molecule capable of selectively binding to an epitope located within or in close proximity to the binding site. The close proximity is defined herein as a distance of about 50 to 500 Å between an amino acid residue of the epitope and an amino acid residue of the binding site. An antibody molecule, which binds to a distant epitope (at a distance of more then 500 Å from an amino acid residue of the binding site), and which binding leads to a conformational change in the Ig1-2-3 module influencing thereby the homophylic binding through the binding site, is also concerned.

A preferred candidate compound is the compound comprising an amino acid sequence derived from the binding site described herein. By "derived" is meant that the amino acid sequence comprises a fragment of the amino sequence Ig the Ig1-2-3 NCAM module, said fragment comprising the binding site or a part of the binding site, or the amino acid sequence comprises a sequence of amino acid residues which are homologous to the residues involved in the interaction between two individual NCAM molecules through the binding site. Homology of the amino acid residues may be about 60%, more preferred is about 70%, even more preferred is about 80%, such as for example 90%, and the most preferred is about 100%. The homology of one amino acid residue to another is defined as above.

Thus, a preferred candidate compound may comprise a sequence derived from the Ig1 module and/or Ig2 module and/or Ig3 module of NCAM. Non-limited examples of such compounds may be the compounds identified in the present application as SEQ ID NOs: 1-20, 40-43.

Thus, the present invention provides in one embodiment a compound having the amino acid sequence WFSPNGEKLSPNQ set forth in SEQ ID NO: 1.

In another embodiment a compound of the invention is having the amino acid sequence YKCVVTAEDGTQSE set forth in SEQ ID NO: 2.

In still another embodiment the invention provides a compound having the amino acid sequence TLVADADGFPEP set forth in SEQ ID NO: 3.

In yet another embodiment the invention provides a compound having the amino acid sequence QIRGIKKTD set forth in SEQ ID NO: 4.

In still yet another embodiment the invention provides a compound having the amino acid sequence DVR set forth in SEQ ID NO: 5.

Yet in another embodiment the compound of the invention is having the amino acid sequence RGIKKTD set forth in SEQ ID NO: 6.

In yet a further embodiment the invention provides a compound is having the amino acid sequence DVRRGIKKTD set forth in SEQ ID NO: 7.

In another aspect the invention concerns a compound is having the amino acid sequence KEGED set forth in SEQ ID NO: 8.

In yet another aspect a compound is having the amino acid sequence IRGIKKTD set forth in SEQ ID NO: 9.

The invention further provides a compound having the amino acid sequence KEGEDGIRGIKKTD set forth in SEQ ID NO: 10.

Moreover, in another embodiment the invention provides a compound having the amino acid sequence DKNDE set forth in SEQ ID NO: 11.

In still another embodiment the invention concerns a compound having the amino acid sequence TVQARNSIVNAT set forth in SEQ ID NO: 12.

In yet another embodiment of the invention the compound is having the amino acid sequence SIHLKVFAK set forth in SEQ ID NO: 13.

In yet another embodiment the compound is having the amino acid sequence LSNNYLQIR set forth in SEQ ID NO: 14.

In a further embodiment the invention provides a compound having the amino acid sequence RFIVLSNNYLQI set forth in SEQ ID NO: 15.

Further, in yet another embodiment the invention provides a compound having the amino acid sequence KKDVRFIVLSNNYLQI set forth in SEQ ID NO: 16.

Furthermore, in yet another embodiment the invention provides a compound having the amino acid sequence QEFKEGEDAVIV set forth in SEQ ID NO: 17.

The invention further provides a compound having the amino acid sequence KEGEDAVIVCD set forth in SEQ ID NO: 18.

In other embodiments the invention concerns the compounds having the amino acid sequences

```
GEISVGESKFFL            (SEQ ID NO: 19)

KHIFSDDSSELTIRNVDKNDE,  (SEQ ID NO: 20)

AFSPNGEKLSPNQ,          (SEQ ID NO: 40)

AKSVVTAEDGTQSE,         (SEQ ID NO: 41)

DVRRGIKKTD              (SEQ ID NO: 42)
or

QIRGIKKTD.              (SEQ ID NO: 43)
```

The above sequences are also concerned as preferred candidate compounds of the invention. Fragments or variants of these sequences are also included in the scope of the invention as candidate compounds capable of the interaction(s) and/or effects of the original sequences, namely the sequences, which they are derived from or homologous.

The identified above sequences according to the invention represent different fragments a homophylic binding site of NCAM in the Ig1-2-3 module and are capable of modulation of differentiation and/or survival of an NCAM-presenting cell.

According to invention the sequences identified above may be used for the manufacture of a medicament for the treatment of a condition or disease wherein the modulation of NCAM homophilic interaction would lead to improvement or rescue.

Additionally, the above sequences may be used for the production of an antibody capable of recognising and specifically binding to the binding site of the invention. Such an antibody according to the invention is capable of at least one of the biological activities of the compound described above and may in some embodiments be advantageously used for medical applications as the compound of the invention Production of Peptide Sequences The peptide compounds of the present invention may be prepared by any conventional synthetic methods, recombinant DNA technologies, enzymatic cleavage of full-length proteins which the peptide sequences are derived from, such as for example NCAM molecules of different species origin, or a combination of said methods.

Recombinant Preparation

Recombinant preparation is a preferred method for the production of long chain polypeptide sequences, such as for example the Ig1-2-3 module, or individual modules of NCAM, such as Ig1, Ig2 or Ig3, or combinations thereof such as Ig1-2, Ig1-3 or Ig2-3. However, shorter peptide fragments of 15-50 amino acids long comprising the sequences derived from the binding site of the invention may also be prepared recombinantly using any of the below described technologies.

The DNA sequence encoding a peptide or the corresponding full-length protein the peptide originates from, or a fragment thereof, may be prepared synthetically by established standard methods, e.g. the phosphoamidine method described by Beaucage and Caruthers, 1981, Tetrahedron Lett. 22:1859-1869, or the method described by Matthes et al., 1984, EMBO J. 3:801-805. According to the phosphoamidine method, oligonucleotides are synthesised, e.g. in an automatic DNA synthesiser, purified, annealed, ligated and cloned in suitable vectors.

The DNA sequence encoding a peptide may also be prepared by fragmentation of the DNA sequences encoding the corresponding full-length protein, e.g. NCAM protein, using DNAase I according to a standard protocol (Sambrook et al., Molecular cloning: A Laboratory manual. 2 rd ed., CSHL Press, Cold Spring Harbor, N.Y., 1989). The DNA encoding a full-length protein may alternatively be fragmented using specific restriction endonucleases. The fragments of DNA are further purified using standard procedures described in Sambrook et al., Molecular cloning: A Laboratory manual. 2 rd ed., CSHL Press, Cold Spring Harbor, N.Y., 1989.

The DNA sequence encoding a full-length protein may also be of genomic or cDNA origin, for instance obtained by preparing a genomic or cDNA library and screening for DNA sequences coding for all or part of the full-length protein by hybridisation using synthetic oligonucleotide probes in accordance with standard techniques (cf. Sambrook et al., Molecular Cloning: A Laboratory Manual, 2nd Ed., Cold Spring Harbor, 1989). The DNA sequence may also be prepared by polymerase chain reaction using specific primers, for instance as described in U.S. Pat. No. 4,683,202 or Saiki et al., 1988, Science 239:487-491.

The DNA sequence is then inserted into a recombinant expression vector, which may be any vector, which may conveniently be subjected to recombinant DNA procedures. The choice of vector will often depend on the host cell into which it is to be introduced. Thus, the vector may be an autonomously replicating vector, i.e. a vector that exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding a peptide or a full-length protein should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the coding DNA sequence in mammalian cells are the SV 40 promoter (Subramani et al., 1981, Mol. Cell. Biol. 1:854-864), the MT-1 (metallothionein gene) promoter (Palmiter et al., 1983, Science 222: 809-814) or the adenovirus 2 major late promoter. A suitable promoter for use in insect cells is the polyhedrin promoter (Vasuvedan et al., 1992, FEBS Lett. 311:7-11). Suitable promoters for use in yeast host cells include promoters from yeast glycolytic genes (Hitzeman et al., 1980, J. Biol. Chem. 255:12073-12080; Alber and Kawasaki, 1982, J. Mol. Appl. Gen. 1: 419-434) or alcohol dehydrogenase genes (Young et al., 1982, in Genetic Engineering of Microorganisms for Chemicals, Hollaender et al, eds., Plenum Press, New York), or the TPI1 (U.S. Pat. No. 4,599,311) or ADH2-4-c (Russell et al., 1983, Nature 304: 652-654) promoters. Suitable promoters for use in filamentous fungus host cells are, for instance, the ADH3 promoter (McKnight et al., 1985, EMBO J. 4:2093-2099) or the tpiA promoter.

The coding DNA sequence may also be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) promoters. The vector may further comprise elements such as polyadenylation signals (e.g. from SV 40 or the adenovirus 5 Elb region), transcriptional enhancer sequences (e.g. the SV 40 enhancer) and translational enhancer sequences (e.g. the ones encoding adenovirus VA RNAs).

The recombinant expression vector may further comprise a DNA sequence enabling the vector to replicate in the host cell in question. An example of such a sequence (when the host cell is a mammalian cell) is the SV 40 origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hydromycin or methotrexate.

The procedures used to ligate the DNA sequences coding the peptides or full-length proteins, the promoter and the terminator, respectively, and to insert them into suitable vectors containing the information necessary for replication, are well known to persons skilled in the art (cf., for instance, Sambrook et al., op.cit.).

To obtain recombinant peptides of the invention the coding DNA sequences may be usefully fused with a second peptide coding sequence and a protease cleavage site coding sequence, giving a DNA construct encoding the fusion protein, wherein the protease cleavage site coding sequence positioned between the HBP fragment and second peptide coding DNA, inserted into a recombinant expression vector, and expressed in recombinant host cells. In one embodiment, said second peptide selected from, but not limited by the group comprising glutathion-S-reductase, calf thymosin, bacterial thioredoxin or human ubiquitin natural or synthetic variants, or peptides thereof. In another embodiment, a peptide sequence comprising a protease cleavage site may be the Factor Xa, with the amino acid sequence IEGR, enterokinase, with the amino acid sequence DDDDK, thrombin, with the amino acid sequence LVPR/GS, or *Acharombacter lyticus*, with the amino acid sequence XKX, cleavage site.

The host cell into which the expression vector is introduced may be any cell which is capable of expression of the peptides or full-length proteins, and is preferably a eukaryotic cell, such as invertebrate (insect) cells or vertebrate cells, e.g. *Xenopus laevis* oocytes or mammalian cells, in particular insect and mammalian cells. Examples of suitable mammalian cell lines are the HEK293 (ATCC CRL-1573), COS (ATCC CRL-1650), BHK (ATCC CRL-1632, ATCC CCL-10) or CHO (ATCC CCL-61) cell lines. Methods of transfecting mammalian cells and expressing DNA sequences introduced in the cells are described in e.g. Kaufman and Sharp, J. Mol. Biol. 159, 1982, pp. 601-621; Southern and Berg, 1982, J. Mol. Appl. Genet. 1:327-341; Loyter et al., 1982, Proc. Natl. Acad. Sci. USA 79: 422-426; Wigler et al., 1978, Cell 14:725; Corsaro and Pearson, 1981, in Somatic Cell Genetics 7, p. 603; Graham and van der Eb, 1973, Virol. 52:456; and Neumann et al., 1982, EMBO J. 1:841-845.

Alternatively, fungal cells (including yeast cells) may be used as host cells. Examples of suitable yeast cells include cells of *Saccharomyces* spp. or *Schizosaccharomyces* spp., in particular strains of *Saccharomyces cerevisiae*. Examples of other fungal cells are cells of filamentous fungi, e.g. *Aspergillus* spp. or *Neurospora* spp., in particular strains of *Aspergillus oryzae* or *Aspergillus niger*. The use of *Aspergillus* spp. for the expression of proteins is described in, e.g., EP 238 023.

The medium used to culture the cells may be any conventional medium suitable for growing mammalian cells, such as a serum-containing or serum-free medium containing appropriate supplements, or a suitable medium for growing insect, yeast or fungal cells. Suitable media are available from commercial suppliers or may be prepared according to published recipes (e.g. in catalogues of the American Type Culture Collection).

The peptides or full-length proteins recombinantly produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. HPLC, ion exchange chromatography, affinity chromatography, or the like.

Synthetic Preparation

Synthetic preparation is preferred when the short sequences of 3 to 50 amino acids are concerned.

The methods for synthetic production of peptides are well known in the art. Detailed descriptions as well as practical advice for producing synthetic peptides may be found in Synthetic Peptides: A User's Guide (Advances in Molecular Biology), Grant G. A. ed., Oxford University Press, 2002, or in: Pharmaceutical Formulation: Development of Peptides and Proteins, Frokjaer and Hovgaard eds., Taylor and Francis, 1999.

Peptides may for example be synthesised by using Fmoc chemistry and with Acm-protected cysteins. After purification by reversed phase HPLC, peptides may be further processed to obtain for example cyclic or C- or N-terminal modified isoforms. The methods for cyclization and terminal modification are well-known in the art and described in detail in the above-cited manuals.

In a preferred embodiment the peptide sequences of the invention are produced synthetically, in particular, by the Sequence Assisted Peptide Synthesis (SAPS) method. Peptides may be synthesised either batchwise in a polyethylene vessel equipped with a polypropylene filter for filtration or in the continuous-flow version of the polyamide solid-phase method (Dryland, A. and Sheppard, R. C., (1986) J. Chem. Soc. Perkin Trans. 1, 125-137.) On a fully automated peptide synthesiser (Cameron E T al., (1987), J. Chem. Soc. Chem. Commun, 270-272) using 9-fluorenylmethyloxycarbonyl (Fmoc) or tert.-Butyloxycarbonyl, (Boc) as N-a-amino protecting group and suitable common protection groups for side-chain functionalities.

Pharmaceutical Composition

Once the candidate compound(s) of the invention has been identified it is further within the scope of the invention to provide a pharmaceutical composition comprising one or more compound(s). In the present context the term pharmaceutical composition is used synonymously with the term medicament.

The invention is further related to a pharmaceutical composition capable of preventing the death of NCAM presenting cells, promote cell differentiation of neural cells and neuronal plasticity, and stimulation of survival and regeneration of NCAM presenting cells and/or NCAM ligand presenting cells in several tissues and organs in vivo or in vitro as discussed herein, said composition comprising an effective amount of one or more of the compounds described above. The medicament of the invention may comprise an effective amount of one or more of the compounds as defined above in combination with pharmaceutically acceptable additives. Such medicament may suitably be formulated for oral, percutaneous, intramuscular, intravenous, intracranial, intrathecal, intracerebroventricular, intranasal or pulmonal administration.

The present invention further concerns a medicament for the treatment of diseases and conditions of the central and peripheral nervous system, of the muscles or of various organs, wherein said medicament comprises an effective amount of one or more of the compounds as defined above or a composition as defined above in combination with pharmaceutically acceptable additives or carriers. Such medicament may suitably be formulated for oral, percutaneous, intramuscular, intravenous, intracranial, intrathecal, intracerebroventricular, intranasal or pulmonal administration.

Formulation

Strategies in formulation development of medicaments and compositions based on the compounds of the present invention generally correspond to formulation strategies for any other protein-based drug product. Potential problems and the guidance required to overcome these problems are dealt with in several textbooks, e.g. "Therapeutic Peptides and Protein Formulation. Processing and Delivery Systems", Ed. A. K. Banga, Technomic Publishing A G, Basel, 1995.

Injectables are usually prepared either as liquid solutions or suspensions, solid forms suitable for solution in, or suspension in, liquid prior to injection. The preparation may also be emulsified. The active ingredient is often mixed with excipients, which are pharmaceutically acceptable and compatible with the active ingredient. Suitable excipients are for example water, saline, dextrose, glycerol, ethanol or the like, and combinations thereof. In addition, if desired, the preparation may contain minor amounts of auxiliary substances such as wetting or emulsifying agents, pH buffering agents, which enhance the effectiveness or transportation of the preparation.

Formulations of the compounds of the invention can be prepared by techniques known to the person skilled in the art. The formulations may contain pharmaceutically acceptable carriers and excipients including microspheres, liposomes, microcapsules, nanoparticles or the like.

Administration

For most indications a localised or substantially localised application is preferred. The compounds are in particular used in combination with a prosthetic device such as a prosthetic nerve guide. Thus, in a further aspect, the present invention relates to a prosthetic nerve guide, characterised in that it comprises one or more of the compounds or the composition defined above. Nerve guides are known in the art.

The preparation may suitably be administered by injection, optionally at the site, where the active ingredient is to exert its effect. Additional formulations which are suitable for other modes of administration include suppositories, nasal, pulmonal and, in some cases, oral formulations. For suppositories, traditional binders and carriers include polyalkylene glycols or triglycerides. Such suppositories may be formed from mixtures containing the active ingredient(s) in the range of from 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and generally contain 10-95% of the active ingredient(s), preferably 25-70%.

Other formulations are such suitable for nasal and pulmonal administration, e.g. inhalators and aerosols.

The active compound may be formulated as neutral or salt forms. Pharmaceutically acceptable salts include acid addition salts (formed with the free amino groups of the peptide compound) and which are formed with inorganic acids such as, for example, hydrochloric or phosphoric acids, or such organic acids as acetic acid, oxalic acid, tartaric acid, mandelic acid, and the like. Salts formed with the free carboxyl group may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The preparations are administered in a manner compatible with the dosage formulation, and in such amount as will be therapeutically effective. The quantity to be administered depends on the subject to be treated, including, e.g. the weight and age of the subject, the disease to be treated and the stage of disease. Suitable dosage ranges are of the order of several hundred µg active ingredient per administration with a preferred range of from about 0.1 µg to 100 mg, such as in the range of from about 1 µg to 100 mg, and especially in the range of from about 10 µg to 50 mg. Administration may be performed once or may be followed by subsequent administrations. The dosage will also depend on the route of administration and will vary with the age and weight of the subject to be treated. A preferred dose would be in the interval 0.5 mg to 50 mg per 70 kg body weight.

Some of the candidate compounds of the present invention are sufficiently active, but for others, the effect will be enhanced if the preparation further comprises pharmaceutically acceptable additives and/or carriers. Such additives and carriers will be known in the art. In some cases, it will be advantageous to include a compound, which promote delivery of the active substance to its target.

In another embodiment it may be advantageous to administer the candidate compound(s) according to the invention with other substances to obtain a synergistic effect. Examples of such other substances may be a growth factor, which can induce differentiation, or a hormone, or a transplant of cells, including a transplant of stem cells, or gene therapy, or immuno-therapy.

In many instances, it will be necessary to administrate the formulation multiple times. Administration may be a continuous infusion, such as intra-ventricular infusion or administration in more doses such as more times a day, daily, more times a week, or weekly. It is preferred that administration of the medicament is initiated before or shortly after the individual has been subjected to the factor(s) that may lead to cell death. Preferably the medicament is administered within 8 hours from the factor onset, such as within 5 hours from the factor onset. Many of the compounds exhibit a long-term effect whereby administration of the compounds may be conducted with long intervals, such as 1 week or 2 weeks.

In one embodiment of the invention the administration of the present compound may be immediately after an acute injury, such as an acute stroke, or at the most 8 hours after said stroke in order for the present compound to have a stimulatory effect on cell survival. Further, in cases concerning proliferation and/or differentiation the administration according to the invention is not time dependent, i.e. it may be administered at any time.

Producing a Pharmaceutical

In another aspect the invention relates to a process of producing a pharmaceutical composition, comprising mixing an effective amount of one or more of the compounds of the invention, or a pharmaceutical composition according to the invention with one or more pharmaceutically acceptable additives or carriers, and administer an effective amount of at least one of said compound, or said pharmaceutical composition to a subject.

In yet a further aspect the invention relates to a method of treating an individual suffering from one or more of the diseases discussed above by administering the said individual a compound as described herein or a pharmaceutical composition comprising said compound.

Medicament

The candidate compounds of the invention may advantageously be used for treating cells presenting NCAM molecules. NCAM is expressed in a variety of cells of the organism where it can serve as an adhesion molecule, receptor and/or as a ligand, depending on cellular type and/or cell environment. The authors of the present invention discovered that the candidate compounds that bind to different parts of the binding site described herein may have different effects on cellular adhesion, differentiation and/or survival and therefore said compounds are suggested herein for using as both direct stimulators of cell differentiation and survival, such as neural cell differentiation and survival, and as modulators of NCAM function in neural plasticity, such as for example synaptic plasticity. Thus, the candidate compounds of the invention may be used in the manufacture of medicaments to be used to treat various pathologic conditions of the peripheral and/or the central nervous system and/or muscles and other tissues expressing NCAM, such as trauma and/or disease, as well as conditions in which a fine modulation of NCAM function may be beneficial, such as stimulation of memory and learning.

Thus, a candidate compound of the invention may be for the manufacture of a medicament for treatment of normal, degenerated or damaged NCAM and/or NCAM ligand presenting cells.

In particular the compound and/or pharmaceutical composition of the invention may be used in the treatment of clinical conditions, such as Neoplasms such as malignant neoplasms, benign neoplasms, carcinoma in situ and neoplasms of uncertain behavior, diseases of endocrine glands, such as diabetes mellitus, psychoses, such as senile and presenile organic psychotic conditions, alcoholic psychoses, drug psychoses, transient organic psychotic conditions, Alzheimer's disease, cerebral lipidoses, epilepsy, general paresis [syphilis], hepatolenticular degeneration, Huntington's chorea, Jakob-Creutzfeldt disease, multiple sclerosis, Pick's disease of the brain, syphilis, Schizophrenic disorders, affective psychoses, neurotic disorders, personality disorders, including character neurosis, non-psychotic personality disorder associated with organic brain syndromes, paranoid personality disorder, fanatic personality, paranoid personality (disorder), paranoid traits, sexual deviations and disorders, mental retardation, disease in the nervous system and sense organs, cognitive anomalies, inflammatory disease of the central nervous system, such as meningitis, encephalitis, cerebral degenerations, such as Alzheimer's disease, Pick's disease, senile degeneration of brain, communicating hydrocephalus, obstructive hydrocephalus, Parkinson's disease including other extra pyramidal disease and abnormal movement disorders, spinocerebellar disease, cerebellar ataxia, Marie's, Sanger-Brown, Dyssynergia cerebellaris myoclonica, primary cerebellar degeneration, such as spinal muscular atrophy, familial, juvenile, adult spinal muscular atrophy, motor neuron disease, amyotrophic lateral sclerosis, motor neuron disease, progressive bulbar palsy, pseudobulbar palsy, primary lateral sclerosis, other anterior horn cell diseases, anterior horn cell disease, unspecified, other diseases of spinal cord, syringomyelia and syringobulbia, vascular myelopathies, acute infarction of spinal cord (embolic) (nonembolic), arterial thrombosis of spinal cord, edema of spinal cord, subacute necrotic myelopathy, subacute combined degeneration of spinal cord in diseases classified elsewhere, myelopathy, drug-induced, radiation-induced myelitis, disorders of the autonomic nervous system, disorders of peripheral autonomic, sympathetic, parasympathetic, or vegetative system, familial dysautonomia [Riley-Day syndrome], idiopathic peripheral autonomic neuropathy, carotid sinus syncope or syndrome, cervical sympathetic dystrophy or paralysis. peripheral autonomic neuropathy in disorders classified elsewhere, amyloidosis, diseases of the peripheral nerve system, brachial plexus lesions, cervical rib syndrome, costoclavicular syndrome, scalenus anterior syndrome, thoracic outlet syndrome, brachial neuritis or radiculitis, including in newborn; inflammatory and toxic neuropathy, including acute infective polyneuritis, Guillain-Barre syndrome, Postinfectious polyneuritis, polyneuropathy in collagen vascular disease, disorders affecting multiple structures of eye, purulent endophthalmitis, diseases of the ear and mastoid process, chronic rheumatic heart disease, ischaemic heart disease, arrhythmia, diseases in the pulmonary system, abnormality of organs and soft tissues in newborn, including in the nerve system, complications of the administration of anesthetic or other sedation in labor and delivery, diseases in the skin including Infection, insufficient circulation problem, injuries, including after surgery, crushing injury, burns. Injuries to nerves and spinal cord, including division of nerve, lesion in continuity (with or without open wound), traumatic neuroma (with or without open wound), traumatic transient paralysis (with or without open wound), accidental puncture or laceration during medical procedure, injury to optic nerve and pathways, optic nerve injury, second cranial nerve, injury to optic chiasm, injury to optic pathways, injury to visual cortex, unspecified blindness, injury to other cranial nerve(s), injury to other and unspecified nerves. Poisoning by drugs, medicinal and biological substances, genetic or traumatic atrophic muscle disorders; or for the treatment of diseases or conditions of various organs, such as degenerative conditions of the gonads, of the pancreas, such as diabetes mellitus type I and II, of the kidney, such as nephrosis.

Conditions of CNS/PNS

In another aspect of the invention the compounds are for the treatment of diseases or conditions of the central and peripheral nervous system, such as postoperative nerve damage, traumatic nerve damage, impaired myelination of nerve fibers, postischaemic damage, e.g. resulting from a stroke, Parkinson's disease, Alzheimer's disease, Huntington's disease, dementias such as multiinfarct dementia, sclerosis, nerve degeneration associated with diabetes mellitus, disorders affecting the circadian clock or neuro-muscular transmission, and schizophrenia, mood disorders, such as manic depression; for treatment of diseases or conditions of the muscles including conditions with impaired function of neuro-muscular connections, such as after organ transplantation, or such as genetic or traumatic atrophic muscle disorders; or for treatment of diseases or conditions of various organs, such as degenerative conditions of the gonads, of the pancreas such as diabetes mellitus type I and II, of the kidney such as nephrosis and of the heart and bowel, and for the treatment of postoperative nerve damage, traumatic nerve damage, impaired myelination of nerve fibers, postischaemic, e.g. resulting from a stroke, Parkinson's disease, Alzheimer's disease, dementias such as multiinfarct dementia, sclerosis, nerve degeneration associated with diabetes mellitus, disorders affecting the circadian clock or neuro-muscular transmission, and schizophrenia, mood disorders, such as manic depression.

Preventing Cell Death

Further, the candidate compounds according to the invention may be used for preventing cell death of cells being implanted or transplanted. This is particularly useful when using compounds having a long-term effect.

In another aspect of the invention the candidate compounds may be synthesised and secreted from implanted or injected gene manipulated cells.

Heart Muscles

Furthermore, the candidate compound and/or pharmaceutical composition may be for preventing cell death of heart muscle cells, such as after acute myocardial infarction, or after angiogenesis. Furthermore, in one embodiment the compound and/or pharmaceutical composition is for the stimulation of the survival of heart muscle cells, such as survival after acute myocardial infarction. In another aspect the compound and/or pharmaceutical composition is for re-vascularisation, such as after injuries.

Memory

In another aspect the candidate compound and/or pharmaceutical composition is used for stimulation of the ability to learn and/or of the short and/or long-term memory.

Regeneration

In one aspect of the invention treatment by the use of the candidate compounds according to the invention is useful for the stimulation of regenerating cells which are degenerating or at risk of dying due to a variety of factors, such as traumas and injuries, acute diseases, chronic diseases and/or disorders, in particular degenerative diseases normally leading to cell death, other external factors, such as medical and/or surgical treatments and/or diagnostic methods that may cause formation of free radicals or otherwise have cytotoxic effects, such as X-rays and chemotherapy.

Prion Disease

The candidate compound or a pharmaceutical composition comprising thereof may also be used for treating the prion diseases. NCAM has been shown to be a molecular interaction partner with the cellular prion protein.

For Wound-Healing

It is also within the scope of the invention to use the candidate compound and/or pharmaceutical composition for the promotion of wound-healing. The present compounds are capable of interfering with cell adhesion and thereby promote the wound healing process.

Cancer

The invention further discloses the use of the candidate compound and/or pharmaceutical composition in the treatment of cancer. NCAM regulates motility and inhibits cancer cells from spreading.

REFERENCES

Atkins, A. R., Osborne, M. J., Lashuel, H. A., Edelman, G. M., Wright, P. E., Cunningham, B. A., and Dyson, H. J. (1999). Association between the first two immunoglobulin-like domains of the neural cell adhesion molecule N-CAM. FEBS Lett. 451, 162-168.

Atkins, A. R, Chung, J., Deechongkit, S., Little, E. B., Edelman, G. M., Wright, P. E., Cunningham, B. A., and Dyson, H. J. (2001). Solution structure of the third immunoglobulin domain of the neural cell adhesion molecule N-CAM: can solution studies define the mechanism of homophilic binding? J. Mol. Biol. 311, 161-172.

Becker, J. W., Erickson, H. P., Hoffman, S., Cunningham, B. A., and Edelman, G. M. (1989). Topology of cell adhesion molecules. Proc. Natl. Acad. Sci. USA 86, 1088-1092.

Berezin, V., Bock, E., and Poulsen, F. M. (2000). The neural cell adhesion molecule. Curr. Opin. Drug Discovery Dev. 3, 605-609.

Bork, P., Downing, A. K., Kieffer, B., and Campbell, I. D. (1996). Structure and distribution of modules in extracellular proteins. Q. Rev. Biophys. 29, 119-167.

Brieher, W. M., Yap, A. S., and Gumbiner, B. M. (1996). Lateral dimerization is required for the homophilic binding activity of C-cadherin. J. Cell Biol. 135, 487-496.

Brünger, A. T., Adams, P. A., Clore, G. M., DeLano, W. L., Gros, P., Grosse-Kunstleve, R. W., Jiang, J-S., Kuszewski, J., Nilges, M., Pannu, N. S., Read, R. J., Rice, L. M., Simonson, T., and Warren, G. L. (1998). Crystallography & NMR system: A new software suite for macromolecular structure determination. Acta Cryst. D54, 905-921.

Casasnovas, J. M., Stehle, T., Liu, J. H., Wang, J. H., and Springer, T. A. (1998). A dimeric crystal structure for the N-terminal two domains of intercellular adhesion molecule-1. Proc. Natl. Acad. Sci. USA. 95, 4134-4139.

Chothia, C., and Jones, E. Y. (1997). The molecular structure of cell adhesion molecules. Annu. Rev. Biochem. 66, 823-862.

Cole, G. J., and Akeson, R. (1989). Identification of a heparin binding domain of the neural cell adhesion molecule N-CAM using synthetic peptides. Neuron 2, 1157-1165.

Collaborative Computational Project, number 4. (1994). The CCP4 Suite: Programs for Protein Crystallography. Acta Cryst. D50, 760-763.

Covault, J., and Sanes, J. R. (1985). Neural cell adhesion molecule (NCAM) accumulates in denervated and paralyzed skeletal muscles. Proc. Natl. Acad. Sci. USA 82, 4544-4548.

Conte, L. L., Chothia, C., and Janin, J. (1999). The atomic structure of protein-protein recognition sites. J. Mol. Biol. 285, 2177-98.

Cremer, H., Lange, R., Christoph, A., Plomann, M., Vopper, G., Roes, J., Brown, R., Baldwin, S., Kraemer, P., Scheff, S., Barthels, D., Rajewsky, K., and Wille, W. (1994). Inactivation of the N-CAM gene in mice results in size reduction of the olfactory bulb and deficits in spatial learning. Nature 367, 455-459.

Cunningham, B. A., Hemperly, J. J., Murray, B. A., Prediger, E. A., Brackenbury, R., and Edelman, G. M. (1987). Neural cell adhesion molecule: Structure, immunoglobulin-like domains, cell surface modulation, and alternative RNA splicing. Science 236, 799-806.

Drejer J. and Schousboe A. (1989) Selection of a pure cerebellar granule cell culture by kainate treatment. Neurochem Res. 14:751-4

Edelman, G. M., and Crossin, K. L. (1991). Cell adhesion molecules: implications for a molecular histology. Annu. Rev. Biochem. 60, 155-190.

Eksterowicz J E, Evensen E, Lemmen C, Brady G P, Lanctot J K, Bradley E K, Saiah E, Robinson L A, Grootenhuis P D, Blaney J M. (2002) Coupling structure-based design with combinatorial chemistry: application of active site derived pharmacophores with informative library design. J Mol Graph Model. 20, 469-77.

Flocco, M. M., and Mowbray, S. L. (1994). Planar stacking interactions of arginine and aromatic side-chains in proteins. J. Mol. Biol. 235, 709-717.

Freigang, J., Proba, K., Leder, L., Diederichs, K., Sonderegger, P., and Welte, W. (2000). The crystal structure of the ligand binding module of axonin-1/TAG-1 suggests a zipper mechanism for neural cell adhesion. Cell 101, 425-433.

Gunning, P., Leavitt, J., Muscat, G., Ng, S. Y., and Kedes, L. (1987). A human beta-actin expression vector system directs high-level accumulation of antisense transcripts. Proc. Natl. Acad. USA. 84, 4831-4835.

Hall, A. K., and Rutishauser, U. (1987). Visualization of neural cell adhesion molecule by electron microscopy. J. Cell Biol. 104, 1579-1586.

Hunter, I., Sawa, H., Edlund, M., and Öbrink, B. (1996). Evidence for regulated dimerization of cell-cell adhesion molecule (C-CAM) in epithelial cells. Biochem. J. 320, 847-853.

Janin, J. (1997). Specific versus non-specific contacts in protein crystals. Nature Struct. Biol. 4, 973-974.

Jensen, P. H., Soroka, V., Thomsen, N. K., Ralets, I., Berezin, V., Bock, E., and Poulsen, F. M. (1999). Structure and interactions of NCAM modules 1 and 2—basic elements in neural cell adhesion. Nature Struct. Biol. 6, 486-493.

Jones, T. A., Zou, J. Y., Cowan, S. W., and Kjeldgaard, M. (1991). Improved methods for building protein models in electron density maps and the location of errors in these models. Acta Crystallogr. A47, 110-119.

Jones, E. Y., Davis, S. J., Williams, A. F., Harlos, K., and Stuart, D. I. (1992). Crystal structure at 2.8 A resolution of a soluble form of the cell adhesion molecule CD2. Nature 360, 232-239.

Jones, S., and Thornton, J. M. (1996). Principles of protein-protein interactions. Proc. Natl. Acad. Sci. USA 93, 13-20.

Jørgensen, O. S., and Bock, E. (1974). Brain-specific synaptosomal membrane proteins demonstrated by crossed immunoelectrophoresis. J. Neurochem. 23, 879-880.

Kallapur, S. G., and Akeson, R. A. (1992). The neural cell adhesion molecule (NCAM) heparin binding domain binds to cell surface heparan sulfate proteoglycans. J. Neurosci. Res. 33, 538-548.

Kasper, C., Stahlhut, M., Berezin, V., Maar, T. E., Edvardsen, K., Kiselyov, V. V., Soroka, V., and Bock, E. (1996). Functional characterization of NCAM fibronectin type III domains: demonstration of modulatory effects of the proline-rich sequence encoded by alternatively spliced exons a and AAG. J. Neurosci. Res. 46, 173-186.

Kasper, C., Rasmussen, H., Kastrup, J. S., Ikemizu, S., Jones, E. Y., Berezin, V., Bock, E., and Larsen, I. K. (2000). Structural basis of cell-cell adhesion by NCAM. Nature Struct. Biol. 7, 389-393.

Kiselyov, V. V., Berezin, V., Maar, T., Soroka, V., Edvardsen, K., Schousboe, A., and Bock, E. (1997). The first Ig-like NCAM domain is involved in both double reciprocal interaction with the second Ig-like NCAM domain and in heparin binding. J. Biol. Chem. 272, 10125-10134.

Kleywegt, G. J., and Jones, T. A. (1996). Phi/psi-chology: Ramachandran revisited. Structure 4, 1395-1400.

Kolkova, K., Novitskaya, V., Pedersen, N., Berezin, V., and Bock, E. (2000). Neural cell adhesion molecule-stimulated neurite outgrowth depends on activation of protein kinase C and the Ras-mitogen-activated protein kinase pathway. J. Neurosci. 20, 2238-2246.

Kostrewa, D., Brockhaus, M., D'Arcy, A.; Dale, G. E., Nelboeck, P., Schmid, G., Mueller, F., Bazzoni, G., Dejana, E., Bartfai, T., Winkler, F. K., and Hennig, M. (2001). X-ray structure of junctional adhesion molecule: structural basis for homophilic adhesion via a novel dimerization motif. EMBO J. 20, 4391-4398.

Kraulis, P. J. (1991). MOLSCRIPT: a program to produce both detailed and schematic plots of protein structures. J. Appl. Cryst. 24, 946-950.

Kristiansen, L. V., Marques, F. A., Soroka, V., Rønn, L. C., Kiselyov, V., Pedersen, N., Berezin, V., and Bock E. (1999). Homophilic NCAM interactions interfere with L1 stimulated neurite outgrowth. FEBS Lett. 464, 30-34.

Leahy, D. J., Aukhil, I., and Erickson, H. P. (1996). 2.0 A crystal structure of a four-domain segment of human fibronectin encompassing the RGD loop and synergy region. Cell 84, 155-164.

Laskowski, R. A., MacArthur, M. W., Moss, D. S., and Thornton, J. M. (1993). PROCHECK: a program to check the stereochemical quality of protein structures. J. Appl. Cryst. 26, 283-291.

Merritt, E. A. and Bacon, D. J. (1997). Raster3D Photorealistic Molecular Graphics. Methods Enzymol. 277, 505-524.

Milev, P., Friedlander, D. R., Sakurai, T., Karthikeyan, L., Flad, M., Margolis, R. K., Grummet, M., and Margolis, R. U. (1994). Interactions of the chondroitin sulfate proteoglican phosphacan, the extracellular domain of a receptor-type protein tyrosine phosphatase, with neurons, glia, and neural cell adhesion molecules. J. Cell Biol. 121, 1409-1421.

Miyahara, M., Nakanishi, H., Takahashi, K., Satoh-Horikawa, K., Tachibana, K., and Takai, Y. (2000). Interaction of nectin with afadin is necessary for its clustering at cell-cell contact sites but not for its cis dimerization or trans interactions. J. Biol. Chem. 275, 613-618.

Muller, D., Wang, C., Skibo, G., Toni, N., Cremer, H., Calaora, V., Rougon, G., and Kiss, J. Z. (1996). PSA-NCAM is required for activity-induced synaptic plasticity. Neuron 3, 413-422.

Navaza, J., and Saludjian, P. (1997). AmoRe: An automated molecular replacement program package. Methods Enzymol. 276, 581-594.

Nybroe, O., Moran, N., and Bock, E. (1989). Equilibrium binding analysis of neural cell adhesion molecule binding to heparin. J. Neurochem. 52, 1947-1949.

Otwinowski, Z., and Minor, W. (1997). Processing of X-ray diffraction data collected in oscillation mode. Methods Enzymol. 276, 307-326.

Perrakis, A., Morris, R., and Lamzin, V. S. (1999). Automated protein model building combined with iterative structure refinement. Nature Struct. Biol. 6, 458-463.

Probstmeier, R., Kuhn, K., and Schachner, M. (1989). Binding properties of the neural cell adhesion molecule to different components of the extracellular matrix. J. Neurochem. 53, 1794-1801.

Ranheim, T. S., Edelman, G. M., and Cunningham, B. A. (1996). Homophilic adhesion mediated by the neural cell adhesion molecule involves multiple immunoglobulin domains. Proc. Natl. Acad. Sci. USA. 93, 4071-4075.

Rao, Y., Wu, X-F., Gariepy J., Rutishauser, Urs., and Siu, C-H. (1992). Identification of a peptide sequence involved in homophilic binding in the neural cell adhesion molecule NCAM. J. Cell Biol. 118, 937-949.

Rao, Y., Zhao, X., and Siu, C. H. (1994). Mechanisms of homophilic binding mediated by the neural cell adhesion molecule NCAM. Evidence for isologous interaction. J. Biol. Chem. 269, 27540-275448.

Rønn, L. C., Ralets, I., Hartz, B. P., Bech, M., Berezin, A., Berezin, V., Moller, A., and Bock, E. (2000). A simple procedure for quantification of neurite outgrowth based on stereological principles. J. Neurosci. Meth. 100, 25-32.

Sandig, M., Rao, Y., and Siu, C-H. (1994). The homophilic binding site of the neural cell adhesion molecule NCAM is directly involved in promoting neurite outgrowth from cultured neural retinal cells. J. Biol. Chem. 269, 14841-14848.

Shapiro, L., Fannon, A. M., Kwong, P. D., Thompson, A., Lehmann, M. S., Grubel, G., Legrand, J-F., Als-Nielsen, J., Colman, D. R., and Hendrickson, W. A. (1995). Structural basis of cell-cell adhesion by cadherins. Nature 374, 327-337.

Soroka, V., Kiryushko, D., Novitskaya, V., Rønn, L. C., Poulsen, F. M., Holm, A., Bock, E., and Berezin, V. (2002). Induction of neuronal differentiation by a peptide corresponding to the homophilic binding site of the second Ig module of NCAM. J. Biol. Chem. 227, 24676-24683.

Su, X-D., Gastinel, L. N., Vaughn, D. E., Faye, I., Poon, P. and Bjorkman P. J. (1998). Crystal structure of hemolin: A horseshoe shape with implications for homophilic adhesion. Science 281, 991-995.

Takeda, H., Shimoyama, Y., Nagafuchi, A., and Hirohashi, S. (1999). E-cadherin functions as a cis-dimer at the cell-cell adhesive interface in vivo. Nature Struct. Biol. 6, 310-312.

Tomasiewicz, H., Ono, K., Yee, D., Thompson, C., Goridis, C., Rutishauser, U., and Magnuson, T. (1993). Genetic deletion of a neural cell adhesion molecule variant (NCAM-180) produces defects in the central nervous system. Neuron 11, 1163-1174.

Thomsen, N. K., Soroka, V., Jensen, P. H., Berezin, V., Bock, E., and Poulsen, F. M. (1996). The three-dimensional structure of the first domain of neural cell adhesion molecule. Nature Struct. Biol. 3, 581-585.

Wu, Y. Y., and Bradshaw, R. A. (1995). PC12-E2 cells: a stable variant with altered responses to growth factor stimulation. J. Cell. Physiol. 164, 522-532.

Wu, H., Kwong, P. D., and Hendrickson, W. A. (1997). Dimeric association and segmental variability in the structure of human CD4. Nature 387, 527-530.

Experimentals

The following is a non-limiting examples of the production of the candidate compounds of the invention, a fragment of NCAM comprising the Ig1-2-3 module and fragments thereof, such as Ig1, Ig2, Ig3, or Ig1-2, or Ig2-3, description of the crystalline protein comprising the Ig1-2-3 module, and the biological testing of selected candidate compounds.

Production of the Ig1-2-3 and Ig3 Fragments of NCAM

The NCAM Ig1-2-3 and Ig3 fragments were produced as recombinant proteins in the yeast *P. pastoris* expression system (Invitrogen). The cDNA fragments encoding Ig1-2-3 and Ig3 of rat NCAM (NCBI accession number NP_113709), corresponding to residues 1-289 and 191-289, respectively, were synthesized by PCR using rat NCAM cDNA as a template. The following DNA primers were used for cloning of Ig1-2-3 and Ig3, respectively: upper (5'-TCT CTC GAG TTC TGC AGG TAG ATA TTG TT-3') (SEQ ID NO: 37) and lower (5'-AAA CCC GGG TTA CTT TGC AAA GAC CTT-3') (SEQ ID NO: 30), upper (5'-GAA TAC GTA ACT GTC CAG GCC AGA C-3') (SEQ ID NO: 31) and lower (5'-AAA CCT AGG TTA CTT TGC AAA GAC CTT G-3') (SEQ ID NO: 32). The amplified cDNA fragments were subcloned into the pHIL-S1 and the pPIC9K plasmids (Invitrogen), respectively. The recombinant plasmids were linearized with the NsiI and SacI restriction enzymes, respectively, and used for transformation of the *P. pastoris* strain His 4 GS-115 (Invitrogen). Large-scale production of the recombinant proteins was performed employing a high-density feed-batch fermentation technique in a Biostat B fermentor (B. Braun Biotech Int. GmbH). Ig1-2-3 and Ig3 were purified from concentrated and desalted medium by anion-exchange chromatography on a HiTrap Q-Sepharose 5 ml column (Pharmacia), followed by gel filtration chromatography on a HiLoad 16/60 Superdex-75 column (Pharmacia). The Ig1-2-3 was enzymatically deglycosylated with PNGase-F endo-N-glycosidase (New England Biolabs) at 37° C. in PBS buffer pH 7.4. The authenticity of the protein fragments was confirmed by DNA sequencing of the recombinant plasmids, by amino acid sequencing of the 10-12 N-terminal residues, and by MALDI-TOF MS. The recombinant Ig1-2-3 and Ig3 fragments contained respectively two (RV) and five (EAEAY) additional N-terminal residues from the cloning vector. The purity of the proteins was at least 95% as estimated by SDS-PAGE.

Production of the Ig1-2-3 and Ig3 Mutants

An Ig1-2-3 mutant (Ig1-2-3mut) containing the substitutions E11A, E16A, and K18A was produced as a recombinant protein in the yeast *P. pastoris* expression system following the procedure described for the Ig1-2-3 fragment. The three mutations were introduced by PCR using the following DNA primer: upper (5'-CTG CAG GTA GAT ATT GTT CCC AGC CAA GGA GCC ATC AGC GTT GGA GCC TCC GCC TTC TTC CTG TGT CAA GTG GCA-3') (SEQ ID NO: 33).

Two Ig3 mutants containing the substitutions: R198A, D249G, E287A (Ig3mut1) and K285A, F287A (Ig3mut2) were produced as recombinant proteins in the yeast *P. pastoris* expression system following the procedure described for the Ig3 fragment. Mutations were introduced by PCR using the following DNA primers: upper1 (5'-AAA TAC GTA ACT GTC CAG GCC GCC CAG AGC ATC GTG-3') (SEQ ID NO: 38), upper2 (5'-GGC GAC AGT TCG GCG TTA ACC ATC AGG AAT GTG GAC-3') (SEQ ID NO: 34), and lower (5'-GGT TAA CGC CGA ACT GTC GCC ACT GAA GAT GTG CTT CTC-3') (SEQ ID NO: 35) for Ig3mut1, and lower (5'-AAA CTT AGG TTA CTT TGC TGC GAC TGC GAG GTG GAT GGA GGC ATC-3') (SEQ ID NO: 36) for Ig3mut2. The DNA constructs of Ig1-2-3mut, Ig3mut1, and Ig3mut2 were verified by DNA sequencing. Folding of the Ig3 module and its mutants, as well as presence of carbohydrates, was confirmed by one-dimensional proton NMR spectra recorded at 800 MHz on a Varian NMR spectrometer (Varian Inc.) at 25° C. in PBS buffer pH 7.4.

Preparation of Peptides

Peptides were synthesized using the 9-fluorenylmethoxycarbonyl (Fmoc) protection strategy on a TentaGel resin (Rapp Polymere) using Fmoc protected amino acids (Calbiochem-Novabiochem). Peptides were at least 85% pure as estimated by MALDI-TOF MS. All peptides were synthesized with free $NH_2$ and carboxy-amidated COOH groups.

Crystallization and Data Collection

Crystals of NCAM Ig1-2-3 were grown at 18° C. using the hanging-drop vapor diffusion method, with drops of equal volumes of reservoir and protein solutions (4 mg ml$^{-1}$ in 5 mM Na phosphate, 150 mM NaCl, pH 7.4). The reservoir solution contained 14-17% w/v PEG 4000, 450 mM Li sulfate, 100 mM Na acetate, pH 5.2. The crystals belong to space group $I2_12_12_1$ with one molecule in the asymmetric unit and cell dimensions of a=51.5, b=108.5, and c=149.0 Å. The crystals were flash cooled in liquid nitrogen using 15% v/v glycerol as cryoprotectant. Two data sets were collected on the same crystal. The high-resolution data were collected to 2.0 Å at 120 K at beamline 1711, Max-Lab, Lund, Sweden, and the low-resolution data were collected to 3.5 Å at 120 K on a Rigaku RU300 rotating anode equipped with a MAR345 image plate detector. The data sets were combined and processed with DENZO/SCALEPACK (Otwinowski and Minor, 1997) and the CCP4 suite of programs (Collaborative Computational Project No. 4, 1994).

Structure Determination and Refinement

The structure was determined by molecular replacement with the programs AmoRe (Navaza and Saludjan, 1997) and CNS version 1.0 (Brünger et al., 1998), using the X-ray structures of the Ig2 and Ig1 modules of NCAM (Kasper et al., 2000) as search models. Initially, the position of the Ig2 module was located using AmoRe. The Ig1 module was subsequently located using CNS. An electron density map was calculated based on phase information from Ig1 and Ig2. Residues of Ig3 were gradually built into this map. Map interpretation and model building were carried out using the program O (Jones et al., 1991). After several building and refinement cycles, ARP/wARP version 5.1 (Perrakis et al., 1999) was used to rebuild 233 out of 291 residues of NCAM Ig1-2-3. CNS was used to carry out the final rounds of refinements. The final model contains amino acids (−1)-238 and 241-289, and 266 water molecules. Amino acids are numbered according to the mature sequence of NCAM. Residues Arg and Val originating from the cloning site were given negative integers −2 and −1, respectively. Using all reflections in the resolution range 50-2.0 Å, the $R_{cryst}$ is 21.8% and the $R_{free}$ is 23.8% (3% test set, corresponding to 828 reflections). Data collection and refinement statistics are given in Table 1 (FIG. 1). Interdomain geometry was determined according to Bork et al. (1996), and buried accessible surface areas were calculated using the Protein-Protein Interaction Server (http://www.biochem.ucl.ac.uk/bsm/PP/server) (Jones and Thornton, 1996). Figures were prepared with the programs MOLSCRIPT, RASTER3D (Kraulis, 1991; Merritt and Bacon, 1997), and Insight II (Accelrys).

The atomic coordinates of the structure is demonstrated in the Table 2 (FIG. 2).

Protein Data Bank ID Code

The coordinates of the structure have been deposited with the Protein Data Bank under ID code 1QZ1.

Cell Culture and Immunostaining

The NCAM-expressing pheochromocytoma PC12-E2 cell line (Wu and Bradshaw, 1995) was a gift from Dr. Klaus Seedorf, Hagedorn Research Institute, Denmark. The cells were grown in Dulbecco's Modified Eagle's Medium (DMEM) supplemented with 5% v/v fetal calf serum (FCS) and 10% v/v horse serum (HS), 100 U ml$^{-1}$ penicillin, 100 µg ml$^{-1}$ streptomycin (all from Gibco BRL) at 37° C. in a humidified atmosphere containing 5% $CO_2$.

The fibroblastoid mouse cell line, L929 (European Cell Culture Collection), was stably transfected with the eukaryotic expression vector pHβ-Apr-1-neo (Gunning et al., 1987) containing a full-length cDNA encoding human 140 kDa NCAM-B or the vector alone. The NCAM cDNA did not contain the exons VASE, a, b, c, or AAG. The cells were routinely grown at 37° C., 5% $CO_2$ in DMEM supplemented with 10% v/v FCS, 100 U ml$^{-1}$ penicillin, and 100 µg ml$^{-1}$ streptomycin. For analysis of neurite outgrowth, PC12-E2 cells (8,000 cells per well) were seeded on top of a confluent monolayer of transfected fibroblastoid L929 cells in four-well LabTek Tissue Culture Chamber Slides (NUNC). The cells were grown for 24 h in DMEM supplemented with 1% v/v HS, before analysis.

Cerebellar granule neurons (CGN) were prepared from Wistar rat pups of postnatal day 3. Cerebellar tissue was dissected in modified Krebs-Ringer solution kept on ice, and treated as described for the hippocampal neurons above. All cell cultures were incubated at 37° C. in a humidified atmosphere containing 5% $CO_2$. All animals were handled in accordance with the national guidelines for animal welfare. Primary cultures of CGN were plated at a density of 100,000 cells/cm² on poly-L-lysine coated 8-well permanox slides in Neurobasal-A medium (Gibco, BRL) supplemented with 2% (v/v) B27, 0.5% (v/v) glutamax, 100 U/ml penicillin, 100 µg/ml streptomycin and KCl, making the final concentration of KCl in the medium 40 mM. 24 hours after plating, cytosine-β-D-arabinofuranoside (Ara-C; Sigma-Aldrich) was added to a final concentration of 10 µM to avoid proliferation of glial cells, after which the neurons were allowed to differentiate for further six days at 37° C.

The glycosylated recombinant rat Ig3 module of NCAM (wildtype and mutated forms) or selected peptides were added immediately after seeding of cells in order to evaluate their inhibitory effects on adhesion, as reflected by interference with NCAM-mediated neurite outgrowth. Ig3 wt, Ig3mut1, and Ig3mut2 were tested at a concentration of 500 µg ml⁻¹. Proper controls were included and the person performing the experiments did not know the identity of the mutants or peptides.

To evaluate the length of processes of PC12-E2 cells, the co-cultures were fixed in 4% w/v paraformaldehyde for 25 min. After washing in PBS, cells were blocked with 10% v/v goat serum (DAKO) for 30 min and subsequently incubated for 1 h at room temperature with a mouse monoclonal anti-Thy-1 antibody (Caltag Laboratories) (1:100 in PBS containing 10% v/v goat serum). After washing, cells were incubated for 1 h at room temperature with Alexa-Fluor 568™ goat anti-mouse IgG (Molecular Probes) (1:1000 in PBS containing 10% goat serum). All washes were performed for 10 min in PBS, and repeated three times.

To evaluate the length of neurites of CGN, the neurons were fixed after 24 hours in culture with 4% (v/v) formaldehyde for 20 minutes and thereafter immunostained using primary rabbit antibodies against GAP-43 and Alexa Fluor secondary goat anti-rabbit antibodies. Images of at least 200 neurons for each group in each individual experiment were obtained systematically by using computer assisted fluorescence microscopy The total neurite length per cell was analyzed using the software ProcessLength (Rønn et al., 2000). Five independent experiments with the Ig3 module, its mutants, and the individual peptides were performed. In each experiment neurites from 200-300 cells were analyzed. In order to compare results of individual experiments and due to the inherently high variability of cell experiments, the data were normalized setting the difference between the average neurite length of PC12-E2 cells grown on NCAM-140-transfected and vector-transfected fibroblasts to 100%. Statistical evaluations were performed using a two-sided Student's t-test.

Dynamic Light Scattering (DLS) Measurements

Measurements were performed using a DynaPro-MS/X instrument (Protein Solutions) at 18° C. The deglycosylated preparations of Ig1-2-3 (4 mg ml⁻¹), Ig1-2-3mut (4 mg ml⁻¹) and Ig3 (10 mg ml⁻¹) in PBS pH 7.4 were used to determine the molecular weight of the recombinant proteins in solution.

Results and Discussion

The X-Ray Structure of the Ig1-2-3 Modules of NCAM

The X-ray structure of NCAM Ig1-2-3 was determined to 2.0 Å resolution (see Table 1 of FIG. 1). In the structure of Ig1-2-3, the Ig1 and Ig2 modules are positioned in an extended conformation with Ig3 oriented at an angle of approximately 45° to the Ig1-Ig2 axis (FIG. 3). The linker regions between Ig1-Ig2 and between Ig2-Ig3 are short and comprise only two (Lys98-Leu99) and one (Asn190) residues, respectively. The overall structure of the Ig1 and Ig2 modules is very similar to the previously determined Ig1-2 structure (Kasper et al., 2000) with root mean square deviations (r.m.s.d.) of 0.7 (96 Cα atoms) and 0.8 Å (93 Cα atoms), respectively. In the Ig1-2-3 structure, the tilt angle between Ig1 and Ig2 is 11° and thereby differs by 13° compared to the Ig1-2 structure.

The 98-residue Ig3 module of rat NCAM adopts the topology of an intermediate type 1 (I1) set Ig module (Casasnovas et al., 1998). In the Ig3 module, the classical β-sandwich consists of two β-sheets with a total of nine β-strands (FIG. 3B). The A, B, D, and E β-strands make up one sheet and the A', C, C', F, and G β-strands the second sheet. A cysteine bridge Cys216-Cys269 connects the two β-sheets. All strands are anti-parallel except for the A' strand, which runs parallel to the C-terminal part of the G strand. Ig3 contains one site for N-linked glycosylation at Asn203 positioned in the A' strand. The E-F loop (residues Lys261-Asp263) forms a $3_{10}$ α-helical turn. The overall structure of rat Ig3 is similar to the structure of chicken Ig3 (Atkins et al., 2001) with r.m.s.d. of 1.65 Å (95 Cα atoms).

Parallel Interactions Between Ig Modules

Several characteristic interactions are observed in the structure of the NCAM Ig1-2-3 fragment which may be divided into two groups: Interactions where the long axes (N- to C-terminus) of two interacting Ig1-2-3 molecules are oriented in a parallel manner and interactions where the long axes are oriented in an anti-parallel manner. One parallel interaction and three major anti-parallel interactions are observed in the crystal.

The parallel, cross-like dimer interaction of NCAM Ig1-2-3 involves the Ig1 and Ig2 modules (FIG. 5). The total buried surface area of this interface is 1594 Å² (per dimer), which is similar to that previously observed in the Ig1-2 cross-like dimers (Kasper et al., 2000). The most prominent feature of the Ig1-to-Ig2 interaction is the intercalation of two aromatic residues of Ig1, Phe19 and Tyr65, into hydrophobic pockets formed by Ig2 residues (FIG. 5A), which was also observed in the Ig1-2 structure. However, a tighter Ig1 to Ig2 binding interface is observed in the Ig1-2-3 structure, where the hydroxyl group of Tyr65 forms a direct hydrogen bond (H-bond) with Glu171, instead of a water-mediated H-bond as observed in Ig1-2. Tyr65 also makes three H-bonds to the side chains of Lys133, Glu171, and Arg173. Arg173 forms part of the Ig2 hydrophobic pocket and makes two H-bonds to Thr63. The parallel orientation of the Arg173 and Phe19 side chains and the distance between the Nηi atom of the guanidinium group of Arg173 and the Cζ atom of the benzene ring of Phe19 (3.4 Å) suggest a cation-π interaction between these two residues (Flocco and Mowbray, 1994).

Dynamic Light Scattering (DLS) measurements showed that deglycosylated Ig1-2-3 forms a single species of molecules in solution with a molecular weight of ~78 kDa, corresponding to a dimer. In order to demonstrate that Ig1-2-3 dimerization is mediated by the observed Ig1 to Ig2 binding, we produced a mutant of Ig1-2-3 (Ig1-2-3mut) containing three Ala substitutions: E11A, E16A, and K18A. These mutations have previously been shown to completely abolish dimerization of the Ig1-2 NCAM fragment in solution (Jensen et al., 1999). In the present structure Glu11 and Glu16 form intramolecular salt bridges, respectively, with Arg177 and Lys98 from the Ig1 to Ig2 linker region (not shown). These salt bridges probably contribute to the proper orientation of Ig1 with respect to Ig2 and therefore are important for the Ig1-to-Ig2 interaction. Lys18 forms an H-bond with the carboxyl group of Arg177 from the Ig2 module stabilizing the Ig1-Ig2 interaction (FIG. 5A). Lys18 is located near Phe19, which is the critical residue for the Ig1-to-Ig2 interaction as it was clearly demonstrated earlier (Atkins et al., 2001). Therefore, disruption of the Lys18-Arg177H-bond may affect the orientation of Phe19 leading to elimination of the Ig1-to-Ig2 interaction. The molecular weight of the Ig1-2-3mut fragment was determined by DLS to be ~34 kDa, indicating a monomer. This confirms that Ig1-2-3 dimerization is mediated by Ig1-to-Ig2 binding.

Parallel (cis) interactions are not uncommon among cell adhesion molecules. Thus, cis dimerization has been demonstrated for the cell adhesion molecules C-CAM1, C-CAM2, ICAM-1, nectin-2α, and JAM belonging to the Ig superfamily (Hunter et al., 1996; Casasnovas et al., 1998; Miyahara et al., 2000; Kostrewa et al., 2001) as well as for N-, E-, and C-cadherins (Shapiro et al., 1995; Takeda et al., 1999; Brieher et al., 1996). It was shown that the dimeric form of C-cadherin is capable of adhesion, whereas the monomeric form is not (Brieher et al., 1996).

Anti-Parallel Interactions Between Ig Modules

An anti-parallel interaction takes place between the Ig2 and Ig3 modules of two Ig1-2-3 molecules, thereby forming arrays of Ig1-2-3 dimers (FIGS. 4A,B). Ig2 of one molecule binds to Ig3 of a second molecule, and vice versa (FIG. 3B). The residues involved are 112-115, 143-146, and 158-161 from the B-strand, CD-loop/D-strand, and E-strand of Ig2, and residues 200-205, 261, and 278-289 from the A'-strand, EF-loop, and G-strand of Ig3. A central element of this interaction is the intercalation of the side chain of Phe287 from Ig3 into a hydrophobic pocket formed by the side chains of Val145, Arg146, and Arg158 of the Ig2 module and Lys285 from Ig3. Arg158 is also involved in water-mediated hydrogen bonding to residues Lys261 and Ala288, and Gly159 makes a direct H-bond to Asn203.

The crystal packing leaves room for glycosylation at Asn203. In order to accommodate N-linked glycosylation at this site, the side chain of Asn203 has to adopt another rotamer conformation. Thereby, the carbohydrate will point away from the binding site and towards a solvent channel in the crystal, and consequently Asn203 will not interfere with Ig2-Ig3 interactions. An interaction between the two Ig3 modules is observed at the interface, as Gln196 makes a water-mediated H-bond with Gln278. The total buried surface of the Ig2-to-Ig3 interface is 1407 Å² per dimer. According to Janin (1997), the probability of finding a non-specific interface of the size of the Ig2-to-Ig3 contact is only 1.9%.

Another anti-parallel interaction between two Ig1-2-3 molecules is formed between two Ig2 modules (FIGS. 4C,D). This interaction involves residues 103-121 and 150-158 of the AA'-loop/A'-strand/A'B-loop and the DE-loop/E-strand and has the total buried surface of 958 Å² per dimer (FIG. 4C). Here, the central residue appears to be Glu114, which makes two H-bonds to Ser151 (side chain and backbone). Apart from an extensive hydrogen-bonding network, especially through water molecules, Val117, Val119, Leu150, and Tyr154 of both Ig2 modules form a number of hydrophobic contacts with each other at the Ig2-to-Ig2 interface (not shown). A slightly smaller anti-parallel interaction (858 Å² of total buried surface per dimer) is formed between the Ig1 and Ig3 modules (FIGS. 4C,D), involving residues 32-47 and 76-88 from the C-strand/CC'-loop/C'-strand/C'D-loop and F-strand/FG-loop/G-strand in Ig1, and residues 198, 213-223, and 248-253 from the A-strand, B-strand/BC-loop, and D-strand/DE-loop in Ig3 (FIG. 5D). Arg198 and Asp249 form direct H-bonds to the backbone oxygen atoms of Ala81 and Glu82 and two salt bridges with Lys76, respectively. Additionally, one water-mediated H-bond is formed between Lys42 and Asp250, one between Ser44 and Gly220, and two between Ser44 and Glu223. The conserved Phe36 and Phe221 are packed against Asp249 and Gln47, respectively. Together two Ig1-to-Ig3 interaction sites and one Ig2-to-Ig2 site make up a predominant contact between Ig1-2-3 dimers in the crystal (2654 Å²) forming the second array of Ig1-2-3 dimers (FIGS. 4C,D) perpendicular to the Ig2-to-Ig3-mediated array (FIGS. 2A,B). Contact areas of similar sizes have been found in other CAMs. Cis dimers of human ICAM-1 and mouse JAM have 1100 Å² and 1200 Å² of total buried surface area (per dimer), respectively (Casasnovas et al. 1998; Kostrewa et al., 2001), whereas trans dimers of rat CD2 and chicken axonin-1/TAG-1 have even larger contact areas of 1300 Å² and 2000 Å² (Jones et al., 1992; Freigang et al., 2000).

Ig3 Inhibits NCAM-Dependent Neurite Outgrowth

NCAM-NCAM interaction is known to induce neurite outgrowth from NCAM-expressing PC12-E2 cells grown on a confluent monolayer of NCAM-expressing fibroblasts (Kolkova et al., 2000). Inhibition of the NCAM-NCAM interaction will therefore inhibit neurite outgrowth in PC12-E2 cells.

In order to examine the biological significance of the observed Ig1-to-Ig3 and Ig2-to-Ig3 contacts in the structure of NCAM Ig1-2-3, we tested the inhibitory effect of the recombinant Ig3 module on NCAM-NCAM adhesion. Furthermore, we prepared two Ig3 mutants containing mutations of the residues R198A, D249G, E253A (Ig3mut1) of the Ig1-to-Ig3 contact site (see FIG. 5D) and K285A, F287A (Ig3mut2) of the Ig2-to-Ig3 contact site (see FIG. 5B). In FIG. 4 it can be seen that the wildtype Ig3 module (Ig3 wt) indeed has an inhibitory effect, whereas both mutants are inactive, thereby strongly supporting that both the Ig1-to-Ig3 and Ig2-to-Ig3 contact sites are participating in homophilic interactions.

A similar co-culture test-system of NCAM-expressing chicken retinal ganglion cells grown on top of NCAM-140-transfected mouse L-cells has been successfully used to demonstrate a disruptive effect of mutations in the Ig3 module homophilic binding site (Ig1-to-Ig3 binding site in the present work) as well as to show an inhibition of neurite outgrowth by synthetic peptides representing this homophilic binding site (Sandig et al. 1994).

Interaction Interface Peptides Inhibit Neurite Outgrowth

It has previously been demonstrated that peptides representing homophilic binding sequences from Ig3 and Ig2 modules of NCAM inhibit NCAM-mediated cell aggregation (Rao et al., 1992; Sandig et al. 1994; Rao et al., 1994; Soroka et al. 2002). Therefore, in order to further examine the biological significance of the observed Ig1-to-Ig2, Ig1-to-Ig3, and Ig2-to-Ig3 contacts in the structure of NCAM Ig1-2-3, we tested the inhibitory effect of a series of peptides representing amino acid sequences from the observed contact areas (FIG. 6, 8-12).

The Ig1-to-Ig2 contact was represented by the P1-B peptide (10-GEISVGESKFFL-21) (SEQ ID NO: 19) that covers the B β-strand of Ig1 and containing the key residue Phe19 in the Ig1-to-Ig2 binding (Kasper et al., 2000; Atkins et al., 2001). As a negative control, two peptides GEISVGESKAFL (P1-B-F19A) (SEQ ID NO:21) and GEISVGESKAAL (P1-B-F19A-F20A) (SEQ ID NO: 22) containing a single Ala substitution of F19 and a double Ala substitution of both F19 and F20, respectively, were used.

The Ig1-to-Ig3 contact was represented by three peptides: AFSPNGEKLSPNQ (P1-CD) (SEQ ID NO: 40), AKSVV-TAEDGTQSE (P1-FG) (SEQ ID NO: 41) and KHIFSDDS-SELTIRNVDKNDE (P3-DE) (SEQ ID NO: 20). The P3-DE peptide covering the sequence of the D and E β-strands and the E-F loop of the Ig3 module is homologous to the sequence previously suggested to be a homophilic binding site in the Ig3 module of chicken NCAM (243-KYSFNYDGSELI-IKKVDKSDE-263) (SEQ ID NO: 23) (Rao et al., 1992). As a negative control, a truncated version of the P3-DE peptide 244-KHIFSDDSSE-253 (P3-DE-trunc) (SEQ ID NO: 24) was used. The P3-DE-trunc peptide is homologous to the 243-KYSFNYDGSE-252 (SEQ ID NO: 25) chicken sequence which was less potent than the longer sequence (Rao et al., 1992).

The Ig2-to-Ig2 contact was represented by the peptide P2-A'B (QEFKEGEDAVIV (SEQ ID NO: 17).

The Ig2-to-Ig3 contact was represented by the peptides P2-CD (DVRRGIKKTD) (SEQ ID NO: 42) and P2-EF (QIR-GIKKTD) (SEQ ID NO: 43) covering the sequences of CD- and EF-β-strands of the Ig2 module correspondingly, and P3-G (SIHLKVFAK) (SEQ ID NO: 13) from the Ig3 module. The sequence SIHLKVFAK (SEQ ID NO: 13) covers the C-terminal part of the G β-strand including the solvent-exposed Phe287. As negative controls, two peptides SIHLA-VAAK (P3-G-K285A-F287S) (SEQ ID NO: 26) and SIHLAVGAK (P3-G-K285A-F287G) (SEQ ID NO: 27) with substitutions of K285 and F287 were used. Both P1-B and P3-G peptides contain two hydrophobic residues (Ile and Val/Leu) close to their N-termini and at least one Phe residue close to their C-termini. As a control peptide with similar hydrophobic properties we selected a peptide 213-TLVA-DADGFPEP-224 (P3-B) (SEQ ID NO: 3) covering the B β-strand and B-C loop of the Ig3 module, and including Gly220, Phe221, and Glu223 involved in Ig1-to-Ig3 binding. In spite of sequence similarity with P1-B and P3-G peptides, the P3-B peptide was not active (FIG. 6G). This is probably due to the fact that Phe221 in Ig3 is partially solvent exposed and Gly220 and Glu223 form water-mediated hydrogen bonds (FIG. 5D). In contrast, the peptides P1-B, P3-DE, and P3-G either contain Phe buried in a hydrophobic pocket or residues forming direct H-bonds (FIG. 5).

Figure 10:
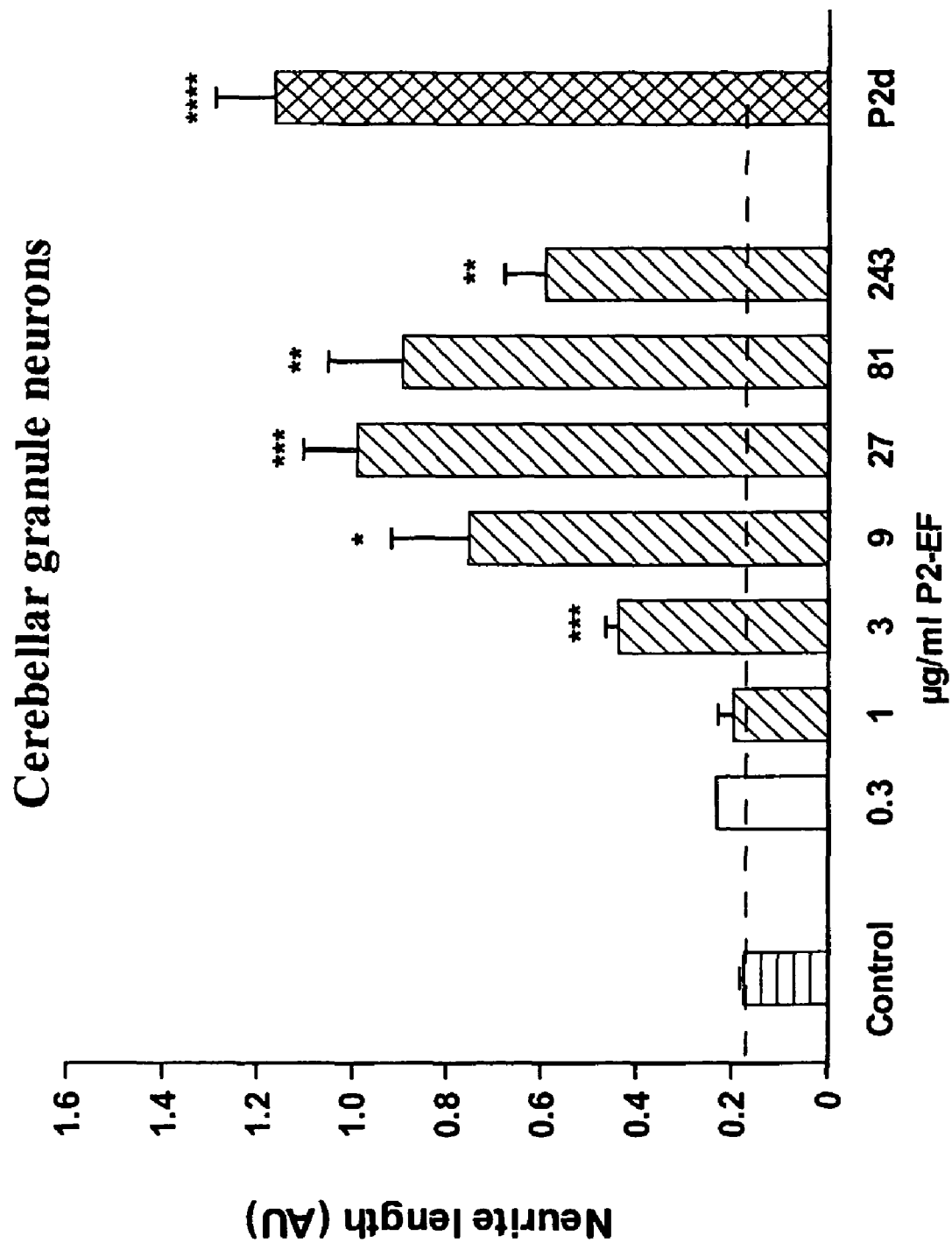
Figure 11:
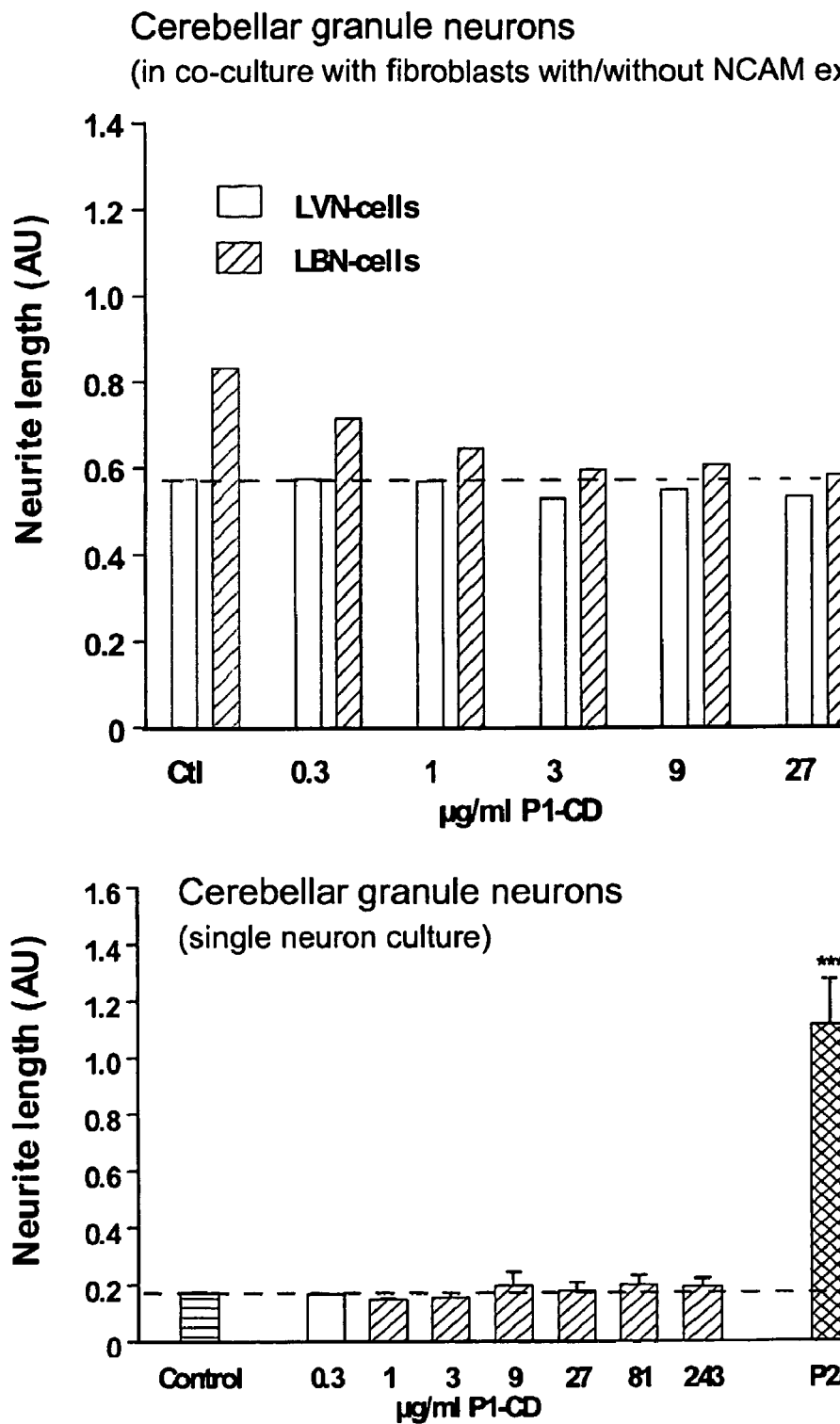

The results of biological testing of the peptides is demonstrated in FIGS. 4, 6-10. In co-cultures of PC12-E2 or CGN cells with fibroblasts expressing NCAM the P1-B, P1-CD, P2-A'B, P3-DE, and P3-G peptides all inhibited NCAM-stimulated neurite outgrowth, indicating an impaired NCAM-NCAM binding between the two cell layers. The corresponding control peptides have little or no inhibitory effect (FIG. 6G). In contrary, the peptides P2-EF, P2-CD and P3-G did not affect NCAM-stimulated neurite outgrowth in co-cultures and are very capable stimulators of neurite outgrowth in primary cultures of single CGN (FIGS. 8-10). The peptides P2-A'B, and P1-CD (FIGS. 8-12) were capable modulating the NCAM homophylic adhesion-mediated neurite outgrowth, but did not stimulate differentiation of single CGN in primary culture.

The P1-B peptide interferes with the Ig1-to-Ig2 interaction and thereby inhibits the Ig1-Ig2-mediated cis dimerization of NCAM. In the crystals of the Ig1-2-3 module zipper-like arrays of NCAM cis dimers are observed, reflecting trans interactions of NCAM. Trans interactions therefore seem to require cis dimerization of NCAM molecules (FIG. 4). The P3-DE and P3-G peptides will not affect cis interactions but interfere with trans interactions. Since the NCAM-dependent neurite outgrowth relies on NCAM-NCAM interactions between the two cell layers, an inhibition of these interactions will directly affect NCAM-mediated neurite outgrowth.

In our study, we show that mutations in the peptides derived from the Ig3 module produce the same effect as that of the similar mutations in the Ig3 module. This demonstrates that in this experimental setup the employed peptides mimic the Ig3 module, and thus can be used as a convenient and simple tool for further analysis. Moreover, the peptides representing the sequence of the Ig3 module homophilic binding site of chicken NCAM (Ig1-to-Ig3 binding site in the present work) have been previously used to identify and characterize the Ig3 module homophilic binding site (Rao et al., 1992; Sandig et al., 1994; Rao et al., 1994). These results, combined with the Ig3 mutation studies, provide strong evidence for a biological role of the observed Ig1-to-Ig2, Ig1-to-Ig3, and Ig2-to-Ig3 contacts.

Novel Zipper Mechanism for NCAM Homophilic Adhesion

The crystal structure of the Ig1-2-3 fragment reveals novel interactions between the Ig1 and Ig3 and the Ig2 and Ig3 modules of NCAM, as well as shows previously observed Ig1-to-Ig2 and Ig2-to-Ig2 interactions (Kasper et al., 2000). Together, these contacts mediate formation of two perpendicular zipper-like arrays of the Ig1-2-3 dimers (FIG. 4). The parallel interaction of the NCAM Ig1-2-3 molecules in the crystal mediated by the Ig1-to-Ig2 contact may reflect an interaction between NCAM molecules present on the same cell surface—cis interaction. The anti-parallel interactions mediated by the Ig1-to-Ig3, Ig2-to-Ig2, and the Ig2-to-Ig3 contacts may reflect the interaction of NCAM molecules present on opposing cells—trans interactions. Based on all presented observations, we propose a model for NCAM homophilic adhesion, consisting of two zipper-like arrays of NCAM molecules (FIG. 7). In the "compact" zipper (FIG. 7A), NCAM cis dimers originating from opposing cell membranes are arranged as arrays through Ig1-to-Ig3 and Ig2-to-Ig2 interactions. We speculate that "compact" zippers are likely to form first as they allow larger distances between opposing cell membranes than the perpendicular "flat" zippers. In the "flat" zipper (FIG. 7B), the Ig2-to-Ig3 interactions suggest a lateral association between the NCAM "compact" zippers thereby forming a double zipper adhesion complex (FIG. 7C). The glycosylation at Asn203 of Ig3 (FIG. 2) is not likely to interfere with the ability to form the zippers as supported by the fact that the glycosylated Ig3 module inhibits NCAM-mediated neurite outgrowth, whereas glycosylated Ig3mut2 containing mutations at the Ig2-Ig3 binding site is inactive (FIG. 6F,G). In the "compact" zipper, the heparin binding sites (133-KHKGRDVILKKDVRFI-148) (SEQ ID NO: 39) (Cole and Akeson, 1989) of Ig1-2-3 molecules are solvent exposed (FIG. 2C,D) and therefore accessible for binding to heparin and heparan sulfate molecules, suggesting that NCAM can be engaged in homophilic and heterophilic interactions simultaneously.

In order to accommodate all seven extracellular modules of NCAM within a typical distance between plasma membranes of ~30 nm (Hall and Rutishauser, 1987), a bend has to be introduced in the NCAM molecules in our model (FIG. 7). Analyses of NCAM by electron microscopy have revealed such a bent rod-like structure (Hall and Rutishauser, 1987; Becker et al., 1989). The angle of the bend at the hinge-region between N-terminal (~18 nm) and C-terminal (~10 nm) parts varies considerably (50-140°) with an average value of 98° (Becker et al., 1989) and presumably provides sufficient internal flexibility for NCAM to fit within the cell-cell distance. Based on these studies and on an average length of ~4.3 nm for an Ig module (present work) and ~3.5 nm for a FnIII module (Leahy et al., 1996), the hinge region is most likely located after Ig4. A multiple sequence alignment of NCAM sequences from various species of vertebrates reveals conserved Pro, Lys, and Gly residues in the PKLQGP sequence connecting the Ig4 and Ig5 modules. Since Pro and Gly are typically associated with polypeptide bends, this sequence is likely to introduce a bend between Ig4 and Ig5 modules. The double zipper observed in the crystal (FIG. 7C) presents Ig modules 1 to 3 at differing heights, implying that the NCAM molecules upon co-existence of the zippers are bent with different angles. This is in accordance with the electron microscopy data (Hall and Rutishauser, 1987; Becker et al., 1989).

Although cis interactions between the Ig1-Ig2 modules do not mediate cell-cell interactions themselves, they probably contribute to the stability of the trans interactions. This contention is supported by the cell co-culture experiments using the P1-B peptide corresponding to the site in Ig1 binding to Ig2 (FIG. 6). Furthermore, an inhibitory effect on cell aggregation was recently demonstrated for a peptide 172-GRILARGEINFK-182 (P2 peptide) (SEQ ID NO: 28) representing the site in the Ig2 module binding to the Ig1 module (Soroka et al., 2002). Therefore, we suggest that the formation of cis dimers may be a prerequisite for the establishment of trans interactions.

To our knowledge, only three X-ray structures of Ig module containing adhesion molecules have been determined comprising three or more Ig modules (axonin-1/TAG1 (Freigang et al., 2000), hemolin (Su et al., 1998), and CD4 (Wu et al., 1997). A similar zipper-like array of trans-interacting cis homodimers has been observed in the crystal structure of the junctional adhesion molecule (JAM) (Kostrewa et al., 2001). A zipper-like mechanism of homophilic interactions was also suggested for axonin-1/TAG-1 (Freigang et al., 2000), where molecules alternately provided by opposed membranes form a linear zipper-like array. However, the double zipper formed by NCAM differs fundamentally from the previously described zippers.

In conclusion, we here present a novel model for NCAM homophilic binding, which is based on the formation of zippers. The model is in agreement with a number of studies demonstrating that the Ig1, Ig2, and Ig3 modules all are involved in NCAM homophilic binding (Rao et al., 1992; Sandig et al., 1994; Kiselyov et al., 1997; Jensen et al., 1999; Kasper et al., 2000; Atkins et al., 2001) and reconciles a large body of conflicting biological data. The crystal structure of the Ig1-2-3 fragment reveals details of two so far unknown interactions between Ig1 and Ig3 and between Ig2 and Ig3. Interestingly, the Ig1 and Ig2 modules of NCAM mediate both cis and trans interactions simultaneously, whereas Ig3 is involved only in trans interactions. All taken together, our study implies that it is the joined forces of the first three Ig modules that confer the strength of the NCAM-mediated adhesion.

The invention claimed is:

1. A purified compound capable of binding to the neural cell adhesion molecule (NCAM) homophylic binding site composed of the Ig1, Ig2 and Ig3 modules, wherein said compound is capable of
   i) binding to the Ig1 module of NCAM at said NCAM homophylic binding site, and thereby mimicking and/or modulating the interaction between the Ig1 and Ig3 modules of NCAM, wherein said modules are from two individual NCAM molecules of opposing contacting cells, and/or
   ii) binding to the Ig3 module of NCAM at said NCAM homophylic binding site, and thereby mimicking and/or modulating the interaction between the Ig3 and Ig1 modules of NCAM, wherein said modules are from two individual NCAM molecules of opposing contacting cells, and/or
   iii) binding to the Ig2 module of NCAM at said NCAM homophylic binding site, and thereby mimicking the interaction between Ig2 and Ig3 modules of NCAM, wherein said modules are from two individual NCAM molecules of opposing contacting cells, and/or
   iv) binding to the Ig3 module of NCAM at said NCAM homophylic binding site, and thereby mimicking and/or modulating the binding between the Ig3 and Ig2 modules of NCAM, wherein said modules are from two individual NCAM molecules of opposing contacting cells, and/or
   v) binding to the Ig2 module of NCAM at said NCAM homophylic binding site, and thereby mimicking and/or modulating the interaction between the Ig2 and Ig2 modules of NCAM, wherein said modules are from two individual NCAM molecules of opposing contacting cells, said compound being
   (I) (a) a peptide sequence identified as SEQ ID NO: 1, 2, 4, 6, 7, 8, 9, 10, 11, 12, 13, 14, 16, 17, 18, 40 or 41,
   (b) a peptide which is a fragment of (a), consisting of at least 5 amino acids,
   (c) a peptide consisting of a peptide sequence according to (a) and up to 10 additional amino acids,
   (d) a peptide which differs from (a), (b) or (c) solely by one or more amino acid substitutions, but (d1) comprises at least a five amino acid fragment of a peptide of (a) or (d2) comprises a sequence at least 85% identical to a peptide of (a), or
   (e) a peptide sequence identified as SEQ ID NO:5; or
   (II) an oligomer or polymer comprising a plurality of peptides according to (I) above, which oligomer or polymer either consists of a plurality of peptides according to (I) above, or comprises a non-NCAM carrier moiety to which said peptides are attached.

2. The compound according to claim 1, said compound consisting of the amino acid sequence WFSPNGEKLSPNQ (SEQ ID NO: 1).

3. The compound according to claim 1, said compound consisting of the amino acid sequence YKCVV-TAEDGTQSE (SEQ ID NO: 2).

4. The compound according to claim 1, said compound consisting of the amino acid sequence QIRGIKKTD (SEQ ID NO: 4).

5. The compound according to claim 1, said compound consisting of the amino acid sequence DVR (SEQ ID NO: 5).

6. The compound according to claim 1, said compound consisting of the amino acid sequence RGIKKTD (SEQ ID NO: 6).

7. The compound according to claim 1, said compound consisting of the amino acid sequence DVRRGIKKTD (SEQ ID NO: 7).

8. The compound according to claim 1, said compound consisting of the amino acid sequence KEGED (SEQ ID NO: 8).

9. The compound according to claim 1, said compound consisting of the amino acid sequence IRGIKKTD (SEQ ID NO: 9).

10. The compound according to claim 1, said compound consisting of the amino acid sequence KEGEDGIRGIKKTD (SEQ ID NO: 10).

11. The compound according to claim 1, said compound consisting of the amino acid sequence DKNDE (SEQ ID NO: 11).

12. The compound according to claim 1, said compound consisting of the amino acid sequence TVQARNSIVNAT (SEQ ID NO: 12).

13. The compound according to claim 1, said compound consisting of the amino acid sequence SIHLKVFAK (SEQ ID NO: 13).

14. The compound according to claim 1, said compound consisting of the amino acid sequence LSNNYLQIR (SEQ ID NO: 14).

15. The compound according to claim 1, said compound consisting of the amino acid sequence RFIVLSNNYLQI (SEQ ID NO: 15).

16. The compound according to claim 1, said compound consisting of the amino acid sequence KKDVRFIVLSN-NYLQI (SEQ ID NO: 16).

17. The compound according to claim 1, said compound consisting of the amino acid sequence QEFKEGEDAVIV (SEQ ID NO: 17).

18. The compound according to claim 1, said compound consisting of the amino acid sequence KEGEDAVIVCD (SEQ ID NO: 18).

19. The compound according to claim 1, said compound consisting of the amino acid sequence AFSPNGEKLSPNQ (SEQ ID NO: 40).

20. The compound according to claim 1, said compound consisting of the amino acid sequence AKSVV-TAEDGTQSE (SEQ ID NO: 41).

21. The compound according to claim 1 wherein the carrier of (II) is a lysine dendrimer backbone.

22. The compound according to claim 1 wherein the carrier of (II) is a protein.

23. The compound according to claim 22 wherein the carrier of (II) is bovine serum albumin.

24. The compound according to claim 1 wherein the carrier of (II) is a lipophilic dendrimer, a micelle-like carrier formed by lipophilic derivatives, a starburst carbon chain polymer conjugate, or a ligand presenting assembly based on a derivative of diethylaminomethane.

25. The compound according to claim 1 wherein (I) applies.

26. The compound of claim 25 wherein the peptide of (I) (d) comprises a sequence at least 85% identical to a peptide of (I) (a).

27. The compound of claim 25 wherein the peptide of (I) (d) comprises a sequence differing from a peptide of (I) (a) solely by a single substitution.

28. The compound of claim 25 wherein the peptide of (I) (d) comprises a sequence which differs from a peptide of (I) (a) solely by one or more conservative substitutions, such being defined as (1) replacement of an amino acid selected from the group consisting of Gly, Ala, Val, Leu and Ile with another amino acid of the same group,
(2) replacement of an amino acid selected from group consisting of Asp, Glu, Asn and Gln with another amino acid of the same group,
(3) replacement of an amino acid selected from the group consisting of Phe, Tyr, Trp, His, and Pro with another amino acid of the same group,
(4) replacement of an amino acid selected from the group consisting of Arg, Lys and His with another amino acid of the same group,
(5) replacement of Cys with an amino acid selected from the group consisting of Asp, Glu, Lys, Arg, His, Asn, Gln, Ser, Thr and Tyr,
(6) replacement of an amino acid selected from the group consisting of Pro, Ala, Gly, Ser and Tyr with another amino acid of the same group, and
(7) replacement of an amino acid selected from the group consisting of Leu, Ile, Val and Met with another amino acid of the same group.

29. The composition of claim 28 wherein the peptide of (I) (c) comprises a sequence differing from a peptide of (I) (a) solely by a single conservative substitution.

30. The compound of claim 25 wherein said fragment of (I) (b) differs from a peptide of (I) (a) by deletion of not more than 8 amino acids.

31. The compound of claim 25 wherein said fragment of (I) (b) differs from a peptide of (I) (a) by deletion of not more than 6 amino acids.

32. The compound of claim 25 wherein said fragment of (I) (b) differs from a peptide of (I) (a) by deletion of not more than 4 amino acids.

33. The compound of claim 25 wherein said fragment of (I) (b) differs from a peptide of (I) (a) by deletion of not more than 2 amino acids.

34. The compound of claim 25 that is a peptide of (I) (a) or (I) (b).

35. The compound of claim 25 that is a peptide of (I) (a).

36. The compound of claim 21 wherein said oligomer or polymer of (II) comprises at least two identical peptides according to (I).

37. The compound of claim 21 wherein said oligomer or polymer of (II) comprises at least four identical peptides according to (I).

38. The compound of claim 37 wherein the carrier is a lysine dendrimer backbone or bovine serum albumin.

39. The compound of claim 38 wherein the fragment of I(b) differs from a peptide of (I) (a) by deletion of not more than 2 amino acids, and the peptide of (I) (d) is at least 85% identical to a peptide of (I) (a).

40. The compound of claim 25 that is a peptide of (I) (a), (I) (b) or (I) (c).

41. The compound of claim 25 that is a peptide of (I) (a) or (I) (c).

42. The compound of claim 25 that is a peptide of (I) (a), (I) (b), (I) (c) or (I) (d).

43. The compound of claim 25 that is a peptide of (I) (a), (I) (b), (I) (c) or I(d1).

44. The compound of claim 25 that is a peptide of (I) (a), (I) (b), (I) (c) or I(d2).

45. The compound of claim 1, in soluble form.

46. The compound of claim 1, which is not part of a combinatorial library.

47. The compound of claim 1 wherein the peptide sequence of (I) (a) is SEQ ID NO:1, 7 or 40.

48. The compound according to claim 47 wherein the carrier of (II) is a protein.

49. The compound according to claim 47 wherein the carrier of (II) is bovine serum albumin.

50. The compound according to claim 47 wherein the carrier of (II) is a lipophilic dendrimer, a micelle-like carrier formed by lipophilic derivatives, a starburst carbon chain polymer conjugate, or a ligand presenting assembly based on a derivative of diethylaminomethane.

51. The compound according to claim 47 wherein (I) applies.

52. The compound of claim 47 wherein the peptide of (I) (d) comprises a sequence at least 90% identical to a peptide of (I) (a).

53. The compound of claim 47 wherein the peptide of (I) (d) comprises a sequence differing from a peptide of (I) (a) solely by a single substitution.

54. The compound of claim 47 wherein the peptide of (I) (d) comprises a sequence which differs from a peptide of (I) (a) solely by one or more conservative substitutions, such being defined as
    (1) replacement of an amino acid selected from the group consisting of Gly, Ala, Val, Leu and Ile with another amino acid of the same group,
    (2) replacement of an amino acid selected from group consisting of Asp, Glu, Asn and Gln with another amino acid of the same group,
    (3) replacement of an amino acid selected from the group consisting of Phe, Tyr, Trp, His, and Pro with another amino acid of the same group,
    (4) replacement of an amino acid selected from the group consisting of Arg, Lys and His with another amino acid of the same group,
    (5) replacement of Cys with an amino acid selected from the group consisting of Asp, Glu, Lys, Arg, His, Asn, Gln, Ser, Thr and Tyr,
    (6) replacement of an amino acid selected from the group consisting of Pro, Ala, Gly, Ser and Tyr with another amino acid of the same group, and
    (7) replacement of an amino acid selected from the group consisting of Leu, Ile, Val and Met with another amino acid of the same group.

55. The composition of claim 47 wherein the peptide of (I) (c) comprises a sequence differing from a peptide of (I) (a) solely by a single conservative substitution.

56. The compound of claim 47 wherein said fragment of (I) (b) differs from a peptide of (I) (a) by deletion of not more than 8 amino acids.

57. The compound of claim 47 wherein said fragment of (I) (b) differs from a peptide of (I) (a) by deletion of not more than 6 amino acids.

58. The compound of claim 47 wherein said fragment of (I) (b) differs from a peptide of (I) (a) by deletion of not more than 4 amino acids.

59. The compound of claim 47 wherein said fragment of (I) (b) differs from a peptide of (I) (a) by deletion of not more than 2 amino acids.

60. The compound of claim 47 that is a peptide of (I) (a) or (I) (b).

61. The compound of claim 47 that is a peptide of (I) (a).

62. The compound of claim 47 wherein said oligomer or polymer of (II) comprises at least two identical peptides according to (I).

63. The compound of claim 47 wherein said oligomer or polymer of (II) comprises at least four identical peptides according to (I).

64. The compound of claim 47 wherein the carrier is a lysine dendrimer backbone or bovine serum albumin.

65. The compound of claim 47 wherein the fragment of I(b) differs from a peptide of (I) (a) by deletion of not more than 2 amino acids, and the peptide of (I) (d) is at least 85% identical to a peptide of (I) (a).

66. The compound of claim 47 that is a peptide of (I) (a), (I) (b) or (I) (c).

67. The compound of claim 47 that is a peptide of (I) (a) or (I) (c).

68. The compound of claim 47 that is a peptide of (I) (a), (I) (b), (I) (c) or (I) (d).

69. The compound of claim 47 that is a peptide of (I) (a), (I) (b), (I) (c) or I(d1).

70. The compound of claim 47 that is a peptide of (I) (a), (I) (b), (I) (c) or I(d2).

71. A pharmaceutical composition comprising one or more compounds as defined in claim 1.

72. A method of treating a disease wherein modulating differentiation, adhesion and/or survival of NCAM presenting cells is essential for the treatment, which comprises administering to a subject in need thereof a therapeutically effective amount of a medicament comprising a compound according to claim 1.

73. The method of claim 72, wherein the medicament is for treating normal, degenerated or damaged NCAM presenting cells.

74. The method of claim 72, wherein the medicament is for treatment comprising the stimulation of differentiation and/or survival of NCAM presenting cells.

75. The method of claim 72, wherein the medicament is for treating the diseases and conditions of the central and peripheral nervous system, or of the muscles or of various organs.

76. The method of claim 72, wherein the medicament is for treating the diseases or conditions of the central and peripheral nervous system, such as postoperative nerve damage, traumatic nerve damage, impaired myelination of nerve fibers, postischaemic damage, e.g. resulting from a stroke, Parkinson's disease, Alzheimer's disease, Huntington's disease, dementias such as multiinfarct dementia, sclerosis, nerve degeneration associated with diabetes mellitus, disorders affecting the circadian clock or neuro-muscular transmission, and schizophrenia, mood disorders, such as manic depression; for treatment of diseases or conditions of the muscles including conditions with impaired function of neuro-muscular connections, such as after organ transplantation, or such as genetic or traumatic atrophic muscle disorders; or for treatment of diseases or conditions of various organs, such as degenerative conditions of the gonads, of the pancreas such as diabetes mellitus type I and II, of the kidney such as nephrosis and of the heart, liver and bowel.

77. The method of claim 72, wherein the medicament is for treating the postoperative nerve damage, traumatic nerve damage, impaired myelination of nerve fibers, postischaemic, e.g. resulting from a stroke, Parkinson's disease, Alzheimer's disease, dementias such as multiinfarct dementia, sclerosis, nerve degeneration associated with diabetes mellitus, disorders affecting the circadian clock or neuro-muscular transmission, and schizophrenia, mood disorders, such as manic depression.

78. The method of claim 72, wherein the medicament is for promoting the wound-healing.

79. The method of claim 72, wherein the medicament is for treating the cancer.

80. The method of claim 72, wherein the medicament is for preventing the cell death of heart muscle cells, such as after acute myocardial infarction, or after angiogenesis.

81. The method of claim 72, wherein the medicament is for promoting the revascularsation.

82. The method of claim 72, wherein the medicament is for stimulating the ability to learn and/or of the short and/or long-term memory.

* * * * *

```
                       SEQUENCE LISTING

<160> NUMBER OF SEQ ID NOS: 46

<210> SEQ ID NO 1
<211> LENGTH: 13
<212> TYPE: PRT
<213> ORGANISM: Artificial sequence
<220> FEATURE:
<223> OTHER INFORMATION: rat NCAM Ig1 fragment: amino acid residues
      35-47

<400> SEQUENCE: 1

Trp Phe Ser Pro Asn Gly Glu Lys Leu Ser Pro Asn Gln
1               5                   10

<210> SEQ ID NO 2
<211> LENGTH: 14
<212> TYPE: PRT
<213> ORGANISM: Artificial sequence
<220> FEATURE:
<223> OTHER INFORMATION: rat NCAM Ig1 fragment: amino acid residues
      75-88

<400> SEQUENCE: 2

Tyr Lys Cys Val Val Thr Ala Glu Asp Gly Thr Gln Ser Glu
1               5                   10

<210> SEQ ID NO 3
<211> LENGTH: 12
<212> TYPE: PRT
<213> ORGANISM: Artificial sequence
<220> FEATURE:
<223> OTHER INFORMATION: rat NCAM Ig3 fragment: amino acid residues
      213-224

<400> SEQUENCE: 3

Thr Leu Val Ala Asp Ala Asp Gly Phe Pro Glu Pro
1               5                   10
```

```
<210> SEQ ID NO 4
<211> LENGTH: 9
<212> TYPE: PRT
<213> ORGANISM: Artificial sequence
<220> FEATURE:
<223> OTHER INFORMATION: rat NCAM Ig2 fragment: amino acid residues
      156-164

<400> SEQUENCE: 4

Gln Ile Arg Gly Ile Lys Lys Thr Asp
1               5

<210> SEQ ID NO 5
<211> LENGTH: 3
<212> TYPE: PRT
<213> ORGANISM: Artificial sequence
<220> FEATURE:
<223> OTHER INFORMATION: rat NCAM Ig2 fragment: amino acid residues
      144-146

<400> SEQUENCE: 5

Asp Val Arg
1

<210> SEQ ID NO 6
<211> LENGTH: 7
<212> TYPE: PRT
<213> ORGANISM: Artificial sequence
<220> FEATURE:
<223> OTHER INFORMATION: rat NCAM Ig2 fragment: amino acid residues
      158-164

<400> SEQUENCE: 6

Arg Gly Ile Lys Lys Thr Asp
1               5

<210> SEQ ID NO 7
<211> LENGTH: 10
<212> TYPE: PRT
<213> ORGANISM: Artificial sequence
<220> FEATURE:
<223> OTHER INFORMATION: rat NCAM Ig2 fragment: amino acid residues
      144-146 and 158-164

<400> SEQUENCE: 7

Asp Val Arg Arg Gly Ile Lys Lys Thr Asp
1               5                   10

<210> SEQ ID NO 8
<211> LENGTH: 5
<212> TYPE: PRT
<213> ORGANISM: Artificial sequence
<220> FEATURE:
<223> OTHER INFORMATION: rat NCAM Ig2 fragment: amino acid residues
      111-115

<400> SEQUENCE: 8

Lys Glu Gly Glu Asp
1               5

<210> SEQ ID NO 9
<211> LENGTH: 8
<212> TYPE: PRT
<213> ORGANISM: Artificial sequence
<220> FEATURE:
<223> OTHER INFORMATION: rat NCAM Ig2 fragment: amino acid residues
      157-164

<400> SEQUENCE: 9
```

```
Ile Arg Gly Ile Lys Lys Thr Asp
1               5
```

<210> SEQ ID NO 10
<211> LENGTH: 14
<212> TYPE: PRT
<213> ORGANISM: Artificial sequence
<220> FEATURE:
<223> OTHER INFORMATION: rat NCAM Ig2 fragment: amino acid residues
      111-115 and 157-164

<400> SEQUENCE: 10

```
Lys Glu Gly Glu Asp Gly Ile Arg Gly Ile Lys Lys Thr Asp
1               5                   10
```

<210> SEQ ID NO 11
<211> LENGTH: 5
<212> TYPE: PRT
<213> ORGANISM: Artificial sequence
<220> FEATURE:
<223> OTHER INFORMATION: rat NCAM Ig3 fragment: amino acid residues
      260-264

<400> SEQUENCE: 11

```
Asp Lys Asn Asp Glu
1               5
```

<210> SEQ ID NO 12
<211> LENGTH: 12
<212> TYPE: PRT
<213> ORGANISM: Artificial sequence
<220> FEATURE:
<223> OTHER INFORMATION: rat NCAM Ig3 fragment: amino acid residues
      194-205

<400> SEQUENCE: 12

```
Thr Val Gln Ala Arg Asn Ser Ile Val Asn Ala Thr
1               5                   10
```

<210> SEQ ID NO 13
<211> LENGTH: 9
<212> TYPE: PRT
<213> ORGANISM: Artificial sequence
<220> FEATURE:
<223> OTHER INFORMATION: rat NCAM Ig3 fragment: amino acid residues
      281-289

<400> SEQUENCE: 13

```
Ser Ile His Leu Lys Val Phe Ala Lys
1               5
```

<210> SEQ ID NO 14
<211> LENGTH: 9
<212> TYPE: PRT
<213> ORGANISM: Artificial sequence
<220> FEATURE:
<223> OTHER INFORMATION: rat NCAM Ig2 fragment: amino acid residues
      150-158

<400> SEQUENCE: 14

```
Leu Ser Asn Asn Tyr Leu Gln Ile Arg
1               5
```

<210> SEQ ID NO 15
<211> LENGTH: 12
<212> TYPE: PRT
<213> ORGANISM: Artificial sequence

```
<220> FEATURE:
<223> OTHER INFORMATION: rat NCAM Ig2 fragment: amino acid residues
      146-157

<400> SEQUENCE: 15

Arg Phe Ile Val Leu Ser Asn Asn Tyr Leu Gln Ile
1               5                   10

<210> SEQ ID NO 16
<211> LENGTH: 16
<212> TYPE: PRT
<213> ORGANISM: Artificial sequence
<220> FEATURE:
<223> OTHER INFORMATION: rat NCAM Ig2 fragment: amino acid residues
      142-157

<400> SEQUENCE: 16

Lys Lys Asp Val Arg Phe Ile Val Leu Ser Asn Asn Tyr Leu Gln Ile
1               5                   10                  15

<210> SEQ ID NO 17
<211> LENGTH: 12
<212> TYPE: PRT
<213> ORGANISM: Artificial sequence
<220> FEATURE:
<223> OTHER INFORMATION: rat NCAM Ig2 fragment: amino acid residues
      108-119

<400> SEQUENCE: 17

Gln Glu Phe Lys Glu Gly Glu Asp Ala Val Ile Val
1               5                   10

<210> SEQ ID NO 18
<211> LENGTH: 11
<212> TYPE: PRT
<213> ORGANISM: Artificial sequence
<220> FEATURE:
<223> OTHER INFORMATION: rat NCAM Ig2 fragment: amino acid residues
      111-121

<400> SEQUENCE: 18

Lys Glu Gly Glu Asp Ala Val Ile Val Cys Asp
1               5                   10

<210> SEQ ID NO 19
<211> LENGTH: 12
<212> TYPE: PRT
<213> ORGANISM: Artificial sequence
<220> FEATURE:
<223> OTHER INFORMATION: rat NCAM Ig1 fragment: amino acid residues
      10-21

<400> SEQUENCE: 19

Gly Glu Ile Ser Val Gly Glu Ser Lys Phe Phe Leu
1               5                   10

<210> SEQ ID NO 20
<211> LENGTH: 21
<212> TYPE: PRT
<213> ORGANISM: Artificial sequence
<220> FEATURE:
<223> OTHER INFORMATION: rat NCAM Ig3 fragment: amino acid residues
      243-263

<400> SEQUENCE: 20

Lys His Ile Phe Ser Asp Asp Ser Ser Glu Leu Thr Ile Arg Asn Val
1               5                   10                  15
```

```
Asp Lys Asn Asp Glu
            20

<210> SEQ ID NO 21
<211> LENGTH: 12
<212> TYPE: PRT
<213> ORGANISM: Artificial sequence
<220> FEATURE:
<223> OTHER INFORMATION: rat NCAM Ig1 fragment: amino acid residues
      10-21 containing mutation F19A

<400> SEQUENCE: 21

Gly Glu Ile Ser Val Gly Glu Ser Lys Ala Phe Leu
1               5                   10

<210> SEQ ID NO 22
<211> LENGTH: 12
<212> TYPE: PRT
<213> ORGANISM: Artificial sequence
<220> FEATURE:
<223> OTHER INFORMATION: rat NCAN Ig1 fragment: amino acid residues
      10-21 containing mutations F19A and F20A

<400> SEQUENCE: 22

Gly Glu Ile Ser Val Gly Glu Ser Lys Ala Ala Leu
1               5                   10

<210> SEQ ID NO 23
<211> LENGTH: 21
<212> TYPE: PRT
<213> ORGANISM: Artificial sequence
<220> FEATURE:
<223> OTHER INFORMATION: chicken NCAM Ig3 fragment: amino acid residues
      243-263

<400> SEQUENCE: 23

Lys Tyr Ser Phe Asn Tyr Asp Gly Ser Glu Leu Ile Ile Lys Lys Val
1               5                   10                  15

Asp Lys Ser Asp Glu
            20

<210> SEQ ID NO 24
<211> LENGTH: 10
<212> TYPE: PRT
<213> ORGANISM: Artificial sequence
<220> FEATURE:
<223> OTHER INFORMATION: rat NCAM Ig3 fragment: amino acid residues
      244-253

<400> SEQUENCE: 24

Lys His Ile Phe Ser Asp Asp Ser Ser Glu
1               5                   10

<210> SEQ ID NO 25
<211> LENGTH: 10
<212> TYPE: PRT
<213> ORGANISM: Artificial sequence
<220> FEATURE:
<223> OTHER INFORMATION: chicken NCAM Ig3 fragment: amino acid residues
      243-252

<400> SEQUENCE: 25

Lys Tyr Ser Phe Asn Tyr Asp Gly Ser Glu
1               5                   10

<210> SEQ ID NO 26
<211> LENGTH: 9
```

```
<212> TYPE: PRT
<213> ORGANISM: Artificial sequence
<220> FEATURE:
<223> OTHER INFORMATION: rat NCAM Ig3 fragment: amino acid residues
      281-289 containing mutations K285A and F287S

<400> SEQUENCE: 26

Ser Ile His Leu Ala Val Ala Ala Lys
1               5

<210> SEQ ID NO 27
<211> LENGTH: 9
<212> TYPE: PRT
<213> ORGANISM: Artificial sequence
<220> FEATURE:
<223> OTHER INFORMATION: rat NCAM Ig3 fragment: amino acid residues
      281-289 containing mutations K285A and F287G

<400> SEQUENCE: 27

Ser Ile His Leu Ala Val Gly Ala Lys
1               5

<210> SEQ ID NO 28
<211> LENGTH: 12
<212> TYPE: PRT
<213> ORGANISM: Artificial sequence
<220> FEATURE:
<223> OTHER INFORMATION: rat NCAM Ig2 fragment: amino acid residues
      172-182

<400> SEQUENCE: 28

Gly Arg Ile Leu Ala Arg Gly Glu Ile Asn Phe Lys
1               5                   10

<210> SEQ ID NO 29
<211> LENGTH: 29
<212> TYPE: DNA
<213> ORGANISM: Artificial sequence
<220> FEATURE:
<223> OTHER INFORMATION: upper PCR primer

<400> SEQUENCE: 29
tctctcgaga actgcaggta gatattgtt                                        29

<210> SEQ ID NO 30
<211> LENGTH: 27
<212> TYPE: DNA
<213> ORGANISM: Artificial sequence
<220> FEATURE:
<223> OTHER INFORMATION: lower PCR primer

<400> SEQUENCE: 30
aaacccgggt tactttgcaa agacctt                                          27

<210> SEQ ID NO 31
<211> LENGTH: 25
<212> TYPE: DNA
<213> ORGANISM: Artificial sequence
<220> FEATURE:
<223> OTHER INFORMATION: upper PCR primer

<400> SEQUENCE: 31
gaatacgtaa ctgtccaggc cagac                                            25

<210> SEQ ID NO 32
<211> LENGTH: 27
<212> TYPE: DNA
```

```
<213> ORGANISM: Artificial sequence
<220> FEATURE:
<223> OTHER INFORMATION: lower PCR primer

<400> SEQUENCE: 32
aaacctaggt tactttgcaa agacctt                                          27

<210> SEQ ID NO 33
<211> LENGTH: 75
<212> TYPE: DNA
<213> ORGANISM: Artificial sequence
<220> FEATURE:
<223> OTHER INFORMATION: upper PCR primer

<400> SEQUENCE: 33
ctgcaggtag atattgttcc cagccaagga gccatcagcg ttggagcctc cgccttcttc      60
ctgtgtcaag tggca                                                      75

<210> SEQ ID NO 34
<211> LENGTH: 36
<212> TYPE: DNA
<213> ORGANISM: Artificial sequence
<220> FEATURE:
<223> OTHER INFORMATION: upper PCR primer

<400> SEQUENCE: 34
ggcgacagtt cggcgttaac catcaggaat gtggac                                36

<210> SEQ ID NO 35
<211> LENGTH: 39
<212> TYPE: DNA
<213> ORGANISM: Artificial sequence
<220> FEATURE:
<223> OTHER INFORMATION: lower PCR primer

<400> SEQUENCE: 35
ggttaacgcc gaactgtcgc cactgaagat gtgcttctc                             39

<210> SEQ ID NO 36
<211> LENGTH: 45
<212> TYPE: DNA
<213> ORGANISM: Artificial sequence
<220> FEATURE:
<223> OTHER INFORMATION: lower PCR primer

<400> SEQUENCE: 36
aaacttaggt tactttgctg cgactgcgag gtggatggag gcatc                      45

<210> SEQ ID NO 37
<211> LENGTH: 29
<212> TYPE: DNA
<213> ORGANISM: Artificial sequence
<220> FEATURE:
<223> OTHER INFORMATION: PCR primer

<400> SEQUENCE: 37
tctctcgagt tctgcaggta gatattgtt                                        29

<210> SEQ ID NO 38
<211> LENGTH: 36
<212> TYPE: DNA
<213> ORGANISM: Artificial sequence
<220> FEATURE:
<223> OTHER INFORMATION: PCR primer

<400> SEQUENCE: 38
```
aaatacgtaa ctgtccaggc cgcccagagc atcgtg                                    36

<210> SEQ ID NO 39
<211> LENGTH: 16
<212> TYPE: PRT
<213> ORGANISM: Artificial sequence
<220> FEATURE:
<223> OTHER INFORMATION: rat NCAM Ig2 fragment: amino acid residues
      133-148

<400> SEQUENCE: 39

Lys His Lys Gly Arg Asp Val Ile Leu Lys Lys Asp Val Arg Phe Ile
1               5                   10                  15

<210> SEQ ID NO 40
<211> LENGTH: 13
<212> TYPE: PRT
<213> ORGANISM: Artificial sequence
<220> FEATURE:
<223> OTHER INFORMATION: NCAM Ig1 fargment: CD-srands

<400> SEQUENCE: 40

Ala Phe Ser Pro Asn Gly Glu Lys Leu Ser Pro Asn Gln
1               5                   10

<210> SEQ ID NO 41
<211> LENGTH: 14
<212> TYPE: PRT
<213> ORGANISM: Artificial sequence
<220> FEATURE:
<223> OTHER INFORMATION: NCAM Ig1 fragment: FG-strands

<400> SEQUENCE: 41

Ala Lys Ser Val Val Thr Ala Glu Asp Gly Thr Gln Ser Glu
1               5                   10

<210> SEQ ID NO 42
<211> LENGTH: 10
<212> TYPE: PRT
<213> ORGANISM: Artificial sequence
<220> FEATURE:
<223> OTHER INFORMATION: NCAM Ig2 fragment: CD-strands

<400> SEQUENCE: 42

Asp Val Arg Arg Gly Ile Lys Lys Thr Asp
1               5                   10

<210> SEQ ID NO 43
<211> LENGTH: 9
<212> TYPE: PRT
<213> ORGANISM: Artificial sequence
<220> FEATURE:
<223> OTHER INFORMATION: NCAM Ig2 fragment: EF-strands

<400> SEQUENCE: 43

Gln Ile Arg Gly Ile Lys Lys Thr Asp
1               5

<210> SEQ ID NO 44
<211> LENGTH: 858
<212> TYPE: PRT
<213> ORGANISM: Rattus norvegicus

<400> SEQUENCE: 44

Met Leu Arg Thr Lys Asp Leu Ile Trp Thr Leu Phe Phe Leu Gly Thr
1               5                   10                  15

-continued

```
Ala Val Ser Leu Gln Val Asp Ile Val Pro Ser Gln Gly Glu Ile Ser
             20                  25                  30

Val Gly Glu Ser Lys Phe Phe Leu Cys Gln Val Ala Gly Asp Ala Lys
         35                  40                  45

Asp Lys Asp Ile Ser Trp Phe Ser Pro Asn Gly Glu Lys Leu Ser Pro
 50                  55                  60

Asn Gln Gln Arg Ile Ser Val Val Trp Asn Asp Asp Ser Ser Thr
65                   70                  75                  80

Leu Thr Ile Tyr Asn Ala Asn Ile Asp Asp Ala Gly Ile Tyr Lys Cys
                 85                  90                  95

Val Val Thr Ala Glu Asp Gly Thr Gln Ser Glu Ala Thr Val Asn Val
             100                 105                 110

Lys Ile Phe Gln Lys Leu Met Phe Lys Asn Ala Pro Thr Pro Gln Glu
         115                 120                 125

Phe Lys Glu Gly Glu Asp Ala Val Ile Val Cys Asp Val Val Ser Ser
 130                 135                 140

Leu Pro Pro Thr Ile Ile Trp Lys His Lys Gly Arg Asp Val Ile Leu
145                 150                 155                 160

Lys Lys Asp Val Arg Phe Ile Val Leu Ser Asn Asn Tyr Leu Gln Ile
                 165                 170                 175

Arg Gly Ile Lys Lys Thr Asp Glu Gly Thr Tyr Arg Cys Glu Gly Arg
             180                 185                 190

Ile Leu Ala Arg Gly Glu Ile Asn Phe Lys Asp Ile Gln Val Ile Val
         195                 200                 205

Asn Val Pro Pro Thr Val Gln Ala Arg Gln Ser Ile Val Asn Ala Thr
 210                 215                 220

Ala Asn Leu Gly Gln Ser Val Thr Leu Val Cys Asp Ala Asp Gly Phe
225                 230                 235                 240

Pro Glu Pro Thr Met Ser Trp Thr Lys Asp Gly Glu Pro Ile Glu Asn
                 245                 250                 255

Glu Glu Glu Asp Asp Glu Lys His Ile Phe Ser Asp Asp Ser Ser Glu
             260                 265                 270

Leu Thr Ile Arg Asn Val Asp Lys Asn Asp Glu Ala Glu Tyr Val Cys
         275                 280                 285

Ile Ala Glu Asn Lys Ala Gly Glu Gln Asp Ala Ser Ile His Leu Lys
 290                 295                 300

Val Phe Ala Lys Pro Lys Ile Thr Tyr Val Glu Asn Gln Thr Ala Met
305                 310                 315                 320

Glu Leu Glu Glu Gln Val Thr Leu Thr Cys Glu Ala Ser Gly Asp Pro
                 325                 330                 335

Ile Pro Ser Ile Thr Trp Arg Thr Ser Thr Arg Asn Ile Ser Ser Glu
             340                 345                 350

Glu Lys Ala Ser Trp Thr Arg Pro Glu Lys Gln Glu Thr Leu Asp Gly
         355                 360                 365

His Met Val Val Arg Ser His Ala Arg Val Ser Ser Leu Thr Leu Lys
 370                 375                 380

Ser Ile Gln Tyr Thr Asp Ala Gly Glu Tyr Ile Cys Thr Ala Ser Asn
385                 390                 395                 400

Thr Ile Gly Gln Asp Ser Gln Ser Met Tyr Leu Glu Val Gln Tyr Ala
                 405                 410                 415

Pro Lys Leu Gln Gly Pro Val Ala Val Tyr Thr Trp Glu Gly Asn Gln
             420                 425                 430
```

-continued

```
Val Asn Ile Thr Cys Glu Val Phe Ala Tyr Pro Ser Ala Thr Ile Ser
        435                 440                 445

Trp Phe Arg Asp Gly Gln Leu Leu Pro Ser Ser Asn Tyr Ser Asn Ile
    450                 455                 460

Lys Ile Tyr Asn Thr Pro Ser Ala Ser Tyr Leu Glu Val Thr Pro Asp
465                 470                 475                 480

Ser Glu Asn Asp Phe Gly Asn Tyr Asn Cys Thr Ala Val Asn Arg Ile
                485                 490                 495

Gly Gln Glu Ser Leu Glu Phe Ile Leu Val Gln Ala Asp Thr Pro Ser
            500                 505                 510

Ser Pro Ser Ile Asp Arg Val Glu Pro Tyr Ser Ser Thr Ala Gln Val
        515                 520                 525

Gln Phe Asp Glu Pro Glu Ala Thr Gly Gly Val Pro Ile Leu Lys Tyr
    530                 535                 540

Lys Ala Glu Trp Lys Ser Leu Gly Glu Glu Ala Trp His Ser Lys Trp
545                 550                 555                 560

Tyr Asp Ala Lys Glu Ala Asn Met Glu Gly Ile Val Thr Ile Met Gly
                565                 570                 575

Leu Lys Pro Glu Thr Arg Tyr Ala Val Arg Leu Ala Ala Leu Asn Gly
            580                 585                 590

Lys Gly Leu Gly Glu Ile Ser Ala Ala Thr Glu Phe Lys Thr Gln Pro
        595                 600                 605

Val Arg Glu Pro Ser Ala Pro Lys Leu Glu Gly Gln Met Gly Glu Asp
    610                 615                 620

Gly Asn Ser Ile Lys Val Asn Leu Ile Lys Gln Asp Asp Gly Gly Ser
625                 630                 635                 640

Pro Ile Arg His Tyr Leu Val Lys Tyr Arg Ala Leu Ala Ser Glu Trp
                645                 650                 655

Lys Pro Glu Ile Arg Leu Pro Ser Gly Ser Asp His Val Met Leu Lys
            660                 665                 670

Ser Leu Asp Trp Asn Ala Glu Tyr Glu Val Tyr Val Val Ala Glu Asn
        675                 680                 685

Gln Gln Gly Lys Ser Lys Ala Ala His Phe Val Phe Arg Thr Ser Ala
    690                 695                 700

Gln Pro Thr Ala Ile Pro Ala Asn Gly Ser Pro Thr Ala Gly Leu Ser
705                 710                 715                 720

Thr Gly Ala Ile Val Gly Ile Leu Ile Val Ile Phe Val Leu Leu Leu
                725                 730                 735

Val Val Met Asp Ile Thr Cys Tyr Phe Leu Asn Lys Cys Gly Leu Leu
            740                 745                 750

Met Cys Ile Ala Val Asn Leu Cys Gly Lys Ala Gly Pro Gly Ala Lys
        755                 760                 765

Gly Lys Asp Met Glu Glu Gly Lys Ala Ala Phe Ser Lys Asp Glu Ser
    770                 775                 780

Lys Glu Pro Ile Val Glu Val Arg Thr Glu Glu Arg Thr Pro Asn
785                 790                 795                 800

His Asp Gly Gly Lys His Thr Glu Pro Asn Glu Thr Thr Pro Leu Thr
                805                 810                 815

Glu Pro Glu Lys Gly Pro Val Thr Lys Ser Glu Pro Gln Glu Ser
            820                 825                 830

Glu Ala Lys Pro Ala Pro Thr Glu Val Lys Thr Val Pro Asn Glu Ala
        835                 840                 845

Thr Gln Thr Lys Glu Asn Glu Ser Lys Ala
```

<210> SEQ ID NO 45
<211> LENGTH: 848
<212> TYPE: PRT
<213> ORGANISM: Homo sapiens

<400> SEQUENCE: 45

Met Leu Gln Thr Lys Asp Leu Ile Trp Thr Leu Phe Phe Leu Gly Thr
1               5                   10                  15

Ala Val Ser Leu Gln Val Asp Ile Val Pro Ser Gln Gly Glu Ile Ser
            20                  25                  30

Val Gly Glu Ser Lys Phe Phe Leu Cys Gln Val Ala Gly Asp Ala Lys
        35                  40                  45

Asp Lys Asp Ile Ser Trp Phe Ser Pro Asn Gly Glu Lys Leu Thr Pro
    50                  55                  60

Asn Gln Gln Arg Ile Ser Val Val Trp Asn Asp Asp Ser Ser Ser Thr
65                  70                  75                  80

Leu Thr Ile Tyr Asn Ala Asn Ile Asp Asp Ala Gly Ile Tyr Lys Cys
                85                  90                  95

Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
        115                 120                 125

Phe Arg Glu Gly Glu Asp Ala Val Ile Val Cys Asp Val Val Ser Ser
    130                 135                 140

Leu Pro Pro Thr Ile Ile Trp Lys His Lys Gly Arg Asp Val Ile Leu
145                 150                 155                 160

Lys Lys Asp Val Arg Phe Ile Val Leu Ser Asn Asn Tyr Leu Gln Ile
                165                 170                 175

Arg Gly Ile Lys Lys Thr Asp Glu Gly Thr Tyr Arg Cys Glu Gly Arg
            180                 185                 190

Ile Leu Ala Arg Gly Glu Ile Asn Phe Lys Asp Ile Gln Val Ile Val
        195                 200                 205

Asn Val Pro Pro Thr Ile Gln Ala Arg Gln Asn Ile Val Asn Ala Thr
    210                 215                 220

Ala Asn Leu Gly Gln Ser Val Thr Leu Val Cys Asp Ala Glu Gly Phe
225                 230                 235                 240

Pro Glu Pro Thr Met Ser Trp Thr Lys Asp Gly Glu Gln Ile Glu Gln
                245                 250                 255

Glu Glu Asp Asp Glu Lys Tyr Ile Phe Ser Asp Asp Ser Ser Gln Leu
            260                 265                 270

Thr Ile Lys Lys Val Asp Lys Asn Asp Glu Ala Glu Tyr Ile Cys Ile
        275                 280                 285

Ala Glu Asn Lys Ala Gly Glu Gln Asp Ala Thr Ile His Leu Lys Val
    290                 295                 300

Phe Ala Lys Pro Lys Ile Thr Tyr Val Glu Asn Gln Thr Ala Met Glu
305                 310                 315                 320

Leu Glu Glu Gln Val Thr Leu Thr Cys Glu Ala Ser Gly Asp Pro Ile
                325                 330                 335

Pro Ser Ile Thr Trp Arg Thr Ser Thr Arg Asn Ile Ser Ser Glu Glu
            340                 345                 350

Lys Thr Leu Asp Gly His Met Val Val Arg Ser His Ala Arg Val Ser
        355                 360                 365

-continued

```
Ser Leu Thr Leu Lys Ser Ile Gln Tyr Thr Asp Ala Gly Glu Tyr Ile
    370                 375                 380

Cys Thr Ala Ser Asn Thr Ile Gly Gln Asp Ser Gln Ser Met Tyr Leu
385                 390                 395                 400

Glu Val Gln Tyr Ala Pro Lys Leu Gln Gly Pro Val Ala Val Tyr Thr
                405                 410                 415

Trp Glu Gly Asn Gln Val Asn Ile Thr Cys Glu Val Phe Ala Tyr Pro
                420                 425                 430

Ser Ala Thr Ile Ser Trp Phe Arg Asp Gly Gln Leu Leu Pro Ser Ser
            435                 440                 445

Asn Tyr Ser Asn Ile Lys Ile Tyr Asn Thr Pro Ser Ala Ser Tyr Leu
    450                 455                 460

Glu Val Thr Pro Asp Ser Glu Asn Asp Phe Gly Asn Tyr Asn Cys Thr
465                 470                 475                 480

Ala Val Asn Arg Ile Gly Gln Glu Ser Leu Glu Phe Ile Leu Val Gln
                485                 490                 495

Ala Asp Thr Pro Ser Ser Pro Ser Ile Asp Gln Val Glu Pro Tyr Ser
            500                 505                 510

Ser Thr Ala Gln Val Gln Phe Asp Glu Pro Glu Ala Thr Gly Gly Val
    515                 520                 525

Pro Ile Leu Lys Tyr Lys Ala Glu Trp Arg Ala Val Gly Glu Glu Val
530                 535                 540

Trp His Ser Lys Trp Tyr Asp Ala Lys Glu Ala Ser Met Glu Gly Ile
545                 550                 555                 560

Val Thr Ile Val Gly Leu Lys Pro Glu Thr Thr Tyr Ala Val Arg Leu
                565                 570                 575

Ala Ala Leu Asn Gly Lys Gly Leu Gly Glu Ile Ser Ala Ala Ser Glu
            580                 585                 590

Phe Lys Thr Gln Pro Val Gln Gly Glu Pro Ser Ala Pro Lys Leu Glu
    595                 600                 605

Gly Gln Met Gly Glu Asp Gly Asn Ser Ile Lys Val Asn Leu Ile Lys
610                 615                 620

Gln Asp Asp Gly Gly Ser Pro Ile Arg His Tyr Leu Val Arg Tyr Arg
625                 630                 635                 640

Ala Leu Ser Ser Glu Trp Lys Pro Glu Ile Arg Leu Pro Ser Gly Ser
                645                 650                 655

Asp His Val Met Leu Lys Ser Leu Asp Trp Asn Ala Glu Tyr Glu Val
            660                 665                 670

Tyr Val Val Ala Glu Asn Gln Gln Gly Lys Ser Lys Ala Ala His Phe
    675                 680                 685

Val Phe Arg Thr Ser Ala Gln Pro Thr Ala Ile Pro Ala Asn Gly Ser
690                 695                 700

Pro Thr Ser Gly Leu Ser Thr Gly Ala Ile Val Gly Ile Leu Ile Val
705                 710                 715                 720

Ile Phe Val Leu Leu Leu Val Val Asp Ile Thr Cys Tyr Phe Leu
                725                 730                 735

Asn Lys Cys Gly Leu Phe Met Cys Ile Ala Val Asn Leu Cys Gly Lys
            740                 745                 750

Ala Gly Pro Gly Ala Lys Gly Lys Asp Met Glu Glu Gly Lys Ala Ala
    755                 760                 765

Phe Ser Lys Asp Glu Ser Lys Glu Pro Ile Val Glu Val Arg Thr Glu
770                 775                 780

Glu Glu Arg Thr Pro Asn His Asp Gly Gly Lys His Thr Glu Pro Asn
```

-continued

```
                785                 790                 795                 800

Glu Thr Thr Pro Leu Thr Glu Pro Glu Lys Gly Pro Val Glu Ala Lys
                805                 810                 815

Pro Glu Cys Gln Glu Thr Glu Thr Lys Pro Ala Pro Ala Glu Val Lys
                820                 825                 830

Thr Val Pro Asn Asp Ala Thr Gln Thr Lys Glu Asn Glu Ser Lys Ala
                835                 840                 845

<210> SEQ ID NO 46
<211> LENGTH: 291
<212> TYPE: PRT
<213> ORGANISM: Artificial sequence
<220> FEATURE:
<223> OTHER INFORMATION: rat NCAM fragment: amino acid residues 20-308
      and cloning artifacts

<400> SEQUENCE: 46

Arg Val Leu Gln Val Asp Ile Val Pro Ser Gln Gly Glu Ile Ser Val
1               5                   10                  15

Gly Glu Ser Lys Phe Phe Leu Cys Gln Val Ala Gly Asp Ala Lys Asp
                20                  25                  30

Lys Asp Ile Ser Trp Phe Ser Pro Asn Gly Glu Lys Leu Ser Pro Asn
            35                  40                  45

Gln Gln Arg Ile Ser Val Val Trp Asn Asp Asp Ser Ser Thr Leu
    50                  55                  60

Thr Ile Tyr Asn Ala Asn Ile Asp Asp Ala Gly Ile Tyr Lys Cys Val
65                  70                  75                  80

Val Thr Ala Glu Asp Gly Thr Gln Ser Glu Ala Thr Val Asn Val Lys
                85                  90                  95

Ile Phe Gln Lys Leu Met Phe Lys Asn Ala Pro Thr Pro Gln Glu Phe
                100                 105                 110

Lys Glu Gly Glu Asp Ala Val Ile Val Cys Asp Val Val Ser Ser Leu
            115                 120                 125

Pro Pro Thr Ile Ile Trp Lys His Lys Gly Arg Asp Val Ile Leu Lys
    130                 135                 140

Lys Asp Val Arg Phe Ile Val Leu Ser Asn Asn Tyr Leu Gln Ile Arg
145                 150                 155                 160

Gly Ile Lys Lys Thr Asp Glu Gly Thr Tyr Arg Cys Glu Gly Arg Ile
                165                 170                 175

Leu Ala Arg Gly Glu Ile Asn Phe Lys Asp Ile Gln Val Ile Val Asn
            180                 185                 190

Val Pro Pro Thr Val Gln Ala Arg Gln Ser Ile Val Asn Ala Thr Ala
    195                 200                 205

Asn Leu Gly Gln Ser Val Thr Leu Val Cys Asp Ala Asp Gly Phe Pro
210                 215                 220

Glu Pro Thr Met Ser Trp Thr Lys Asp Gly Glu Pro Ile Glu Asn Glu
                225                 230                 235                 240

Glu Glu Asp Asp Glu Lys His Ile Phe Ser Asp Ser Ser Glu Leu
                245                 250                 255

Thr Ile Arg Asn Val Asp Lys Asn Asp Glu Ala Glu Tyr Val Cys Ile
            260                 265                 270

Ala Glu Asn Lys Ala Gly Glu Gln Asp Ala Ser Ile His Leu Lys Val
    275                 280                 285

Phe Ala Lys
    290
```